US012723106B2

(12) United States Patent
Langer et al.

(10) Patent No.: US 12,723,106 B2
(45) Date of Patent: Sep. 1, 2026

(54) PROTEASE-PROCESSED MOLECULES

(71) Applicant: SANOFI, Paris (FR)

(72) Inventors: Thomas Langer, Frankfurt am Main (DE); Ercole Rao, Frankfurt am Main (DE); Sandra Weil, Frankfurt am Main (DE)

(73) Assignee: SANOFI, Paris (FR)

(*) Notice: Subject to any disclaimer, the term of this patent is extended or adjusted under 35 U.S.C. 154(b) by 949 days.

(21) Appl. No.: 17/908,216

(22) PCT Filed: Mar. 5, 2021

(86) PCT No.: PCT/EP2021/055673
§ 371 (c)(1),
(2) Date: Aug. 30, 2022

(87) PCT Pub. No.: WO2021/176090
PCT Pub. Date: Sep. 10, 2021

(65) Prior Publication Data

US 2023/0279151 A1 Sep. 7, 2023

(30) Foreign Application Priority Data

Mar. 5, 2020 (EP) .................................... 20305233

(51) Int. Cl.
*C12P 21/06* (2006.01)
*C07K 16/46* (2006.01)

(52) U.S. Cl.
CPC ........ *C07K 16/468* (2013.01); *C07K 2317/31* (2013.01); *C07K 2317/55* (2013.01); *C07K 2317/622* (2013.01); *C07K 2317/64* (2013.01)

(58) Field of Classification Search
CPC .... C12N 9/6454; C12P 21/06; C07K 2317/64
USPC ...................................................... 424/136.1
See application file for complete search history.

(56) References Cited

FOREIGN PATENT DOCUMENTS

| | | | |
|---|---|---|---|
| JP | 2014-155581 | A | 7/2014 |
| RU | 2014147684 | A | 6/2016 |
| RU | 2713121 | C2 | 2/2020 |
| WO | WO 2012/025530 | A1 | 3/2012 |
| WO | WO 2012/158948 | A1 | 11/2012 |
| WO | WO 2013/006544 | A1 | 1/2013 |
| WO | WO 2013/100534 | A1 | 7/2013 |
| WO | WO 2013/163631 | A2 | 10/2013 |
| WO | WO 2016/046778 | A2 | 3/2016 |
| WO | WO 2019/222282 | A1 | 11/2019 |
| WO | WO 2019/222296 | A1 | 11/2019 |

OTHER PUBLICATIONS

NCT05564078 (sanofi_IL4_IL13 _ClinicalTrialsgov); pp. (Oct. 27, 2025)).*
Liu et al (Anim Biotechnol (2016;27(1):1-8. doi: 10.1080/10495398.2014.977906; Abstract).*
Duckert et al., "Prediction of proprotein convertase cleavage sites", Protein Engineering, Design and Selection, Jan. 1, 2004, vol. 17, No. 1, pp. 107-112.
International Preliminary Report on Patentability for PCT International Patent Application No. PCT/EP2021/055673, mailed Sep. 15, 2022.
International Search Report and Written Opinion for PCT International Patent Application No. PCT/EP2021/055673, mailed May 28, 2021.
Izidoro et al., "A study of human furin specificity using synthetic peptides derived from natural substrates, and effects of potassium ions", Archives of Biochemistry and Biophysics, Jul. 15, 2009, vol. 487, No. 2, pp. 105-114.
Chen et al., "Fusion protein linkers: property, design and functionality", Adv. Drug Deliv. Rev., Oct. 2013, 65(10): 1357-1369, Epublished Sep. 29, 2012.
Keskin et al., "A new, structurally nonredundant, diverse data set of protein-protein interfaces and its implications", Protein Science, Apr. 2004, 13(4): 1043-1055, first published Jan. 1, 2004.
Pakula et al., "Genetic Analysis of Protein Stability and Function", Annual Review of Genetics, Jan. 1, 1989, 23: 289-310.
Izidoro et al., "A study of human furin specificity using synthetic peptides derived from natural substrates, and effects of potassium ions", Archives of Biochemistry and Biophysics, May 27, 2009, 487(2): 105-114.
Matthews et al., "A survey of furin substrate specificity using substrate phage display", Protein Science, Aug. 1994, 3(8): 1197-1205.
Remacle et al., "Substrate Cleavage Analysis of Furin and Related Proprotein Convertases", The Journal of Biological Chemistry, Jul. 25, 2008, 283(30): 20897-20906.

* cited by examiner

*Primary Examiner* — Lynn A Bristol
(74) *Attorney, Agent, or Firm* — LATHROP GPM LLP; James H. Velema, Esq.

(57) ABSTRACT

The present invention relates to protein molecules comprising at least one protease-cleavable linker. It also relates to protein molecules obtainable by protease-cleavage of such protein molecules and their use in therapy.

26 Claims, 13 Drawing Sheets

Specification includes a Sequence Listing.

C SDS-PAGE

A analytical SEC B analytical HIC

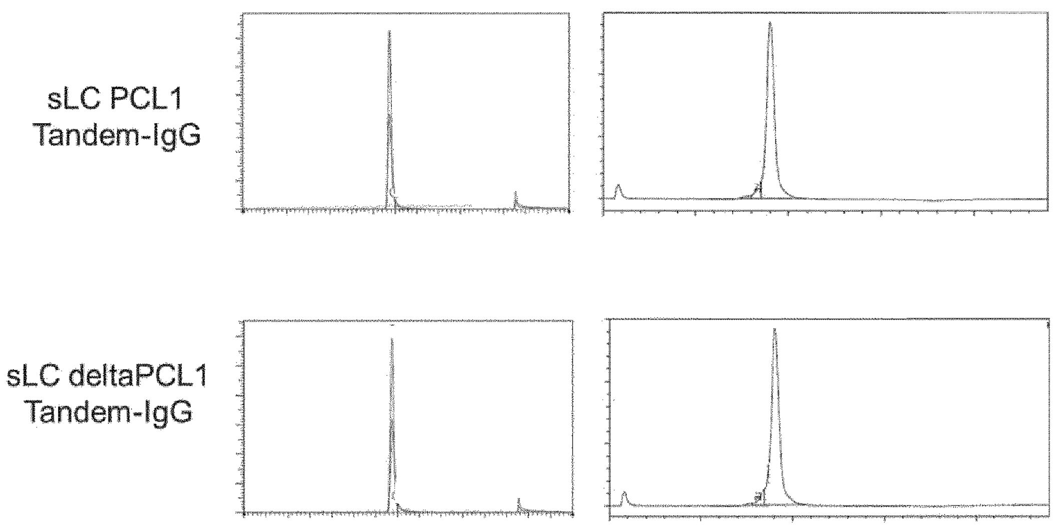

D LC-MS of sLC-PCL1 Tandem-IgG co-expressd with Furin and Furin-KDEL

| Seq ID | Construct Name | Expected (Da) | Measured (Da) | Differece (Da) | Comment | Chain |
|---|---|---|---|---|---|---|
| Seq 17, Seq 13 with Seq 37 | sLC-Tandem-(anti-IL4 x anti-IL13)-His8-PCL1-hulgG1 | 74621.92 | 74631.26 | 9.43 | correct | HC |
| | | 23746.05 | 23744.60 | -1.45 | correct | LC1 |
| | | 23914.5 | 23754.76 | -159.74 | R-loss | LC2 |
| | | 23914.5 | 23627.58 | -286.92 | KR-loss | LC2 |
| | | 23914.5 | 23470.97 | -443.53 | RKR-loss | LC2 |
| Seq 17, Seq 13 with Seq 38 | sLC-Tandem-(anti-IL4 x anti-IL13)-His8-PCL1-hulgG1 | 74621.92 | 74625.99 | 4.07 | correct | HC |
| | | 23746.05 | 23744.65 | -1.40 | correct | LC1 |
| | | 23914.5 | 23754.47 | -160.03 | R-loss | LC2 |
| | | 23914.5 | 23627.21 | -287.29 | KR-loss | LC2 |
| | | 23914.5 | 23470.75 | -443.75 | RKR-loss | LC2 |

Figure 5

PROTEASE-PROCESSED MOLECULES

RELATED APPLICATIONS

This application is a 35 U.S.C. § 371 filing of International Patent Application No. PCT/EP2021/055673, filed Mar. 5, 2021, which claims priority to European Patent Application No. 20305233.7, filed Mar. 5, 2020, the contents of which are incorporated herein by reference in their entirety.

SEQUENCE LISTING

The instant application contains a Sequence Listing which has been submitted electronically in ASCII format and is hereby incorporated by reference in its entirety. Said ASCII file, created on Aug. 30, 2022, is named 732358_SA9-343US_ST25.txt and is 333,475 bytes in size.

TECHNICAL FIELD OF THE INVENTION

The present invention relates to protein molecules comprising at least one protease-cleavable linker. It also relates to protein molecules obtainable by protease-processing of such protein molecules as well as their use in therapy.

BACKGROUND OF THE INVENTION

Naturally occurring IgG antibodies are bivalent and monospecific. Multispecific, e.g., bispecific antibodies having binding specificities for multiple different antigens can be produced using recombinant technologies and are projected to have broad clinical applications. It is well known that complete IgG antibody molecules are Y-shaped molecules comprising four polypeptide chains: two heavy chains and two light chains. Each light chain consists of two domains, the N-terminal domain being known as the variable or VL domain (or region) and the C-terminal domain being known as the constant or CL domain/region (constant kappa (Cκ) or constant lambda (Cλ) domain). Each heavy chain consists of four or five domains, depending on the class of the antibody. The N-terminal domain is known as the variable (or VH) domain (or region), which is followed by the first constant (or CH1) domain, the hinge region, and then the second and third constant (or CH2 and CH3) domains. In an assembled antibody, the VL and VH domains associate together to form an antigen binding site. Also, the CL and CH1 domains associate together to keep one heavy chain associated with one light chain. The two heavy-light chain heterodimers associate together by interaction of the CH2 and CH3 domains and interaction between the hinge regions on the two heavy chains.

One of the main problems coming along with the generation of multispecific antibodies is the light chain mispairing. While the pairing of two different heavy chains can be addressed by technologies like knobs-into-holes, it is also essential to impose correct light chain association. This is probably a bigger challenge from a structural point of view, since the modifications should be applied within the Fab fragment interface, which requires more modifications. In any case, the heterodimerization of heavy chains and their association with the cognate light chain require a quite intensive number of different designs to achieve proper chain association, avoiding the formation of unwanted species. Furthermore, expression of multispecific molecules from different vectors/plasmids, encoding light chains and heavy chains, requires translation of all plasmids to the same extent to provide optimal ratios for correct chain pairing.

The present invention addresses the light chain pairing problem by a change of paradigm, from design-derived multispecific formats to process-derived multispecific formats. Here, no modifications of antibody sequences are needed.

SUMMARY OF THE INVENTION

In one aspect, the present invention relates to a protein comprising at least one polypeptide chain having the formula $$PP_1-PCL-PP_2,$$

wherein $PP_1$ is a first polypeptide, $PP_2$ is a second polypeptide, and

PCL is a protease-cleavable linker comprising at least one protease-cleavage site comprising the amino acid sequence $HRRX_1X_2RSVDE$ (SEQ ID NO: 42), wherein $X_1$ and $X_2$ are independently selected from the group consisting of amino acids, preferably naturally occurring amino acids.

In one embodiment, the protease is a furin and/or furin-like protease.

In one embodiment, the at least one protease-cleavage site comprises the amino acid sequence HRRRKRSVDE (SEQ ID NO: 43) or the amino acid sequence HRRQQRSVDE (SEQ ID NO: 44).

In one embodiment, protease-cleavage of the linker results in a change in activity of the protein.

In one embodiment, the change in activity is binding or increased binding to at least one antigen.

In one embodiment, protease-cleavage occurs intracellularly.

In one embodiment, the protease-cleavable linker comprises two protease-cleavage sites, wherein the two protease-cleavage sites are located at the N-terminus and at the C-terminus of the protease-cleavable linker, respectively, wherein the two protease-cleavage sites may be the same or different.

In one embodiment, the protease-cleavable linker has a length of 10 to 80 amino acid residues.

In one embodiment, the at least one protease-cleavage site is preceded and/or followed by at least 2, at least 3, at least 4, at least 5 or at least 10 contiguous amino acid residues independently selected from the group consisting of glycine and serine.

In one embodiment, the protease-cleavable linker further comprises an amino acid sequence selected from the group consisting of $(GS)_n$, $(G_4S)_n$ (SEQ ID NO: 51), $(HH)_n$, $(EAAAK)_n$ (SEQ ID NO: 52), $(AP)_nA$ (SEQ ID NO: 53), $(KQGKQ)_n$ (SEQ ID NO: 54) and combinations thereof, wherein n is an integer selected from 1 to 10.

In one embodiment, the protease-cleavable linker further comprises an amino acid sequence selected from the group consisting of GSHHHHHHHHGGGGS (SEQ ID NO: 45), GGGGSEAAAKEAAAKGGGGS (SEQ ID NO: 46), APAPAPAPAPAPA (SEQ ID NO: 47), GSKQGKQKQGKQGS (SEQ ID NO: 48) and combinations thereof.

In one embodiment, $PP_1$ comprises at least one immunoglobulin constant region and/or at least one immunoglobulin variable region, and/or $PP_2$ comprises at least one immunoglobulin constant region and/or at least one immunoglobulin variable region.

In one embodiment,

- $PP_1$ comprises an immunoglobulin constant region and $PP_2$ comprises an immunoglobulin variable region,
- $PP_1$ comprises an immunoglobulin variable region and $PP_2$ comprises an immunoglobulin constant region,
- $PP_1$ comprises an immunoglobulin constant region and $PP_2$ comprises an immunoglobulin constant region, or
- $PP_1$ comprises an immunoglobulin variable region and $PP_2$ comprises an immunoglobulin variable region.

In one embodiment, the protein is an antibody or antibody derivative.

In one embodiment, the protein is a single chain antibody, preferably a multispecific single chain antibody.

In one embodiment, the protein comprises a polypeptide chain having a formula selected from the group consisting of:

VL-CL-PCL-VH-CH1-hinge-CH2-CH3, (a)

wherein

VL is an immunoglobulin light chain variable region;
CL is an immunoglobulin light chain constant region;
VH is an immunoglobulin heavy chain variable region;
CH1 is an immunoglobulin CH1 heavy chain constant region;
hinge is an immunoglobulin hinge region;
CH2 is an immunoglobulin CH2 heavy chain constant region;
CH3 is an immunoglobulin CH3 heavy chain constant region; and
PCL is the protease-cleavable linker;

$VL_a$-$CL_a$-PCL-$VL_b$-$CL_b$, (b)

wherein $VL_a$ is a first immunoglobulin light chain variable region;
$VL_b$ is a second immunoglobulin light chain variable region;
$CL_a$ is a first immunoglobulin light chain constant region;
$CL_b$ is a second immunoglobulin light chain constant region; and
PCL is the protease-cleavable linker; and $VL_a$-$CL_a$-PCL-$VL_b$-$CL_b$-L-hinge-CH2-CH3 (c)

wherein $VL_a$ is a first immunoglobulin light chain variable region;
$VL_b$ is a second immunoglobulin light chain variable region;
$CL_a$ is a first immunoglobulin light chain constant region;
$CL_b$ is a second immunoglobulin light chain constant region;
L is an optional linker;
hinge is an immunoglobulin hinge region;
CH2 is an immunoglobulin CH2 heavy chain constant region;
CH3 is an immunoglobulin CH3 heavy chain constant region; and
PCL is the protease-cleavable linker.

In one embodiment, the protein comprises a polypeptide chain having the formula VL-CL-PCL-VH-CH1-hinge-CH2-CH3, wherein VL pairs with VH to form an antigen binding site.

In one embodiment, the antigen binding site becomes active or exhibits increased activity upon protease-cleavage of the protease-cleavable linker.

In one embodiment, the protein comprises two copies of the polypeptide chain having the formula VL-CL-PCL-VH-CH1-hinge-CH2-CH3, wherein the two copies are associated with each other via at least two disulfide bonds.

In one embodiment, the protein comprises a first polypeptide chain having the formula $VL_a$-$CL_a$-PCL-$VH_a$-$CH1_a$-hinge-CH2-CH3, and a second polypeptide chain having the formula $VL_b$-$CL_b$-PCL-$VH_b$-$CH1_b$-hinge-CH2-CH3, wherein $VL_a$ is a first immunoglobulin light chain variable region;
$VL_b$ is a second immunoglobulin light chain variable region;
$CL_a$ is a first immunoglobulin light chain constant region;
$CL_b$ is a second immunoglobulin light chain constant region;
$VH_a$ is a first immunoglobulin heavy chain variable region;
$VH_b$ is a second immunoglobulin heavy chain variable region;
$CH1_a$ is a first immunoglobulin CH1 heavy chain constant region; and
$CH1_b$ is a second immunoglobulin CH1 heavy chain constant region;
wherein $VL_a$ pairs with $VH_a$ to form an antigen binding site binding to antigen A, and wherein $VL_b$ pairs with $VH_b$ to form an antigen binding site binding to antigen B; and
wherein the first polypeptide chain is associated with the second polypeptide chain via at least two disulfide bonds and, optionally, via at least one additional Fc interaction.

In one embodiment, the antigen binding site A and/or the antigen binding site B become active or exhibit increased activity upon protease-cleavage of the protease-cleavable linkers.

In one embodiment, the at least one additional Fc interaction is at least one knob-into-hole interaction.

In one embodiment, the protein comprises a first polypeptide chain having the formula $VL_b$-L1-$VL_a$-L2-CL, a second polypeptide chain having the formula $VH_a$-L3-$VH_b$-L4-CH1-hinge-CH2-CH3 and a third polypeptide chain having the formula $VL_c$-$CL_c$-PCL-$VH_c$-$CH1_c$-hinge-CH2-CH3, wherein $VL_a$ is a first immunoglobulin light chain variable region;
$VL_b$ is a second immunoglobulin light chain variable region;
$VL_c$ is a third immunoglobulin light chain variable region;
CL is an immunoglobulin light chain constant region;
$CL_c$ is an immunoglobulin light chain constant region;
$VH_a$ is a first immunoglobulin heavy chain variable region;
$VH_b$ is a second immunoglobulin heavy chain variable region;
$VH_c$ is a third immunoglobulin heavy chain variable region;
CH1 is an immunoglobulin CH1 heavy chain constant region;
$CH1_c$ is an immunoglobulin CH1 heavy chain constant region;
hinge is an immunoglobulin hinge region;
CH2 is an immunoglobulin CH2 heavy chain constant region; and
CH3 is an immunoglobulin CH3 heavy chain constant region;
L1, L2, L3 and L4 are linkers;

wherein $VL_a$ pairs with $VH_a$ to form an antigen binding site binding to antigen A, wherein $VL_b$ pairs with $VH_b$ to form an antigen binding site binding to antigen B, and wherein $VL_c$ pairs with $VH_c$ to form an antigen binding site binding to antigen C; and wherein the second polypeptide chain is associated with the third polypeptide chain via at least two disulfide bonds and, optionally, via at least one additional Fc interaction.

In one embodiment, the antigen binding site C becomes active or exhibits increased activity upon protease-cleavage of the protease-cleavable linker.

In one embodiment, the at least one additional Fc interaction is at least one knob-into-hole interaction.

In one embodiment, the protein comprises a first polypeptide chain having the formula $VL_a$-$CL_a$-PCL-$VL_b$-$CL_b$, and a second polypeptide chain having the formula $VH_a$-$CH1_a$-L-$VH_b$-$CH1_b$-hinge-CH2-CH3, wherein $VH_a$ is a first immunoglobulin heavy chain variable region;

VH, is a second immunoglobulin heavy chain variable region;

$CH1_a$ is a first immunoglobulin CH1 heavy chain constant region;

$CH1_b$ is a second immunoglobulin CH1 heavy chain constant region;

L is an optional linker;

hinge is an immunoglobulin hinge region;

CH2 is an immunoglobulin CH2 heavy chain constant region; and

CH3 is an immunoglobulin CH3 heavy chain constant region;

wherein $VL_a$ pairs with $VH_a$ to form an antigen binding site binding to antigen A, and wherein $VL_b$ pairs with $VH_b$ to form an antigen binding site binding to antigen B.

In one embodiment, the antigen binding site B becomes active or exhibits increased activity upon protease-cleavage of the protease-cleavable linker.

In one embodiment, the protein comprises two copies of the first polypeptide chain and two copies of the second polypeptide chain, wherein the two copies of the second polypeptide chain are associated with each other via at least two disulfide bonds.

In one embodiment, the protein comprises a first polypeptide chain having the formula $VL_b$-$CL_b$-PCL-$VL_a$-$CL_a$, a second polypeptide chain having the formula $VL_c$-$CL_c$-PCL-$VL_a$-$CL_a$, a third polypeptide chain having the formula $VH_a$-$CH1_a$-L-$VH_b$-$CH1_b$-hinge-CH2-CH3, and a fourth polypeptide chain having the formula $VH_c$-$CH1_c$-L-$VH_a$-$CH1_c$-hinge-CH2-CH3, wherein $VL_a$ is a first immunoglobulin light chain variable region;

$VL_b$ is a second immunoglobulin light chain variable region;

VL, is a third immunoglobulin light chain variable region;

$VL_a$ is a fourth immunoglobulin light chain variable region;

$CL_a$ is a first immunoglobulin light chain constant region;

$CL_b$ is a second immunoglobulin light chain constant region;

$CL_c$ is a third immunoglobulin light chain constant region;

$CL_a$ is a fourth immunoglobulin light chain constant region;

$VH_a$ is a first immunoglobulin heavy chain variable region;

$VH_b$ is a second immunoglobulin heavy chain variable region;

$VH_c$ is a third immunoglobulin heavy chain variable region;

$VH_a$ is a fourth immunoglobulin heavy chain variable region;

$CH1_a$ is a first immunoglobulin CH1 heavy chain constant region;

$CH1_b$ is a second immunoglobulin CH1 heavy chain constant region;

$CH1_c$ is a third immunoglobulin CH1 heavy chain constant region;

$CH1_d$ is a fourth immunoglobulin CH1 heavy chain constant region;

L is an optional linker;

hinge is an immunoglobulin hinge region;

CH2 is an immunoglobulin CH2 heavy chain constant region; and

CH3 is an immunoglobulin CH3 heavy chain constant region;

wherein $VL_a$ pairs with $VH_a$ to form an antigen binding site binding to antigen A, wherein $VL_b$ pairs with $VH_b$ to form an antigen binding site binding to antigen B, wherein $VL_c$ pairs with $VH_c$ to form an antigen binding site binding to antigen C, and wherein $VL_a$ pairs with $VH_d$ to form an antigen binding site binding to antigen D; and wherein the third polypeptide chain is associated with the fourth polypeptide chain via at least two disulfide bonds and, optionally, via at least one additional Fc interaction.

In one embodiment, the antigen binding site B and/or the antigen binding site D become active or exhibit increased activity upon protease-cleavage of the protease-cleavable linkers.

In one embodiment, the at least one additional Fc interaction is at least one knob-into-hole interaction.

In one embodiment, the protein comprises a first polypeptide chain having the formula $VL_a$-$CL_a$-PCL-$VL_b$-$CL_b$-L-hinge-CH2-CH3, and a second polypeptide chain having the formula $VH_a$-$CH1_a$-L-$VH_b$-$CH1_b$-hinge-CH2-CH3, wherein $VH_a$ is a first immunoglobulin heavy chain variable region;

$VH_b$ is a second immunoglobulin heavy chain variable region;

$CH1_a$ is a first immunoglobulin CH1 heavy chain constant region;

$CH1_b$ is a second immunoglobulin CH1 heavy chain constant region;

L is an optional linker;

hinge is an immunoglobulin hinge region;

CH2 is an immunoglobulin CH2 heavy chain constant region; and

CH3 is an immunoglobulin CH3 heavy chain constant region;

wherein $VL_a$ pairs with $VH_a$ to form an antigen binding site binding to antigen A, and wherein $VL_b$ pairs with $VH_b$ to form an antigen binding site binding to antigen B; and wherein the first polypeptide chain is associated with the second polypeptide chain via at least two disulfide bonds and, optionally, via at least one additional Fc interaction.

In one embodiment, the antigen binding site B becomes active or exhibits increased activity upon protease-cleavage of the protease-cleavable linker.

In one embodiment, the at least one additional Fc interaction is at least one knob-into-hole interaction.

In another aspect, the present invention relates to a nucleic acid or set of nucleic acids encoding the protein as defined above.

In another aspect, the present invention relates to a vector or set of vectors comprising the nucleic acid or set of nucleic acids as defined above.

In another aspect, the present invention relates to a host cell comprising a protein as defined above, a nucleic acid or set of nucleic acids as defined above, or a vector or set of vectors as defined above.

In one embodiment, the host cell expresses an endogenous or exogenous furin and/or furin-like protease.

In one embodiment, the host cell is a mammalian cell.

In one aspect, the present invention relates to a method of producing a protein comprising the steps:

i) culturing a host cell as defined above; and ii) isolating the protein from the host cell.

In another aspect, the present invention relates to a protein obtainable by the method as defined above.

In yet another aspect, the present invention relates to a protein obtainable by furin and/or furin-like protease-cleavage of a protein as defined above.

In one embodiment, the protein as defined above is a therapeutically active protein.

In one aspect, the present invention relates to a protein as defined above for use in therapy.

In another aspect, the present invention relates to the use of a protein as defined above in the manufacture of a medicament.

In yet another aspect, the present invention relates to a method of treating or preventing a disease or disorder, comprising administering an effective amount of a protein as defined above to a subject in need thereof.

In yet another aspect, the present invention relates to a pharmaceutical composition or kit comprising a protein as defined above.

In another aspect, the present invention relates to a peptide comprising the amino acid sequence of any one of SEQ ID NOs: 42 to 44, to a protein comprising said peptide, to a nucleic acid encoding said peptide or protein, to a vector comprising said nucleic acid, or to a host cell comprising said peptide, protein, nucleic acid or vector.

DETAILED DESCRIPTION OF THE INVENTION

Figure 1:
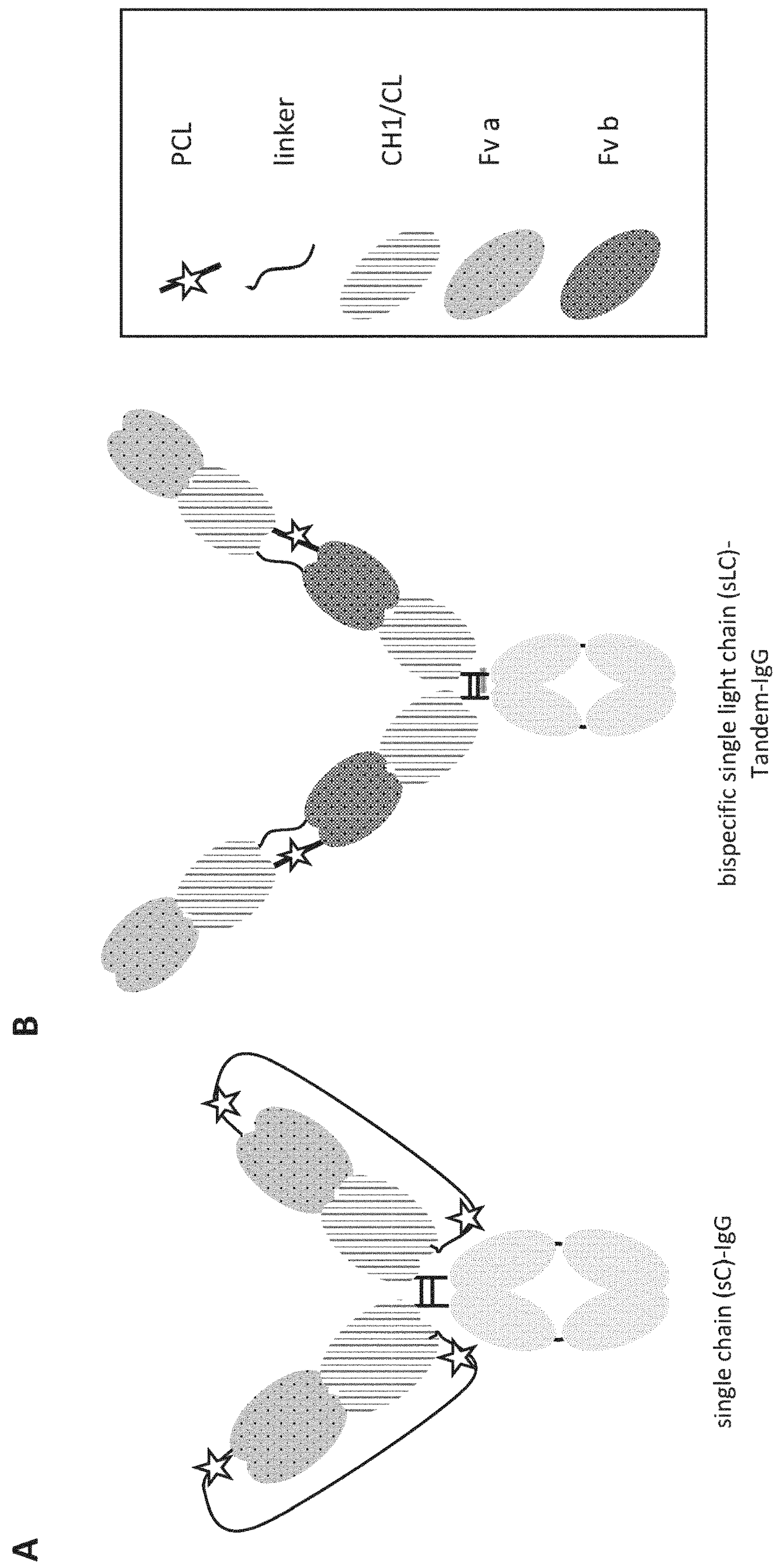
FIG. 1: Protease-cleavable homodimeric antibody formats. (A) Single chain (sC) monoclonal IgG. The CL (e.g., CK) domain is elongated at its C-terminus via a protease-cleavable linker (PCL) sequence with the N-terminus of the VH domain of the heavy chain. (B) Single light chain (sLC) bivalent, bispecific Tandem-IgG. The VH-CH1 (VHb) domain of the heavy chain is elongated at its N-terminus with a second VH-CH1 domain (VHa), e.g., via a $(G_4S)_3$ linker (SEQ ID NO: 55). The VL-CL domain (VLb) of the light chain is elongated at its N-terminus with a second VL-CL domain (VLa) using a PCL sequence.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred/particular embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

In one aspect, the present invention relates to a protein comprising at least one polypeptide chain having the formula $$PP_1 - PCL - PP_2,$$

wherein $PP_1$ is a first polypeptide, $PP_2$ is a second polypeptide, and

PCL is a protease-cleavable linker comprising at least one protease-cleavage site comprising the amino acid sequence $HRRX_1X_2RSVDE$ (SEQ ID NO: 42), wherein $X_1$ and $X_2$ are independently selected from the group consisting of amino acids, preferably naturally occurring amino acids.

If the protein comprises more than one polypeptide chains as defined above, these polypeptide chains may be the same or different.

The term "peptide" according to the invention refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" or "polypeptide" refers to large peptides, preferably to peptides with more than 100 amino acid residues, but in general the terms "peptides", "polypeptides" and "proteins" are synonyms and are used interchangeably herein.

In one embodiment, the protein is a recombinant protein. In one embodiment, the protein is a fusion protein.

The term "recombinant" in the context of the present invention means "made through genetic engineering". Preferably, a "recombinant object" is not naturally occurring.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "fusion protein" (or "chimeric protein") generally refers to proteins created by joining, in particular covalently linking, two or more distinct proteins and/or peptides resulting in a single protein with functional properties derived from each of the original proteins and/or peptides.

The term "linker", as used herein, preferably refers to a peptide linker, i.e., a linker composed of amino acids connected via peptide bonds. A linker in accordance with the present invention may, however, also include non-peptidic components, such as non-peptidic polymers (e.g., PEG).

A peptide linker in accordance with the present invention may have any length, i.e., comprise any number of amino acid residues. However, it is preferably long enough to provide an adequate degree of flexibility so that the connected/linked moieties can, for example, interact/pair with each other or other moieties, and to allow for proper protein folding; yet it is preferably short enough to provide stability (e.g., proteolytic stability) in the cell. Suitable peptide linkers are described in, e.g., Chen et al., Adv Drug Deliv Rev. 2013, 65(10):1357-69, which is incorporated herein in its entirety. Preferably, a peptide linker according to the present invention has a length of 1 to 100 amino acids.

Flexibility of a peptide linker is generally increased if its amino acids are small and do not have bulky side chains that impede rotation or bending of the amino acid chain. Thus, a peptide linker of the present invention preferably has an increased content of small amino acids, in particular of glycines, alanines, serines, threonines, leucines and isoleucines. Preferably, at least 20%, 30%, 40%, 50%, 60%, 70%, 80%, 90% or more of the amino acids of the peptide linker are such small amino acids. In particular embodiments, the peptide linkers according to the present invention are glycine-serine-rich linkers, wherein at least 50%, preferably at least 60%, more preferably at least 70%, more preferably at least 80%, even more preferably at least 85% of the amino acids are a glycine or serine residue, respectively. Peptide linkers in accordance with the present invention can also be exclusively composed of glycine and/or serine residues (referred to as glycine linkers, serine linkers or glycine-serine linkers, respectively). Exemplary peptide linkers comprise a sequence of the amino acid formula $(G_lS_m)_n$, wherein l is an integer from 1 to 4, m is 1 or 2, and n is an integer from 1 to 12, preferably 1 to 10, e.g., 2 to 10 or 4 to 10. Peptide linkers according to the present invention may also comprise or consist of other sequence elements, e.g., a His-tag.

In some embodiments, a peptide linker according to the present invention may also be a rigid peptide linker. Such rigid peptide linkers are known to a person skilled in the art and include, for example, proline-rich peptide linkers with the general formula $(XP)_n$, with X designating any amino acid, preferably alanine, lysine or glutamic acid, and n being an integer, preferably an integer from 1 to 12. A particular example of this motif is $(AP)_nA$ (SEQ ID NO: 53). Another example of a rigid peptide linker sequence motif is $(EAAAK)_n$ (SEQ ID NO: 52), wherein n is an integer, preferably an integer from 1 to 12.

The term "protease-cleavable linker" ("PCL"), as used herein, refers to a linker comprising at least one protease-cleavage site.

A "protease-cleavage site" ("PCS"; also referred to as protease recognition site herein) according to the present invention is a type of enzymatic cleavage site in a protein which is the target for enzymes (proteases) that function after translation of the protein. In one embodiment, such enzymes function during transport from the Golgi lumen to the trans-Golgi compartment. Intracellular processing enzymes (proteases) cleave polypeptides prior to secretion of the protein from the cell.

In one embodiment, the protease is a furin and/or furin-like protease. The terms "furin" and "furin-like protease" refer to the enzymes corresponding to EC No. 3.4.21.75. Furin is subtilisin-like proprotein convertase, which is also known as PACE (Paired basic Amino acid Cleaving Enzyme). Furin deletes sections of inactive precursor proteins to convert them into biologically active proteins. Examples of furin and/or furin-like proteases (which can also be referred to as members of the furin family of proteases) include, but are not limited to PCSK1 (also known as PC1/Pc3), PCSK2 (also known as PC2), PCSK3 (also known as furin or PACE), PCSK4 (also known as PC4), PCSK5 (also known as PCS or PC6), PCSK6 (also known as PACE4) and PCSK7 (also known as PC7/LPC, PC8, or SPC7).

The term "amino acid" or "amino acid residue", as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

When used in connection with amino acids, the term "naturally occurring" refers to the conventional amino acids (i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine(S), threonine (T), valine (V), tryptophan (W), and tyrosine (Y)), as well as selenocysteine, pyrrolysine, and pyrroline-carboxylysine.

The term "unnatural amino acid", as used herein, is meant to refer to amino acids that are not naturally encoded or found in the genetic code of any organism. They may, for example, be purely synthetic compounds. Examples of unnatural amino acids include, but are not limited to, hydroxyproline, gamma-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, D-ornithine, D-arginine, p-aminophenylalanine, pentylglycine, pipecolic acid and thioproline.

The term "amino acid analogue", as used herein, refers to compounds that have the same basic chemical structure as a naturally occurring amino acid. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(betamethylester), N-ethylglycine, alanine carboxamide, homoserine, norleucine and methionine methyl sulfonium.

The term "amino acid mimetics", as used herein, refers to chemical compounds that have a structure that is different from the general chemical structure of an amino acid, but function in a manner similar to a naturally occurring amino acid.

In one embodiment, $X_1$ and $X_2$ are independently selected from the group consisting of lysine (K), glutamine (Q) and arginine (R). In one embodiment, $X_1X_2$ is selected from the group consisting of KK, KQ, KR, QK, QQ, QR, RK, RQ and RR.

In one embodiment, the at least one protease-cleavage site comprises the amino acid sequence HRRRKRSVDE (SEQ ID NO: 43) or the amino acid sequence HRRQQRSVDE (SEQ ID NO: 44).

In one embodiment, protease-cleavage of the linker results in a change in activity of the protein.

In one embodiment, the change in activity is binding or increased binding to at least one antigen.

The term "binding" according to the invention preferably relates to a specific binding. A binding agent, such as an antibody or antibody derivative, is specific for a predetermined target if it is capable of binding to said predetermined target while it is not (substantially) capable of binding to other targets.

) According to the present invention, a binding agent, such as an antibody or antibody derivative, is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 μg/ml or higher. Preferably, an agent has no significant affinity for a target if it binds to said target with a $K_D$ that is at least 10-fold, 100-fold, 103-fold, 104-fold, 105-fold, or 106-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

Binding of an agent to a target can be determined experimentally using any suitable method; see, for example, Berzofsky et al., "Antibody-Antigen Interactions" In Fundamental Immunology, Paul, W. E., Ed., Raven Press New York, NY (1984), Kuby, Janis Immunology, W. H. Freeman and Company New York, NY (1992), and methods described herein. Affinities may be readily determined using conventional techniques, such as by equilibrium dialysis; by using the BIACORE™ (surface plasmon resonance biosensor) 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

The term "increased binding" may refer to binding which is increased by at least 50%, at least 100%, at least 200%, at least 300%, at least 400% or at least 500% as compared to binding prior to protease-cleavage.

In one embodiment, protease-cleavage occurs intracellularly, e.g., within host cells as defined herein. Thus, the protease-cleavage site contained in the protease-cleavable linker may also be referred to as an intracellular processing site. A protease-cleavable linker according to the present invention may also be referred to as an in vivo cleavable linker.

Preferably, a protease-cleavable linker according to the present invention comprising at least one protease-cleavage site according to the present invention is cleaved/processed intracellularly/in vivo without co-expression of a protease (e.g., a furin and/or furin-like protease), in particular an exogenous protease. The term "co-expression", as used herein, is meant to refer to an artificial co-expression, e.g., by genetically manipulating host cells to express the protease, for example via transfection of host cells with a nucleic acid encoding the protease.

In one embodiment, the protease-cleavable linker comprises two protease-cleavage sites, wherein the two protease-cleavage sites are located at the N-terminus and at the C-terminus of the protease-cleavable linker, respectively, wherein the two protease-cleavage sites may be the same or different.

In one embodiment, the protease-cleavable linker has a length of 10 to 80 amino acid residues, preferably 20 to 80 amino acids, more preferably 20 to 70 amino acids, more preferably 30 to 70 amino acids, even more preferably 30 to 60 amino acids.

In one embodiment, the at least one protease-cleavage site is preceded and/or followed by at least 2, at least 3, at least 4, at least 5 or at least 10 contiguous amino acid residues independently selected from the group consisting of glycine and serine.

In one embodiment, the protease-cleavable linker further comprises an amino acid sequence selected from the group consisting of $(GS)_n$, $(G_4S)_n$ (SEQ ID NO: 51), $(HH)_n$, $(EAAAK)_n$ (SEQ ID NO: 52), $(AP)_nA$ (SEQ ID NO: 53), $(KQGKQ)_n$ (SEQ ID NO: 54) and combinations thereof, wherein n is an integer selected from 1 to 12, preferably 1 to 10. In one embodiment, the protease-cleavable linker comprises the amino acid sequence $(G_4S)_n$ (SEQ ID NO: 51), wherein n is an integer selected from 2 to 10, preferably 4 to 10.

In one embodiment, the protease-cleavable further linker comprises an amino acid sequence selected from the group consisting of GSHHHHHHHHGGGGS (SEQ ID NO: 45), GGGGSEAAAKEAAAKGGGGS (SEQ ID NO: 46), APAPAPAPAPAPAPA (SEQ ID NO: 47), GSKQGKQKQGKQGS (SEQ ID NO: 48) and combinations thereof.

In one embodiment, the protease-cleavable linker (PCL) has the structure $PCS_A$-L-$PCS_B$, wherein $PCS_A$ and $PCS_B$ are protease-cleavage sites as defined herein, which may be the same or different, and wherein L is a linker comprising or consisting of an amino acid sequence selected from the group consisting of SEQ ID NOs: 45 to 48 and 51 to 54, $(GS)_n$, $(HH)_n$ and combinations thereof, as defined above.

In one embodiment, $PP_1$ comprises at least one immunoglobulin constant region and/or at least one immunoglobulin variable region, and/or $PP_2$ comprises at least one immunoglobulin constant region and/or at least one immunoglobulin variable region.

In one embodiment, the protein is an antibody or antibody derivative.

In one embodiment, the protein is a single chain antibody, preferably a multispecific (e.g., bispecific, trispecific, tetraspecific, pentaspecific, hexaspecific etc.) single chain antibody. The term "single chain antibody", as used herein, also refers to antibodies or antibody derivatives comprising more than one (e.g., two) single chains, which, preferably, are associated with each other via at least one covalent or non-covalent bond (e.g., two disulfide bonds).

The term "antibody" (or "immunoglobulin") refers to a glycoprotein comprising at least two heavy (H) chains and two light (L) chains inter-connected by disulfide bonds. The term "antibody" includes monoclonal antibodies, recombinant antibodies, human antibodies, humanized antibodies, chimeric antibodies and combinations of any of the foregoing. Each heavy chain is comprised of a heavy chain variable region (VH) and a heavy chain constant region (CH). Each light chain is comprised of a light chain variable region (VL) and a light chain constant region (CL). The variable regions and constant regions are also referred to herein as variable domains and constant domains, respectively. The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. The CDRs of a VH are termed HCDR1, HCDR2 and HCDR3, the CDRs of a VL are termed LCDR1, LCDR2 and LCDR3. The variable regions of the heavy and light chains contain a binding domain that interacts with an antigen. The constant regions of an antibody comprise the heavy chain constant region (CH) and the light chain constant region (CL), wherein CH can be further subdivided into constant domain CH1, a hinge region, and constant domains CH2 and CH3 (arranged from amino-terminus to carboxy-terminus in the following order: CH1, CH2, CH3). The constant regions of the antibodies may mediate the binding of the immunoglobulin to host tissues or factors, including various cells of the immune system (e.g., effector cells) and the first component (Clq) of the classical complement system. In one embodiment, the CL region/domain referred to herein is a Ck region/domain.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1 kappa or IgG1 lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ). In one embodiment, the antibody or antibody derivative is an IgG1 antibody or IgG1 antibody derivative, respectively.

As used herein, "isotype" refers to the antibody class (e.g., IgM or IgG1) that is encoded by heavy chain constant region genes. "Isotype switching" refers to the phenomenon by which the class, or isotype, of an antibody changes from one Ig class to one of the other Ig classes.

The term "monoclonal antibody", as used herein, refers to a preparation of antibody molecules of single molecular composition. A monoclonal antibody displays a single binding specificity and affinity. In one embodiment, the monoclonal antibodies are produced by a hybridoma which includes a B-cell obtained from a non-human animal, e.g., a mouse, fused to an immortalized cell.

The term "hinge" or "hinge region", as used herein, refers to the flexible amino acid stretch in the central part of the heavy chains of the IgG and IgA, in particular the IgG (i.e., IgG1, IgG2, IgG3 or IgG4, especially IgG1) immunoglobulin classes, which links these two chains by disulfide bonds.

The term "antibody derivative", as used herein, refers to a molecule comprising at least the domains it is specified to comprise, but not having the overall structure of an antibody such as IgA, IgD, IgE, IgG, IgM, IgY or IgW, although still being capable of binding a target molecule. Said derivatives may be, but are not limited to functional (i.e. target binding, particularly specific target binding) antibody fragments thereof, such as Fab2, or combinations of such derivatives, for example bivalent Fabs. It also relates to an antibody to which further antibody domains have been added, such as further variable domains. In one embodiment, the term "antibody derivative" refers to the single chain antibodies as described herein. Thus, the term "antibody derivative" also includes multispecific (e.g., bispecific, trispecific, tetraspecific, pentaspecific, hexaspecific etc.) and multivalent (e.g., bivalent, trivalent, tetravalent etc.) antibodies.

In one embodiment,

- $PP_1$ comprises an immunoglobulin constant region and $PP_2$ comprises an immunoglobulin variable region,
- $PP_1$ comprises an immunoglobulin variable region and $PP_2$ comprises an immunoglobulin constant region,
- $PP_1$ comprises an immunoglobulin constant region and $PP_2$ comprises an immunoglobulin constant region, or
- $PP_1$ comprises an immunoglobulin variable region and $PP_2$ comprises an immunoglobulin variable region.

In one embodiment, the protein is selected from the group consisting of a single chain (sC) monoclonal IgG (e.g., as described in Spies et al., J Mol Imm. 2015, 67:95-106), a single light chain (sLC) bivalent, bispecific Tandem-IgG (e.g., as described in WO 2009/052081 A2), a single light chain (sLC) multispecific Tandem-IgG (e.g., as described in Wu et al., Nat. Biotechnol. 2007, 25:1290-1297), a single chain (sC) monovalent, bispecific Tandem-like-IgG (e.g., as described in Brinkmann & Kontermann, MAbs 2017, 9:182-212), a trispecific CODV-sC-Fab-IgG (e.g., as described in WO 2017/180913 A2 and/or Xu et al., Science 2017, 358 (6359):85-90) and a single chain (sC) bispecific IgG (e.g., as described in Fitzgerald et al., Mol Cancer Ther. 2013, 13:410-25).

In one embodiment, the protein comprises a polypeptide chain having a formula selected from the group consisting of:

VL-CL-PCL-VH-CH1-hinge-CH2-CH3, (a)

wherein

- VL is an immunoglobulin light chain variable region;
- CL is an immunoglobulin light chain constant region;
- VH is an immunoglobulin heavy chain variable region;
- CH1 is an immunoglobulin CH1 heavy chain constant region;
- hinge is an immunoglobulin hinge region;
- CH2 is an immunoglobulin CH2 heavy chain constant region;

CH3 is an immunoglobulin CH3 heavy chain constant region; and

PCL is the protease-cleavable linker;

$VL_a$-$CL_a$-PCL-$VL_b$-$CL_b$, (b)

wherein $VL_a$ is a first immunoglobulin light chain variable region;

$VL_b$ is a second immunoglobulin light chain variable region;

$CL_a$ is a first immunoglobulin light chain constant region;

CL is a second immunoglobulin light chain constant region; and

PCL is the protease-cleavable linker; and $VL_a$-$CL_a$-PCL-$VL_b$-$CL_b$-L-hinge-CH2-CH3 (c)

wherein $VL_a$ is a first immunoglobulin light chain variable region;

$VL_b$ is a second immunoglobulin light chain variable region;

$CL_a$ is a first immunoglobulin light chain constant region;

$CL_b$ is a second immunoglobulin light chain constant region;

L is an optional linker;

hinge is an immunoglobulin hinge region;

CH2 is an immunoglobulin CH2 heavy chain constant region;

CH3 is an immunoglobulin CH3 heavy chain constant region; and

PCL is the protease-cleavable linker.

The symbol (-), when used in connection with the formulas disclosed herein, is meant to refer to a covalent bond, in particular a peptide bond, or one or more amino acid residues, e.g., a peptide linker as described herein.

In one embodiment, L is a peptide linker as defined herein, preferably having a length of 5 to 25 amino acid residues, preferably 10 to 20 amino acid residues, preferably 12 to 18 amino acid residues, more preferably 13 to 17 amino acid residues, even more preferably 14 to 16 amino acid residues, e.g., 15 amino acid residues. In one embodiment, L is a glycine-serine-rich linker, wherein at least 50%, preferably at least 60%, more preferably at least 70%, more preferably at least 80%, even more preferably at least 85% of the amino acids are a glycine or serine residue, respectively. In one embodiment, L is a glycine linker, serine linker or glycine-serine linker. In one embodiment, L has the sequence $(G_4S)_n$ (SEQ ID NO: 51), wherein n is an integer selected from 1 to 5, e.g., 1 to 3 or 2 to 4. In one embodiment, L has the sequence $(G_4S)_3$ (SEQ ID NO: 55).

In one embodiment, the protein comprises a polypeptide chain having the formula VL-CL-PCL-VH-CH1-hinge-CH2-CH3, wherein VL pairs with VH to form an antigen binding site.

In one embodiment, the antigen binding site becomes active or exhibits increased activity upon protease-cleavage of the protease-cleavable linker.

Preferably, the term "pairs with", as used herein, refers to the dimerization of immunoglobulin constant regions or immunoglobulin variable regions as it occurs in a regular, e.g., naturally occurring, immunoglobulin, in particular IgG.

The term "antigen binding site" (also called "paratope"), as used herein, refers to the part of an antibody which recognizes and binds to an antigen.

In one embodiment, the protein comprises two copies of the polypeptide chain having the formula VL-CL-PCL-VH-CH1-hinge-CH2-CH3, wherein the two copies are associated with each other via at least two disulfide bonds.

In one embodiment, the protein comprises a first polypeptide chain having the formula $VL_a$-$CL_a$-PCL-$VH_a$-$CH1_a$-hinge-CH2-CH3, and a second polypeptide chain having the formula $VL_b$-$CL_b$-PCL-$VH_b$-$CH1_b$-hinge-CH2-CH3, wherein $VL_a$ is a first immunoglobulin light chain variable region;

$VL_b$ is a second immunoglobulin light chain variable region;

$CL_a$ is a first immunoglobulin light chain constant region;

$CL_b$ is a second immunoglobulin light chain constant region;

$VH_a$ is a first immunoglobulin heavy chain variable region;

VH, is a second immunoglobulin heavy chain variable region;

$CH1_a$ is a first immunoglobulin CH1 heavy chain constant region; and $CH1_b$ is a second immunoglobulin CH1 heavy chain constant region;

wherein $VL_a$ pairs with $VH_a$ to form an antigen binding site binding to antigen A, and wherein $VL_b$ pairs with $VH_b$ to form an antigen binding site binding to antigen B; and wherein the first polypeptide chain is associated with the second polypeptide chain via at least two disulfide bonds and, optionally, via at least one additional Fc interaction.

In one embodiment, the antigen binding site A and/or the antigen binding site B become active or exhibit increased activity upon protease-cleavage of the protease-cleavable linkers.

The term "additional Fc interaction", as used herein, refers to an interaction between two Fc molecules (e.g., two heterologous Fc molecules), in particular between the CH3 domains of two Fc molecules, in addition to the at least two disulfide bonds referred to herein. Examples of additional Fc interactions include, but are not limited to, knob-into-hole interactions (see below for details), hydrophobic interactions (e.g., due to the introduction of specific mutations; see, e.g., Von Kreudenstein et al., MAbs 2013, 5(5):646-654), electrostatic interactions (e.g., due to electrostatic steering; see, e.g., Gunasekaran et al., J Biol Chem 2010, 285(25):19637-19646), interactions due to alternating CH3 segments of IgG and IgA (SEED technology; see, e.g., Davis et al., Protein Eng Des Sel 2010, 23(4):195-202), interactions due to the fusion of a heterodimeric module, such as a cleavable leucine zipper, in the C-terminus of the CH3 domain (LUZ-Y technology; see, e.g., Wranik et al., J Biol Chem 2012, 287(52):43331-43339).

In one embodiment, the at least one additional Fc interaction is at least one knob-into-hole interaction (e.g., two knob-into-hole interactions).

The term "knob-into-hole interaction", as used herein, refers to an interaction which is based on knob-into-hole amino acid changes. Such changes represent a well-known rational design strategy in antibody engineering used for heterodimerization of the heavy (H) immunoglobulin chains, e.g., in the production of bispecific antibodies, as described in, e.g., Merchant et al., Nat. Biotechnol. 1998, 16:677-681. Amino acid changes are engineered in order to create a knob on the constant region (e.g., on the CH3) of a first immunoglobulin chain or first antibody and a hole on the constant region (e.g., on the CH3) of a second immunoglobulin chain or second antibody. The knob is represented by an amino acid that belongs to the "very large" IMGT volume class of amino acids (e.g., tyrosine, Y), whereas the hole is represented by an amino acid that belongs to the "small" IMGT volume class (e.g., threonine; T)—for the IMGT classes of the 20 conventional amino acids, see Pommie et al., J. Mol. Recognit. 2004, 17:17-32. Particularly preferred knob-into-hole amino acid changes, in accordance with the present invention, include, but are not limited to those described in Spies et al., J Mol Imm. 2015, 67:95-106.

In one embodiment, the protein comprises a first polypeptide chain having the formula $VL_b$-L1-$VL_a$-L2-CL, a second polypeptide chain having the formula $VH_a$-L3-$VH_b$-L4-CH1-hinge-CH2-CH3 and a third polypeptide chain having the formula $VL_c$-$CL_c$-PCL-$VH_c$-$CH1_c$-hinge-CH2-CH3, wherein

- $VL_a$ is a first immunoglobulin light chain variable region;
- $VL_b$ is a second immunoglobulin light chain variable region;
- $VL_c$ is a third immunoglobulin light chain variable region;
- CL is an immunoglobulin light chain constant region;
- $CL_c$ is an immunoglobulin light chain constant region;
- $VH_a$ is a first immunoglobulin heavy chain variable region;
- $VH_b$ is a second immunoglobulin heavy chain variable region;
- $VH_c$ is a third immunoglobulin heavy chain variable region;
- CH1 is an immunoglobulin CH1 heavy chain constant region;
- $CH1_c$ is an immunoglobulin CH1 heavy chain constant region;
- hinge is an immunoglobulin hinge region;
- CH2 is an immunoglobulin CH2 heavy chain constant region; and
- CH3 is an immunoglobulin CH3 heavy chain constant region;
- L1, L2, L3 and L4 are linkers;
- wherein $VL_a$ pairs with $VH_a$ to form an antigen binding site binding to antigen A, wherein $VL_b$ pairs with $VH_b$ to form an antigen binding site binding to antigen B, and wherein VL, pairs with $VH_c$ to form an antigen binding site binding to antigen C; and
- wherein the second polypeptide chain is associated with the third polypeptide chain via at least two disulfide bonds and, optionally, via at least one additional Fc interaction.

In one embodiment, the antigen binding site C becomes active or exhibits increased activity upon protease-cleavage of the protease-cleavable linker.

In one embodiment, the at least one additional Fc interaction is at least one knob-into-hole interaction (e.g., two knob-into-hole interactions).

In one embodiment, L1, L2, L3 and L4 are independently selected from peptide linkers as defined herein, preferably having a length of between 1 to 25, preferably 2 to 25, more preferably 5 to 20, more preferably 10 to 20 amino acid residues. In one embodiment, L1, L2, L3 and L4 are glycine-serine-rich linkers, wherein at least 50%, preferably at least 60%, more preferably at least 70%, more preferably at least 80%, even more preferably at least 85% of the amino acids are a glycine or serine residue, respectively. In one embodiment, L1, L2, L3 and L4 are glycine linkers, serine linkers or glycine-serine linkers, respectively. In one embodiment, L1, L2, L3 and L4 have the sequence $(G_4S)_n$ (SEQ ID NO: 51), wherein n is an integer independently selected from 1 to 5, e.g., 1 to 3 or 2 to 4.

In one embodiment, the protein comprises a first polypeptide chain having the formula $VL_a$-$CL_a$-PCL-$VL_b$-$CL_b$, and a second polypeptide chain having the formula $VH_a$-$CH1_a$-L-$VH_b$-$CH1_b$-hinge-CH2-CH3, wherein

- $VH_a$ is a first immunoglobulin heavy chain variable region;
- $VH_b$ is a second immunoglobulin heavy chain variable region;
- $CH1_a$ is a first immunoglobulin CH1 heavy chain constant region;
- $CH1_b$ is a second immunoglobulin CH1 heavy chain constant region;
- L is an optional linker;
- hinge is an immunoglobulin hinge region;
- CH2 is an immunoglobulin CH2 heavy chain constant region; and
- CH3 is an immunoglobulin CH3 heavy chain constant region;
- wherein $VL_a$ pairs with $VH_a$ to form an antigen binding site binding to antigen A, and wherein $VL_b$ pairs with $VH_b$ to form an antigen binding site binding to antigen B.

In one embodiment, the antigen binding site B becomes active or exhibits increased activity upon protease-cleavage of the protease-cleavable linker.

In one embodiment, L is a peptide linker as defined herein. In one embodiment, L has a length of 5 to 25 amino acid residues, preferably 10 to 20 amino acid residues.

In one embodiment, the protein comprises two copies of the first polypeptide chain and two copies of the second polypeptide chain, wherein the two copies of the second polypeptide chain are associated with each other via at least two disulfide bonds.

In one embodiment, the protein comprises a first polypeptide chain having the formula $VL_a$-$CL_a$-PCL-$VL_b$-$CL_b$, a second polypeptide chain having the formula $VL_c$-$CL_c$-PCL-$VL_a$-$CL_a$, a third polypeptide chain having the formula $VH_a$-$CH1_a$-L-$VH_b$-$CH1_b$-hinge-CH2-CH3, and a fourth polypeptide chain having the formula $VH_c$-$CH1_c$-L-$VH_a$-$CH1_a$-hinge-CH2-CH3, wherein

- $VL_a$ is a first immunoglobulin light chain variable region;
- $VL_b$ is a second immunoglobulin light chain variable region;
- $VL_c$ is a third immunoglobulin light chain variable region;
- $VL_a$ is a fourth immunoglobulin light chain variable region;
- $CL_a$ is a first immunoglobulin light chain constant region;
- $CL_b$ is a second immunoglobulin light chain constant region;
- $CL_c$ is a third immunoglobulin light chain constant region;
- $CL_a$ is a fourth immunoglobulin light chain constant region;
- $VH_a$ is a first immunoglobulin heavy chain variable region;
- $VH_b$ is a second immunoglobulin heavy chain variable region;
- $VH_c$ is a third immunoglobulin heavy chain variable region;
- $VH_a$ is a fourth immunoglobulin heavy chain variable region;
- $CH1_a$ is a first immunoglobulin CH1 heavy chain constant region;
- $CH1_b$ is a second immunoglobulin CH1 heavy chain constant region;
- $CH1_c$ is a third immunoglobulin CH1 heavy chain constant region;

$CH1_a$ is a fourth immunoglobulin CH1 heavy chain constant region;

L is an optional linker;

hinge is an immunoglobulin hinge region;

CH2 is an immunoglobulin CH2 heavy chain constant region; and

CH3 is an immunoglobulin CH3 heavy chain constant region;

wherein $VL_a$ pairs with $VH_a$ to form an antigen binding site binding to antigen A, wherein $VL_b$ pairs with $VH_b$ to form an antigen binding site binding to antigen B, wherein $VL_c$ pairs with $VH_c$ to form an antigen binding site binding to antigen C, and wherein $VL_a$ pairs with $VH_a$ to form an antigen binding site binding to antigen D; and wherein the third polypeptide chain is associated with the fourth polypeptide chain via at least two disulfide bonds and, optionally, via at least one additional Fc interaction.

In one embodiment, the antigen binding site B and/or the antigen binding site D become active or exhibit increased activity upon protease-cleavage of the protease-cleavable linkers.

In one embodiment, the at least one additional Fc interaction is at least one knob-into-hole interaction (e.g., two knob-into-hole interactions).

In one embodiment, L is a peptide linker as defined herein. In one embodiment, L has a length of 5 to 25 amino acid residues, preferably 10 to 20 amino acid residues.

In one embodiment, the protein comprises a first polypeptide chain having the formula $VL_a$-$CL_a$-PCL-$VL_b$-$CL_b$-L-hinge-CH2-CH3, and a second polypeptide chain having the formula $VH_a$-$CH1_a$-L-$VH_b$-$CH1_b$-hinge-CH2-CH3, wherein $VH_a$ is a first immunoglobulin heavy chain variable region;

$VH_b$ is a second immunoglobulin heavy chain variable region;

$CH1_a$ is a first immunoglobulin CH1 heavy chain constant region;

$CH1_b$ is a second immunoglobulin CH1 heavy chain constant region;

L is an optional linker;

hinge is an immunoglobulin hinge region;

CH2 is an immunoglobulin CH2 heavy chain constant region; and

CH3 is an immunoglobulin CH3 heavy chain constant region;

wherein $VL_a$ pairs with $VH_a$ to form an antigen binding site binding to antigen A, and wherein $VL_b$ pairs with $VH_b$ to form an antigen binding site binding to antigen B; and wherein the first polypeptide chain is associated with the second polypeptide chain via at least two disulfide bonds and, optionally, via at least one additional Fc interaction.

In one embodiment, the antigen binding site B becomes active or exhibits increased activity upon protease-cleavage of the protease-cleavable linker.

In one embodiment, the at least one additional Fc interaction is at least one knob-into-hole interaction (e.g., two knob-into-hole interactions).

In one embodiment, L is a peptide linker as defined herein. In one embodiment, L has a length of 5 to 25 amino acid residues, preferably 10 to 20 amino acid residues.

In another aspect, the present invention relates to a nucleic acid or set of nucleic acids encoding the protein as defined herein.

A "nucleic acid" (or "nucleic acid molecule") is, according to the invention, preferably deoxyribonucleic acid (DNA) or ribonucleic acid (RNA). A nucleic acid molecule may according to the invention be in the form of a molecule, which is single-stranded or double-stranded and linear or covalently closed to form a circle.

The term "DNA" relates to a molecule which comprises deoxyribonucleotide residues and preferably is entirely or substantially composed of deoxyribonucleotide residues. "Deoxyribonucleotide" relates to a nucleotide which lacks a hydroxyl group at the 2'-position of a beta-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogues or analogues of naturally-occurring DNA. When used in connection with nucleotides, the term "naturally occurring" refers to the bases adenine (A), cytosine (C), guanine (G), thymine (T), and uracil (U).

The term "RNA" relates to a molecule which comprises ribonucleotide residues and preferably is entirely or substantially composed of ribonucleotide residues. "Ribonucleotide" relates to a nucleotide with a hydroxyl group at the 2'-position of a beta-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogues or analogues of naturally-occurring RNA. According to the invention, "RNA" refers to single-stranded RNA or double-stranded RNA. In one embodiment, the RNA is mRNA, e.g., in vitro transcribed RNA (IVT RNA) or synthetic RNA. The RNA may also be modified, e.g., with one or more modifications increasing the stability (e.g., the half-life) of the RNA. Such modifications are known to a person skilled in the art and include, for example, 5'-caps or 5'cap analogues In another aspect, the present invention relates to a vector or set of vectors comprising the nucleic acid or set of nucleic acids as defined herein.

The term "vector", as used herein, includes all vectors known to the skilled person, including plasmid vectors, cosmid vectors, phage vectors, such as lambda phage, viral vectors, such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

Alternatively, the nucleic acid molecule according to the present invention may be integrated into a genome, e.g., the genome of a host cell. Means and methods to integrate a particular nucleic acid molecule into a genome are known to a person skilled in the art.

In another aspect, the present invention relates to a host cell comprising a protein as defined herein, a nucleic acid or set of nucleic acids as defined herein, or a vector or set of vectors as defined herein.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (Tor example *Saccharomyces cerevisiae*), *Schizosaccharomyces* (for example *Schizosaccharomyces pombe*), *Pichia* (for example *Pichia pastoris* and *Pichia methanolica*), and *Hansenula*. Suitable mammalian cells include for example CHO cells, BHK cells, Hela cells, COS cells, HEK 293 (e.g., HEK 293-FS) and the like. However, amphibian cells, insect cells, plant cells, and any other cells used in the art for the expression of heterologous proteins can be used as well. The "cell" or "host cell" may be isolated or part of a tissue or organism, in particular a "non-human organism". The term "non-human organism", as used herein, is meant to include non-human primates or other animals, in particular mammals, such as cows, horses, pigs, sheep, goats, dogs, cats, rabbits or rodents, such as mice, rats, guinea pigs and hamsters.

In one embodiment, the host cell expresses an endogenous or exogenous furin and/or furin-like protease.

In one embodiment, the host cell is a mammalian cell. In one embodiment, the mammalian cell is a CHO cell, preferably selected from the group consisting of CHO 9E4, EXPICHO™, CHO DG44 and CHO K1.

In one aspect, the present invention relates to a method of producing a protein, e.g., a protein as defined herein, comprising the steps:

i) culturing a host cell as defined herein; and ii) isolating the protein from the host cell.

In one embodiment, said host cell is cultured under conditions allowing the expression of said protein.

In another aspect, the present invention relates to a protein obtainable (or obtained) by the method as defined herein.

In yet another aspect, the present invention relates to a protein obtainable (or obtained) by furin and/or furin-like protease-cleavage of a protein as defined herein.

In one embodiment, the protein as defined herein is a therapeutically active protein.

The term "therapeutically active protein", as used herein, refers to a protein which is suitable for therapy, i.e., can be used to treat a disease or disorder. In one embodiment, the therapeutically active protein is an antibody or antibody-derivative binding to a therapeutically relevant antigen.

For all antibodies and antibody derivatives, as described herein, the therapeutically relevant antigen is for example independently selected for each specificity from the group consisting of IL-4, IL-13, PD-1, 4.1BB, OX40 and GITR. For all bispecific antibodies and antibody derivatives, as described herein, the antigen pair is for example selected from the group consisting of the antigen pairs IL-4 and IL-13, PD-1 and OX40, PD-1 and GITR, and PD-1 and 4.1BB. For all trispecific antibodies or antibody derivatives described herein, two antigens are for example selected from the group consisting of the antigen pairs IL-4 and IL-13, PD-1 and OX40, PD-1 and GITR, and PD-1 and 4.1BB. The third and fourth antigens can be another antigen selected from the list above. In one embodiment of a trispecific antibody or antibody derivative, as described herein, the antigens are PD-1, GITR and OX40.

In one aspect, the present invention relates to a protein as defined herein for use in therapy.

In another aspect, the present invention relates to the use of a protein as defined herein in the manufacture of a medicament.

In yet another aspect, the present invention relates to a method of treating a disease or disorder, comprising administering an effective amount of a protein as defined herein to a subject in need thereof.

The term "medicament", as used herein, refers to a substance/composition used in therapy, i.e., in the treatment of a disease or disorder.

By "treat" is meant to administer a compound or composition or a combination of compounds or compositions to a subject in order to prevent or eliminate a disease or disorder; arrest or slow a disease or disorder in a subject; inhibit or slow the development of a new disease or disorder in a subject; decrease the frequency or severity of symptoms and/or recurrences in a subject who currently has or who previously has had a disease or disorder; and/or prolong, i.e., increase, the lifespan of the subject.

In particular, the term "treating/treatment of a disease or disorder" includes curing, shortening the duration, ameliorating, preventing, slowing down or inhibiting progression or worsening, or preventing or delaying the onset of a disease or disorder or the symptoms thereof.

According to the invention, the term "disease" refers to any pathological state, in particular cancer, infectious diseases, inflammatory diseases, autoimmune disorders, and transplant rejections.

As used herein, the term "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease. The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above.

The term “cancer” according to the invention also comprises cancer metastases. By “metastasis” is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term “metastasis” according to the invention relates to “distant metastasis” which relates to a metastasis which is remote from the primary tumor and the regional lymph node system.

The term “infectious disease” refers to any disease which can be transmitted from individual to individual or from organism to organism, and is caused by a microbial agent (e.g. common cold). Examples of infectious diseases include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), and severe acute respiratory syndrome (SARS), bacterial infectious diseases, such as Legionnaire’s disease (*Legionella*), sexually transmitted diseases (e.g. *chlamydia* or gonorrhea), gastric ulcer (*Helicobacter*), cholera (*Vibrio*), tuberculosis, diphtheria, infections by *E. coli*, Staphylococci, *Salmonella* or Streptococci (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused, e.g., by *Cryptococcus neoformans, Histoplasma capsulatum, Coccidioides immitis, Blastomyces dermatitidis* or *Candida albicans*.

The term “inflammatory disease” refers to any disease, which is characterized by or associated with high levels of inflammation in tissues, in particular connective tissues, or degeneration of these tissues. A chronic inflammatory disease is a medical condition which is characterized by persistent inflammation. Examples of (chronic) inflammatory diseases include celiac disease, vasculitis, lupus, chronic obstructive pulmonary disease (COPD), irritable bowel disease, atherosclerosis, arthritis, ankylosing spondylitis, Crohn’s disease, colitis, chronic active hepatitis, dermatitis and psoriasis.

The term “autoimmune disorder” refers to any disease/disorder in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto’s thyroiditis, Grave’s disease, lupus, multiple sclerosis, rheumatic arthritis, hemolytic anemia, anti-immune thyroiditis, systemic lupus erythematosus, celiac disease, Crohn’s disease, colitis, diabetes, scleroderma, psoriasis, and the like.

The term “transplant rejection” refers to the rejection of a transplanted tissue or organ by the recipient’s immune system, which may, ultimately, destroy the transplanted tissue or organ.

The term “effective amount”, as used herein, refers, in particular, to a “therapeutically effective amount”, which is an amount that achieves a desired therapeutic reaction or a desired therapeutic effect alone or together with further doses, preferably without causing unacceptable side-effects. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount of a protein described herein will depend on the condition to be treated, the severeness of the disease, the individual parameters of the subject, including age, physiological condition, size and weight, the duration of treatment, the type of an accompanying therapy (if present), the specific route of administration and similar factors. Accordingly, the doses administered of the agents described herein may depend on several of such parameters. In the case that a reaction in a subject is insufficient with an initial dose, higher doses (or effectively higher doses achieved by a different, more localized route of administration) may be used.

The term “subject” means according to the invention a subject for treatment, in particular a diseased subject (also referred to as “patient”), including human beings, non-human primates or other animals, in particular mammals, such as cows, horses, pigs, sheep, goats, dogs, cats, rabbits or rodents, such as mice, rats, guinea pigs and hamsters. In one embodiment, the subject/patient is a human being.

In yet another aspect, the present invention relates to a pharmaceutical composition or kit comprising a protein as defined above. In one embodiment, the pharmaceutical composition further comprises a pharmaceutically acceptable carrier.

The pharmaceutical compositions of the invention can be selected for parenteral delivery. Alternatively, the compositions can be selected for inhalation or for delivery through the digestive tract, such as orally. The preparation of such pharmaceutically acceptable compositions is within the skill of the art.

The term “pharmaceutically acceptable carrier” or “physiologically acceptable carrier” as used herein refers to one or more formulation materials suitable for accomplishing or enhancing the delivery of an antibody-like binding protein. The primary carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise TRIS™ (tris(hydroxymethyl)aminomethane buffer) buffer of about pH 7.0-8.5, or acetate buffer of about pH 4.0-5.5, which can further include sorbitol or a suitable substitute. In one embodiment of the invention, antibody-like binding protein compositions can be prepared for storage by mixing the selected composition having the desired degree of purity with optional formulation agents in the form of a lyophilized cake or an aqueous solution. Further, the antibody-like binding protein can be formulated as a lyophilizate using appropriate excipients such as sucrose.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediaminetetraacetic acid (EDTA)), complexing agents (such as caffeine, polyvinylpyrrolidone, beta-cyclodextrin, or hydroxypropylbeta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; TRITON™ (non-ionic surfactant or polyethylene glycol tert-octylphenyl ether); tromethamine; lecithin; cholesterol or tyloxapal), stability enhancing agents (such as sucrose or sorbitol), tonicity enhancing agents (such as alkali metal halides, preferably sodium or potassium chloride—or mannitol sorbitol), delivery vehicles, diluents, excipients and/or pharmaceutical adjuvants (see, e.g., REMINGTON's PHARMACEUTICAL SCIENCES (18th Ed., A.R. Gennaro, ed., Mack Publishing Company 1990), and subsequent editions of the same).

As used herein, the term "kit of parts (in short: kit)" refers to an article of manufacture comprising one or more containers and, optionally, a data carrier. Said one or more containers may be filled with one or more of the above mentioned (re-) agents. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the agents of the present invention, e.g., proteins and pharmaceutical compositions as well as related agents, such as nucleic acid molecules and host cells, as described herein.

In another aspect, the present invention relates to a protein comprising a first polypeptide chain having the formula $VL_b$-L1-$VL_a$-L2-CL, a second polypeptide chain having the formula $VH_a$-L3-$VH_b$-L4-CH1-hinge-CH2-CH3 and a third polypeptide chain having the formula $VL_c$-$CL_c$-PCL-$VH_c$-$CH1_c$-hinge-CH2-CH3, wherein

- $VL_a$ is a first immunoglobulin light chain variable region;
- $VL_b$ is a second immunoglobulin light chain variable region;
- $VL_c$ is a third immunoglobulin light chain variable region;
- CL is an immunoglobulin light chain constant region;
- $CL_c$ is an immunoglobulin light chain constant region;
- $VH_a$ is a first immunoglobulin heavy chain variable region;
- $VH_b$ is a second immunoglobulin heavy chain variable region;
- $VH_c$ is a third immunoglobulin heavy chain variable region;
- CH1 is an immunoglobulin CH1 heavy chain constant region;
- $CH1_c$ is an immunoglobulin CH1 heavy chain constant region;
- hinge is an immunoglobulin hinge region;
- CH2 is an immunoglobulin CH2 heavy chain constant region; and
- CH3 is an immunoglobulin CH3 heavy chain constant region;
- PCL is a protease-cleavable linker;
- L1, L2, L3 and L4 are linkers;
- wherein $VL_a$ pairs with $VH_a$ to form an antigen binding site binding to antigen A, wherein $VL_b$ pairs with $VH_b$ to form an antigen binding site binding to antigen B, and wherein VL pairs with $VH_c$ to form an antigen binding site binding to antigen C; and
- wherein the second polypeptide chain is associated with the third polypeptide chain via at least two disulfide bonds and, optionally, via at least one additional Fc interaction.

In one embodiment, the antigen binding site C becomes active or exhibits increased activity upon protease-cleavage of the protease-cleavable linker.

In one embodiment, the protease-cleavable linker is a protease-cleavable linker as defined herein.

In one embodiment, the at least one additional Fc interaction is at least one knob-into-hole interaction (e.g., two knob-into-hole interactions).

In one embodiment, L1, L2, L3 and L4 are independently selected from peptide linkers as defined herein, preferably having a length of between 1 to 25, preferably 2 to 25, more preferably 5 to 20, more preferably 10 to 20 amino acid residues. In one embodiment, L1, L2, L3 and L4 are glycine-serine-rich linkers, wherein at least 50%, preferably at least 60%, more preferably at least 70%, more preferably at least 80%, even more preferably at least 85% of the amino acids are a glycine or serine residue, respectively. In one embodiment, L1, L2, L3 and L4 are glycine linkers, serine linkers or glycine-serine linkers, respectively. In one embodiment, L1, L2, L3 and L4 have the sequence $(G_4S)_n$ (SEQ ID NO: 51), wherein n is an integer independently selected from 1 to 5, e.g., 1 to 3 or 2 to 4.

The present invention also includes (the use of) a functional (i.e., protease-cleavable) variant of the amino acid sequence of any one of SEQ ID NOs: 42 to 44 in any aspect of the present invention as described herein. In one embodiment, the variant comprises up to 3, 2 or 1 amino acid substitution(s), preferably conservative amino acid substitution(s), a deletion of up to 3, 2 or 1 amino acid residues (e.g., at the N-terminus and/or C-terminus) and/or an addition of up to 3, 2 or 1 amino acid residues (e.g., to the N-terminus and/or C-terminus) in/from/to the amino acid sequence of any one of SEQ ID NOs: 42 to 44. A conservative amino acid substitution involves substitution of an amino acid with another one of the same family of amino acids, i.e., amino acids which are related in their side chains (e.g., in terms of the electrical charge and/or size). Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. Conservative substitutions are well known in the art (see for example Creighton (1984) Proteins. W.H. Freeman and Company). In one embodiment, the variant comprises one or more (e.g., up to 3, 2 or 1) of the following amino acid substitutions: R→K, S→T/A (i.e., S→T or S→A), V→A/I/L (i.e., V→A or V→I or V→L), D→E, E→D. In one embodiment, the variant (e.g., a variant of SEQ ID NO: 42) comprises one or more (e.g., up to 3, 2 or 1) of the following amino acid substitutions: S→T/A, V→A/I/L, D→E, E→D.

The present invention is now further described by reference to the following Examples, which are intended to illustrate, not to limit the scope of the present invention.

EXAMPLES

Example 1: Materials and Methods

Expression of Protease-Cleavable Monospecific and Bispecific Molecules in HEK 293-FS, EXPICHO™ Cells and Stable CHO 9E4 Cell Pools For monoclonal antibodies, the expression plasmids encoded a single chain comprising the heavy and light chain (anti-IL4-hIgG1) linked via protease-cleavable linkers; for bispecific Tandem-IgG antibodies, expression plasmids encoded either heavy chain or single-light chains (2 Fab fragments linked with protease-cleavable linkers); for bispecific Tandem-like antibodies, expression plasmids encoded either heavy chain or heavy-light chain linked constructs. For proteases, the expression plasmids encoded the human propeptide sequences of either Furin, PCSK5, PCSK6, PCSK7, or Furin with an additional KDEL (SEQ ID NO: 38)-signal peptide. All expression plasmids were propagated in *E. coli* DH5a. Plasmids used for transfection were prepared from *E. coli* using the Qiagen ENDOFREE™ (low-endotoxin plasmid purification system) Plasmid Mega Kit.

HEK 293-FS cells growing in F17 serum free suspension culture (Invitrogen) were transfected with indicated single chain or LC and HC plasmids using polyethylenimine transfection reagent. EXPICHO™ cells growing in F17 serum free suspension cultures (Invitrogen) were transfected with indicated plasmids using a suitable transfection reagent.

After 7 days of cultivation at 37° C., cells were removed by centrifugation and the supernatant was passed over a 0.22 μm filter to remove particles.

For co-transfections of HEK293-FS or EXPICHO™ cells, plasmids for the antibody constructs were mixed in a 1:1 molar ratio with individual expression plasmids encoding the pro-peptide sequences of the proteases.

For the generation of stable CHO 9E4 cell pools, CHO 9E4 cells were cultured in CD CHO serum-free media (Invitrogen) and electroporated using the MAXCYTE STX™ (high-efficiency electroporation platform) instrument and buffer reagents (MaxCyte Inc.) with transposon-based plasmids encoding single light chains and heavy chains, respectively. For protease co-expression, 30% of plasmid content were transposon-based protease-encoding plasmids. Stable cell pools were selected for 6 days in CD CHO media containing MSX selection marker. For expression of antibodies, cells were cultivated for 13 days at 37° C. in OPTI CHO media (Invitrogen) containing FeedB (Invitrogen) under selection pressure, before supernatants were separated by centrifugation and passed over a 0.22 μm filter to remove particles.

For purification, the antibody was captured on a MAB-SELECT SURE™ (protein A affinity chromatography resin) column (Cat. No.: 11-0034-93, GE Healthcare) and eluted with 0.1 M Citrate buffer pH 3.0. Elution fractions were directly neutralized by adding 1:6 (v/v) TRIZMA™ (tris (hydroxymethyl)aminomethane buffer) pH 8.0 (Sigma Aldrich). After polishing the protein by size exclusion chromatography (SEC) using a SUPERDEX200™ (size-exclusion chromatography medium) 16/60 (GE) and a final ultrafiltration concentration step, the protein was used for further characterization.

Sodium Dodecyl Sulfate Polyacrylamide Gel Electrophoresis (SDS-PAGE) and Capillary Electrophoresis For SDS-PAGE, 2 μg protein sample was mixed with NUPAGE™ (polyacrylamide gel electrophoresis system or precast polyacrylamide gel) LDS Sample Buffer (ThermoFisher Scientific); for reducing conditions, 2 μg protein was mixed with NUPAGE™ LDS Sample Buffer containing DTT (Dithiothreitol) and heated for five minutes at 95° C. Samples and Color Protein Standard Broad Range ladder (New England Biolabs) were loaded on 4-12% Bis/TRIS™ (tris(hydroxymethyl)aminomethane buffer) gels (Invitrogen) and run in NUPAGE™ MOPS SDS Running Buffer (ThermoFisher Scientific) at 200 V for 45 minutes. Gels were stained with Instant Blue Coomassie protein stain (Expedeon). For capillary electrophoreses, protein samples were prepared under reducing and oxidizing conditions according to manufacturer's protocol using Protein Clear HR Assay Kit and LABCHIP™ (microfluidic electrophoresis system) Touch SP2 instrument (Perkin Elmer).

Analytical Size-Exclusion Chromatography (SEC)

Analytical SEC was performed using a BioSECcurity instrument (PSS Polymer) with a ADVANCEBIO 300™ (bioinert liquid chromatography column) (4.6 mm×300 mm) and AdvanceBio 300 guard column (Agilent Technologies) at 25° C. The analysis was run at a flow rate of 0.5 ml/min using 2× concentrated D-PBS buffer (Thermo Fisher Scientific) with detection at 280 nm. 10 μl of protein sample (at 1 mg/ml) were applied onto the column. Data evaluation was performed using WINGPC™ (gel permeation chromatography data analysis software) v8.1 (PSS Polymer). For estimation of the molecular weight, the SEC column was calibrated with a protein calibration standard mix (Agilent Technologies).

Analytical Hydrophobic-Interaction Chromatography (HIC)

Analytical HIC was performed using a LC10 HPLC instrument (Shimadzu) or a Vanquish HPLC instrument (Thermo Fisher Scientific) equipped with a TSKGEL™ (size-exclusion chromatography resin) Butyl-NPR column (2.5 μm, 4.6×35 mm) (Tosoh Bioscience) at 25° C. The analysis was run at a flow rate of 1 ml/min with detection at 280 nm. 5 μg of undiluted protein sample were applied onto the column. Gradient elution was from 15% B to 85% B in 7 min followed by 1 min to 100% B, then 1 min to 15% B and then 3 minutes equilibration at 15% B. Buffer A was composed of 1.5 M ammonium sulfate, 25 mM sodium phosphate pH 7.0. Buffer B was composed of 25 mM sodium phosphate pH 7.0. Data evaluation was performed using either LabSolutionsLABSOLUTIONS™ software v5.85 (chromatography and mass spectrometry data analysis software) (Shimadzu) or CHROMELEON 7™ software (chromatography data system software) (Thermo Fisher Scientific).

Mass spectrometry (MS)

Protein integrity and potential mispairing of heterodimeric constructs was analyzed by LC-mass spectrometry (LC-MS). Protein samples were deglycosylated with 12.5 μg of protein diluted to 0.17 mg/ml in LC-MS grade water (Thermo Scientific) treated with 0.5 μl PNGaseF (glycerol free, New England Biolabs) at 37° C. for 16 hours. The LC-MS analysis was performed using a Thermo Fisher ORBITRAP™ (high-resolution mass spectrometer) Lumos LC/MS instrument. Reversed phase (RP) chromatography was done using a MabPac RP HPLC column, analytical 4 μm particle size, 2.1×100 mm (Thermo Scientific) at 300 μL/min. Eluents were LC water, 0.1% formic acid (A) and 90% acetonitrile, 10% LC water, 0.1% formic acid (B). 2 μg of protein were injected onto the column and eluted using a linear gradient from 0% to 95% B in 12 minutes. Data analysis was done using EXPRESSIONIST™ software (liquid chromatography-mass spectrometry data analysis) 13.0.3 (Genedata). Molecular masses were calculated based on the amino acid sequences of the proteins using GPMAW software version 10.32b1 (Lighthouse data).

Surface Plasmon Resonance (SPR)

Binding of antigens to the antibody constructs was measured using surface plasmon resonance (SPR) with a BIACORE™ (surface plasmon resonance biosensor) 3000 instrument (GE Healthcare) with HBS-EP buffer (GE Healthcare). As antigens, human IL4 (IL004, Millipore) and human IL13 (IL012, Millipore) were used. The anti-human Fc capture antibody (human antibody capture kit, GE Life Sciences) was immobilized via primary amine groups (11000 RU) on a research grade CM5 chip (GE Life Sciences) using standard procedures. The ligands were captured at a flow rate of 10 μl/min with an adjusted RU value that resulted in maximal analyte binding of 30 RU. The tested antibody constructs were used as analytes and injected at 100 nM concentration for 240 sec with a dissociation time of 300 sec at a flow rate of 30 μL/min. For human IL4 and IL13, a dilution series of 0.1 nM to 3 nM and 0.8 nM to 25 nM, respectively were used. Chip surfaces were regenerated with 2 min injects of the regeneration buffer provided with the capture kit. Sensorgrams were double-referenced with a blank chip surface and HBS-EP buffer blanks. Data analysis was performed using the BIAevaluation software v4.1.

Figure 3:
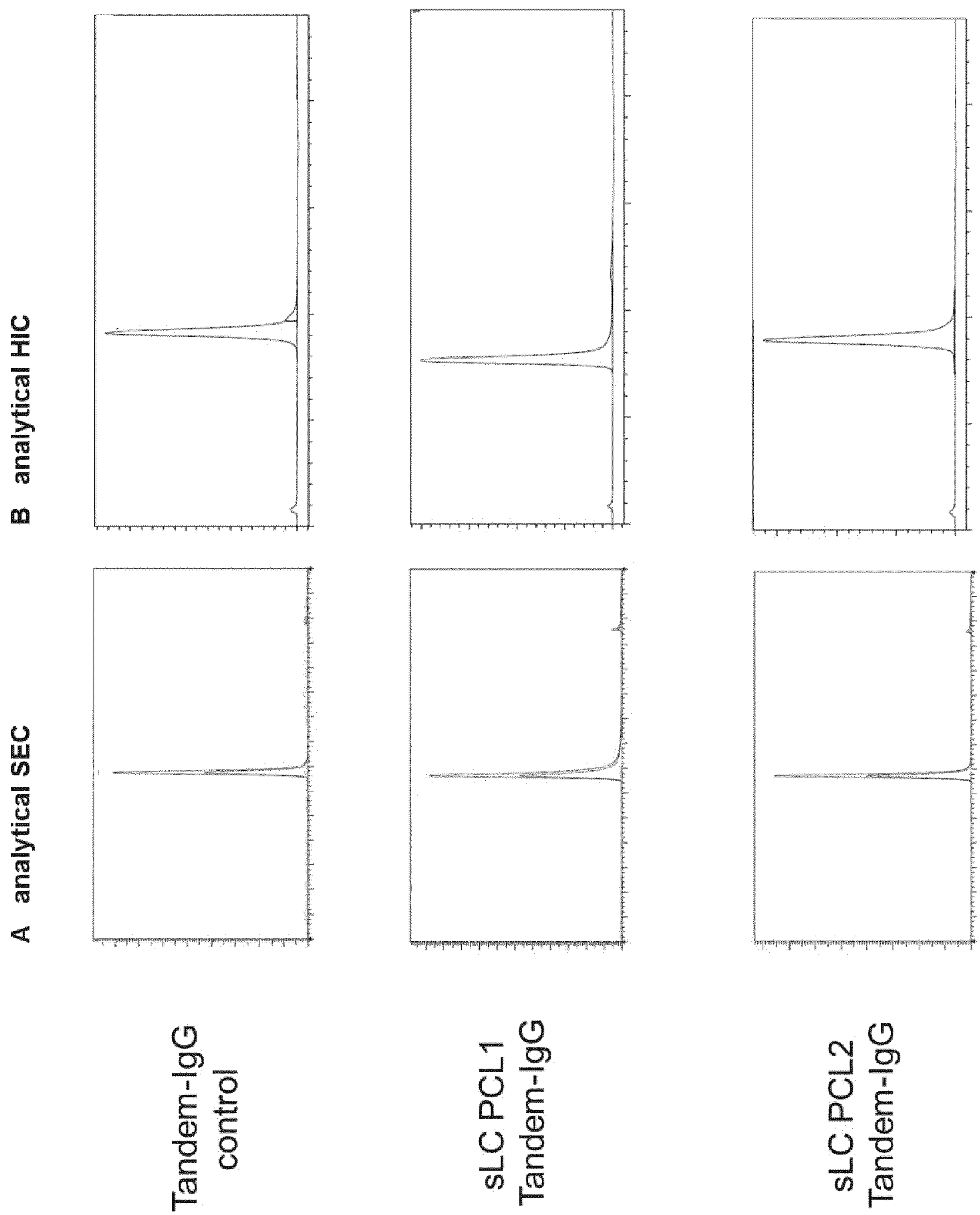
FIG. 3: Analysis of Tandem-anti-IL4 x anti-IL13-huIgG1 constructs from HEK293-FS cells. Panel (A) shows the purity of the Tandem-IgG products (Tandem-IgG control; sLC-PCL1-Tandem-IgG and sLC-PCL2-Tandem-IgG) after affinity and preparative SEC using analytical size exclusion chromatography. Panel (B) shows the homogeneity of the antibody products using analytical hydrophobic-interaction chromatography. Panel (C) shows the reduced (one heavy chain and two light chains/one single LC, respectively) and oxidized form (intact Tandem-IgG) of the antibody using 4-12% Bis/TRIS™ (tris(hydroxymethyl)aminomethane buffer) MOPS sodium dodecyl sulfate polyacrylamide gel electrophoresis (SDS-PAGE).
Figure 3:
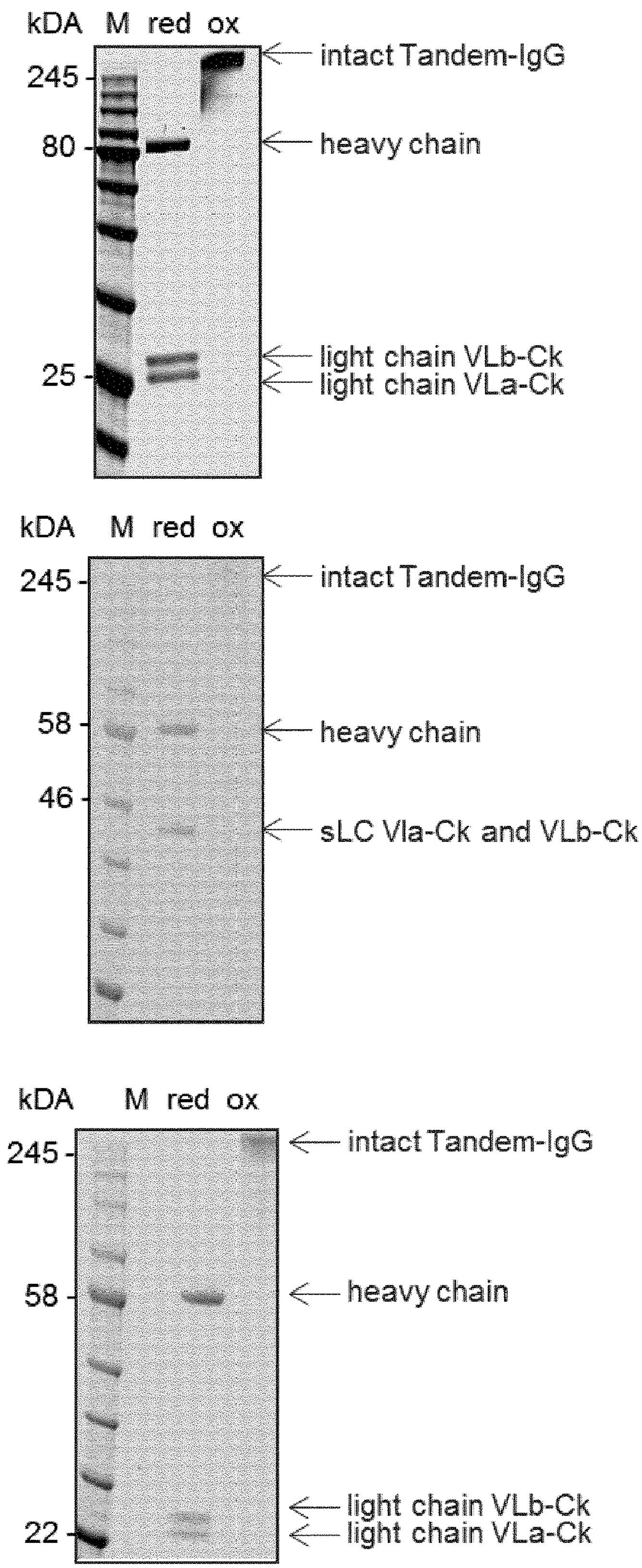

Example 2: Expression and In Vivo Processing of Protease-Cleavable Tandem-IgGs in HEK293-FS cells Bispecific Tandem-IgG (FIG. 1B; Table 1) constructs were expressed in HEK293-FS cells after transient transfection of two plasmids encoding the heavy chain (HC) and a single light chain (sLC) wherein the VLa-Cκ and VLb-Cκ chains were connected via different protease-cleavable linker sequences. As control, a Tandem-(anti-IL4xanti-IL13)-huIgG1 with VLa-Cκ and VLb-Cκ expressed as two separate chains (Tandem-IgG control) was used. The sLC Tandem-IgGs showed comparable expression and purification characteristics as the control Tandem-IgG (FIG. 3A-B; selected constructs depicted in bold in Table 1).

TABLE 1

Expression and purification results for Tandem-IgG constructs with protease-cleavable linkers from HEK293-FS cultures.

| SEQ ID NO | Construct Name | Monomeric Fraction after Protein A [%] | Yield after prep. SEC [mg/L] |
|---|---|---|---|
| 11, 12, 13 | Tandem-(anti-IL4xanti-IL13)-hulgG1 | 100.0 | 71.3 |
| 14, 13 | sLC-Tandem-(anti-IL4xanti-IL13)-singlePCL1-hulgG1 | 80.9 | 44.8 |
| 15, 13 | **sLC-Tandem-(anti-IL4xanti-IL13)-PCL1-hulgG1** | 83.1 | 34.8 |
| 16, 13 | LC-Tandem-(anti-IL4xanti-IL13)-ΔPCL1-hulgG1 | 63.2 | 78.4 |
| 17, 13 | sLC-Tandem-(anti-IL4xanti-IL13)-His8-PCL1-hulgG1 | 91.0 | 33.1 |
| 18, 13 | sLC-Tandem-(anti-IL4xanti-IL13)-His8-ΔPCL1-hulgG1 | 83.1 | 28.3 |
| 19, 13 | **sLC-Tandem-(anti-IL4xanti-IL13)-PCL2-hulgG1** | 100.0 | 38.2 |
| 20, 13 | sLC-Tandem-(anti-IL4xanti-IL13)-PCL3-hulgG1 | 84.3 | 20.4 |
| 21, 22 | sLC-Tandem-(anti-IL4xanti-IL13)-rigidL1-PCL1-hulgG1 | 73.0 | 21.4 |
| 23, 13 | sLC-Tandem-(anti-IL4xanti-IL13)-rigidL2-PCL1-hulgG1 | 84.8 | 18.3 |
| 24, 13 | sLC-Tandem-(anti-IL4xanti-IL13)-charL-PCL1-hulgG1 | 100.0 | 18.3 |
| 70, 71 | sLC-Tandem-(anti-PD-1)x(anti-4.1BB)-PCL2-hulgG1-LALA_AB0-2 | 100.0 | 7.5 |
| 72, 71 | sLC-Tandem-(anti-PD-1)x(anti-4.1BB)-PCL2a hulgG1-LALA_AB0-2 | 100.0 | 6.9 |
| 73, 74 | sLC-Tandem-(anti-PD-1)x(anti-OX40)-PCL2 hulgG1-LALA_AC0-2 | 100.0 | 3.7 |
| 75, 74 | sLC-Tandem-(anti-PD-1)x(anti-OX40)-PCL2a hulgG1-LALA_AC0-2 | 100.0 | 7.2 |

SDS-PAGE analysis under reducing conditions of in vivo processing of the Tandem-IgG constructs with protease-cleavable linkers revealed that the sLCs containing the linker sequences with the modified protease recognition/cleavage site HRRRKRSVDE (PCS2; SEQ ID NO: 43; "PCL2" refers to a PCL containing PCS2) showed two separate light chains (FIG. 3C) as seen for the Tandem-IgG control. Similar results were obtained with the modified protease recognition/cleavage site HRRQQRSVDE (PCS2a; SEQ ID NO: 44; "PCL2a" refers to a PCL containing PCS2a). In contrast, all constructs containing the minimal protease recognition sequence (PCS1; SEQ ID NO: 49; "PCL1" refers to a PCL containing PCS1), different linker sequences or the deleted recognition sequence (deltaPCS/PCL) were not processed in vivo during expression in HEK293-FS cells and showed the same profile of a single LC and a HC under reducing conditions (FIG. 3C; exemplary profile shown for sLC PCL1 Tandem-IgG).

Protein integrity and in vivo processing of Tandem-IgG constructs was further analyzed by LC-mass spectrometry (LC-MS). Samples were measured after deglycosylation under reducing and non-reducing conditions. Molecular masses were calculated based on the amino acid sequences of the proteins (Table 2). LC-MS analysis confirmed complete in vivo processing of linker sequences in Tandem-IgG constructs containing PCS2 recognition sites. In contrast, no processing was detected in protein samples of Tandem-IgGs with deleted (deltaPCS/PCL) or minimal PCS (PCS1) recognition sites. Furthermore, control Tandem-IgG consisting of two separate LCs showed mispairing of LCs to HCs (3*LC1+1*LC2+2*HC), which was not observed in sLC Tandem-IgG-PCL2 after processing of the sLC into LC1 and LC2. Thus, sLC Tandem-IgG constructs reduce/avoid LC-HC mispairing in this bispecific IgG-format. Moreover, in fully processed samples, further processing of the C-terminal charged amino acids comprising the protease recognition site RRKR (SEQ ID NO: 49) by carboxy-terminal proteases was observed (RRKR-loss). In contrast, no further N-terminal processing could be seen by Edman-Sequencing (data not shown).

TABLE 2

LC-MS results of HEK293-FS expressed Tandem-IgG under deglycosylated reducing or non-reducing conditions.

| SEQ ID NO | Construct Name | Expected (Da)* | Measured (Da) | Difference (Da) | Comment | Pairing | Processing |
|---|---|---|---|---|---|---|---|
| 11 12, 13 | Tandem-(anti-IL4xanti-IL13)-hulgG1 | 243319.08 | 243343.67 | 24.59 | correct | 2*LC1 2*LC2 2*HC | ctrl. |
| | | | 242905.05 | −414.03 | minor peak-mispairing | 3*LC1 1*LC2 2*HC | |
| | | | 243203.21 | −115.87 | minor preak 2*Gly-loss | 2*LC1 1*LC2 2*HC | |
| 15, 13 | sLC-Tandem-(anti-IL4xanti-IL13)-PCL1-hulgG1 | 49185.11 | 49180.34 | −4.77 | correct | SLC | no |
| | | 74621.92 | 74621.92 | 6.18 | correct | HC | |
| 16, 13 | sLC-Tandem-(anti-IL4xanti-IL13)-ΔPCL1-hulgG1 | 49128.91 | 49124.10 | −4.81 | correct | SLC | no |
| | | 74621.92 | 74617.48 | −4.44 | correct | HC | |
| 19, 13 | sLC-Tandem-(anti-IL4xanti-IL13)-PCL2-hulgG1 | 24176.46 | 24173.94 | −2.52 | correct | LC1 | yes |
| | | 24207.83 | 23608.71 | −599.12 | correct but RRKR-loss | LC2 | |
| | | 24207.83 | 23452.24 | −755.59 | correct but RRKR-loss | LC2 | |
| | | 74621.92 | 746625.48 | 3.56 | correct | HC | |
| 72, 71 | sLC-Tandem-(anti-PD-1)x(anti-4.1BB)-PCL2a hulgG1-LALA_AB0-2 | 244161.57 | 244169.00 | 30 | correct | 2*LC1 2*LC2 HC | yes |
| | | 244161.57 | 244007.00 | −154.57 | correct but RR-loos on 1LC1 | 2*LC1 2*LC2 HC | |
| | | 244161.57 | 243850.00 | −1276 | correct but R-loss on 2LC1 | 2*LC1 2*LC2 HC | |
| 75, 74 | sLC-Tandem-(anti-PD-1)x(anti-OX40)-PCL2a hulgG1-LALA_AC0-2 | 243246.66 | 242933.00 | −3 | correct | 2*LC1 2*LC2 HC | yes |
| | | 243246.66 | 243092.00 | −636 | correct but RR-loos on 1LC1 | 2*LC1 2*LC2 HC | |
| | | 243246.66 | 243246.00 | −1289 | correct but R-loss on 2LC1 | 2*LC1 2*LC2 HC | |

Figure 4:
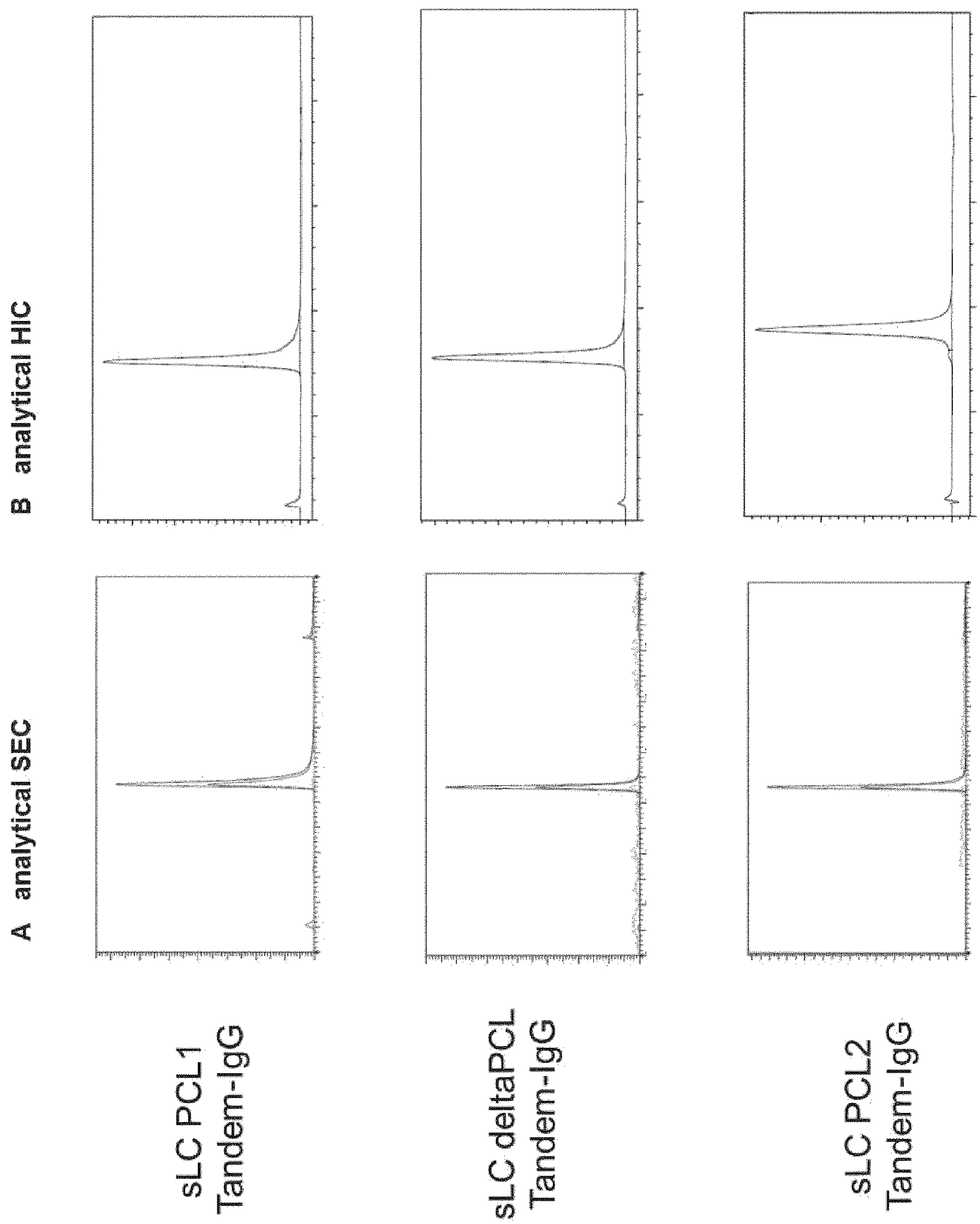
FIG. 4: Analysis of Tandem-anti-IL4 x anti-IL13-huIgG1 constructs from HEK293-FS cells. Panel (A) shows the purity of the Tandem-IgG products (sLC-PCL1-Tandem-IgG, sLC deltaPCL Tandem-IgG and sLC-PCL2-Tandem-IgG) after affinity and preparative SEC using analytical size exclusion chromatography. Panel (B) shows the homogeneity of the antibody products using analytical hydrophobic-interaction chromatography. Panel (C) shows the reduced (one heavy chain and two light chains/one single LC, respectively) and oxidized form (intact Tandem-IgG) of the antibody using 4-12% Bis/TRIS™ (tris(hydroxymethyl) aminomethane buffer) MOPS sodium dodecyl sulfate polyacrylamide gel electrophoresis (SDS-PAGE).
Figure 4:
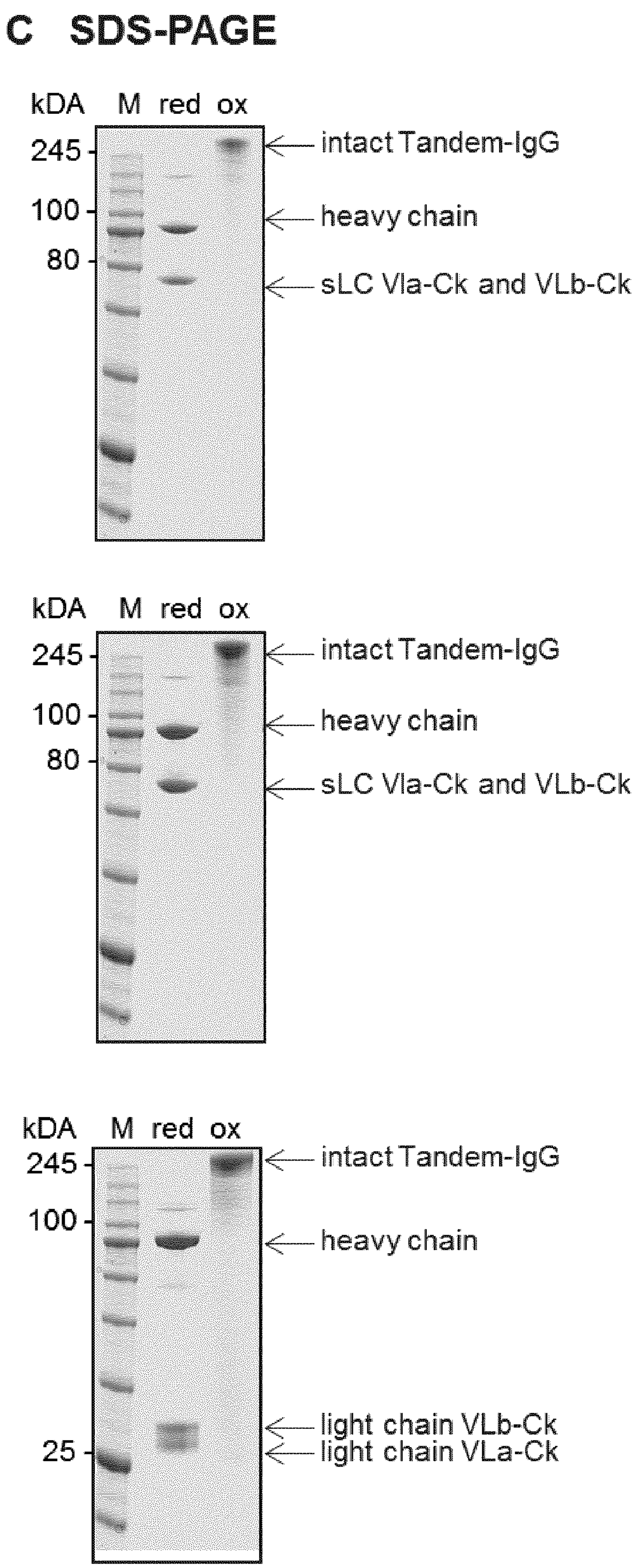

Example 3: Expression and In Vivo Processing of Protease-Cleavable Tandem-IgGs in EXPICHO™ (Chinese Hamster Ovary (CHO) Suspension Cell Line Optimized for High-Density Transient Expression) Cells For transient expression of Tandem-IgGs in EXPICHO™ cells, selected sLC constructs are shown in Table 3. The sLC Tandem-IgGs with different protease recognition sites showed comparable expression and purification characteristics as the control Tandem-IgG (FIG. 4A-B). However, expression levels were lower compared to transient transfection and expression in HEK293-FS cells.

TABLE 3

Expression and purification results Tandem-IgG constructs with protease-cleavable linkers from EXPICHO ™ cultures.

| SEQ ID NO | Construct Name | Monomeric Fraction after Protein A [%] | Yield after prep. SEC [mg/L] |
|---|---|---|---|
| 15, 13 | sLC-Tandem-(anti-IL4xanti-IL13)-PCL1-hulgG1 | 80.1 | 1.4 |
| 16, 13 | sLC-Tandem-(anti-IL4xanti-IL13)-ΔPCL1-hulgG1 | 90.3 | 3.4 |
| 19, 13 | sLC-Tandem-(anti-IL4xanti-IL13)-PCL2-hulgG1 | 95.4 | 4.1 |

SDS-PAGE analysis under reducing conditions of in vivo processing of the Tandem-IgG revealed, that the sLCs containing the linker sequences with the modified protease recognition site HRRRKRSVDE (PCS2; SEQ ID NO: 43) showed two separate light chains (FIG. 4C). Constructs containing the minimal protease recognition sequence (PCS1; SEQ ID NO: 49) or the deleted recognition sequence (deltaPCS/PCL) were not processed in vivo by endogenously expressed proteases in EXPICHO™ cells. Thus, expression of protease-cleavable sLC Tandem-IgGs in EXPICHO™ cells confirmed the results from HEK293-FS cultures.

LC-MS analysis confirmed SDS-PAGE results of fully processed sLC-PCL2 Tandem-IgG in EXPICHO™ cells with further processing profile of C-terminal charged amino acids by carboxy-terminal proteases (RRKR-loss).

TABLE 4

LC-MS results of EXPICHO ™ expressed Tandem-IgG under deglycosylated reducing conditions.

| SEQ ID NO | Construct Name | Expected (Da)* | Measured (Da) | Difference (Da) | Comment | Pairing | Processing |
|---|---|---|---|---|---|---|---|
| 15, 13 | sLC-Tandem-(anti-IL4xanti-IL13)-PCL1-hulgG1 | 49185.11 | 49179.68 | −5.43 | correct | SLC | no |
| | | 74621.92 | 74620.47 | −1.45 | correct | HC | |
| 16, 13 | sLC-Tandem-(anti-IL4xanti-IL13)-ΔPCL1-hulgG1 | 49128.91 | 49123.63 | −5.28 | correct | SLC | no |
| | | 74621.92 | 74620.93 | −0.99 | correct | HC | |
| 19, 13 | sLC-Tandem-(anti-IL4xanti-IL13)-PCL2-hulgG1 | 24176.46 | 24174.19 | −2.27 | correct | LC1 | yes |
| | | 24207.83 | 24212.20 | 4.37 | correct | LC2 | |
| | | 24207.83 | 24049.16 | −158.67 | correct but R-loss | LC2 | |
| | | 24207.83 | 23764.18 | −443.65 | correct but RKR-loss | LC2 | |
| | | 24207.83 | 23608.55 | −599.28 | correct but RRKR-loss | LC2 | |
| | | 24207.83 | 23452.18 | −755.65 | correct but RRRKR-loss | LC2 | |
| | | 74621.92 | 74622.13 | 0.25 | correct | HC | |

Figure 5:
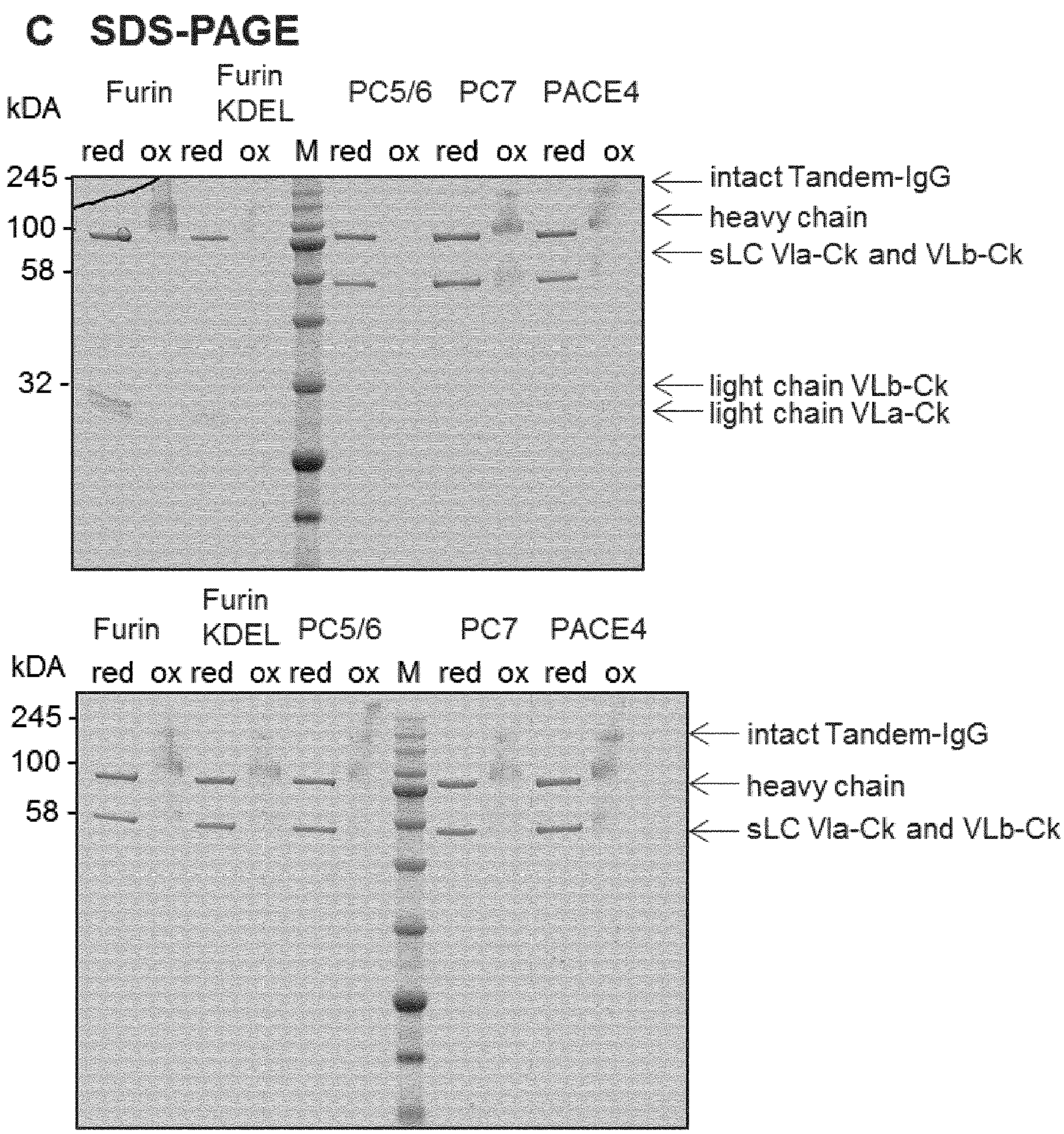
FIG. 5: Analysis of sLC Tandem-IgG co-expressed with proteases in HEK293-FS cells. Panel (A) shows the purity of the Tandem-IgG products (sLC-PCL1-Tandem-IgG, sLC deltaPCL Tandem-IgG) after affinity and preparative SEC using analytical size exclusion chromatography. Panel (B) shows the homogeneity of the antibody products using analytical hydrophobic-interaction chromatography. Panel (C) shows the reduced (one heavy chain and two light chains/one single LC, respectively) and oxidized form (intact Tandem-IgG) of the antibody using 4-12% Bis/TRIS™ (tris(hydroxymethyl)aminomethane buffer) MOPS sodium dodecyl sulfate polyacrylamide gel electrophoresis (SDS-PAGE). Panel (D) shows LC-MS analysis after deglycosylation and under reducing conditions of sLC Tandem-IgG-PCL1 after co-expression with furin and furin-KDEL (SEQ ID NO: 38).
Figure 7:
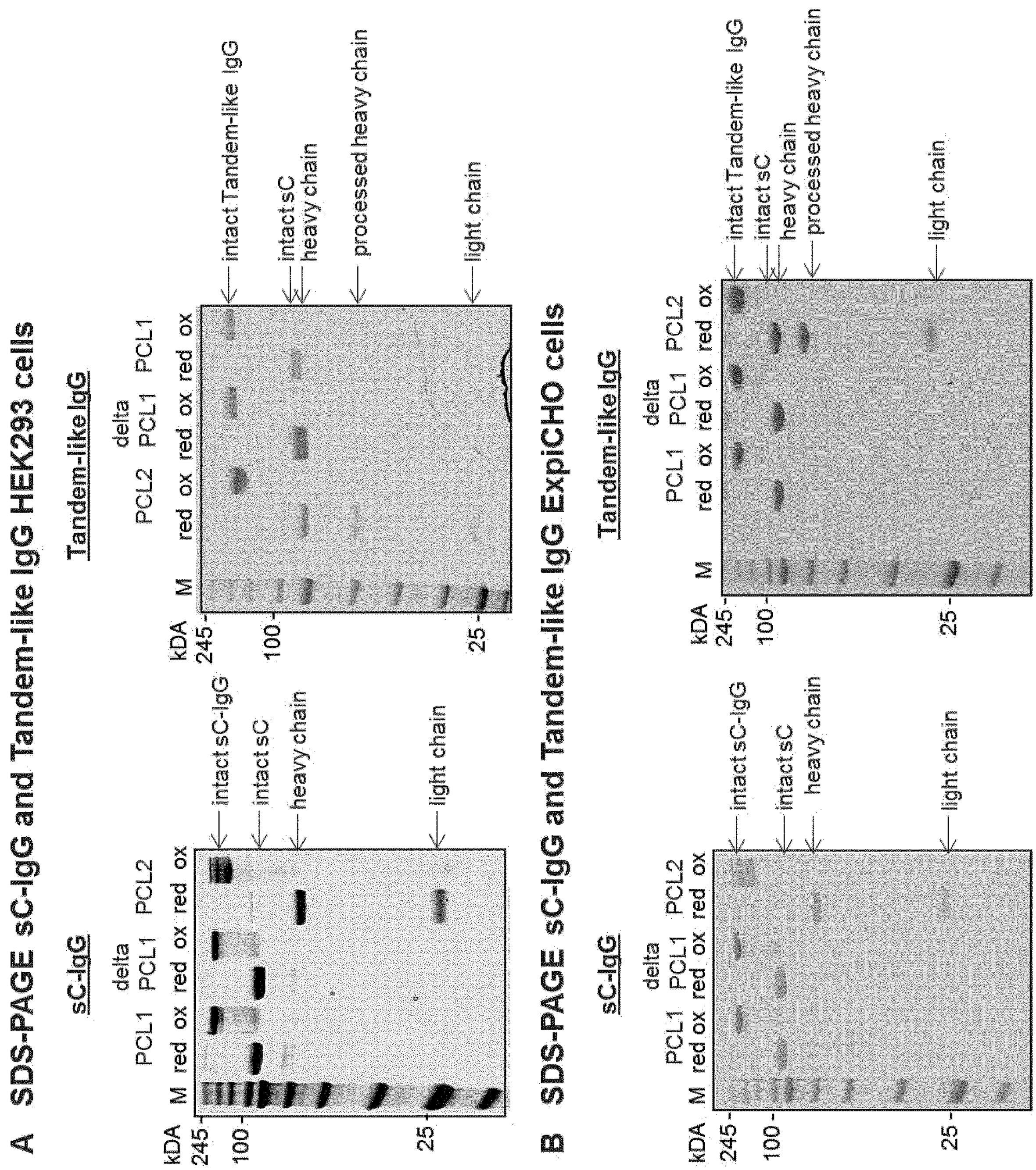
FIG. 7: Analysis of sC-IgG and Tandem-like IgGs expressed in HEK293-FS and ExpiCHO™ cells with SDS-PAGE. Panel (A) shows the reduced (one heavy chain and one light chain/one sC (left), one heavy chain and un-/processed sC (right)) and oxidized form (intact Tandem-IgG) of the two antibody formats expressed in HEK293-FS cells and panel (B) corresponding constructs expressed in ExpiCHO™ cells using 4-12% Bis/TRIS™ (tris(hydroxymethyl)aminomethane buffer) MOPS sodium dodecyl sulfate polyacrylamide gel electrophoresis (SDS-PAGE) after Protein A and SEC purification.

Example 4: Co-Transfection of Proteases and Protease-Cleavable Constructs in HEK293-FS Cells Tandem-IgG constructs with sLC containing PCS1 and deltaPCS recognition sites in the linker sequence of the sLC were co-transfected with proteases of the PCSK family in HEK293-FS cells (Table 5) to induce in vivo processing by overexpression of the proteases. The sLC Tandem-IgG constructs showed comparable expression and purification characteristics as the single transfected antibodies (FIGS. 5A and B). Reduced expression yields were due to a lower plasmid amount in the co-transfection (1:1 molar ratio with plasmids encoding individual proteases). Analysis of in vivo processing in SDS-PAGE and LC-MS confirmed processing of sLC Tandem-IgGs containing PCS1 recognition sites with recombinantly expressed human Furin and human Furin with a KDEL (SEQ ID NO: 38)-retention sequence (FIGS. 5C and D). In contrast, overexpression of other protease family members did not lead to sLC Tandem-IgG processing. Comparable results were obtained for sC-IgG and Tandem-like IgG constructs (FIGS. 7A and B).

TABLE 5

Expression and purification results Tandem-IgG constructs with protease-cleavable linkers from HEK293-FS cultures after co-expression with proteases of the PCSK family.

| SEQ ID NO | Construct Name | Yield after prep. SEC [mg/L] |
|---|---|---|
| 17, 13 with 37 | sLC-Tandem-(anti-IL4xanti-IL13)-His8-PCL1-huIgG1 | 12.5 |
| 17, 13 with 38 | sLC-Tandem-(anti-IL4xanti-IL13)-His8-PCL1-huIgG1 | 12.5 |
| 17, 13 with 39 | sLC-Tandem-(anti-IL4xanti-IL13)-His8-PCL1-huIgG1 | 7.8 |
| 17, 13 with 40 | sLC-Tandem-(anti-IL4xanti-IL13)-His8-PCL1-huIgG1 | 3.8 |
| 17, 13 with 41 | sLC-Tandem-(anti-IL4xanti-IL13)-His8-PCL1-huIgG1 | 9.0 |
| 18, 13 with 37 | sLC-Tandem-(anti-IL4xanti-IL13)-His8-ΔPCL1-huIgG1 | 5.8 |
| 18, 13 with 38 | sLC-Tandem-(anti-IL4xanti-IL13)-His8-ΔPCL1-huIgG1 | 8.8 |
| 18, 13 with 39 | sLC-Tandem-(anti-IL4xanti-IL13)-His8-ΔPCL1-huIgG1 | 5.3 |
| 18, 13 with 40 | sLC-Tandem-(anti-IL4xanti-IL13)-His8-ΔPCL1-huIgG1 | 3.8 |
| 18, 13 with 41 | sLC-Tandem-(anti-IL4xanti-IL13)-His8-ΔPCL1-huIgG1 | 7.5 |

Figure 6:
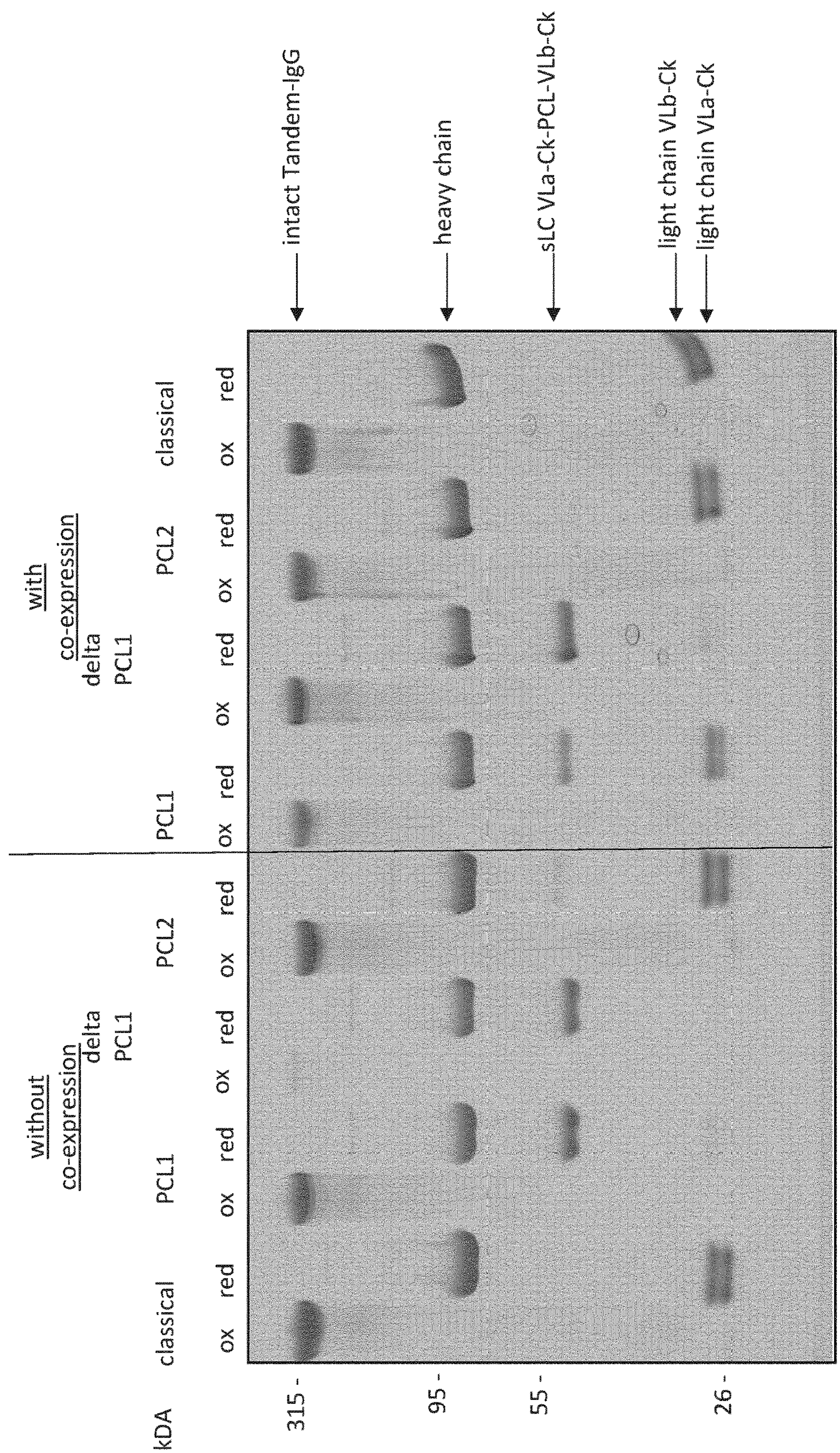
FIG. 6: Analysis of sLC Tandem-IgGs with and without co-expression of protease in stable CHO 9E4 cell pools. The oxidized (intact Tandem-IgG) and reduced forms (one heavy chain and two light chains/one single LC, respectively) of purified antibodies expressed in stable cell pools with (left panel) and without (right panel) protease co-expression are shown using 4-12% Bis/TRIS™ (tris(hydroxymethyl)aminomethane buffer) MOPS sodium dodecyl sulfate polyacrylamide gel electrophoresis (SDS-PAGE).

For generation of stable CHO cell pools, transposon-based plasmids encoding Tandem-IgG constructs with sLC containing PCS1, PCS2 and deltaPCS recognition sites in the linker sequence of the sLC, as well as the Tandem-IgG control (2 LC plasmids) were used for electroporation of CHO 9E4 cells with and without protease co-expression. The sLC Tandem-IgG constructs showed comparable expression and purification characteristics as the Tandem-IgG control. Analysis of in vivo processing in SDS-PAGE confirmed processing of sLC Tandem-IgGs containing PCS2 recognition sites in the samples expressed without protease co-expression and processed sLC for Tandem-IgGs with PCS1 and PCS2 recognition sites with recombinantly expressed human Furin (FIG. 6).

Example 5: Evaluation of Antigen Binding of Bispecific sLC Tandem-IgGs with Protease-Cleavable Linkers The binding of the different bispecific Tandem-IgG constructs expressed in HEK293-FS or EXPICHO™ cells as well as in vivo processed Tandem-IgG from the co-transfection with Furin variants was measured via surface plasmon resonance (SPR). The binding to the two human antigens IL4 and IL13 were compared to the binding characteristics of the individual monoclonal antibodies. The binding characteristics of the monoclonal anti-IL4 and anti-IL13 mAbs and bispecific Tandem-IgGs are shown in Table 6. Specific binding to IL4 was measured for all Tandem-IgGs and was comparable to the specific binding of anti-IL4 control antibody. In contrast, specific binding to IL13 was only detectable for in vivo processed Tandem-IgGs as well as the Tandem-IgG control comprising two LCs. Unprocessed sLC Tandem-IgGs showed no binding. Thus, processing of the linker sequence connecting the VLb (VL against IL13) at the inner position of the Tandem-IgG with the CK domain of the IL4 binding Fab at the outer position is required for a functional IL13 binding site. In vivo processing can thereby be mediated via endogenously expressed proteases or via co-transfected Furin variants.

TABLE 6

Binding kinetics by SPR: Comparison of anti-IL4 and anti-IL13 mAbs with bispecific Tandem-IgGs

| | | Antigen IL4 | | | Antigen IL13 | | |
|---|---|---|---|---|---|---|---|
| SEQ ID NO | Construct Name | KD [M] | ka [1/Ms] | kd [1/s] | KD [M] | ka [1/Ms] | kd [1/s] |
| | HEK293-FS expression | | | | | | |
| | anti-IL4 mAb ctrl | 8.87E−13 | 7.90E+08 | 7.01E−04 | — | — | — |
| | anti-IL13 mAb ctrl | — | | | 8.88E−11 | 5.08E+05 | 4.52E−05 |
| 11, 12, 13 | Tandem-(anti-IL4)xanti-IL13)-huIgG1 | 2.32E−12 | 6.39E+07 | 1.49E−04 | 1.14E−10 | 2.25E+05 | 2.56E−05 |
| 15, 13 | sLC-Tandem-(anti-IL4)xanti-IL13)-PCL1-huIgG1 | 9.01E−13 | 4.20E+09 | 3.79E−04 | — | — | — |
| 16, 13 | sLC-Tandem-(anti-IL4xanti-IL13)-ΔPCL1-huIgG1 | 2.29E−12 | 6.75E+07 | 1.55E−04 | — | — | — |
| 19, 13 | sLC-Tandem-(anti-IL4xanti-IL13)-PCL2-huIgG1 | 1.05E−12 | 1.79E+08 | 1.89E−04 | 1.81E−10 | 2.00E+05 | 3.62E−05 |
| 17, 13 with 37 | sLC-Tandem-(anti-IL4xanti-IL13)-His8-PCL1-huIgG1 | 1.53E−12 | 1.38E+08 | 2.11E−04 | 8.70E−11 | 1.79E+05 | 1.56E−05 |
| 17, 13 with 38 | sLC-Tandem-(anti-IL4xanti-IL13)-His8-PCL1-huIgG1 | 1.86E−12 | 1.61E+08 | 2.99E−04 | 1.49E−10 | 1.89E+05 | 2.82E−05 |
| | EXPICHO ™ expression | | | | | | |
| 15, 13 | sLC-Tandem-(anti-IL4xanti-IL13)-PCL1-huIgG1 | 1.42E−12 | 1.13E+08 | 1.61E−04 | — | — | — |
| 16, 13 | sLC-Tandem-(anti-IL4xanti-IL13)-ΔPCL1-huIgG1 | 2.75E−12 | 5.43E+07 | 1.49E−04 | — | — | — |
| 19, 13 | sLC-Tandem-(anti-IL4xanti-IL13)-PCL2-huIgG1 | 1.33E−12 | 1.87E+08 | 2.49E−04 | 6.33E−12 | 1.27E+05 | 8.05E−07 |

Example 6: Expression and Purification of sC-IgGs and Tandem-Like IgGs with Protease-Cleavable Linkers in HEK293-FS and EXPICHO™ Cells Table 6 and Table 7 show expression and purification data of sC-IgG and Tandem-like IgG constructs with protease-cleavable linker sequence from HEK293-FS and EXPICHO™ cultures after transient transfection, respectively.

After Protein A purification and preparative SEC, sC-IgGs showed high purity with 83-99% monomeric peak fractions. Protein yield dropped for sC-IgGs with decreasing length of the $(G_4S)_n$ (SEQ ID NO: 51) linker sequences.

In contrast to sC-IgGs, the Tandem-like IgG format showed only low protein purity (23-75% monomeric peak fraction) with high aggregation potential as seen in high molecular weight species in preparative SEC.

TABLE 7

Expression and purification results of sc-IgGs and Tandem-like IgG constructs with protease-cleavable linkers from HEK293-FS cultures.

| SEQ ID NO | Construct Name | Yield after Protein A [mg/L] | Monomeric Fraction after Protein A [%] |
|---|---|---|---|
| 1 | sc-anti-IL4-(G4S)10-PCL1-hulgG1 | 32.3 | 98.4 |
| 2 | sc-anti-IL4-(G4S)8-PCL1-hulgG1 | 13.8 | 99.1 |
| 3 | sc-anti-IL4-(G4S)6-PCL1-hulgG1 | 8.3 | 92.3 |
| 4 | sc-anti-IL4-(G4S)4-PCL1-hulgG1 | 9.4 | 93.2 |
| 5 | sc-anti-IL4-(G4S)2-PCL1-hulgG1 | 1.6 | 88.5 |
| 6 | sc-anti-IL4-ΔPCL1-hulgG1 | 94.3 | 83.8 |
| 7 | sc-anti-IL4-His8-PCL1-hulgG1 | 8.1 | 87.1 |
| 8 | sc-anti-IL4-His8-ΔPCL1-hulgG1 | 43.9 | 90.4 |
| 9 | sc-anti-IL4-His8-PCL2-hulgG1 | 61.8 | 98.7 |
| 10 | sc-anti-IL4-His8-PCL3-hulgG1 | 22.8 | 98.2 |
| 25, 26 | scTandem-(anti-IL4xanti-IL13)-PCL1-hulgG1-OL-KIH | 36.7 | 39.6 |
| 27, 26 | scTandem-(anti-IL4xanti-IL13)-singlePCL1-hulgG1-OL-KIH | 19.2 | 33.9 |
| 28, 26 | scTandem-(anti-IL4xanti-IL13)-ΔPCL1-hulgG1-OL-KIH | 15.6 | 23.6 |
| 29, 26 | scTandem-(anti-IL4xanti-IL13)-His8-PCL1-hulgG1-OL-KIH | 5.9 | 73.3 |
| 30, 26 | scTandem-(anti-IL4xanti-IL13)-His8-ΔPCL1-hulgG1-OL-KIH | 6.3 | 69.3 |
| 31, 26 | scTandem-(anti-IL4xanti-IL13)-PCL2-hulgG1-OL-KIH | 17.6 | 54 |
| 32, 26 | scTandem-(anti-IL4xanti-IL13)-PCL3-hulgG1-OL-KIH | 13.0 | 61.9 |
| 33, 34 | scTandem-(anti-IL4xanti-IL13)-rigidL-PCL1-hulgG1-OL-KIH | 20.2 | 29 |
| 35, 26 | scTandem-(anti-IL4xanti-IL13)-rigidL2-PCL1-hulgG1-OL-KIH | 25.0 | 60 |
| 36, 26 | scTandem-(anti-IL4xanti-IL13)-charL-PCL1-hulgG1-OL-KIH | 6.3 | 75.1 |

TABLE 8

Expression and purification results of sc-IgGs and Tandem-like IgG constructs with protease-cleavable linkers from EXPICHO ™ cultures.

| SEQ ID NO | Construct name | Monomeric Fraction after Protein A [%] | Yield after prep. SEC [mg/L] |
|---|---|---|---|
| 3 | sc-anti-IL4-(G4S)6-PCL1-hulgG1 | 94.6 | 1.1 |
| 6 | sc-anti-IL4-ΔPCL1-hulgG1 | 96.3 | 1.6 |
| 9 | sc-anti-IL4-His8-PCL2-hulgG1 | 100.0 | 3.7 |
| 25, 26 | scTandem-(anti-IL4xanti-IL13)-PCL1-hulgG1-OL-KIH | | 1.2 |
| 28, 26 | scTandem-(anti-IL4xanti-IL13)-ΔPCL1-hulgG1-OL-KIH | | 2.1 |
| 31, 26 | scTandem-(anti-IL4xanti-IL13)-PCL2-hulgG1-OL-KIH | | 3.5 |

In both cell lines, only sC-IgGs and Tandem-like IgGs with PCS2 recognition sites were cleaved into the respective chain fragments by endogenous proteases during protein expression (FIGS. 7A and B) as shown for the sLC Tandem-IgG format.

Figure 8:
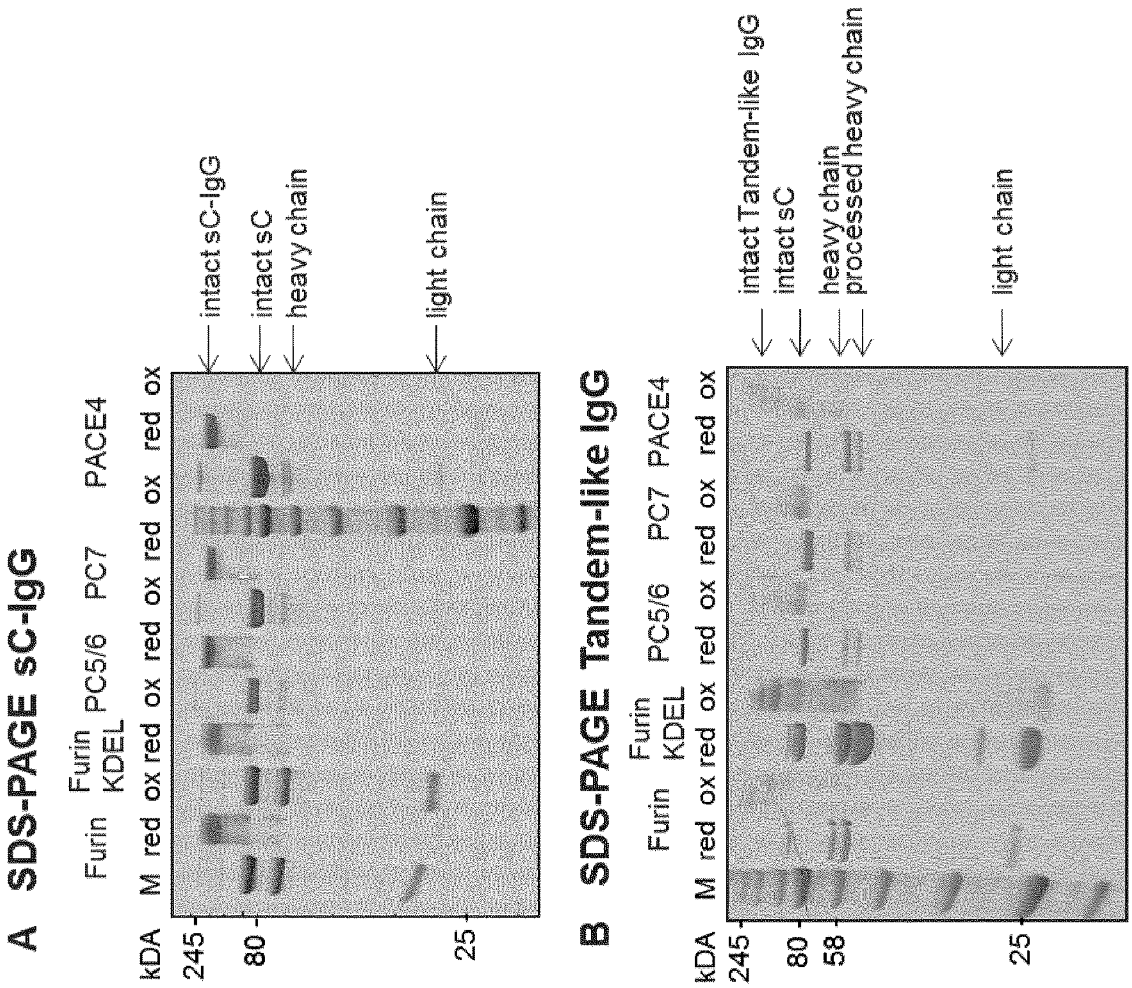
FIG. 8: Analysis of sC-IgG and Tandem-like IgGs co-expressed with proteases in HEK293-FS cells. Panel (A) shows the reduced (one heavy chain and one light chain/one sC) and oxidized form of sC-IgG and panel (B) the reduced (one heavy chain and un-/processed sLC) and oxidized form (intact Tandem-like IgG) of the Tandem-like IgG after co-expression with PCSK family members in HEK293-FS cells using 4-12% Bis/TRIS™ (tris(hydroxymethyl)aminomethane buffer) MOPS sodium dodecyl sulfate polyacrylamide gel electrophoresis (SDS-PAGE) after Protein A and SEC purification. Furin-KDEL (SEQ ID NO: 38) is depicted in each of panel (A) and (B).

Example 7: Co-Transfection of Proteases and Protease-Cleavable Constructs in HEK293-FS Cells Single chain Ig and Tandem-like IgG constructs with sLC containing PCS1 and deltaPCS recognition sites in the linker sequence were co-transfected with proteases of the PCSK family in HEK293-FS cells to induce in vivo processing by overexpression of the proteases. Analysis of in vivo processing in SDS-PAGE confirmed induced processing of sC-IgG and Tandem-like IgG containing PCS1 recognition sites with recombinantly expressed human Furin and human Furin with a KDEL (SEQ ID NO: 38)-retention sequence (FIGS. 8A and B). Furthermore, overexpression of PACE4 lead to partially processed constructs.

Figure 2:
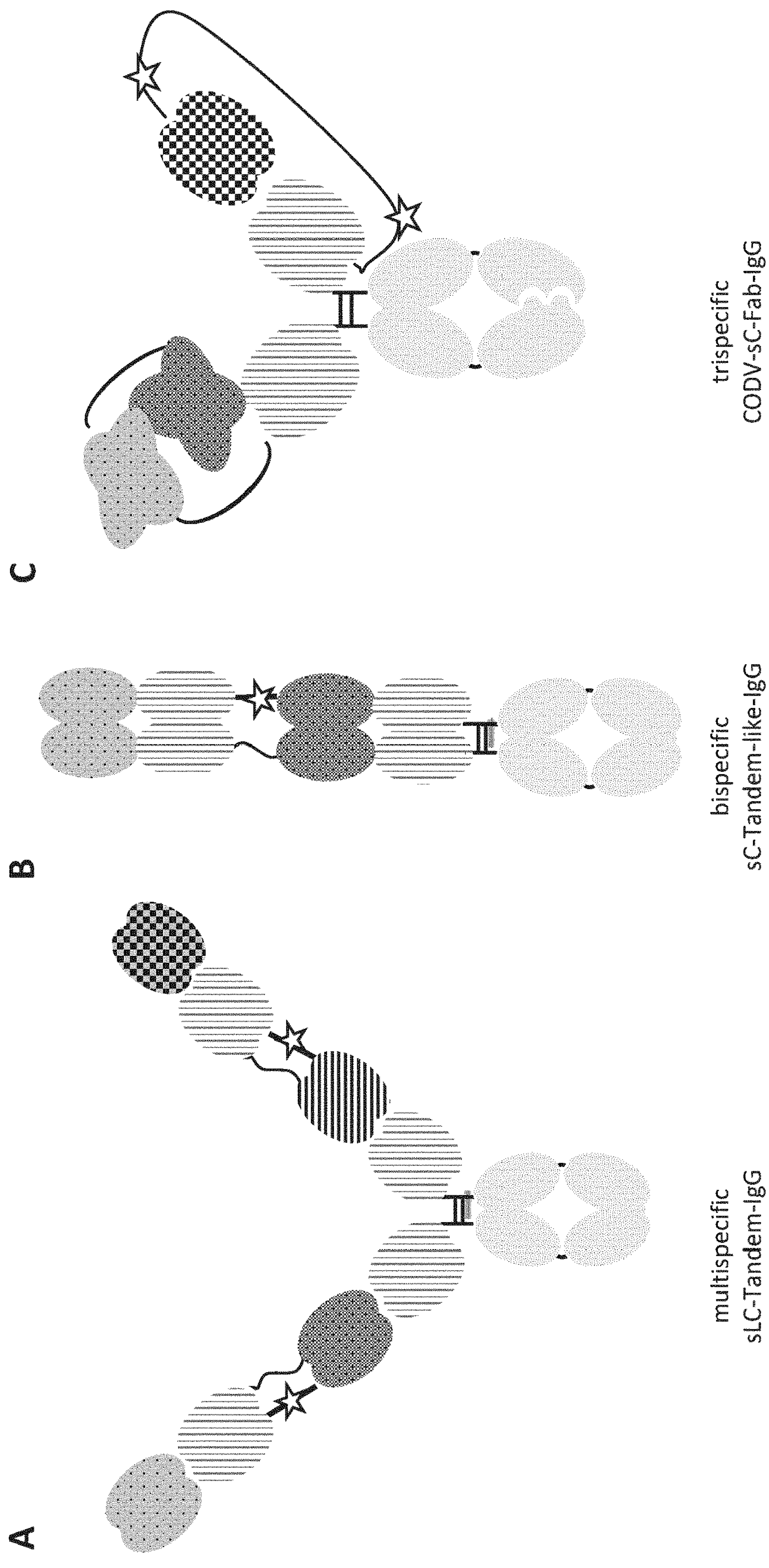
FIG. 2: Protease-cleavable homodimeric antibody formats. (A) Single light chain (sLC) multispecific Tandem-IgG. The VH-CH1 (VHb and VHd) domains of the heavy chains are elongated at the N-termini with a second VH-CH1 domain (VHa and VHc), e.g., via a $(G_4S)_3$ linker (SEQ ID NO: 55). The VL-CL domains (VLb and VLd) of the light chains are elongated at the N-termini with a second VL-CL domain (VLa and VLc) using a PCL sequence. (B) Single chain (sC) monovalent, bispecific Tandem-like-IgG. The VH-CH1 domain (VHb) of the first heavy chain is elongated at its N-terminus with a second VH-CH1 domain (VHa), e.g., via a $(G_4S)_3$ linker (SEQ ID NO: 55); the hinge region of the second heavy chain is elongated with two VL-CL-domains, wherein VLb and Fv a are connected via a PCL sequence. (C) Single chain (sC) Fab containing trispecific CODV-IgG. One arm of the antibody comprises a CODV-LC (VLb-linker-VLa-linker-CL) associated with a CODV-HC (VHa-linker-VHb-linker-CH1-hinge-CH2-CH3) the other arm comprises a single chain (sC) Fab arm, where the VHc domain is elongated at its N-terminus with a VLc-CL domain using a PCL sequence. (D) Single chain (sC) bispecific IgG. The VHa and VHb domains of each HC are elongated at the N-termini with a VLa-CL and VLb-CL domain, respectively, using a PCL sequence. The heavy chains of all heterodimeric molecules preferably comprise one or more knops-into-holes (KIH) mutations forming an asymmetric antibody.
Figure 2:
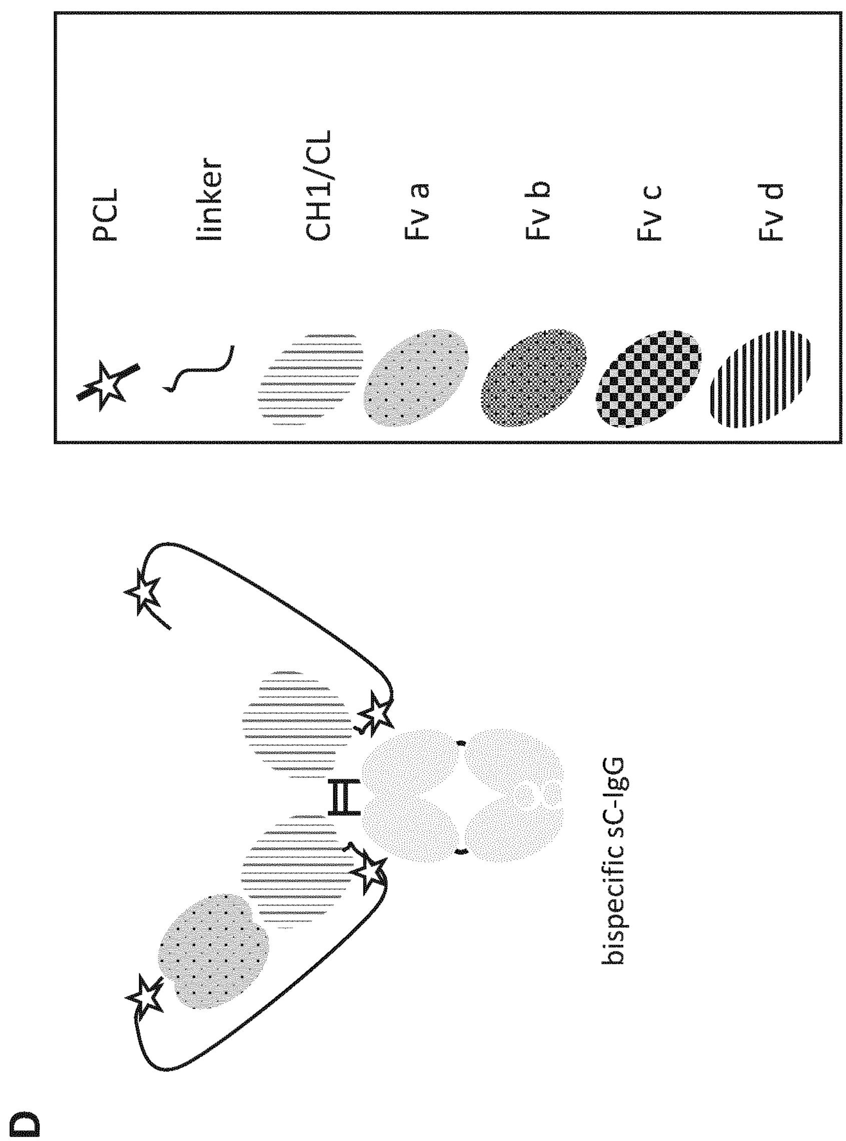

Example 8: Expression and In Vivo Processing of Protease-Cleavable CODV-scFab-IgG in HEK293-FS Cells Trispecific CODV-scFab-IgG (FIG. 2C; Table 8) constructs were expressed in HEK293-FS cells after transient transfection of three plasmids encoding the CODV HC, CODV LC and a single chain (sC) wherein the VLc-CK and VHc-CH1-CH2-CH3 chains were connected via different protease-cleavable linker sequences. As control, a trispecific CODV-Fab-IgG with Fab-LC and HC expressed as two separate chains (classical CODV-Fab-IgG control) was used. The single chain Fab CODVs showed comparable expression and purification characteristics as the control, with reduction of aggregate peaks in SEC (Table 9, FIG. 9A).

TABLE 9

Expression and purification results of trispecific CODV-Fab-IgG constructs with protease-cleavable linkers from HEK293-FS cultures.

| SEQ ID NO | Construct Name | Monomeric Fraction after Protein A [%] | Yield after prep. SEC [mg/L] |
|---|---|---|---|
| 56, 57, 58, 59 | TRI-(CODV-anti-PD-1 x anti-OX40) x anti-GITR-hulgG1-LALA-KIH-RF | 56.3 | 40.3 |
| 56, 57, 60 | TRI-(CODV-anti-PD-1 x anti-OX40) x sc-PCL2-anti-GITR-hulgG1-LALA-KIH-RF | 73.6 | 24.5 |
| 56, 57, | TRI-(CODV) x sc-PCL2a-anti-GITR-hulgG1-LALA-KIH- | 75.8 | 19.0 |

TABLE 9-continued

| Expression and purification results of trispecific CODV-Fab-IgG constructs with protease-cleavable linkers from HEK293-FS cultures. | | | |
|---|---|---|---|
| SEQ ID NO | Construct Name | Monomeric Fraction after Protein A [%] | Yield after prep. SEC [mg/L] |
| 61 | RF | | |
| 62, 63, 64 | TRI-(CODV-anti-GITR x anti-PD-1) x sc-PCL2-anti-OX40-hulgG1-LALA-KIH-RF | 89.4 | 30.7 |
| 62, 63, 65 | TRI-(CODV-anti-GITR x anti-PD-1)x sc-PCL2a-anti-OX40-hulgG1-LALA-KIH-RF | 92.3 | 28.0 |
| 66, 67, 68 | TRI-(CODV-anti-PD-1 x anti-GITR) x sc-PCL2-anti-OX40-hulgG1-LALA-KIH-RF | 88.1 | 33.7 |
| 66, 67, 69 | TRI-(CODV-anti-PD-1 x anti-GITR) x sc-hPCL2a-anti-OX40-hulgG1-LALA-KIH-RF | 93.7 | 28.2 |

Figure 9:
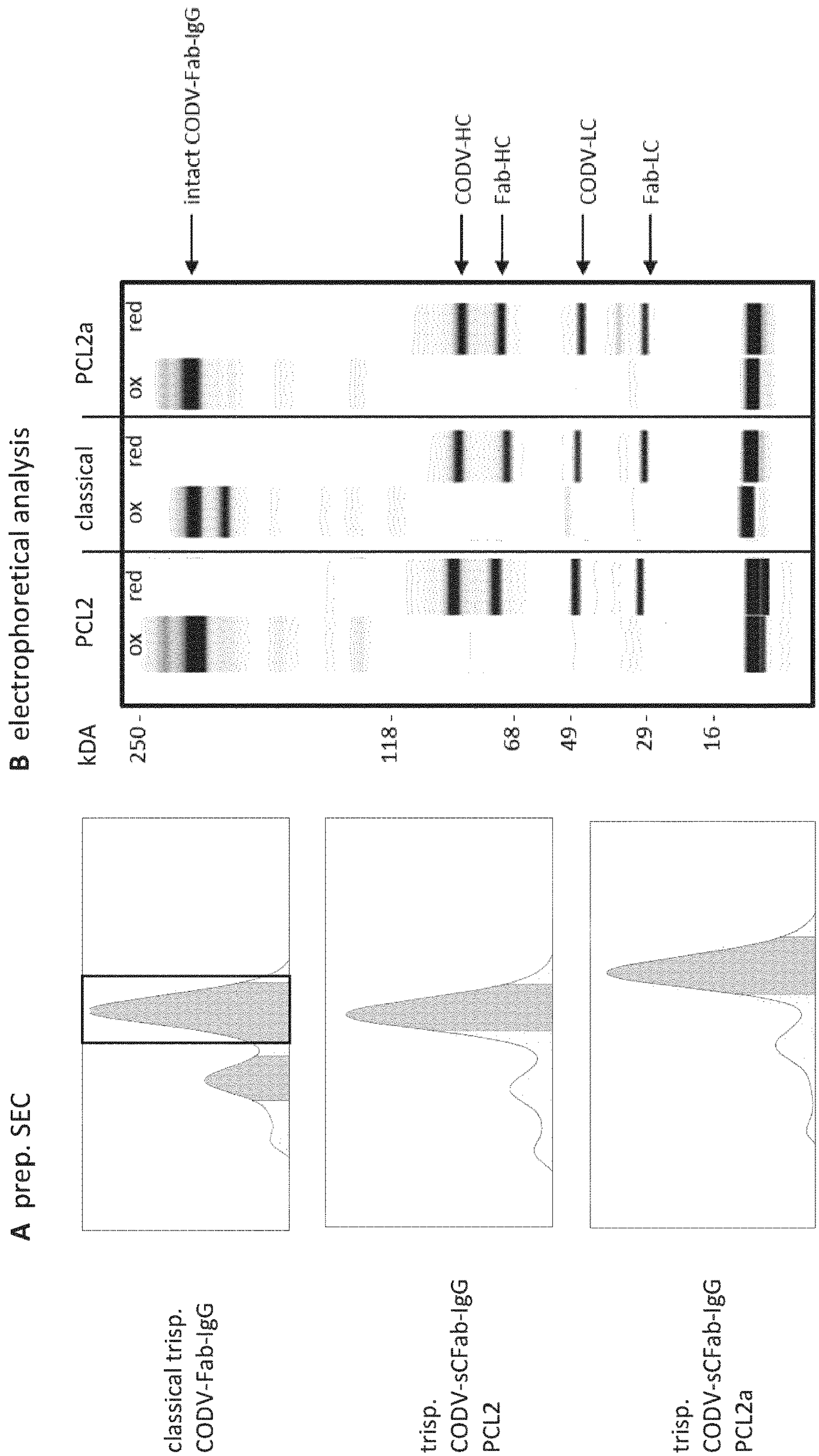
FIG. 9: Analysis of trispecific CODV-sCFab-IgG expressed in HEK293FS cells. Panel (A) shows the preparative SEC chromatograms and panel (B) shows the oxidized (intact trispecific CODV-Fab-IgG and reduced (CODV heavy and light chains and single/processed Fab heavy and light chain) after preparative SEC using LABCHIP™ electrophoresis device.

Electrophoretic analysis under reducing conditions showed that the single chains of the Fab arm containing either PCS2 (SEQ ID NO: 43) or PCS2a (SEQ ID NO: 44) sequences were processed after expression in HEK293-FS cells leading to Fab-LC and Fab-HC parts (FIG. 9B).

TABLE 10

| List of Sequences/Constructs. | | | |
|---|---|---|---|
| Name | SEQ ID NO | Amino acid sequence | Annotation/ Comments |
| sc-anti-IL4-(G4S)10-PCL1-hulgG1 | 1 | **DIQMTQSPASLSVSVGDTITLTCHASQNIDVWLSWFQQK**<br>**PGNIPKLLIYKASNLHTGVPSRFSGSGSGTGFTLTISSLQPED**<br>**IATYYCQQAHSYPFTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC*RRKR*GGGGSGGGGSGGGGSGGGGSGGGGSG<br>GGGSGGGGSGGGGSGGGGSGGGGS*RRKR*QVQLQQSGP<br>**ELVKPGASVKISCKASGYSFTSYWIHWIKQRPGQGLEWIG**<br>**MIDPSDGETRLNQRFQGRATLTVDESTSTAYMQLRSPTSE**<br>**DSAVYYCTRLKEYGNYDSFYFDVWGAGTLVTVSS**ASTKGP<br>SVFPLAPSSKSTSGGTAALGCLVKDYFPEPVTVSWNSGALTS<br>GVHTFPAVLQSSGLYSLSSVVTVPSSSLGTQTYICNVNHKPS<br>NTKVDKKVEPKSCDKTHTCPPCPAPELLGGPSVFLFPPKPKD<br>TLMISRTPEVTCVVVDVSHEDPEVKFNWYVDGVEVHNAKT<br>KPREEQYNSTYRVVSVLTVLHQDWLNGKEYKCKVSNKALP<br>APIEKTISKAKGQPREPQVYTLPPSRDELTKNQVSLTCLVKGF<br>YPSDIAVEWESNGQPENNYKTTPPVLDSDGSFFLYSKLTVD<br>KSRWQQGNVFSCSVMHEALHNHYTQKSLSLSPG | **anti-IL4-VL**-hulGKC-[*PCS1*]-<(G4S)10>-[*PCS1*]-**anti-IL4-VH**-hulGHG1 |
| sc-anti-IL4-(G4S)8-PCL1-hulgG1 | 2 | **DIQMTQSPASLSVSVGDTITLTCHASQNIDVWLSWFQQK**<br>**PGNIPKLLIYKASNLHTGVPSRFSGSGSGTGFTLTISSLQPED**<br>**IATYYCQQAHSYPFTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC*RRKR*GGGGGGGGSGGGGSGGGGSGGGGSG<br>GGGSGGGGSGGGGS*RRKR*QVQLQQSGPELVKPGASVKIS<br>**CKASGYSFTSYWIHWIKQRPGQGLEWIGMIDPSDGETRL**<br>**NQRFQGRATLTVDESTSTAYMQLRSPTSEDSAVYYCTRLK**<br>**EYGNYDSFYFDVWGAGTLVTVSS**ASTKGPSVFPLAPSSKST<br>SGGTAALGCLVKDYFPEPVTVSWNSGALTSGVHTFPAVLQS<br>SGLYSLSSVVTVPSSSLGTQTYICNVNHKPSNTKVDKKVEPK<br>SCDKTHTCPPCPAPELLGGPSVFLFPPKPKDTLMISRTPEVTC<br>VVVDVSHEDPEVKFNWYVDGVEVHNAKTKPREEQYNSTY<br>RVVSVLTVLHQDWLNGKEYKCKVSNKALPAPIEKTISKAKG<br>QPREPQVYTLPPSRDELTKNQVSLTCLVKGFYPSDIAVEWES<br>NGQPENNYKTTPPVLDSDGSFFLYSKLTVDKSRWQQGNVF<br>SCSVMHEALHNHYTQKSLSLSPG | **anti-IL4-VL**-hulGKC-[*PCS1*]-<(G4S)8>-[*PCS1*]-**anti-IL4-VH**-hulGHG1 |
| sc-anti-IL4-(G4S)6-PCL1-hulgG1 | 3 | **DIQMTQSPASLSVSVGDTITLTCHASQNIDVWLSWFQQK**<br>**PGNIPKLLIYKASNLHTGVPSRFSGSGSGTGFTLTISSLQPED**<br>**IATYYCQQAHSYPFTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC*RRKR*GGGGSGGGGSGGGGSGGGGSGGGGSG<br>GGGS*RRKR*QVQLQQSGPELVKPGASVKISCKASGYSFTSY<br>**WIHWIKQRPGQGLEWIGMIDPSDGETRLNQRFQGRATL** | **anti-IL4-VL**-hulGKC-[*PCS1*]-<(G4S)6>-[*PCS1*]-**anti-IL4-VH**-hulGHG1 |

TABLE 10-continued

List of Sequences/Constructs.

| Name | SEQ ID NO | Amino acid sequence | Annotation/ Comments |
|---|---|---|---|
| | | TVDESTSTAYMQLRSPTSEDSAVYYCTRLKEYGNYDSFYFD<br>VWGAGTLVTVSSASTKGPSVFPLAPSSKSTSGGTAALGCLV<br>KDYFPEPVTVSWNSGALTSGVHTFPAVLQSSGLYSLSSVVT<br>VPSSSLGTQTYICNVNHKPSNTKVDKKVEPKSCDKTHTCPPC<br>PAPELLGGPSVFLFPPKPKDTLMISRTPEVTCVVVDVSHEDP<br>EVKFNWYVDGVEVHNAKTKPREEQYNSTYRVVSVLTVLHQ<br>DWLNGKEYKCKVSNKALPAPIEKTISKAKGQPREPQVYTLPP<br>SRDELTKNQVSLTCLVKGFYPSDIAVEWESNGQPENNYKTT<br>PPVLDSDGSFFLYSKLTVDKSRWQQGNVFSCSVMHEALHN<br>HYTQKSLSLSPG | |
| sc-anti-IL4-(G4S)4-PCL1-hulgG1 | 4 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRRKRGGGGSGGGGSGGGGSGGGGSRRKRQV<br>QLQQSGPELVKPGASVKISCKASGYSFTSYWIHWIKQRPG<br>QGLEWIGMIDPSDGETRLNQRFQGRATLTVDESTSTAYM<br>QLRSPTSEDSAVYYCTRLKEYGNYDSFYFDVWGAGTLVTV<br>SSASTKGPSVFPLAPSSKSTSGGTAALGCLVKDYFPEPVTVS<br>WNSGALTSGVHTFPAVLQSSGLYSLSSVVTVPSSSLGTQTYI<br>CNVNHKPSNTKVDKKVEPKSCDKTHTCPPCPAPELLGGPSV<br>FLFPPKPKDTLMISRTPEVTCVVVDVSHEDPEVKFNWYVDG<br>VEVHNAKTKPREEQYNSTYRVVSVLTVLHQDWLNGKEYKC<br>KVSNKALPAPIEKTISKAKGQPREPQVYTLPPSRDELTKNQV<br>SLTCLVKGFYPSDIAVEWESNGQPENNYKTTPPVLDSDGSF<br>FLYSKLTVDKSRWQQGNVFSCSVMHEALHNHYTQKSLSLS<br>PG | anti-IL4-VL-hulGKC-[PCS1]-<(G4S)4>-[PCS1]-anti-IL4-VH-hulGHG1 |
| sc-anti-IL4-(G4S)2-PCL1-hulgG1 | 5 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRRKRGGGGSGGGGSRRKRQVQLQQSGPELVK<br>PGASVKISCKASGYSFTSYWIHWIKQRPGQGLEWIGMIDP<br>SDGETRLNQRFQGRATLTVDESTSTAYMQLRSPTSEDSAV<br>YYCTRLKEYGNYDSFYFDVWGAGTLVTVSSASTKGPSVFPL<br>APSSKSTSGGTAALGCLVKDYFPEPVTVSWNSGALTSGVHT<br>FPAVLQSSGLYSLSSVVTVPSSSLGTQTYICNVNHKPSNTKV<br>DKKVEPKSCDKTHTCPPCPAPELLGGPSVFLFPPKPKDTLMI<br>SRTPEVTCVVVDVSHEDPEVKFNWYVDGVEVHNAKTKPRE<br>EQYNSTYRVVSVLTVLHQDWLNGKEYKCKVSNKALPAPIEK<br>TISKAKGQPREPQVYTLPPSRDELTKNQVSLTCLVKGFYPSDI<br>AVEWESNGQPENNYKTTPPVLDSDGSFFLYSKLTVDKSRW<br>QQGNVFSCSVMHEALHNHYTQKSLSLSPG | anti-IL4-VL-hulGKC-[PCS1]-<(G4S)2>-[PCS1]-anti-IL4-VH-hulGHG1 |
| sc-anti-IL4-ΔPCL1-hulgG1 | 6 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRQQRGGGGGGGSGGGGGGGGSGGGGS<br>GGGGSGGGGSGGGGSGGGGSGGGGSRQQRQVQLQQSG<br>PELVKPGASVKISCKASGYSFTSYWIHWIKQRPGQGLEWI<br>GMIDPSDGETRLNQRFQGRATLTVDESTSTAYMQLRSPTS<br>EDSAVYYCTRLKEYGNYDSFYFDVWGAGTLVTVSSASTKG<br>PSVFPLAPSSKSTSGGTAALGCLVKDYFPEPVTVSWNSGALT<br>SGVHTFPAVLQSSGLYSLSSVVTVPSSSLGTQTYICNVNHKP<br>SNTKVDKKVEPKSCDKTHTCPPCPAPELLGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKALP<br>APIEKTISKAKGQPREPQVYTLPPSRDELTKNQVSLTCLVKGF<br>YPSDIAVEWESNGQPENNYKTTPPVLDSDGSFFLYSKLTVD<br>KSRWQQGNVFSCSVMHEALHNHYTQKSLSLSPG | anti-IL4-VL-hulGKC-[deltaPCS]-<(G4S)10>-[deltaPCS]-anti-IL4-VH-hulGHG1 |
| sc-anti-IL4-His8-PCL1-hulgG1 | 7 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESV<br>TEQDSKDSTYSLSSTLTLSKADYEKHKVYACEVTHQGLSSP<br>VTKSFNRGECRRKRGGGGSGGGGSGGGGSGGGGSHHHH<br>HHHHGGGGSGGGGSGGGGSGGGGSRRKRQVQLQQSGP | anti-IL4-VL-hulGKC-[PCS1]-<(G4S)4>-His(8)-<(G4S)4>-[PCS1]-anti-IL4-VH-hulGHG1 |

TABLE 10-continued

List of Sequences/Constructs.

| Name | SEQ ID NO | Amino acid sequence | Annotation/ Comments |
|---|---|---|---|
| | | ELVKPGASVKISCKASGYSFTSYWIHWIKQRPGQGLEWIG<br>MIDPSDGETRLNQRFQGRATLTVDESTSTAYMQLRSPTSE<br>DSAVYYCTRLKEYGNYDSFYFDVWGAGTLVTVSSASTKGP<br>SVFPLAPSSKSTSGGTAALGCLVKDYFPEPVTVSWNSGALTS<br>GVHTFPAVLQSSGLYSLSSVVTVPSSSLGTQTYICNVNHKPS<br>NTKVDKKVEPKSCDKTHTCPPCPAPELLGGPSVFLFPPKPKD<br>TLMISRTPEVTCVVVDVSHEDPEVKFNWYVDGVEVHNAKT<br>KPREEQYNSTYRVVSVLTVLHQDWLNGKEYKCKVSNKALP<br>APIEKTISKAKGQPREPQVYTLPPSRDELTKNQVSLTCLVKGF<br>YPSDIAVEWESNGQPENNYKTTPPVLDSDGSFFLYSKLTVD<br>KSRWQQGNVFSCSVMHEALHNHYTQKSLSLSPG | |
| sc-anti-IL4-His8-ΔPCL1-hulgG1 | 8 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRQQRGGGGSGGGGSGGGGSGGGGSHHHHH<br>HHHGGGGSGGGGSGGGGSGGGGSRQQRQVQLQQSGPE<br>LVKPGASVKISCKASGYSFTSYWIHWIKQRPGQGLEWIG<br>MIDPSDGETRLNQRFQGRATLTVDESTSTAYMQLRSPTSE<br>DSAVYYCTRLKEYGNYDSFYFDVWGAGTLVTVSSASTKGP<br>SVFPLAPSSKSTSGGTAALGCLVKDYFPEPVTVSWNSGALTS<br>GVHTFPAVLQSSGLYSLSSVVTVPSSSLGTQTYICNVNHKPS<br>NTKVDKKVEPKSCDKTHTCPPCPAPELLGGPSVFLFPPKPKD<br>TLMISRTPEVTCVVVDVSHEDPEVKFNWYVDGVEVHNAKT<br>KPREEQYNSTYRVVSVLTVLHQDWLNGKEYKCKVSNKALP<br>APIEKTISKAKGQPREPQVYTLPPSRDELTKNQVSLTCLVKGF<br>YPSDIAVEWESNGQPENNYKTTPPVLDSDGSFFLYSKLTVD<br>KSRWQQGNVFSCSVMHEALHNHYTQKSLSLSPG | anti-IL4-VL-hulGKC-[deltaPCS]-<(G4S)4>-His(8)-<(G4S)4>-[deltaPCS]-anti-IL4-VH-hulGHG1 |
| sc-anti-IL4-His8-PCL2-hulgG1 | 9 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECHRRRKRSVDEGGGGSGGGGSGGGGSHHHHH<br>HHHGGGGSGGGGSGGGGSHRRRKRSVDEQVQLQQSGPE<br>LVKPGASVKISCKASGYSFTSYWIHWIKQRPGQGLEWIG<br>MIDPSDGETRLNQRFQGRATLTVDESTSTAYMQLRSPTSE<br>DSAVYYCTRLKEYGNYDSFYFDVWGAGTLVTVSSASTKGP<br>SVFPLAPSSKSTSGGTAALGCLVKDYFPEPVTVSWNSGALTS<br>GVHTFPAVLQSSGLYSLSSVVTVPSSSLGTQTYICNVNHKPS<br>NTKVDKKVEPKSCDKTHTCPPCPAPELLGGPSVFLFPPKPKD<br>TLMISRTPEVTCVVVDVSHEDPEVKFNWYVDGVEVHNAKT<br>KPREEQYNSTYRVVSVLTVLHQDWLNGKEYKCKVSNKALP<br>APIEKTISKAKGQPREPQVYTLPPSRDELTKNQVSLTCLVKGF<br>YPSDIAVEWESNGQPENNYKTTPPVLDSDGSFFLYSKLTVD<br>KSRWQQGNVFSCSVMHEALHNHYTQKSLSLSPG | anti-IL4-VL-hulGKC-[PCS2]-<(G4S)4>-His(8)-<(G4S)4>-[PCS2]-anti-IL4-VH-hulGHG1 |
| sc-anti-IL4-His8-PCL3-hulgG1 | 10 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECPMKKRRAGVPGGGGSGGGGSGGGGSHHHHH<br>HHHGGGGSGGGGSGGGGSPMKKRRAGVPQVQLQQSGP<br>ELVKPGASVKISCKASGYSFTSYWIHWIKQRPGQGLEWIG<br>MIDPSDGETRLNQRFQGRATLTVDESTSTAYMQLRSPTSE<br>DSAVYYCTRLKEYGNYDSFYFDVWGAGTLVTVSSASTKGP<br>SVFPLAPSSKSTSGGTAALGCLVKDYFPEPVTVSWNSGALTS<br>GVHTFPAVLQSSGLYSLSSVVTVPSSSLGTQTYICNVNHKPS<br>NTKVDKKVEPKSCDKTHTCPPCPAPELLGGPSVFLFPPKPKD<br>TLMISRTPEVTCVVVDVSHEDPEVKFNWYVDGVEVHNAKT<br>KPREEQYNSTYRVVSVLTVLHQDWLNGKEYKCKVSNKALP<br>APIEKTISKAKGQPREPQVYTLPPSRDELTKNQVSLTCLVKGF<br>YPSDIAVEWESNGQPENNYKTTPPVLDSDGSFFLYSKLTVD<br>KSRWQQGNVFSCSVMHEALHNHYTQKSLSLSPG | anti-IL4-VL-hulGKC-[PCS3]-<(G4S)4>-His(8)-<(G4S)4>-[PCS3]-anti-IL4-VH-hulGHG1 |

TABLE 10-continued

List of Sequences/Constructs.

| Name | SEQ ID NO | Amino acid sequence | Annotation/ Comments |
| --- | --- | --- | --- |
| Tandem-(anti-IL4xanti-IL13)-hulgG1 | 11 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC | anti-IL4-VL-hulGKC |
| | 12 | DIVLTQSPASLAVSLGQRATISCRASESVDSYGQSYMHWY<br>QQKAGQPPKLLIYLASNLESGVPARFSGSGSRTDFTLTIDP<br>VQAEDAATYYCQQNAEDSRTFGGGTKLEIKRTVAAPSVFIF<br>PPSDEQLKSGTASVVCLLNNFYPREAKVQWKVDNALQSGN<br>SQESVTEQDSKDSTYSLSSTLTLSKADYEKHKVYACEVTHQG<br>LSSPVTKSFNRGEC | anti-IL13-IGKC |
| | 13 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPSRDELTKN<br>QVSLTCLVKGFYPSDIAVEWESNGQPENNYKTTPPVLDSDG<br>SFFLYSKLTVDKSRWQQGNVFSCSVMHEALHNHYTQKSLS<br>LSPG | anti-IL4-VH-hulGH-G11-hulGH-H1-<(G4S)3>-anti-IL13-VH-hulGHG1 |
| sLC-Tandem-(anti-IL4xanti-IL13)-singlePCL1-1-hulgG1 | 14 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECGGGGSRRKRGGGGSDIVLTQSPASLAVSLGQR<br>ATISCRASESVDSYGQSYMHWYQQKAGQPPKLLIYLASNL<br>SGVPARFSGSGSRTDFTLTIDPVQAEDAATYYCQQNAED<br>SRTFGGGTKLEIKRTVAAPSVFIFPPSDEQLKSGTASVVCLLN<br>NFYPREAKVQWKVDNALQSGNSQESVTEQDSKDSTYSLSS<br>TLTLSKADYEKHKVYACEVTHQGLSSPVTKSFNRGEC | anti-IL4-VL-hulGKC-<G4S>-[PCS1]-<G4S>-anti-IL13-VL-hulGKC |
| | 13 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPSRDELTKN<br>QVSLTCLVKGFYPSDIAVEWESNGQPENNYKTTPPVLDSDG<br>SFFLYSKLTVDKSRWQQGNVFSCSVMHEALHNHYTQKSLS<br>LSPG | anti-IL4-VH-hulGH-G11-hulGH-H1-<(G4S)3>-anti-IL13-VH-hulGHG1 |
| sLC-Tandem-(anti-IL4xanti-IL13)-PCL1-hulgG1 | 15 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRRKRGGGGGGGGSGGGGSRRKRDIVLTQSPA<br>SLAVSLGQRATISCRASESVDSYGQSYMHWYQQKAGQP<br>PKLLIYLASNLESGVPARFSGSGSRTDFTLTIDPVQAEDAAT<br>YYCQQNAEDSRTFGGGTKLEIKRTVAAPSVFIFPPSDEQLKS<br>GTASVVCLLNNFYPREAKVQWKVDNALQSGNSQESVTEQ<br>DSKDSTYSLSSTLTLSKADYEKHKVYACEVTHQGLSSPVTKSF<br>NRGEC | anti-IL4-VL-hulGKC-[PCS1]-<(G4S)3>-[PCS1]-anti-IL13-VL-hulGKC |

TABLE 10-continued

| List of Sequences/Constructs. | | | |
|---|---|---|---|
| Name | SEQ ID NO | Amino acid sequence | Annotation/ Comments |
| | 13 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPSRDELTKN<br>QVSLTCLVKGFYPSDIAVEWESNGQPENNYKTTPPVLDSDG<br>SFFLYSKLTVDKSRWQQGNVFSCSVMHEALHNHYTQKSLS<br>LSPG | anti-IL4-VH-hulGH-G11-hulGH-H1-<(G4S)3>-anti-IL13-VH-hulGHG1 |
| sLC-Tandem-(anti-IL4xanti-IL13)-ΔPCL1-hulgG1 | 16 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRQQRGGGGSGGGGSGGGGSRQQRDIVLTQSP<br>ASLAVSLGQRATISCRASESVDSYGQSYMHWYQQKAGQ<br>PPKLLIYLASNLESGVPARFSGSGSRTDFTLTIDPVQAEDAA<br>TYYCQQNAEDSRTFGGGTKLEIKRTVAAPSVFIFPPSDEQLK<br>SGTASVVCLLNNFYPREAKVQWKVDNALQSGNSQESVTEQ<br>DSKDSTYSLSSTLTLSKADYEKHKVYACEVTHQGLSSPVTKSF<br>NRGEC | anti-IL4-VL-hulGKC-[deltaPCS]-<(G4S)3>-[deltaPCS]-anti-IL13-VL-hulGKC |
| | 13 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPSRDELTKN<br>QVSLTCLVKGFYPSDIAVEWESNGQPENNYKTTPPVLDSDG<br>SFFLYSKLTVDKSRWQQGNVFSCSVMHEALHNHYTQKSLS<br>LSPG | anti-IL4-VH-hulGH-G11-hulGH-H1-<(G4S)3>-anti-IL13-VH-hulGHG1 |
| sLC-Tandem-(anti-IL4xanti-IL13)-His8-PCL1-hulgG1 | 17 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRRKRGSHHHHHHHHGGGGSRRKRDIVLTQSP<br>ASLAVSLGQRATISCRASESVDSYGQSYMHWYQQKAGQ<br>PPKLLIYLASNLESGVPARFSGSGSRTDFTLTIDPVQAEDAA<br>TYYCQQNAEDSRTFGGGTKLEIKRTVAAPSVFIFPPSDEQLK<br>SGTASVVCLLNNFYPREAKVQWKVDNALQSGNSQESVTEQ<br>DSKDSTYSLSSTLTLSKADYEKHKVYACEVTHQGLSSPVTKSF<br>NRGEC | anti-IL4-VL-hulGKC-[PCS1]-<GS>-His(8)-<G4S>-[PCS1]-anti-IL13-VL-hulGKC |
| | 13 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP | anti-IL4-VH-hulGH-G11-hulGH-H1-<(G4S)3>-anti-IL13-VH-hulGHG1 |

TABLE 10-continued

List of Sequences/Constructs.

| Name | SEQ ID NO | Amino acid sequence | Annotation/ Comments |
|---|---|---|---|
| | | SVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | |
| sLC-Tandem-(anti-IL4xanti-IL13)-His8-ΔPCL1-hulgG1 | 18 | **DIQMTQSPASLSVSVGDTITLTCHASQNIDVWLSWFQQKPGNIPKLLIYKASNLHTGVPSRFSGSGSGTGFTLTISSLQPEDIATYYCQQAHSYPFTFGGGTKLEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*RQQR*GSHHHHHHHHGGGGS*RQQR* **DIVLTQSPASLAVSLGQRATISCRASESVDSYGQSYMHWYQQKAGQPPKLLIYLASNLESGVPARFSGSGSRTDFTLTIDPVQAEDAATYYCQQNAEDSRTFGGGTKLEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | **anti-IL4-VL**-hulGKC-[*deltaPCS*]-<GS>-His(8)-<G4S>-[*deltaPCS*]-**anti-IL13-VL**-hulGKC |
| | 13 | **QVQLQQSGPELVKPGASVKISCKASGYSFTSYWIHWIKQRPGQGLEWIGMIDPSDGETRLNQRFQGRATLTVDESTSTAYMQLRSPTSEDSAVYYCTRLKEYGNYDSFYFDVWGAGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTGGGGSGGGGSGGGGS**EVQLKESGPGLVAPGGSLSITCTVSGFSLTDSSINWVRQPPGKGLEWLGMIWGDGRIDYADALKSRLSISKDSSKSQVFLEMTSLRTDDTATYYCARDGYFPYAMDFWGQGTSVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | **anti-IL4-VH**-hulGH-G11-hulGH-H1-<(*G4S*)*3*>-**anti-IL13-VH**-hulGHG1 |
| sLC-Tandem-(anti-IL4xanti-IL13)-PCL2-hulgG1 | 19 | **DIQMTQSPASLSVSVGDTITLTCHASQNIDVWLSWFQQKPGNIPKLLIYKASNLHTGVPSRFSGSGSGTGFTLTISSLQPEDIATYYCQQAHSYPFTFGGGTKLEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*HRRRKRSVDE*GGGGS*HRRRKRSVDE* **DIVLTQSPASLAVSLGQRATISCRASESVDSYGQSYMHWYQQKAGQPPKLLIYLASNLESGVPARFSGSGSRTDFTLTIDPVQAEDAATYYCQQNAEDSRTFGGGTKLEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | **anti-IL4-VL**-hulGKC-[*PCS2*]-<(*G4S*)*3*>-[*PCS2*]-**anti-IL13-VL**-hulGKC |
| | 13 | **QVQLQQSGPELVKPGASVKISCKASGYSFTSYWIHWIKQRPGQGLEWIGMIDPSDGETRLNQRFQGRATLTVDESTSTAYMQLRSPTSEDSAVYYCTRLKEYGNYDSFYFDVWGAGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTGGGGSGGGGSGGGGS**EVQLKESGPGLVAPGGSLSITCTVSGFSLTDSSINWVRQPPGKGLEWLGMIWGDGRIDYADALKSRLSISKDSSKSQVFLEMTSLRTDDTATYYCARDGYFPYAMDFWGQGTSVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | **anti-IL4-VH**-hulGH-G11-hulGH-H1-<(*G4S*)*3*>-**anti-IL13-VH**-hulGHG1 |

TABLE 10-continued

List of Sequences/Constructs.

| Name | SEQ ID NO | Amino acid sequence | Annotation/ Comments |
|---|---|---|---|
| sLC-Tandem-(anti-IL4xanti-IL13)-PCL3-hulgG1 | 20 | **DIQMTQSPASLSVSVGDTITLTCHASQNIDVWLSWFQQK**<br>**PGNIPKLLIYKASNLHTGVPSRFSGSGSGTGFTLTISSLQPED**<br>**IATYYCQQAHSYPFTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC*PMKKRRAGVP*GGGGS*PMKKRRAGVP*DIVLTQ<br>S**PASLAVSLGQRATISCRASESVDSYGQSYMHWYQQKAG**<br>**QPPKLLIYLASNLESGVPARFSGSGSRTDFTLTIDPVQAEDA**<br>**ATYYCQQNAEDSRTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC | **anti-IL4-VL**-hulGKC-[*PCS3*]-<(G4S)>-[*PCS3*]-**anti-IL13-VL**-hulGKC |
| | 13 | **QVQLQQSGPELVKPGASVKISCKASGYSFTSYWIHWIKQR**<br>**PGQGLEWIGMIDPSDGETRLNQRFQGRATLTVDESTSTA**<br>**YMQLRSPTSEDSAVYYCTRLKEYGNYDSFYFDVWGAGTL**<br>**VTVSS**ASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGS**EVQLKESGPGLVAPGGSLSITCTVSGFSLTDSSINWV**<br>**RQPPGKGLEWLGMIWGDGRIDYADALKSRLSISKDSSKS**<br>**QVFLEMTSLRTDDTATYYCARDGYFPYAMDFWGQGTSV**<br>**TVSS**ASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPSRDELTKN<br>QVSLTCLVKGFYPSDIAVEWESNGQPENNYKTTPPVLDSDG<br>SFFLYSKLTVDKSRWQQGNVFSCSVMHEALHNHYTQKSLS<br>LSPG | **anti-IL4-VH**-hulGH-G11-hulGH-H1-<(*G4S)3*>-**anti-IL13-VH**-hulGHG1 |
| sLC-Tandem-(anti-IL4xanti-IL13)-rigidL1-PCL1-hulgG1 | 21 | **DIQMTQSPASLSVSVGDTITLTCHASQNIDVWLSWFQQK**<br>**PGNIPKLLIYKASNLHTGVPSRFSGSGSGTGFTLTISSLQPED**<br>**IATYYCQQAHSYPFTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC*RRKR*GGGGSEAAAKEAAAKGGGGS*RRKR*D**IVL**<br>**TQSPASLAVSLGQRATISCRASESVDSYGQSYMHWYQQK**<br>**AGQPPKLLIYLASNLESGVPARFSGSGSRTDFTLTIDPVQAE**<br>**DAATYYCQQNAEDSRTFGGGTKLEIK**RTVAAPSVFIFPPSD<br>EQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | **anti-IL4-VL**-hulGKC-[*PCS1*]-<G4S>-<(EAAAK)2>-<G4S>-[*PCS1*]-**anti-IL13-VL**-hulGKC |
| | 22 | **QVQLQQSGPELVKPGASVKISCKASGYSFTSYWIHWIKQR**<br>**PGQGLEWIGMIDPSDGETRLNQRFQGRATLTVDESTSTA**<br>**YMQLRSPTSEDSAVYYCTRLKEYGNYDSFYFDVWGAGTL**<br>**VTVSS**ASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSEAAAKE<br>AAAKGGGGS**EVQLKESGPGLVAPGGSLSITCTVSGFSLTDS**<br>**SINWVRQPPGKGLEWLGMIWGDGRIDYADALKSRLSISK**<br>**DSSKSQVFLEMTSLRTDDTATYYCARDGYFPYAMDFWG**<br>**QGTSVTVSS**ASTKGPSVFPLAPSSKSTSGGTAALGCLVKDYF<br>PEPVTVSWNSGALTSGVHTFPAVLQSSGLYSLSSVVTVPSSS<br>LGTQTYICNVNHKPSNTKVDKKVEPKSCDKTHTCPPCPAPE<br>LLGGPSVFLFPPKPKDTLMISRTPEVTCVVVDVSHEDPEVKF<br>NWYVDGVEVHNAKTKPREEQYNSTYRVVSVLTVLHQDWL<br>NGKEYKCKVSNKALPAPIEKTISKAKGQPREPQVYTLPPSRD<br>ELTKNQVSLTCLVKGFYPSDIAVEWESNGQPENNYKTTPPV<br>LDSDGSFFLYSKLTVDKSRWQQGNVFSCSVMHEALHNHYT<br>QKSLSLSPG | **anti-IL4-VH**-hulGH-G11-hulGH-H1-<G4S>-<(EAAAK)2>-<G4S>-**anti-IL13-VH**-hulGHG1 |

TABLE 10-continued

| List of Sequences/Constructs. | | | |
|---|---|---|---|
| Name | SEQ ID NO | Amino acid sequence | Annotation/ Comments |
| sLC-Tandem-(anti-IL4xanti-IL13)-rigidL2-PCL1-hulgG1 | 23 | **DIQMTQSPASLSVSVGDTITLTCHASQNIDVWLSWFQQK PGNIPKLLIYKASNLHTGVPSRFSGSGSGTGFTLTISSLQPED IATYYCQQAHSYPFTFGGGTKLEIK**RTVAAPSVFIFPPSDEQ LKSGTASVVCLLNNFYPREAKVQWKVDNALQSGNSQESVT EQDSKDSTYSLSSTLTLSKADYEKHKVYACEVTHQGLSSPVT KSFNRGEC*RRKR*APAPAPAPAPAPAPA*RRKR***DIVLTQSPAS LAVSLGQRATISCRASESVDSYGQSYMHWYQQKAGQPP KLLIYLASNLESGVPARFSGSGSRTDFTLTIDPVQAEDAATY YCQQNAEDSRTFGGGTKLEIK**RTVAAPSVFIFPPSDEQLKS GTASVVCLLNNFYPREAKVQWKVDNALQSGNSQESVTEQ DSKDSTYSLSSTLTLSKADYEKHKVYACEVTHQGLSSPVTKSF NRGEC | **anti-IL4-VL**-hulGKC-[*PCS1*]><(AP)7A>-[*PCS1*]-**anti-IL13-VL**-hulGKC |
| | 13 | **QVQLQQSGPELVKPGASVKISCKASGYSFTSYWIHWIKQR PGQGLEWIGMIDPSDGETRLNQRFQGRATLTVDESTSTA YMQLRSPTSEDSAVYYCTRLKEYGNYDSFYFDVWGAGTL VTVSS**ASTKGPSVFPLAPSSKSTSGGTAALGCLVKDYFPEPV TVSWNSGALTSGVHTFPAVLQSSGLYSLSSVVTVPSSSLGTQ TYICNVNHKPSNTKVDKKVEPKSCDKTHTGGGGSGGGGSG GGGS**EVQLKESGPGLVAPGGSLSITCTVSGFSLTDSSINWV RQPPGKGLEWLGMIWGDGRIDYADALKSRLSISKDSSKS QVFLEMTSLRTDDTATYYCARDGYFPYAMDFWGQGTSV TVSS**ASTKGPSVFPLAPSSKSTSGGTAALGCLVKDYFPEPVT VSWNSGALTSGVHTFPAVLQSSGLYSLSSVVTVPSSSLGTQT YICNVNHKPSNTKVDKKVEPKSCDKTHTCPPCPAPELLGGP SVFLFPPKPKDTLMISRTPEVTCVVVDVSHEDPEVKFNWYV DGVEVHNAKTKPREEQYNSTYRVVSVLTVLHQDWLNGKEY KCKVSNKALPAPIEKTISKAKGQPREPQVYTLPPSRDELTKN QVSLTCLVKGFYPSDIAVEWESNGQPENNYKTTPPVLDSDG SFFLYSKLTVDKSRWQQGNVFSCSVMHEALHNHYTQKSLS LSPG | **anti-IL4-VH**-hulGH-G11-hulGH-H1-<(*G4S*)*3*>-**anti-IL13-VH**-hulGHG1 |
| sLC-Tandem-(anti-IL4xanti-IL13)-charL-PCL1-hulgG1 | 24 | **DIQMTQSPASLSVSVGDTITLTCHASQNIDVWLSWFQQK PGNIPKLLIYKASNLHTGVPSRFSGSGSGTGFTLTISSLQPED IATYYCQQAHSYPFTFGGGTKLEIK**RTVAAPSVFIFPPSDEQ LKSGTASVVCLLNNFYPREAKVQWKVDNALQSGNSQESVT EQDSKDSTYSLSSTLTLSKADYEKHKVYACEVTHQGLSSPVT KSFNRGEC*RRKR*GSKQGKQKQGKQGS*RRKR***DIVLTQSPAS LAVSLGQRATISCRASESVDSYGQSYMHWYQQKAGQPP KLLIYLASNLESGVPARFSGSGSRTDFTLTIDPVQAEDAATY YCQQNAEDSRTFGGGTKLEIK**RTVAAPSVFIFPPSDEQLKS GTASVVCLLNNFYPREAKVQWKVDNALQSGNSQESVTEQ DSKDSTYSLSSTLTLSKADYEKHKVYACEVTHQGLSSPVTKSF NRGEC | **anti-IL4-VL**-hulGKC-[*PCS1*]-<*GS*>-<(KQGKQ)2>-<*GS*>-[*PCS1*]-**anti-IL13-VL**-hulGKC |
| | 13 | **QVQLQQSGPELVKPGASVKISCKASGYSFTSYWIHWIKQR PGQGLEWIGMIDPSDGETRLNQRFQGRATLTVDESTSTA YMQLRSPTSEDSAVYYCTRLKEYGNYDSFYFDVWGAGTL VTVSS**ASTKGPSVFPLAPSSKSTSGGTAALGCLVKDYFPEPV TVSWNSGALTSGVHTFPAVLQSSGLYSLSSVVTVPSSSLGTQ TYICNVNHKPSNTKVDKKVEPKSCDKTHTGGGGSGGGGSG GGGS**EVQLKESGPGLVAPGGSLSITCTVSGFSLTDSSINWV RQPPGKGLEWLGMIWGDGRIDYADALKSRLSISKDSSKS QVFLEMTSLRTDDTATYYCARDGYFPYAMDFWGQGTSV TVSS**ASTKGPSVFPLAPSSKSTSGGTAALGCLVKDYFPEPVT VSWNSGALTSGVHTFPAVLQSSGLYSLSSVVTVPSSSLGTQT YICNVNHKPSNTKVDKKVEPKSCDKTHTCPPCPAPELLGGP SVFLFPPKPKDTLMISRTPEVTCVVVDVSHEDPEVKFNWYV DGVEVHNAKTKPREEQYNSTYRVVSVLTVLHQDWLNGKEY KCKVSNKALPAPIEKTISKAKGQPREPQVYTLPPSRDELTKN QVSLTCLVKGFYPSDIAVEWESNGQPENNYKTTPPVLDSDG SFFLYSKLTVDKSRWQQGNVFSCSVMHEALHNHYTQKSLS LSPG | **anti-IL4-VH**-hulGH-G11-hulGH-H1-<(*G4S*)*3*>-**anti-IL13**-VH-hulGHG1 |
| scTandem-(anti-IL4xanti-IL13)-PCL1-hulgG1-OL-KIH | 25 | **DIQMTQSPASLSVSVGDTITLTCHASQNIDVWLSWFQQK PGNIPKLLIYKASNLHTGVPSRFSGSGSGTGFTLTISSLQPED IATYYCQQAHSYPFTFGGGTKLEIK**RTVAAPSVFIFPPSDEQ LKSGTASVVCLLNNFYPREAKVQWKVDNALQSGNSQESVT EQDSKDSTYSLSSTLTLSKADYEKHKVYACEVTHQGLSSPVT KSFNRGEC*RRKR*GGGGSGGGGSGGGGS*RRKR***DIVLTQSPA SLAVSLGQRATISCRASESVDSYGQSYMHWYQQKAGQP PKLLIYLASNLESGVPARFSGSGSRTDFTLTIDPVQAEDAAT YYCQQNAEDSRTFGGGTKLEIK**RTVAAPSVFIFPPSDEQLKS GTASVVCLLNNFYPREAKVQWKVDNALQSGNSQESVTEQ DSKDSTYSLSSTLTLSKADYEKHKVYACEVTHQGLSSPVTKSF | **anti-IL4-VL**-hulGKC-[*PCS1*]-<(*G4S*)*3*>-[*PCS1*]-**anti-IL13-VL**-hulGKC-<G4S>-*Fc-hulgG1*(*hole-RF*) |

TABLE 10-continued

List of Sequences/Constructs.

| Name | SEQ ID NO | Amino acid sequence | Annotation/ Comments |
|---|---|---|---|
| | | NRGECGGGGSDKTHTCPPCPAPELLGGPSVFLFPPKPKDTL<br>MISRTPEVTCVVVDVSHEDPEVKFNWYVDGVEVHNAKTKP<br>REEQYNSTYRVVSVLTVLHQDWLNGKEYKCKVSNKALPAPI<br>EKTISKAKGQPREPQVCTLPPSRDELTKNQVSLSCAVKGFYP<br>SDIAVEWESNGQPENNYKTTPPVLDSDGSFFLVSKLTVDKS<br>RWQQGNVFSCSVMHEALHNRFTQKSLSLSPG | |
| | 26 | **QVQLQQSGPELVKPGASVKISCKASGYSFTSYWIHWIKQR**<br>**PGQGLEWIGMIDPSDGETRLNQRFQGRATLTVDESTSTA**<br>**YMQLRSPTSEDSAVYYCTRLKEYGNYDSFYFDVWGAGTL**<br>**VTVSS**ASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGS**EVQLKESGPGLVAPGGSLSITCTVSGFSLTDSSINWV**<br>**RQPPGKGLEWLGMIWGDGRIDYADALKSRLSISKDSSKS**<br>**QVFLEMTSLRTDDTATYYCARDGYFPYAMDFWGQGTSV**<br>**TVSS**ASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKSL<br>SLSPG | **anti-IL4-VH**-hulGH-<br>G11-hulGH-H1-<br><(G4S)3>-**anti-IL13-**<br>**VH**-hulGHG1(knob) |
| scTandem-<br>(anti-<br>IL4xanti-<br>IL13)-<br>single PCL1-<br>hulgG1-OL-<br>KIH | 27 | **DIQMTQSPASLSVSVGDTITLTCHASQNIDVWLSWFQQK**<br>**PGNIPKLLIYKASNLHTGVPSRFSGSGSGTGFTLTISSLQPED**<br>**IATYYCQQAHSYPFTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECGGGGS*RRKR*GGGGS**DIVLTQSPASLAVSLGQR**<br>**ATISCRASESVDSYGQSYMHWYQQKAGQPPKLLIYLASNL**<br>**ESGVPARFSGSGSRTDFTLTIDPVQAEDAATYYCQQNAED**<br>**SRTFGGGTKLEIK**RTVAAPSVFIFPPSDEQLKSGTASVVCLLN<br>NFYPREAKVQWKVDNALQSGNSQESVTEQDSKDSTYSLSS<br>TLTLSKADYEKHKVYACEVTHQGLSSPVTKSFNRGECGGGG<br>*SDKTHTCPPCPAPELLGGPSVFLFPPKPKDTLMISRTPEVTCV*<br>*VVDVSHEDPEVKFNWYVDGVEVHNAKTKPREEQYNSTYR*<br>*VVSVLTVLHQDWLNGKEYKCKVSNKALPAPIEKTISKAKGQ*<br>*PREPQVCTLPPSRDELTKNQVSLSCAVKGFYPSDIAVEWESN*<br>*GQPENNYKTTPPVLDSDGSFFLVSKLTVDKSRWQQGNVFS*<br>*CSVMHEALHNRFTQKSLSLSPG* | **anti-IL4-VL**-hulGKC-<br><G4S>-[*PCS1*]-<G4S>-<br>**anti-IL13-VL**-hulGKC-<br><G4S>-*Fc*-<br>*hulgG1*(*hole-RF*) |
| | 26 | **QVQLQQSGPELVKPGASVKISCKASGYSFTSYWIHWIKQR**<br>**PGQGLEWIGMIDPSDGETRLNQRFQGRATLTVDESTSTA**<br>**YMQLRSPTSEDSAVYYCTRLKEYGNYDSFYFDVWGAGTL**<br>**VTVSS**ASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGS**EVQLKESGPGLVAPGGSLSITCTVSGFSLTDSSINWV**<br>**RQPPGKGLEWLGMIWGDGRIDYADALKSRLSISKDSSKS**<br>**QVFLEMTSLRTDDTATYYCARDGYFPYAMDFWGQGTSV**<br>**TVSS**ASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKSL<br>SLSPG | **anti-IL4-VH**-hulGH-<br>G11-hulGH-H1-<br><(G4S)3>-**anti-IL13-**<br>**VH**-hulGHG1(knob) |
| scTandem-<br>(anti-<br>IL4xanti-<br>IL13)-<br>ΔPCL1-<br>hulgG1-OL-<br>KIH | 28 | **DIQMTQSPASLSVSVGDTITLTCHASQNIDVWLSWFQQK**<br>**PGNIPKLLIYKASNLHTGVPSRFSGSGSGTGFTLTISSLQPED**<br>**IATYYCQQAHSYPFTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC*RQQR*GGGGSGGGGSGGGGS*RQQR***DIVLTQSP**<br>**ASLAVSLGQRATISCRASESVDSYGQSYMHWYQQKAGQ**<br>**PPKLLIYLASNLESGVPARFSGSGSRTDFTLTIDPVQAEDAA**<br>**TYYCQQNAEDSRTFGGGTKLEIK**RTVAAPSVFIFPPSDEQLK<br>SGTASVVCLLNNFYPREAKVQWKVDNALQSGNSQESVTEQ<br>DSKDSTYSLSSTLTLSKADYEKHKVYACEVTHQGLSSPVTKSF<br>NRGECGGGGS*DKTHTCPPCPAPELLGGPSVFLFPPKPKDTL*<br>*MISRTPEVTCVVVDVSHEDPEVKFNWYVDGVEVHNAKTKP* | **anti-IL4-VL**-hulGKC-<br>[*deltaPCS*]-<(G4S)3>-<br>[*deltaPCS*]-**anti-IL13-**<br>**VL**-hulGKC-<G4S>-*Fc*-<br>*hulgG1*(*hole-RF*) |

TABLE 10-continued

List of Sequences/Constructs.

| Name | SEQ ID NO | Amino acid sequence | Annotation/ Comments |
|---|---|---|---|
| | | *REEQYNSTYRVVSVLTVLHQDWLNGKEYKCKVSNKALPAPI*<br>*EKTISKAKGQPREPQVCTLPPSRDELTKNQVSLSCAVKGFYP*<br>*SDIAVEWESNGQPENNYKTTPPVLDSDGSFFLVSKLTVDKS*<br>*RWQQGNVFSCSVMHEALHNRFTQKSLSLSPG* | |
| | 26 | **QVQLQQSGPELVKPGASVKISCKASGYSFTSYWIHWIKQR**<br>**PGQGLEWIGMIDPSDGETRLNQRFQGRATLTVDESTSTA**<br>**YMQLRSPTSEDSAVYYCTRLKEYGNYDSFYFDVWGAGTL**<br>**VTVSS**ASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGS**EVQLKESGPGLVAPGGSLSITCTVSGFSLTDSSINWV**<br>**RQPPGKGLEWLGMIWGDGRIDYADALKSRLSISKDSSKS**<br>**QVFLEMTSLRTDDTATYYCARDGYFPYAMDFWGQGTSV**<br>**TVSS**ASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKSL<br>SLSPG | **anti-IL4-VH**-hulGH-<br>G11-hulGH-H1-<br><(G4S)3>-**anti-IL13-**<br>**VH**-hulGHG1(knob) |
| scTandem-<br>(anti-<br>IL4xanti-<br>IL13)-His8-<br>PCL1-<br>hulgG1-OL-<br>KIH | 29 | **DIQMTQSPASLSVSVGDTITLTCHASQNIDVWLSWFQQK**<br>**PGNIPKLLIYKASNLHTGVPSRFSGSGSGTGFTLTISSLQPED**<br>**IATYYCQQAHSYPFTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC*RRKR*GSHHHHHHHHGGGGS*RRKR***DIVLTQSP**<br>**ASLAVSLGQRATISCRASESVDSYGQSYMHWYQQKAGQ**<br>**PPKLLIYLASNLESGVPARFSGSGSRTDFTLTIDPVQAEDAA**<br>**TYYCQQNAEDSRTFGGGTKLEIK**RTVAAPSVFIFPPSDEQLK<br>SGTASVVCLLNNFYPREAKVQWKVDNALQSGNSQESVTEQ<br>DSKDSTYSLSSTLTLSKADYEKHKVYACEVTHQGLSSPVTKSF<br>NRGECGGGGS*DKTHTCPPCPAPELLGGPSVFLFPPKPKDTL*<br>*MISRTPEVTCVVVDVSHEDPEVKFNWYVDGVEVHNAKTKP*<br>*REEQYNSTYRVVSVLTVLHQDWLNGKEYKCKVSNKALPAPI*<br>*EKTISKAKGQPREPQVCTLPPSRDELTKNQVSLSCAVKGFYP*<br>*SDIAVEWESNGQPENNYKTTPPVLDSDGSFFLVSKLTVDKS*<br>*RWQQGNVFSCSVMHEALHNRFTQKSLSLSPG* | **anti-IL4-VL**-hulGKC-<br>[*PCS1*]-<GS>-His(8)-<br><G4S>-[*PCS1*]-**anti-**<br>**IL13-VL**-hulGKC-<br><G4S>-*Fc-*<br>*hulgG1*(*hole-RF*) |
| | 26 | **QVQLQQSGPELVKPGASVKISCKASGYSFTSYWIHWIKQR**<br>**PGQGLEWIGMIDPSDGETRLNQRFQGRATLTVDESTSTA**<br>**YMQLRSPTSEDSAVYYCTRLKEYGNYDSFYFDVWGAGTL**<br>**VTVSS**ASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGS**EVQLKESGPGLVAPGGSLSITCTVSGFSLTDSSINWV**<br>**RQPPGKGLEWLGMIWGDGRIDYADALKSRLSISKDSSKS**<br>**QVFLEMTSLRTDDTATYYCARDGYFPYAMDFWGQGTSV**<br>**TVSS**ASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKSL<br>SLSPG | **anti-IL4-VH**-hulGH-<br>G11-hulGH-H1-<br><(*G4S*)*3*>-**anti-IL13-**<br>**VH**-hulGHG1(knob) |
| scTandem-<br>(anti-<br>IL4xanti-<br>IL13)-His8-<br>ΔPCL1-<br>hulgG1-OL-<br>KIH | 30 | **DIQMTQSPASLSVSVGDTITLTCHASQNIDVWLSWFQQK**<br>**PGNIPKLLIYKASNLHTGVPSRFSGSGSGTGFTLTISSLQPED**<br>**IATYYCQQAHSYPFTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGEC*RQQR*GSHHHHHHHHGGGGS*RQQR***DIVLTQS**<br>**PASLAVSLGQRATISCRASESVDSYGQSYMHWYQQKAG**<br>**QPPKLLIYLASNLESGVPARFSGSGSRTDFTLTIDPVQAEDA**<br>**ATYYCQQNAEDSRTFGGGTKLEIK**RTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECGGGGS*DKTHTCPPCPAPELLGGPSVFLFPPKPK*<br>*DTLMISRTPEVTCVVVDVSHEDPEVKFNWYVDGVEVHNAK*<br>*TKPREEQYNSTYRVVSVLTVLHQDWLNGKEYKCKVSNKALP*<br>*APIEKTISKAKGQPREPQVCTLPPSRDELTKNQVSLSCAVKG* | **anti-IL4-VL**-hulGKC-<br>[*deltaPCS*]-<GS>-<br>His(8)-<G4S>-<br>[*deltaPCS*]-**anti-IL13-**<br>**VL**-hulGKC-<G4S>-*Fc-*<br>*hulgG1*(*hole-RF*) |

TABLE 10-continued

List of Sequences/Constructs.

| Name | SEQ ID NO | Amino acid sequence | Annotation/ Comments |
|---|---|---|---|
| | | FYPSDIAVEWESNGQPENNYKTTPPVLDSDGSFFLVSKLTV<br>DKSRWQQGNVFSCSVMHEALHNRFTQKSLSLSPG | |
| | 26 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKSL<br>SLSPG | **anti-IL4-VH**-hulGH-G11-hulGH-H1-<(G4S)3>-**anti-IL13-VH**-hulGHG1(knob) |
| scTandem-(anti-IL4xanti-IL13)-PCL2-hulgG1-OL-KIH | 31 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECHRRRKRSVDEGGGGSHRRRKRSVDEDIVLTQS<br>PASLAVSLGQRATISCRASESVDSYGQSYMHWYQQKAG<br>QPPKLLIYLASNLESGVPARFSGSGSRTDFTLTIDPVQAEDA<br>ATYYCQQNAEDSRTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECGGGGSDKTHTCPPCPAPELLGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKALP<br>APIEKTISKAKGQPREPQVCTLPPSRDELTKNQVSLSCAVKG<br>FYPSDIAVEWESNGQPENNYKTTPPVLDSDGSFFLVSKLTV<br>DKSRWQQGNVFSCSVMHEALHNRFTQKSLSLSPG | **anti-IL4-VL**-hulGKC-[*PCS2*]-<(G4S)3>-[*PCS2*]-**anti-IL13-VL**-hulGKC-<G4S>-*Fc-hulgG1*(*hole-RF*) |
| | 26 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKSL<br>SLSPG | **anti-IL4-VH**-hulGH-G11-hulGH-H1-<(G4S)3>-**anti-IL13-VH**-hulGHG1(knob) |
| scTandem-(anti-IL4xanti-IL13)-PCL3-hulgG1-OL-KIH | 32 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECPMKKRRAGVPGGGGSPMKKRRAGVPDIVLT<br>QSPASLAVSLGQRATISCRASESVDSYGQSYMHWYQQKA<br>GQPPKLLIYLASNLESGVPARFSGSGSRTDFTLTIDPVQAED<br>AATYYCQQNAEDSRTFGGGTKLEIKRTVAAPSVFIFPPSDE<br>QLKSGTASVVCLLNNFYPREAKVQWKVDNALQSGNSQESV<br>TEQDSKDSTYSLSSTLTLSKADYEKHKVYACEVTHQGLSSPV<br>TKSFNRGECGGGGSDKTHTCPPCPAPELLGGPSVFLFPPKP<br>KDTLMISRTPEVTCVVVDVSHEDPEVKFNWYVDGVEVHNA<br>KTKPREEQYNSTYRVVSVLTVLHQDWLNGKEYKCKVSNKAL<br>PAPIEKTISKAKGQPREPQVCTLPPSRDELTKNQVSLSCAVK | **anti-IL4-VL**-hulGKC-[*PCS3*]-<(G4S)3>-[*PCS3*]-**anti-IL13-VL**-hulGKC-<G4S>-*Fc-hulgG1*(*hole-RF*) |

TABLE 10-continued

List of Sequences/Constructs.

| Name | SEQ ID NO | Amino acid sequence | Annotation/ Comments |
|---|---|---|---|
| | | GFYPSDIAVEWESNGQPENNYKTTPPVLDSDGSFFLVSKLT<br>VDKSRWQQGNVFSCSVMHEALHNRFTQKSLSLSPG | |
| | 26 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKSL<br>SLSPG | anti-IL4-VH-hulGH-G11-hulGH-H1-<(G4S)3>-anti-IL13-VH-hulGHG1(knob) |
| scTandem-(anti-IL4xanti-IL13)-rigidL-PCL1-hulgG1-OL-KIH | 33 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRRKRGGGGSEAAAKEAAAKGGGGSRRKRDIVL<br>TQSPASLAVSLGQRATISCRASESVDSYGQSYMHWYQQK<br>AGQPPKLLIYLASNLESGVPARFSGSGSRTDFTLTIDPVQAE<br>DAATYYCQQNAEDSRTFGGGTKLEIKRTVAAPSVFIFPPSD<br>EQLKSGTASVVCLLNNFYPREAKVQWKVDNALQSGNSQES<br>VTEQDSKDSTYSLSSTLTLSKADYEKHKVYACEVTHQGLSSP<br>VTKSFNRGECGGGGSDKTHTCPPCPAPELLGGPSVFLFPPK<br>PKDTLMISRTPEVTCVVVDVSHEDPEVKFNWYVDGVEVHN<br>AKTKPREEQYNSTYRVVSVLTVLHQDWLNGKEYKCKVSNK<br>ALPAPIEKTISKAKGQPREPQVCTLPPSRDELTKNQVSLSCAV<br>KGFYPSDIAVEWESNGQPENNYKTTPPVLDSDGSFFLVSKLT<br>VDKSRWQQGNVFSCSVMHEALHNRFTQKSLSLSPG | anti-IL4-VL-hulGKC-[PCS1]-<G4S>-<(EAAAK)2>-<G4S>-[PCS1]-anti-IL13-VL-hulGKC-<G4S>-Fc-hulgG1(hole-RF) |
| | 34 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSEAAAKE<br>AAAKGGGGSEVQLKESGPGLVAPGGSLSITCTVSGFSLTDS<br>SINWVRQPPGKGLEWLGMIWGDGRIDYADALKSRLSISK<br>DSSKSQVFLEMTSLRTDDTATYYCARDGYFPYAMDFWG<br>QGTSVTVSSASTKGPSVFPLAPSSKSTSGGTAALGCLVKDYF<br>PEPVTVSWNSGALTSGVHTFPAVLQSSGLYSLSSVVTVPSSS<br>LGTQTYICNVNHKPSNTKVDKKVEPKSCDKTHTCPPCPAPE<br>LLGGPSVFLFPPKPKDTLMISRTPEVTCVVVDVSHEDPEVKF<br>NWYVDGVEVHNAKTKPREEQYNSTYRVVSVLTVLHQDWL<br>NGKEYKCKVSNKALPAPIEKTISKAKGQPREPQVYTLPPCRD<br>ELTKNQVSLWCLVKGFYPSDIAVEWESNGQPENNYKTTPP<br>VLDSDGSFFLYSKLTVDKSRWQQGNVFSCSVMHEALHNHY<br>TQKSLSLSPG | anti-IL4-VH-hulGH-G11-hulGH-H1-<G4S>-<(EAAAK)2>-<G4S>-anti-IL13-VH-hulGHG1(knob) |
| scTandem-(anti-IL4xanti-IL13)-rigidL2-PCL1-hulgG1-OL-KIH | 35 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRRKRAPAPAPAPAPAPAPARRKRDIVLTQSPAS<br>LAVSLGQRATISCRASESVDSYGQSYMHWYQQKAGQPP<br>KLLIYLASNLESGVPARFSGSGSRTDFTLTIDPVQAEDAATY<br>YCQQNAEDSRTFGGGTKLEIKRTVAAPSVFIFPPSDEQLKS<br>GTASVVCLLNNFYPREAKVQWKVDNALQSGNSQESVTEQ<br>DSKDSTYSLSSTLTLSKADYEKHKVYACEVTHQGLSSPVTKSF<br>NRGECGGGGSDKTHTCPPCPAPELLGGPSVFLFPPKPKDTL<br>MISRTPEVTCVVVDVSHEDPEVKFNWYVDGVEVHNAKTKP<br>REEQYNSTYRVVSVLTVLHQDWLNGKEYKCKVSNKALPAPI<br>EKTISKAKGQPREPQVCTLPPSRDELTKNQVSLSCAVKGFYP<br>SDIAVEWESNGQPENNYKTTPPVLDSDGSFFLVSKLTVDKS<br>RWQQGNVFSCSVMHEALHNRFTQKSLSLSPG | anti-IL4-VL-hulGKC-[PCS1]-<(AP)7A>-[PCS1]-anti-IL13-VL-hulGKC-<G4S>-Fc-hulgG1(hole-RF) |

TABLE 10-continued

List of Sequences/Constructs.

| Name | SEQ ID NO | Amino acid sequence | Annotation/ Comments |
|---|---|---|---|
| | 26 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKSL<br>SLSPG | anti-IL4-VH-hulGH-G11-hulGH-H1-<(G4S)3>-anti-IL13-VH-hulGHG1(knob) |
| scTandem-(anti-IL4xanti-IL13)-charL-PCL1-hulgG1-OL-KIH | 36 | DIQMTQSPASLSVSVGDTITLTCHASQNIDVWLSWFQQK<br>PGNIPKLLIYKASNLHTGVPSRFSGSGSGTGFTLTISSLQPED<br>IATYYCQQAHSYPFTFGGGTKLEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPVT<br>KSFNRGECRRKRGSKQGKQKQGKQGSRRKRDIVLTQSPAS<br>LAVSLGQRATISCRASESVDSYGQSYMHWYQQKAGQPP<br>KLLIYLASNLESGVPARFSGSGSRTDFTLTIDPVQAEDAATY<br>YCQQNAEDSRTFGGGTKLEIKRTVAAPSVFIFPPSDEQLKS<br>GTASVVCLLNNFYPREAKVQWKVDNALQSGNSQESVTEQ<br>DSKDSTYSLSSTLTLSKADYEKHKVYACEVTHQGLSSPVTKSF<br>NRGECGGGGSDKTHTCPPCPAPELLGGPSVFLFPPKPKDTL<br>MISRTPEVTCVVVDVSHEDPEVKFNWYVDGVEVHNAKTKP<br>REEQYNSTYRVVSVLTVLHQDWLNGKEYKCKVSNKALPAPI<br>EKTISKAKGQPREPQVCTLPPSRDELTKNQVSLSCAVKGFYP<br>SDIAVEWESNGQPENNYKTTPPVLDSDGSFFLVSKLTVDKS<br>RWQQGNVFSCSVMHEALHNRFTQKSLSLSPG | anti-IL4-VL-hulGKC-[PCS1]-<GS>-<(KQGKQ)2>-<GS>-[PCS1]-anti-IL13-VL-hulGKC-<G4S>-Fc-hulgG1(hole-RF) |
| | 26 | QVQLQQSGPELVKPGASVKISCKASGYSFTSYWIHWIKQR<br>PGQGLEWIGMIDPSDGETRLNQRFQGRATLTVDESTSTA<br>YMQLRSPTSEDSAVYYCTRLKEYGNYDSFYFDVWGAGTL<br>VTVSSASTKGPSVFPLAPSSKSTSGGTAALGCLVKDYFPEPV<br>TVSWNSGALTSGVHTFPAVLQSSGLYSLSSVVTVPSSSLGTQ<br>TYICNVNHKPSNTKVDKKVEPKSCDKTHTGGGGSGGGGSG<br>GGGSEVQLKESGPGLVAPGGSLSITCTVSGFSLTDSSINWV<br>RQPPGKGLEWLGMIWGDGRIDYADALKSRLSISKDSSKS<br>QVFLEMTSLRTDDTATYYCARDGYFPYAMDFWGQGTSV<br>TVSSASTKGPSVFPLAPSSKSTSGGTAALGCLVKDYFPEPVT<br>VSWNSGALTSGVHTFPAVLQSSGLYSLSSVVTVPSSSLGTQT<br>YICNVNHKPSNTKVDKKVEPKSCDKTHTCPPCPAPELLGGP<br>SVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPCRDELTKN<br>QVSLWCLVKGFYPSDIAVEWESNGQPENNYKTTPPVLDSD<br>GSFFLYSKLTVDKSRWQQGNVFSCSVMHEALHNHYTQKSL<br>SLSPG | anti-IL4-VH-hulGH-G11-hulGH-H1-<(G4S)3>-anti-IL13-VH-hulGHG1(knob) |
| hFurin | 37 | QKVFTNTWAVRIPGGPAVANSVARKHGFLNLGQIFGDYYH<br>FWHRGVTKRSLSPHRPRHSRLQREPQVQWLEQQVAKRRT<br>KRDVYQEPTDPKFPQQWYLSGVTQRDLNVKAAWAQGYT<br>GHGIVVSILDDGIEKNHPDLAGNYDPGASFDVNDQDPDPQ<br>PRYTQMNDNRHGTRCAGEVAAVANNGVCGVGVAYNARI<br>GGVRMLDGEVTDAVEARSLGLNPNHIHIYSASWGPEDDGK<br>TVDGPARLAEEAFFRGVSQGRGGLGSIFVWASGNGGREH<br>DSCNCDGYTNSIYTLSISSATQFGNVPWYSEACSSTLATTYSS<br>GNQNEKQIVTTDLRQKCTESHTGTSASAPLAAGIIALTLEAN<br>KNLTWRDMQHLVVQTSKPAHLNANDWATNGVGRKVSHS<br>YGYGLLDAGAMVALAQNWTTVAPQRKCIIDILTEPKDIGKR<br>LEVRKTVTACLGEPNHITRLEHAQARLTLSYNRRGDLAIHLV<br>SPMGTRSTLLAARPHDYSADGFNDWAFMTTHSWDEDPS<br>GEWVLEIENTSEANNYGTLTKFTLVLYGTAPEGLPVPPESSG<br>CKTLTSSQACVVCEEGFSLHQKSCVQHCPPGFAPQVLDTHY<br>STENDVETIRASVCAPCHASCATCQGPALTDCLSCPSHASLD<br>PVEQTCSRQSQSSRESPPQQQPPRLPPEVEAGQRLRAGLLP<br>SHLPEVVAGLSCAFIVLVFVTVFLVLQLRSGFSFRGVKVYTM<br>DRGLISYKGLPPEAWQEECPSDSEEDEGRGERTAFIKDQSAL | Propeptide Furin-mature Furin |

TABLE 10-continued

List of Sequences/Constructs.

| Name | SEQ ID NO | Amino acid sequence | Annotation/ Comments |
|---|---|---|---|
| hFurin-KDEL | 38 | QKVFTNTWAVRIPGGPAVANSVARKHGFLNLGQIFGDYYH<br>FWHRGVTKRSLSPHRPRHSRLQREPQVQWLEQQVAKRRT<br>KRDVYQEPTDPKFPQQWYLSGVTQRDLNVKAAWAQGYT<br>GHGIVVSILDDGIEKNHPDLAGNYDPGASFDVNDQDPDPQ<br>PRYTQMNDNRHGTRCAGEVAAVANNGVCGVGVAYNARI<br>GGVRMLDGEVTDAVEARSLGLNPNHIHIYSASWGPEDDGK<br>TVDGPARLAEEAFFRGVSQGRGGLGSIFVWASGNGGREH<br>DSCNCDGYTNSIYTLSISSATQFGNVPWYSEACSSTLATTYSS<br>GNQNEKQIVTTDLRQKCTESHTGTSASAPLAAGIIALTLEAN<br>KNLTWRDMQHLVVQTSKPAHLNANDWATNGVGRKVSHS<br>YGYGLLDAGAMVALAQNWTTVAPQRKCIIDILTEPKDIGKR<br>LEVRKTVTACLGEPNHITRLEHAQARLTLSYNRRGDLAIHLV<br>SPMGTRSTLLAARPHDYSADGFNDWAFMTTHSWDEDPS<br>GEWVLEIENTSEANNYGTLTKFTLVLYGTAPEGLPVPPESSG<br>CKTLTSSQACVVCEEGFSLHQKSCVQHCPPGFAPQVLDTHY<br>STENDVETIRASVCAPCHASCATCQGPALTDCLSCPSHASLD<br>PVEQTCSRQSQSSRESPPQQQPPRLPPEVEAGQRLRAGLLP<br>SHLPEVVAGLSCAFIVLVFVTVFLVLQLRSGFSFRGVKVYTM<br>DRGLISYKGLPPEAWQEECPSDSEEDEGRGERTAFIKDQSAL<br>GAAKDEL | Propeptide Furin-mature Furin-<GAA>-**KDEL signal peptide** |
| hPC5/6 | 39 | RVYTNHWAVKIAGGFPEANRIASKYGFINIGQIGALKDYYHF<br>YHSRTIKRSVISSRGTHSFISMEPKVEWIQQQVVKKRTKRDY<br>DFSRAQSTYFNDPKWPSMWYMHCSDNTHPCQSDMNIEG<br>AWKRGYTGKNIVVTILDDGIERTHPDLMQNYDALASCDVN<br>GNDLDPMPRYDASNENKHGTRCAGEVAAAANNSHCTVGI<br>AFNAKIGGVRMLDGDVTDMVEAKSVSFNPQHVHIYSASW<br>GPDDDGKTVDGPAPLTRQAFENGVRMGRRGLGSVFVWA<br>SGNGGRSKDHCSCDGYTNSIYTISISSTAESGKKPWYLEECSS<br>TLATTYSSGESYDKKIITTDLRQRCTDNHTGTSASAPMAAGII<br>ALALEANPFLTWRDVQHVIVRTSRAGHLNANDWKTNAAG<br>FKVSHLYGFGLMDAEAMVMEAEKWTTVPRQHVCVESTDR<br>QIKTIRPNSAVRSIYKASGCSDNPNRHVNYLEHVVVRITITHP<br>RRGDLAIYLTSPSGTRSQLLANRLFDHSMEGFKNWEFMTIH<br>CWGERAAGDWVLEVYDTPSQLRNFKTPGKLKEWSLVLYGT<br>SVQPYSPTNEFPKVERFRYSRVEDPTDDYGTEDYAGPCDPE<br>CSEVGCDGPGPDHCNDCLHYYYKLKNNTRICVSSCPPGHYH<br>ADKKRCRKCAPNCESCFGSHGDQCMSCKYGYFLNEETNSC<br>VTHCPDGSYQDTKKNLCRKCSENCKTCTEFHNCTECRDGLS<br>LQGSRCSVSCEDGRYFNGQDCQPCHRFCATCAGAGADGCI<br>NCTEGYFMEDGRCVQSCSISYYFDHSSENGYKSCKKCDISCL<br>TCNGPGFKNCTSCPSGYLLDLGMCQMGAICKDGEYVDEH<br>GHCQTCEASCAKCQGPTQEDCTTCPMTRIFDDGRCVSNCP<br>SWKFEFENQCHPCHHTCQRCQGSGPTHCTSCGADNYGRE<br>HFLYQGECGDSCPEGHYATEGNTCLPCPDNCELCHSVHVC<br>TRCMKGYFIAPTNHTCQKLECGQGEVQDPDYEECVPCEEG<br>CLGCSLDDPGTCTSCAMGYYRFDHHCYKTCPEKTYSEEVEC<br>KACDSNCGSCDQNGCYWCEEGFFLLGGSCVRKCGPGFYG<br>DQEMGECESCHRACETCTGPGHDECSSCQEGLQLLRGMC<br>VHATKTQEEGKFWNDILRKLQPCHSSCKTCNGSATLCTSCP<br>KGAYLLAQACVSSCPQGTWPSVRSGSCENCTEACAICSGAD<br>LCKKCQMQPGHPLFLHEGRCYSKCPEGSYAEDGICERCSSP<br>CRTCEGNATNCHSCEGGHVLHHGVCQENCPERHVAVKGV<br>CKHCPEMCQDCIHEKTCKECTPEFFLHDDMCHQSCPRGFY<br>ADSRHCVPCHKDCLECSGPKADDCELCLESSWVLYDGLCLE<br>ECPAGTYYEKETKECRDCHKSCLTCSSSGTCTTCQKGLIMNP<br>RGSCMANEKCSPSEYWDEDAPGCKPCHVKCFHCMGPAED<br>QCQTCPMNSLLLNTTCVKDCPEGYYADEDSNRCAHCHSSC<br>RTCEGRHSRQCHSCRPGWFQLGKECLLQCREGYYADNSTG<br>RCERCNRSCKGCQGPRPTDCLSCDRFFFLLRSKGECHRSCP<br>DHYYVEQSTQTCERCHPTCDQCKGKGALNCLSCVWSYHL<br>MGGICTSDCLVGEYRVGEGEKFNCEKCHESCMECKGPGAK<br>NCTLCPANLVLHMDDSHCLHCCNTSDPPSAQECCDCQDTT<br>DECILRTSKVRPATEHFKTALFITSSMMLVLLLGAAVVVWKK<br>SRGRVQPAAKAGYEKLADPNKSYSSYKSSYRESTSFEEDQVI<br>EYRDRDYDEDDDDDIVYMGQDGTVYRKFKYGLLDDDDIDE<br>LEYDDESYSYYQ | Propeptide PCSK5-mature PCSK5 |
| hPC7 | 40 | LAGTGGPDGQGTGGPSWAVHLESLEGDGEEETLEQQADA<br>LAQAAGLVNAGRIGELQGHYLFVQPAGHRPALEVEAIRQQ<br>VEAVLAGHEAVRWHSEQRLLRRAKRSVHFNDPKYPQQWH<br>LNNRRSPGRDINVTGVWERNVTGRGVTVVVVDDGVEHTI<br>QDIAPNYSPEGSYDLNSNDPDPMPHPDVENGNHHGTRCA | Propeptide PCSK7-mature PCSK7 |

TABLE 10-continued

List of Sequences/Constructs.

| Name | SEQ ID NO | Amino acid sequence | Annotation/ Comments |
|---|---|---|---|
| | | GEIAAVPNNSFCAVGVAYGSRIAGIRVLDGPLTDSMEAVAF<br>NKHYQINDIYSCSWGPDDDGKTVDGPHQLGKAALQHGVI<br>AGRQGFGSIFVVASGNGGQHNDNCNYDGYANSIYTVTIGA<br>VDEEGRMPFYAEECASMLAVTFSGGDKMLRSIVTTDWDL<br>QKGTGCTEGHTGTSAAAPLAAGMIALMLQVRPCLTWRDV<br>QHIIVFTATRYEDRRAEWVTNEAGFSHSHQHGFGLLNAWR<br>LVNAAKIWTSVPYLASYVSPVLKENKAIPQSPRSLEVLWNVS<br>RMDLEMSGLKTLEHVAVTVSITHPRRGSLELKLFCPSGMMS<br>LIGAPRSMDSDPNGFNDWTFSTVRCWGERARGTYRLVIRD<br>VGDESFQVGILRQWQLTLYGSVWSAVDIRDRQRLLESAMS<br>GKYLHDDFALPCPPGLKIPEEDGYTITPNTLKTLVLVGCFTVF<br>WTVYYMLEVYLSQRNVASNQVCRSGPCHWPHRSRKAKEE<br>GTELESVPLCSSKDPDEVETESRGPPTTSDLLAPDLLEQGDW<br>SLSQNKSALDCPHQHLDVPHGKEEQIC | |
| hPACE4 | 41 | PPPRPVYTNHWAVQVLGGPAEADRVAAAHGYLNLGQIGN<br>LEDYYHFYHSKTFKRSTLSSRGPHTFLRMDPQVKWLQQQE<br>VKRRVKRQVRSDPQALYFNDPIWSNMWYLHCGDKNSRCR<br>SEMNVQAAWKRGYTGKNVVVTILDDGIERNHPDLAPNYD<br>SYASYDVNGNDYDPSPRYDASNENKHGTRCAGEVAASAN<br>NSYCIVGIAYNAKIGGIRMLDGDVTDVVEAKSLGIRPNYIDIY<br>SASWGPDDDGKTVDGPGRLAKQAFEYGIKKGRQGLGSIFV<br>WASGNGGREGDYCSCDGYTNSIYTISVSSATENGYKPWYLE<br>ECASTLATTYSSGAFYERKIVTTDLRQRCTDGHTGTSVSAPM<br>VAGIIALALEANSQLTWRDVQHLLVKTSRPAHLKASDWKV<br>NGAGHKVSHFYGFGLVDAEALVVEAKKWTAVPSQHMCVA<br>ASDKRPRSIPLVQVLRTTALTSACAEHSDQRVVYLEHVVVRT<br>SISHPRRGDLQIYLVSPSGTKSQLLAKRLLDLSNEGFTNWEF<br>MTVHCWGEKAEGQWTLEIQDLPSQVRNPEKQGKLKEWSL<br>ILYGTAEHPYHTFSAHQSRSRMLELSAPELEPPKAALSPSQV<br>EVPEDEEDYTAQSTPGSANILQTSVCHPECGDKGCDGPNA<br>DQCLNCVHFSLGSVKTSRKCVSVCPLGYFGDTAARRCRRCH<br>KGCETCSSRAATQCLSCRRGFYHHQEMNTCVTLCPAGFYA<br>DESQKNCLKCHPSCKKCVDEPEKCTVCKEGFSLARGSCIPDC<br>EPGTYFDSELIRCGECHHTCGTCVGPGREECIHCAKNFHFH<br>DWKCVPACGEGFYPEEMPGLPHKVCRRCDENCLSCAGSSR<br>NCSRCKTGFTQLGTSCITNHTCSNADETFCEMVKSNRLCER<br>KLFIQFCCRTCLLAG | Propeptide PCSK6-mature PCSK6 |
| PCS General Formula | 42 | HRR$X_1X_2$RSVDE | |
| PCS2 | 43 | *HRRRKRSVDE* | |
| PCS2a | 44 | HR*RQQR*SVDE | |
| Linker | 45 | GSHHHHHHHHGGGGS | |
| Linker | 46 | GGGGSEAAAKEAAAKGGGGS | |
| Linker | 47 | APAPAPAPAPAPAPA | |
| Linker | 48 | GSKQGKQKQGKQGS | |
| PCS1 | 49 | *RRKR* | |
| PCS3 | 50 | *PMKKRRAGVP* | |
| Linker | 51 | $(G_4S)_n$ | n = 1-10 |
| Linker | 52 | $(EAAAK)_n$ | n = 1-10 |
| Linker | 53 | $(AP)_nA$ | n = 1-10 |
| Linker | 54 | (KQGKQ)n | n = 1-10 |

TABLE 10-continued

List of Sequences/Constructs.

| Name | SEQ ID NO | Amino acid sequence | Annotation/ Comments |
|---|---|---|---|
| Linker | 55 | GGGGSGGGGSGGGGS | |
| TRI-(CODV-anti-PD-1 x anti-OX40) x anti-GITR-hulgG1-LALA-KIH-RF | 56 | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIKGGGGSGGGGSEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKGGGGSGGGGSRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | anti-OX40-VL-<(G4S)2>-anti-PD1-VL-<(G4S)2>-hulGKC |
| | 57 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSEVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPG | anti-PD1-VH-anti-OX40-VH-hulGHG1(LALA-knob) |
| | 58 | AIQLTQSPSSLSASVGDRVTITCRASQGISSALAWYQQKPGKAPKLLIYDASSLESGVPSRFSGSGSGTDFTLTISSLQPEDFATYYCQQFNSYPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | anti-GITR-VL-hulGKC |
| | 59 | QVQLVESGGGVVQPGRSLRLSCAASGFTFSSYGMHWVRQAPGKGLEWVAVIWYEGSNKYYADSVKGRFTISRDNSKNTLYLQMNSLRAEDTAVYYCARGGSMVRGDYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPG | anti-GITR-VH-hulGHG1(LALA-hole-RF) |
| TRI-(CODV-anti-PD-1 x anti-OX40) x sc- PCL2-anti-GITR-hulgG1-LALA-KIH-RF | 56 | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIKGGGGSGGGGSEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKGGGGSGGGGSRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | anti-OX40-VL-<(G4S)2>-anti-PD1-VL-<(G4S)2>-hulGKC |
| | 57 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSEVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPG | anti-PD1-VH-anti-OX40-VH-hulGHG1(LALA-knob) |
| | 60 | AIQLTQSPSSLSASVGDRVTITCRASQGISSALAWYQQKPGKAPKLLIYDASSLESGVPSRFSGSGSGTDFTLTISSLQPEDFATYYCQQFNSYPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECHRRRKRSVDEGGGGSGGGGSGGGGSGGGGSGGGGSGGGGSHRRRKRSVDEQVQLVESGGGVVQPGRSL | anti-GITR-VL-hulGKC-[PCS2]-<(G4S)6>[PCS2]-anti-GITR-VH-hulGHG1(LALA-hole-RF) |

TABLE 10-continued

List of Sequences/Constructs.

| Name | SEQ ID NO | Amino acid sequence | Annotation/ Comments |
|---|---|---|---|
| | | RLSCAASGFTFSSYGMHWVRQAPGKGLEWVAVIWYEGSNKYYADSVKGRFTISRDNSKNTLYLQMNSLRAEDTAVYYCARGGSMVRGDYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPG | |
| TRI-(CODV-anti-PD-1 x anti-OX40) x sc- PCL2a-anti-GITR-hulgG1-LALA-KIH-RF | 56 | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIKGGGGSGGGGSEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKGGGGSGGGGSRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | anti-OX40-VL-<(G4S)2>-anti-PD1-VL-<(G4S)2>-hulGKC |
| | 57 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSEVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPG | anti-PD1-VH-anti-OX40-VH-hulGHG1(LALA-knob) |
| | 61 | AIQLTQSPSSLSASVGDRVTITCRASQGISSALAWYQQKPGKAPKLLIYDASSLESGVPSRFSGSGSGTDFTLTISSLQPEDFATYYCQQFNSYPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECHRRQQRSVDEGGGGSGGGGSGGGGSGGGGSGGGGSGGGGSHRRQQRSVDEQVQLVESGGGVVQPGRSLRLSCAASGFTFSSYGMHWVRQAPGKGLEWVAVIWYEGSNKYYADSVKGRFTISRDNSKNTLYLQMNSLRAEDTAVYYCARGGSMVRGDYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPG | anti-GITR-VL-hulGKC-[PCS2a]-<(G4S)6>-[PCS2a]-anti-GITR-VH-hulGHG1(LALA-hole-RF) |
| TRI-(CODV-anti-GITR x anti-PD-1) x sc-PCL2-anti-OX40-hulgG1-LALA-KIH-RF | 62 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKGGGGSGGGGSAIQLTQSPSSLSASVGDRVTITCRASQGISSALAWYQQKPGKAPKLLIYDASSLESGVPSRFSGSGSGTDFTLTISSLQPEDFATYYCQQFNSYPYTFGQGTKLEIKGGGGSGGGGSRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | anti-PD1-VL-<(G4S)2>-anti-GITR-VL-<(G4S)2>-hulGKC |
| | 63 | QVQLVESGGGVVQPGRSLRLSCAASGFTFSSYGMHWVRQAPGKGLEWVAVIWYEGSNKYYADSVKGRFTISRDNSKNTLYLQMNSLRAEDTAVYYCARGGSMVRGDYYYGMDVWGQGTTVTVSSQVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGK | anti-GITR-VH-anti-PD1-VH-hulGHG1(LALA-knob) |

TABLE 10-continued

List of Sequences/Constructs.

| Name | SEQ ID NO | Amino acid sequence | Annotation/ Comments |
|---|---|---|---|
| | | EYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPG | |
| | 64 | **DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*HRRRKRSVDE*GGGGSGGGGSGGGGSGGGGSGGGGSGGGGS*HRRRKRSVDE****EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS***ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPG | **anti-OX40-VL**-hulGKC-[*PCS2*]-<(G4S)6>-[*PCS2*]-anti-OX40-VH-hulGHG1(LALA-hole-RF) |
| TRI-(CODV-anti-GITR x anti-PD-1)x sc-PCL2a-anti-OX40-hulgG1-LALA-KIH-RF | 62 | **EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK**GGGGSGGGGS***AIQLTQSPSSLSASVGDRVTITCRASQGISSALAWYQQKPGKAPKLLIYDASSLESGVPSRFSGSGSGTDFTLTISSLQPEDFATYYCQQFNSYPYTFGQGTKLEIK***GGGGSGGGGSRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | **anti-PD1-VL-**<(G4S)2>-***anti-GITR-VL***-<(G4S)2>-hulGKC |
| | 63 | **QVQLVESGGGVVQPGRSLRLSCAASGFTFSSYGMHWVRQAPGKGLEWVAVIWYEGSNKYYADSVKGRFTISRDNSKNTLYLQMNSLRAEDTAVYYCARGGSMVRGDYYYGMDVWGQGTTVTVSS*****QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS***ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPG | **anti-GITR-VH-*anti-PD1-VH-*** hulGHG1(LALA-knob) |
| | 65 | **DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*HRRQQRSVDE*GGGGSGGGGSGGGGSGGGGSGGGGSGGGGS*HRRQQRSVDE****EVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSS***ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPG | **anti-OX40-VL**-hulGKC-[*PCS2a*]-<(G4S)6>-[*PCS2a*]-***anti-OX40-VH***-hulGHG1(LALA-hole-RF) |

TABLE 10-continued

List of Sequences/Constructs.

| Name | SEQ ID NO | Amino acid sequence | Annotation/ Comments |
|---|---|---|---|
| TRI-(CODV-anti-PD-1 x anti-GITR) x sc-PCL2-anti-OX40-hulgG1-LALA-KIH-RF | 66 | AIQLTQSPSSLSASVGDRVTITCRASQGISSALAWYQQKPGKAPKLLIYDASSLESGVPSRFSGSGSGTDFTLTISSLQPEDFATYYCQQFNSYPYTFGQGTKLEIKGGGGSGGGGSEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKGGGGSGGGGSRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | anti-GITR-VL-<(G4S)2>-anti-PD1-VL-<(G4S)2>-hulGKC |
| | 67 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSQVQLVESGGGVVQPGRSLRLSCAASGFTFSSYGMHWVRQAPGKGLEWVAVIWYEGSNKYYADSVKGRFTISRDNSKNTLYLQMNSLRAEDTAVYYCARGGSMVRGDYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPG | anti-PD1-VH-anti-GITR-VH-hulGHG1(LALA-knob) |
| | 68 | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECHRRRKRSVDEGGGGSGGGGSGGGGSGGGGSGGGGSGGGGSHRRRKRSVDEEVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPG | anti-OX40-VL-hulGKC-[PCS2]-<(G4S)6>-[PCS2]-anti-OX40-VH-hulGHG1(LALA-hole-RF) |
| TRI-(CODV-anti-PD-1 x anti-GITR) x sc-PCL2a-anti-OX40-hulgG1-LALA-KIH-RF | 66 | AIQLTQSPSSLSASVGDRVTITCRASQGISSALAWYQQKPGKAPKLLIYDASSLESGVPSRFSGSGSGTDFTLTISSLQPEDFATYYCQQFNSYPYTFGQGTKLEIKGGGGSGGGGSEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKGGGGSGGGGSRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | anti-GITR-VL-<(G4S)2>-anti-PD1-VL-<(G4S)2>-hulGKC |
| | 67 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSQVQLVESGGGVVQPGRSLRLSCAASGFTFSSYGMHWVRQAPGKGLEWVAVIWYEGSNKYYADSVKGRFTISRDNSKNTLYLQMNSLRAEDTAVYYCARGGSMVRGDYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPG | anti-PD1-VH-anti-GITR-VH-hulGHG1(LALA-knob) |
| | 69 | DIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECHRRQQRSVDEGGGGSGGGGSGGGGSGGG | anti-OX40-VL-hulGKC-[PCS2a]-<(G4S)6>-[PCS2a]-anti-OX40-VH-hulGHG1(LALA-hole-RF) |

TABLE 10-continued

List of Sequences/Constructs.

| Name | SEQ ID NO | Amino acid sequence | Annotation/ Comments |
|---|---|---|---|
| | | GSGGGGSGGGGSHRRQQRSVDEEVQLVQSGAEVKKPGA<br>SVKVSCKASGYTFTDSYMSWVRQAPGQGLEWIGDMYPD<br>NGDSSYNQKFRERVTITRDTSTSTAYLELSSLRSEDTAVYYC<br>VLAPRWYFSVWGQGTLVTVSSASTKGPSVFPLAPSSKSTS<br>GGTAALGCLVKDYFPEPVTVSWNSGALTSGVHTFPAVLQSS<br>GLYSLSSVVTVPSSSLGTQTYICNVNHKPSNTKVDKKVEPKS<br>CDKTHTCPPCPAPEAAGGPSVFLFPPKPKDTLMISRTPEVTC<br>VVVDVSHEDPEVKFNWYVDGVEVHNAKTKPREEQYNSTY<br>RVVSVLTVLHQDWLNGKEYKCKVSNKALPAPIEKTISKAKG<br>QPREPQVCTLPPSRDELTKNQVSLSCAVKGFYPSDIAVEWE<br>SNGQPENNYKTTPPVLDSDGSFFLVSKLTVDKSRWQQGNV<br>FSCSVMHEALHNRFTQKSLSLSPG | |
| sLC-Tandem-(anti-PD-1)x(anti-4.1BB)-PCL2 hulgG1-LALA_AB0-2 | 70 | EIVLTQSPATLSLSPGERATLSCRASQSVSSYLAWYQQKPG<br>QAPRLLIYDASNRATGIPARFSGSGSGTDFTLTISSLEPEDF<br>AVYYCQQSSNWPRTFGQGTKVEIKRTVAAPSVFIFPPSDE<br>QLKSGTASVVCLLNNFYPREAKVQWKVDNALQSGNSQESV<br>TEQDSKDSTYSLSSTLTLSKADYEKHKVYACEVTHQGLSSPV<br>TKSFNRGECHRRRKRSVDEGGGGSGGGGSGGGGSHRRRK<br>RSVDEEIVLTQSPATLSLSPGERATLSCRASQSVSSYLAWYQ<br>QKPGQAPRLLIYDASNRATGIPARFSGSGSGTDFTLTISSLE<br>PEDFAVYYCQQRSNWPPALTFGGGTKVEIKRTVAAPSVFIF<br>PPSDEQLKSGTASVVCLLNNFYPREAKVQWKVDNALQSGN<br>SQESVTEQDSKDSTYSLSSTLTLSKADYEKHKVYACEVTHQG<br>LSSPVTKSFNRGEC | anti-PD1-VL-hulGKC-[PCS2]-<(G4S)3>-[PCS2]-anti-4.1BB-VL-hulGKC |
| | 71 | QVQLVESGGGVVQPGRSLRLDCKASGITFSNSGMHWVR<br>QAPGKGLEWVAVIWYDGSKRYYADSVKGRFTISRDNSKN<br>TLFLQMNSLRAEDTAVYYCATNDDYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKKVEPKSCDKTHTGGGGSGGGGSGGGGSQV<br>QLQQWGAGLLKPSETLSLTCAVYGGSFSGYYWSWIRQSP<br>EKGLEWIGEINHGGYVTYNPSLESRVTISVDTSKNQFSLKLS<br>SVTAADTAVYYCARDYGPGNYDWYFDLWGRGTLVTVSS<br>ASTKGPSVFPLAPSSKSTSGGTAALGCLVKDYFPEPVTVSW<br>NSGALTSGVHTFPAVLQSSGLYSLSSVVTVPSSSLGTQTYICN<br>VNHKPSNTKVDKKVEPKSCDKTHTCPPCPAPEAAGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSRDELTKNQVS<br>LTCLVKGFYPSDIAVEWESNGQPENNYKTTPPVLDSDGSFFL<br>YSKLTVDKSRWQQGNVFSCSVMHEALHNHYTQKSLSLSPG | anti-PD1-VH-hulGH-G11-hulGH-H1-<(G4S)3>-anti-4.1BB-VH-hulGHG1-(LALA) |
| sLC-Tandem-(anti-PD-1)x(anti-4.1BB)-PCL2a hulgG1-LALA_AB0-2 | 72 | EIVLTQSPATLSLSPGERATLSCRASQSVSSYLAWYQQKPG<br>QAPRLLIYDASNRATGIPARFSGSGSGTDFTLTISSLEPEDF<br>AVYYCQQSSNWPRTFGQGTKVEIKRTVAAPSVFIFPPSDE<br>QLKSGTASVVCLLNNFYPREAKVQWKVDNALQSGNSQESV<br>TEQDSKDSTYSLSSTLTLSKADYEKHKVYACEVTHQGLSSPV<br>TKSFNRGECHRRQQRSVDEGGGGSGGGGSGGGGSHRRQ<br>QRSVDEEIVLTQSPATLSLSPGERATLSCRASQSVSSYLAWY<br>QQKPGQAPRLLIYDASNRATGIPARFSGSGSGTDFTLTISSL<br>EPEDFAVYYCQQRSNWPPALTFGGGTKVEIKRTVAAPSVFI<br>FPPSDEQLKSGTASVVCLLNNFYPREAKVQWKVDNALQSG<br>NSQESVTEQDSKDSTYSLSSTLTLSKADYEKHKVYACEVTHQ<br>GLSSPVTKSFNRGEC | anti-PD1-VL-hulGKC-[PCS2a]-<(G4S)3>-[PCS2a]-anti-4.1BB-VL-hulGKC |
| | 71 | QVQLVESGGGVVQPGRSLRLDCKASGITFSNSGMHWVR<br>QAPGKGLEWVAVIWYDGSKRYYADSVKGRFTISRDNSKN<br>TLFLQMNSLRAEDTAVYYCATNDDYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKKVEPKSCDKTHTGGGGSGGGGSGGGGSQV<br>QLQQWGAGLLKPSETLSLTCAVYGGSFSGYYWSWIRQSP<br>EKGLEWIGEINHGGYVTYNPSLESRVTISVDTSKNQFSLKLS<br>SVTAADTAVYYCARDYGPGNYDWYFDLWGRGTLVTVSS<br>ASTKGPSVFPLAPSSKSTSGGTAALGCLVKDYFPEPVTVSW<br>NSGALTSGVHTFPAVLQSSGLYSLSSVVTVPSSSLGTQTYICN<br>VNHKPSNTKVDKKVEPKSCDKTHTCPPCPAPEAAGGPSVFL<br>FPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSRDELTKNQVS<br>LTCLVKGFYPSDIAVEWESNGQPENNYKTTPPVLDSDGSFFL<br>YSKLTVDKSRWQQGNVFSCSVMHEALHNHYTQKSLSLSPG | anti-PD1-VH-hulGH-G11-hulGH-H1-<(G4S)3>-anti-4.1BB-VH-hulGHG1-(LALA) |

TABLE 10-continued

List of Sequences/Constructs.

| Name | SEQ ID NO | Amino acid sequence | Annotation/ Comments |
|---|---|---|---|
| sLC-Tandem-(anti-PD-1)x(anti-OX40)-PCL2 hulgG1-LALA_AC0-2 | 73 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECHRRRKRSVDEGGGGSGGGGSGGGGSHRRRKRSVDEDIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | anti-PD1-VL-hulGKC-[PCS2]-<(G4S)3>-[PCS2]-anti-OX40-VL-hulGKC |
| | 74 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTGGGGSGGGGSGGGGSEVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | anti-PD1-VH-hulGH-G11-hulGH-H1-<(G4S)3>-anti-OX40-VH-hulGHG1-(LALA) |
| sLC-Tandem-(anti-PD-1)x(anti-OX40)-PCL2a hulgG1-LALA_ACO-2 | 75 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECHRRQQRSVDEGGGGSGGGGSGGGGSHRRQQRSVDEDIQMTQSPSSLSASVGDRVTITCRASQDISNYLNWYQQKPGKAPKLLIYYTSRLRSGVPSRFSGSGSGTDFTLTISSLQPEDFATYYCQQGHTLPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | anti-PD1-VL-hulGKC-[PCS2a]><(G4S)3>-[PCS2a]-anti-OX40-VL-hulGKC |
| | 74 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTGGGGSGGGGSGGGGSEVQLVQSGAEVKKPGASVKVSCKASGYTFTDSYMSWVRQAPGQGLEWIGDMYPDNGDSSYNQKFRERVTITRDTSTSTAYLELSSLRSEDTAVYYCVLAPRWYFSVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | anti-PD1-VH-hulGH-G11-hulGH-H1-<(G4S)3>-anti-OX40-VH-hulGHG1-(LALA) |

The invention claimed is:

1. A protein comprising at least one polypeptide chain having the formula $PP_1$-PCL-$PP_2$, wherein $PP_1$ is a first polypeptide, $PP_2$ is a second polypeptide, and PCL is a furin and/or furin-like protease-cleavable linker comprising at least one furin and/or furin-like protease-cleavage site comprising the amino acid sequence $HRRX_1X_2RSVDE$ (SEQ ID NO: 42), wherein $X_1$ and $X_2$ are independently selected from the group consisting of KK, KQ, KR, QK, QQ, QR, RK, RQ and RR.

2. The protein of claim 1, wherein the at least one protease-cleavage site comprises the amino acid sequence HRRRKRSVDE (SEQ ID NO: 43) or the amino acid sequence HRRQQRSVDE (SEQ ID NO: 44).

3. The protein of claim 1, wherein protease-cleavage of the linker results in a change in activity of the protein.

4. The protein of claim 1, wherein the protease-cleavable linker comprises two protease-cleavage sites, wherein the two protease-cleavage sites are located at the N-terminus and at the C-terminus of the protease-cleavable linker, respectively, wherein the two protease-cleavage sites are the same or different.

5. The protein of claim 1, wherein $PP_1$ comprises at least one immunoglobulin constant region and/or at least one immunoglobulin variable region, and/or wherein $PP_2$ comprises at least one immunoglobulin constant region and/or at least one immunoglobulin variable region.

6. The protein of claim 1, wherein the protein is an antibody, antibody derivative, a single chain antibody, or a multispecific single chain antibody.

7. The protein of claim 1, comprising a polypeptide chain having a formula selected from the group consisting of:

VL-CL-PCL-VH-CH1-hinge-CH2-CH3, (a)

wherein

VL is an immunoglobulin light chain variable region;

CL is an immunoglobulin light chain constant region;

VH is an immunoglobulin heavy chain variable region;

CH1 is an immunoglobulin CH1 heavy chain constant region;

hinge is an immunoglobulin hinge region;

CH2 is an immunoglobulin CH2 heavy chain constant region;

CH3 is an immunoglobulin CH3 heavy chain constant region; and

PCL is the protease-cleavable linker;

$VL_a$-$CL_a$-PCL-$VL_b$-$CL_b$, (b)

wherein $VL_a$ is a first immunoglobulin light chain variable region;

$VL_b$ is a second immunoglobulin light chain variable region;

$CL_a$ is a first immunoglobulin light chain constant region;

$CL_b$ is a second immunoglobulin light chain constant region; and

PCL is the protease-cleavable linker; and $VL_a$-$CL_a$-PCL-$VL_b$-$CL_b$-L-hinge-CH2-CH3 (c)

wherein $VL_a$ is a first immunoglobulin light chain variable region;

$VL_b$ is a second immunoglobulin light chain variable region;

$CL_a$ is a first immunoglobulin light chain constant region;

$CL_b$ is a second immunoglobulin light chain constant region;

L is an optional linker;

hinge is an immunoglobulin hinge region;

CH2 is an immunoglobulin CH2 heavy chain constant region;

CH3 is an immunoglobulin CH3 heavy chain constant region; and

PCL is the protease-cleavable linker.

8. A nucleic acid or set of nucleic acids encoding the protein of claim 1.

9. A vector or set of vectors comprising the nucleic acid or set of nucleic acids of claim 8.

10. A host cell comprising a protein of claim 1.

11. A method of producing a protein comprising the steps:

i) culturing a host cell according to claim 10; and ii) isolating the protein from the host cell.

12. A protein obtained by the method of claim 11.

13. A protein obtained by furin and/or furin-like protease-cleavage of a protein of claim 1.

14. The protein of claim 1, wherein the protein is a therapeutically active protein.

15. The protein of claim 12, wherein the protein is a therapeutically active protein.

16. The protein of claim 13, wherein the protein is a therapeutically active protein.

17. A host cell comprising a nucleic acid or set of nucleic acids of claim 8.

18. A host cell comprising a vector or set of vectors of claim 9.

19. The protein of claim 3, wherein the change in activity is binding or increased binding to at least one antigen.

20. The host cell of claim 10, wherein the host cell is a mammalian cell.

21. The protein of claim 1, wherein $PP_1$ comprises an immunoglobulin constant region and $PP_2$ comprises an immunoglobulin variable region.

22. The protein of claim 1, wherein $PP_1$ comprises an immunoglobulin variable region and $PP_2$ comprises an immunoglobulin constant region.

23. The protein of claim 1, wherein $PP_1$ comprises an immunoglobulin constant region and $PP_2$ comprises an immunoglobulin constant region.

24. The protein of claim 1, wherein $PP_1$ comprises an immunoglobulin variable region and $PP_2$ comprises an immunoglobulin variable region.

25. The host cell of claim 17, wherein the host cell is a mammalian cell.

26. The host cell of claim 18, wherein the host cell is a mammalian cell.

* * * * *

SEQUENCE LISTING

<160> NUMBER OF SEQ ID NOS: 75

<210> SEQ ID NO 1
<211> LENGTH: 724
<212> TYPE: PRT
<213> ORGANISM: Artificial Sequence
<220> FEATURE:
<223> OTHER INFORMATION: anti-IL4-VL-huIGKC-[PCS1]-<(G4S)10>-[PCS1]-
anti-IL4-VH-huIGHG1

<400> SEQUENCE: 1

```
Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Gly Gly Gly Ser Gly
    210                 215                 220

Gly Gly Gly Ser Gly Gly Gly Gly Ser Gly Gly Gly Gly Ser Gly Gly
225                 230                 235                 240

Gly Gly Ser Gly Gly Gly Gly Ser Gly Gly Gly Gly Ser Gly Gly Gly
                245                 250                 255

Gly Ser Gly Gly Gly Gly Ser Gly Gly Gly Gly Ser Arg Arg Lys Arg
            260                 265                 270

Gln Val Gln Leu Gln Gln Ser Gly Pro Glu Leu Val Lys Pro Gly Ala
        275                 280                 285

Ser Val Lys Ile Ser Cys Lys Ala Ser Gly Tyr Ser Phe Thr Ser Tyr
    290                 295                 300

Trp Ile His Trp Ile Lys Gln Arg Pro Gly Gln Gly Leu Glu Trp Ile
305                 310                 315                 320

Gly Met Ile Asp Pro Ser Asp Gly Glu Thr Arg Leu Asn Gln Arg Phe
                325                 330                 335

Gln Gly Arg Ala Thr Leu Thr Val Asp Glu Ser Thr Ser Thr Ala Tyr
            340                 345                 350
```

-continued

```
Met Gln Leu Arg Ser Pro Thr Ser Glu Asp Ser Ala Val Tyr Tyr Cys
        355                 360                 365

Thr Arg Leu Lys Glu Tyr Gly Asn Tyr Asp Ser Phe Tyr Phe Asp Val
    370                 375                 380

Trp Gly Ala Gly Thr Leu Val Thr Val Ser Ser Ala Ser Thr Lys Gly
385                 390                 395                 400

Pro Ser Val Phe Pro Leu Ala Pro Ser Ser Lys Ser Thr Ser Gly Gly
                405                 410                 415

Thr Ala Ala Leu Gly Cys Leu Val Lys Asp Tyr Phe Pro Glu Pro Val
            420                 425                 430

Thr Val Ser Trp Asn Ser Gly Ala Leu Thr Ser Gly Val His Thr Phe
        435                 440                 445

Pro Ala Val Leu Gln Ser Ser Gly Leu Tyr Ser Leu Ser Ser Val Val
    450                 455                 460

Thr Val Pro Ser Ser Ser Leu Gly Thr Gln Thr Tyr Ile Cys Asn Val
465                 470                 475                 480

Asn His Lys Pro Ser Asn Thr Lys Val Asp Lys Lys Val Glu Pro Lys
                485                 490                 495

Ser Cys Asp Lys Thr His Thr Cys Pro Pro Cys Pro Ala Pro Glu Leu
            500                 505                 510

Leu Gly Gly Pro Ser Val Phe Leu Phe Pro Pro Lys Pro Lys Asp Thr
        515                 520                 525

Leu Met Ile Ser Arg Thr Pro Glu Val Thr Cys Val Val Val Asp Val
    530                 535                 540

Ser His Glu Asp Pro Glu Val Lys Phe Asn Trp Tyr Val Asp Gly Val
545                 550                 555                 560

Glu Val His Asn Ala Lys Thr Lys Pro Arg Glu Glu Gln Tyr Asn Ser
                565                 570                 575

Thr Tyr Arg Val Val Ser Val Leu Thr Val Leu His Gln Asp Trp Leu
            580                 585                 590

Asn Gly Lys Glu Tyr Lys Cys Lys Val Ser Asn Lys Ala Leu Pro Ala
        595                 600                 605

Pro Ile Glu Lys Thr Ile Ser Lys Ala Lys Gly Gln Pro Arg Glu Pro
    610                 615                 620

Gln Val Tyr Thr Leu Pro Pro Ser Arg Asp Glu Leu Thr Lys Asn Gln
625                 630                 635                 640

Val Ser Leu Thr Cys Leu Val Lys Gly Phe Tyr Pro Ser Asp Ile Ala
                645                 650                 655

Val Glu Trp Glu Ser Asn Gly Gln Pro Glu Asn Asn Tyr Lys Thr Thr
            660                 665                 670

Pro Pro Val Leu Asp Ser Asp Gly Ser Phe Phe Leu Tyr Ser Lys Leu
        675                 680                 685

Thr Val Asp Lys Ser Arg Trp Gln Gln Gly Asn Val Phe Ser Cys Ser
    690                 695                 700

Val Met His Glu Ala Leu His Asn His Tyr Thr Gln Lys Ser Leu Ser
705                 710                 715                 720

Leu Ser Pro Gly


<210> SEQ ID NO 2
<211> LENGTH: 714
<212> TYPE: PRT
<213> ORGANISM: Artificial Sequence
<220> FEATURE:
<223> OTHER INFORMATION: anti-IL4-VL-huIGKC-[PCS1]-<(G4S)8>-[PCS1]-anti-
      IL4-VH-huIGHG1
```

<400> SEQUENCE: 2

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Gly Gly Gly Ser Gly
    210                 215                 220

Gly Gly Gly Ser Gly Gly Gly Gly Ser Gly Gly Gly Gly Ser Gly Gly
225                 230                 235                 240

Gly Gly Ser Gly Gly Gly Gly Ser Gly Gly Gly Gly Ser Gly Gly Gly
                245                 250                 255

Gly Ser Arg Arg Lys Arg Gln Val Gln Leu Gln Gln Ser Gly Pro Glu
            260                 265                 270

Leu Val Lys Pro Gly Ala Ser Val Lys Ile Ser Cys Lys Ala Ser Gly
        275                 280                 285

Tyr Ser Phe Thr Ser Tyr Trp Ile His Trp Ile Lys Gln Arg Pro Gly
    290                 295                 300

Gln Gly Leu Glu Trp Ile Gly Met Ile Asp Pro Ser Asp Gly Glu Thr
305                 310                 315                 320

Arg Leu Asn Gln Arg Phe Gln Gly Arg Ala Thr Leu Thr Val Asp Glu
                325                 330                 335

Ser Thr Ser Thr Ala Tyr Met Gln Leu Arg Ser Pro Thr Ser Glu Asp
            340                 345                 350

Ser Ala Val Tyr Tyr Cys Thr Arg Leu Lys Glu Tyr Gly Asn Tyr Asp
        355                 360                 365

Ser Phe Tyr Phe Asp Val Trp Gly Ala Gly Thr Leu Val Thr Val Ser
    370                 375                 380

Ser Ala Ser Thr Lys Gly Pro Ser Val Phe Pro Leu Ala Pro Ser Ser
385                 390                 395                 400

Lys Ser Thr Ser Gly Gly Thr Ala Ala Leu Gly Cys Leu Val Lys Asp

```
                405                 410                 415

Tyr Phe Pro Glu Pro Val Thr Val Ser Trp Asn Ser Gly Ala Leu Thr
            420                 425                 430

Ser Gly Val His Thr Phe Pro Ala Val Leu Gln Ser Ser Gly Leu Tyr
        435                 440                 445

Ser Leu Ser Ser Val Val Thr Val Pro Ser Ser Ser Leu Gly Thr Gln
    450                 455                 460

Thr Tyr Ile Cys Asn Val Asn His Lys Pro Ser Asn Thr Lys Val Asp
465                 470                 475                 480

Lys Lys Val Glu Pro Lys Ser Cys Asp Lys Thr His Thr Cys Pro Pro
                485                 490                 495

Cys Pro Ala Pro Glu Leu Leu Gly Gly Pro Ser Val Phe Leu Phe Pro
            500                 505                 510

Pro Lys Pro Lys Asp Thr Leu Met Ile Ser Arg Thr Pro Glu Val Thr
        515                 520                 525

Cys Val Val Val Asp Val Ser His Glu Asp Pro Glu Val Lys Phe Asn
    530                 535                 540

Trp Tyr Val Asp Gly Val Glu Val His Asn Ala Lys Thr Lys Pro Arg
545                 550                 555                 560

Glu Glu Gln Tyr Asn Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
        595                 600                 605

Gly Gln Pro Arg Glu Pro Gln Val Tyr Thr Leu Pro Pro Ser Arg Asp
    610                 615                 620

Glu Leu Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Lys Leu Thr Val Asp Lys Ser Arg Trp Gln Gln Gly
        675                 680                 685

Asn Val Phe Ser Cys Ser Val Met His Glu Ala Leu His Asn His Tyr
    690                 695                 700

Thr Gln Lys Ser Leu Ser Leu Ser Pro Gly
705                 710


<210> SEQ ID NO 3
<211> LENGTH: 704
<212> TYPE: PRT
<213> ORGANISM: Artificial Sequence
<220> FEATURE:
<223> OTHER INFORMATION: anti-IL4-VL-huIGKC-[PCS1]-<(G4S)6>-[PCS1]-anti-
      IL4-VH-huIGHG1

<400> SEQUENCE: 3

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45
```

-continued

```
Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Gly Gly Gly Ser Gly
    210                 215                 220

Gly Gly Gly Ser Gly Gly Gly Gly Ser Gly Gly Gly Gly Ser Gly Gly
225                 230                 235                 240

Gly Gly Ser Gly Gly Gly Gly Ser Arg Arg Lys Arg Gln Val Gln Leu
                245                 250                 255

Gln Gln Ser Gly Pro Glu Leu Val Lys Pro Gly Ala Ser Val Lys Ile
            260                 265                 270

Ser Cys Lys Ala Ser Gly Tyr Ser Phe Thr Ser Tyr Trp Ile His Trp
        275                 280                 285

Ile Lys Gln Arg Pro Gly Gln Gly Leu Glu Trp Ile Gly Met Ile Asp
    290                 295                 300

Pro Ser Asp Gly Glu Thr Arg Leu Asn Gln Arg Phe Gln Gly Arg Ala
305                 310                 315                 320

Thr Leu Thr Val Asp Glu Ser Thr Ser Thr Ala Tyr Met Gln Leu Arg
                325                 330                 335

Ser Pro Thr Ser Glu Asp Ser Ala Val Tyr Tyr Cys Thr Arg Leu Lys
            340                 345                 350

Glu Tyr Gly Asn Tyr Asp Ser Phe Tyr Phe Asp Val Trp Gly Ala Gly
        355                 360                 365

Thr Leu Val Thr Val Ser Ser Ala Ser Thr Lys Gly Pro Ser Val Phe
    370                 375                 380

Pro Leu Ala Pro Ser Ser Lys Ser Thr Ser Gly Gly Thr Ala Ala Leu
385                 390                 395                 400

Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
        435                 440                 445

Ser Ser Leu Gly Thr Gln Thr Tyr Ile Cys Asn Val Asn His Lys Pro
    450                 455                 460

Ser Asn Thr Lys Val Asp Lys Lys Val Glu Pro Lys Ser Cys Asp Lys
```

```
465                 470                 475                 480

Thr His Thr Cys Pro Pro Cys Pro Ala Pro Glu Leu Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Ser Arg Asp Glu Leu Thr Lys Asn Gln Val Ser Leu Thr
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
        675                 680                 685

Ala Leu His Asn His Tyr Thr Gln Lys Ser Leu Ser Leu Ser Pro Gly
    690                 695                 700
```

<210> SEQ ID NO 4
<211> LENGTH: 694
<212> TYPE: PRT
<213> ORGANISM: Artificial Sequence
<220> FEATURE:
<223> OTHER INFORMATION: anti-IL4-VL-huIGKC-[PCS1]-<(G4S)4>-[PCS1]-anti-IL4-VH-huIGHG1

<400> SEQUENCE: 4

```
Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Gly Gly Gly Ser Gly
    210                 215                 220

Gly Gly Gly Ser Gly Gly Gly Gly Ser Gly Gly Gly Gly Ser Arg Arg
225                 230                 235                 240

Lys Arg Gln Val Gln Leu Gln Gln Ser Gly Pro Glu Leu Val Lys Pro
                245                 250                 255

Gly Ala Ser Val Lys Ile Ser Cys Lys Ala Ser Gly Tyr Ser Phe Thr
            260                 265                 270

Ser Tyr Trp Ile His Trp Ile Lys Gln Arg Pro Gly Gln Gly Leu Glu
        275                 280                 285

Trp Ile Gly Met Ile Asp Pro Ser Asp Gly Glu Thr Arg Leu Asn Gln
    290                 295                 300

Arg Phe Gln Gly Arg Ala Thr Leu Thr Val Asp Glu Ser Thr Ser Thr
305                 310                 315                 320

Ala Tyr Met Gln Leu Arg Ser Pro Thr Ser Glu Asp Ser Ala Val Tyr
                325                 330                 335

Tyr Cys Thr Arg Leu Lys Glu Tyr Gly Asn Tyr Asp Ser Phe Tyr Phe
            340                 345                 350

Asp Val Trp Gly Ala Gly Thr Leu Val Thr Val Ser Ser Ala Ser Thr
        355                 360                 365

Lys Gly Pro Ser Val Phe Pro Leu Ala Pro Ser Ser Lys Ser Thr Ser
    370                 375                 380

Gly Gly Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
                405                 410                 415

Thr Phe Pro Ala Val Leu Gln Ser Ser Gly Leu Tyr Ser Leu Ser Ser
            420                 425                 430

Val Val Thr Val Pro Ser Ser Ser Leu Gly Thr Gln Thr Tyr Ile Cys
        435                 440                 445

Asn Val Asn His Lys Pro Ser Asn Thr Lys Val Asp Lys Lys Val Glu
    450                 455                 460

Pro Lys Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
            500                 505                 510

Asp Val Ser His Glu Asp Pro Glu Val Lys Phe Asn Trp Tyr Val Asp
        515                 520                 525

Gly Val Glu Val His Asn Ala Lys Thr Lys Pro Arg Glu Glu Gln Tyr
    530                 535                 540

Asn Ser Thr Tyr Arg Val Val Ser Val Leu Thr Val Leu His Gln Asp
```

-continued

```
545                 550                 555                 560

Trp Leu Asn Gly Lys Glu Tyr Lys Cys Lys Val Ser Asn Lys Ala Leu
                565                 570                 575

Pro Ala Pro Ile Glu Lys Thr Ile Ser Lys Ala Lys Gly Gln Pro Arg
            580                 585                 590

Glu Pro Gln Val Tyr Thr Leu Pro Pro Ser Arg Asp Glu Leu Thr Lys
        595                 600                 605

Asn Gln Val Ser Leu Thr Cys Leu Val Lys Gly Phe Tyr Pro Ser Asp
    610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Tyr Ser
                645                 650                 655

Lys Leu Thr Val Asp Lys Ser Arg Trp Gln Gln Gly Asn Val Phe Ser
            660                 665                 670

Cys Ser Val Met His Glu Ala Leu His Asn His Tyr Thr Gln Lys Ser
        675                 680                 685

Leu Ser Leu Ser Pro Gly
    690


<210> SEQ ID NO 5
<211> LENGTH: 684
<212> TYPE: PRT
<213> ORGANISM: Artificial Sequence
<220> FEATURE:
<223> OTHER INFORMATION: anti-IL4-VL-huIGKC-[PCS1]-<(G4S)2>-[PCS1]-anti-
      IL4-VH-huIGHG1

<400> SEQUENCE: 5

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

-continued

```
Phe Asn Arg Gly Glu Cys Arg Arg Lys Arg Gly Gly Gly Gly Ser Gly
    210                 215                 220

Gly Gly Gly Ser Arg Arg Lys Arg Gln Val Gln Leu Gln Gln Ser Gly
225                 230                 235                 240

Pro Glu Leu Val Lys Pro Gly Ala Ser Val Lys Ile Ser Cys Lys Ala
                245                 250                 255

Ser Gly Tyr Ser Phe Thr Ser Tyr Trp Ile His Trp Ile Lys Gln Arg
            260                 265                 270

Pro Gly Gln Gly Leu Glu Trp Ile Gly Met Ile Asp Pro Ser Asp Gly
        275                 280                 285

Glu Thr Arg Leu Asn Gln Arg Phe Gln Gly Arg Ala Thr Leu Thr Val
    290                 295                 300

Asp Glu Ser Thr Ser Thr Ala Tyr Met Gln Leu Arg Ser Pro Thr Ser
305                 310                 315                 320

Glu Asp Ser Ala Val Tyr Tyr Cys Thr Arg Leu Lys Glu Tyr Gly Asn
                325                 330                 335

Tyr Asp Ser Phe Tyr Phe Asp Val Trp Gly Ala Gly Thr Leu Val Thr
            340                 345                 350

Val Ser Ser Ala Ser Thr Lys Gly Pro Ser Val Phe Pro Leu Ala Pro
        355                 360                 365

Ser Ser Lys Ser Thr Ser Gly Gly Thr Ala Ala Leu Gly Cys Leu Val
    370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
        435                 440                 445

Val Asp Lys Lys Val Glu Pro Lys Ser Cys Asp Lys Thr His Thr Cys
    450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
            500                 505                 510

Phe Asn Trp Tyr Val Asp Gly Val Glu Val His Asn Ala Lys Thr Lys
        515                 520                 525

Pro Arg Glu Glu Gln Tyr Asn Ser Thr Tyr Arg Val Val Ser Val Leu
    530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Asp Glu Leu Thr Lys Asn Gln Val Ser Leu Thr Cys Leu Val Lys
        595                 600                 605

Gly Phe Tyr Pro Ser Asp Ile Ala Val Glu Trp Glu Ser Asn Gly Gln
    610                 615                 620

Pro Glu Asn Asn Tyr Lys Thr Thr Pro Pro Val Leu Asp Ser Asp Gly
```

```
625                 630                 635                 640

Ser Phe Phe Leu Tyr Ser Lys Leu Thr Val Asp Lys Ser Arg Trp Gln
                645                 650                 655

Gln Gly Asn Val Phe Ser Cys Ser Val Met His Glu Ala Leu His Asn
            660                 665                 670

His Tyr Thr Gln Lys Ser Leu Ser Leu Ser Pro Gly
        675                 680


<210> SEQ ID NO 6
<211> LENGTH: 724
<212> TYPE: PRT
<213> ORGANISM: Artificial Sequence
<220> FEATURE:
<223> OTHER INFORMATION: anti-IL4-VL-huIGKC-[deltaPCS]-<(G4S)10>-
      [deltaPCS]-anti-IL4-VH-huIGHG1

<400> SEQUENCE: 6

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Gln Gln Arg Gly Gly Gly Gly Ser Gly
    210                 215                 220

Gly Gly Gly Ser Gly Gly Gly Gly Ser Gly Gly Gly Gly Ser Gly Gly
225                 230                 235                 240

Gly Gly Ser Gly Gly Gly Gly Ser Gly Gly Gly Gly Ser Gly Gly Gly
                245                 250                 255

Gly Ser Gly Gly Gly Gly Ser Gly Gly Gly Gly Ser Arg Gln Gln Arg
            260                 265                 270

Gln Val Gln Leu Gln Gln Ser Gly Pro Glu Leu Val Lys Pro Gly Ala
        275                 280                 285

Ser Val Lys Ile Ser Cys Lys Ala Ser Gly Tyr Ser Phe Thr Ser Tyr
    290                 295                 300
```

-continued

```
Trp Ile His Trp Ile Lys Gln Arg Pro Gly Gln Gly Leu Glu Trp Ile
305                 310                 315                 320

Gly Met Ile Asp Pro Ser Asp Gly Glu Thr Arg Leu Asn Gln Arg Phe
                325                 330                 335

Gln Gly Arg Ala Thr Leu Thr Val Asp Glu Ser Thr Ser Thr Ala Tyr
            340                 345                 350

Met Gln Leu Arg Ser Pro Thr Ser Glu Asp Ser Ala Val Tyr Tyr Cys
        355                 360                 365

Thr Arg Leu Lys Glu Tyr Gly Asn Tyr Asp Ser Phe Tyr Phe Asp Val
    370                 375                 380

Trp Gly Ala Gly Thr Leu Val Thr Val Ser Ser Ala Ser Thr Lys Gly
385                 390                 395                 400

Pro Ser Val Phe Pro Leu Ala Pro Ser Ser Lys Ser Thr Ser Gly Gly
                405                 410                 415

Thr Ala Ala Leu Gly Cys Leu Val Lys Asp Tyr Phe Pro Glu Pro Val
            420                 425                 430

Thr Val Ser Trp Asn Ser Gly Ala Leu Thr Ser Gly Val His Thr Phe
        435                 440                 445

Pro Ala Val Leu Gln Ser Ser Gly Leu Tyr Ser Leu Ser Ser Val Val
    450                 455                 460

Thr Val Pro Ser Ser Ser Leu Gly Thr Gln Thr Tyr Ile Cys Asn Val
465                 470                 475                 480

Asn His Lys Pro Ser Asn Thr Lys Val Asp Lys Lys Val Glu Pro Lys
                485                 490                 495

Ser Cys Asp Lys Thr His Thr Cys Pro Pro Cys Pro Ala Pro Glu Leu
            500                 505                 510

Leu Gly Gly Pro Ser Val Phe Leu Phe Pro Pro Lys Pro Lys Asp Thr
        515                 520                 525

Leu Met Ile Ser Arg Thr Pro Glu Val Thr Cys Val Val Val Asp Val
    530                 535                 540

Ser His Glu Asp Pro Glu Val Lys Phe Asn Trp Tyr Val Asp Gly Val
545                 550                 555                 560

Glu Val His Asn Ala Lys Thr Lys Pro Arg Glu Glu Gln Tyr Asn Ser
                565                 570                 575

Thr Tyr Arg Val Val Ser Val Leu Thr Val Leu His Gln Asp Trp Leu
            580                 585                 590

Asn Gly Lys Glu Tyr Lys Cys Lys Val Ser Asn Lys Ala Leu Pro Ala
        595                 600                 605

Pro Ile Glu Lys Thr Ile Ser Lys Ala Lys Gly Gln Pro Arg Glu Pro
    610                 615                 620

Gln Val Tyr Thr Leu Pro Pro Ser Arg Asp Glu Leu Thr Lys Asn Gln
625                 630                 635                 640

Val Ser Leu Thr Cys Leu Val Lys Gly Phe Tyr Pro Ser Asp Ile Ala
                645                 650                 655

Val Glu Trp Glu Ser Asn Gly Gln Pro Glu Asn Asn Tyr Lys Thr Thr
            660                 665                 670

Pro Pro Val Leu Asp Ser Asp Gly Ser Phe Phe Leu Tyr Ser Lys Leu
        675                 680                 685

Thr Val Asp Lys Ser Arg Trp Gln Gln Gly Asn Val Phe Ser Cys Ser
    690                 695                 700

Val Met His Glu Ala Leu His Asn His Tyr Thr Gln Lys Ser Leu Ser
705                 710                 715                 720

Leu Ser Pro Gly
```

<210> SEQ ID NO 7
<211> LENGTH: 722
<212> TYPE: PRT
<213> ORGANISM: Artificial Sequence
<220> FEATURE:
<223> OTHER INFORMATION: anti-IL4-VL-huIGKC-[PCS1]-<(G4S)4>-His(8)-
<(G4S)4>-[PCS1]-anti-IL4-VH-huIGHG1

<400> SEQUENCE: 7

```
Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Gly Gly Gly Ser Gly
    210                 215                 220

Gly Gly Gly Ser Gly Gly Gly Gly Ser Gly Gly Gly Gly Ser His His
225                 230                 235                 240

His His His His His His Gly Gly Gly Gly Ser Gly Gly Gly Gly Ser
                245                 250                 255

Gly Gly Gly Gly Ser Gly Gly Gly Gly Ser Arg Arg Lys Arg Gln Val
            260                 265                 270

Gln Leu Gln Gln Ser Gly Pro Glu Leu Val Lys Pro Gly Ala Ser Val
        275                 280                 285

Lys Ile Ser Cys Lys Ala Ser Gly Tyr Ser Phe Thr Ser Tyr Trp Ile
    290                 295                 300

His Trp Ile Lys Gln Arg Pro Gly Gln Gly Leu Glu Trp Ile Gly Met
305                 310                 315                 320

Ile Asp Pro Ser Asp Gly Glu Thr Arg Leu Asn Gln Arg Phe Gln Gly
                325                 330                 335

Arg Ala Thr Leu Thr Val Asp Glu Ser Thr Ser Thr Ala Tyr Met Gln
            340                 345                 350

Leu Arg Ser Pro Thr Ser Glu Asp Ser Ala Val Tyr Tyr Cys Thr Arg
```

-continued

```
        355                 360                 365

Leu Lys Glu Tyr Gly Asn Tyr Asp Ser Phe Tyr Phe Asp Val Trp Gly
    370                 375                 380

Ala Gly Thr Leu Val Thr Val Ser Ser Ala Ser Thr Lys Gly Pro Ser
385                 390                 395                 400

Val Phe Pro Leu Ala Pro Ser Ser Lys Ser Thr Ser Gly Gly Thr Ala
                405                 410                 415

Ala Leu Gly Cys Leu Val Lys Asp Tyr Phe Pro Glu Pro Val Thr Val
            420                 425                 430

Ser Trp Asn Ser Gly Ala Leu Thr Ser Gly Val His Thr Phe Pro Ala
        435                 440                 445

Val Leu Gln Ser Ser Gly Leu Tyr Ser Leu Ser Ser Val Val Thr Val
    450                 455                 460

Pro Ser Ser Ser Leu Gly Thr Gln Thr Tyr Ile Cys Asn Val Asn His
465                 470                 475                 480

Lys Pro Ser Asn Thr Lys Val Asp Lys Lys Val Glu Pro Lys Ser Cys
                485                 490                 495

Asp Lys Thr His Thr Cys Pro Pro Cys Pro Ala Pro Glu Leu Leu Gly
            500                 505                 510

Gly Pro Ser Val Phe Leu Phe Pro Pro Lys Pro Lys Asp Thr Leu Met
        515                 520                 525

Ile Ser Arg Thr Pro Glu Val Thr Cys Val Val Val Asp Val Ser His
    530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
            580                 585                 590

Lys Glu Tyr Lys Cys Lys Val Ser Asn Lys Ala Leu Pro Ala Pro Ile
        595                 600                 605

Glu Lys Thr Ile Ser Lys Ala Lys Gly Gln Pro Arg Glu Pro Gln Val
    610                 615                 620

Tyr Thr Leu Pro Pro Ser Arg Asp Glu Leu Thr Lys Asn Gln Val Ser
625                 630                 635                 640

Leu Thr Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
        675                 680                 685

Asp Lys Ser Arg Trp Gln Gln Gly Asn Val Phe Ser Cys Ser Val Met
    690                 695                 700

His Glu Ala Leu His Asn His Tyr Thr Gln Lys Ser Leu Ser Leu Ser
705                 710                 715                 720

Pro Gly
```

<210> SEQ ID NO 8
<211> LENGTH: 722
<212> TYPE: PRT
<213> ORGANISM: Artificial Sequence
<220> FEATURE:
<223> OTHER INFORMATION: anti-IL4-VL-huIGKC-[deltaPCS]-<(G4S)4>-His(8)-
<(G4S)4>-[deltaPCS]-anti-IL4-VH-huIGHG1

<400> SEQUENCE: 8

```
Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Gln Gln Arg Gly Gly Gly Gly Ser Gly
    210                 215                 220

Gly Gly Gly Ser Gly Gly Gly Gly Ser Gly Gly Gly Gly Ser His His
225                 230                 235                 240

His His His His His His Gly Gly Gly Gly Ser Gly Gly Gly Gly Ser
                245                 250                 255

Gly Gly Gly Gly Ser Gly Gly Gly Gly Ser Arg Gln Gln Arg Gln Val
            260                 265                 270

Gln Leu Gln Gln Ser Gly Pro Glu Leu Val Lys Pro Gly Ala Ser Val
        275                 280                 285

Lys Ile Ser Cys Lys Ala Ser Gly Tyr Ser Phe Thr Ser Tyr Trp Ile
    290                 295                 300

His Trp Ile Lys Gln Arg Pro Gly Gln Gly Leu Glu Trp Ile Gly Met
305                 310                 315                 320

Ile Asp Pro Ser Asp Gly Glu Thr Arg Leu Asn Gln Arg Phe Gln Gly
                325                 330                 335

Arg Ala Thr Leu Thr Val Asp Glu Ser Thr Ser Thr Ala Tyr Met Gln
            340                 345                 350

Leu Arg Ser Pro Thr Ser Glu Asp Ser Ala Val Tyr Tyr Cys Thr Arg
        355                 360                 365

Leu Lys Glu Tyr Gly Asn Tyr Asp Ser Phe Tyr Phe Asp Val Trp Gly
    370                 375                 380

Ala Gly Thr Leu Val Thr Val Ser Ser Ala Ser Thr Lys Gly Pro Ser
385                 390                 395                 400

Val Phe Pro Leu Ala Pro Ser Ser Lys Ser Thr Ser Gly Gly Thr Ala
                405                 410                 415
```

```
Ala Leu Gly Cys Leu Val Lys Asp Tyr Phe Pro Glu Pro Val Thr Val
            420                 425                 430

Ser Trp Asn Ser Gly Ala Leu Thr Ser Gly Val His Thr Phe Pro Ala
        435                 440                 445

Val Leu Gln Ser Ser Gly Leu Tyr Ser Leu Ser Ser Val Val Thr Val
    450                 455                 460

Pro Ser Ser Ser Leu Gly Thr Gln Thr Tyr Ile Cys Asn Val Asn His
465                 470                 475                 480

Lys Pro Ser Asn Thr Lys Val Asp Lys Lys Val Glu Pro Lys Ser Cys
                485                 490                 495

Asp Lys Thr His Thr Cys Pro Pro Cys Pro Ala Pro Glu Leu Leu Gly
            500                 505                 510

Gly Pro Ser Val Phe Leu Phe Pro Pro Lys Pro Lys Asp Thr Leu Met
        515                 520                 525

Ile Ser Arg Thr Pro Glu Val Thr Cys Val Val Val Asp Val Ser His
    530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
            580                 585                 590

Lys Glu Tyr Lys Cys Lys Val Ser Asn Lys Ala Leu Pro Ala Pro Ile
        595                 600                 605

Glu Lys Thr Ile Ser Lys Ala Lys Gly Gln Pro Arg Glu Pro Gln Val
    610                 615                 620

Tyr Thr Leu Pro Pro Ser Arg Asp Glu Leu Thr Lys Asn Gln Val Ser
625                 630                 635                 640

Leu Thr Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
        675                 680                 685

Asp Lys Ser Arg Trp Gln Gln Gly Asn Val Phe Ser Cys Ser Val Met
    690                 695                 700

His Glu Ala Leu His Asn His Tyr Thr Gln Lys Ser Leu Ser Leu Ser
705                 710                 715                 720

Pro Gly
```

<210> SEQ ID NO 9
<211> LENGTH: 724
<212> TYPE: PRT
<213> ORGANISM: Artificial Sequence
<220> FEATURE:
<223> OTHER INFORMATION: anti-IL4-VL-huIGKC-[PCS2]-<(G4S)4>-His(8)-<(G4S)4>-[PCS2]-anti-IL4-VH-huIGHG1

<400> SEQUENCE: 9

```
Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45
```

```
Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Arg Lys Arg Ser Val Asp Glu
    210                 215                 220

Gly Gly Gly Gly Ser Gly Gly Gly Gly Ser Gly Gly Gly Gly Ser His
225                 230                 235                 240

His His His His His His His Gly Gly Gly Gly Ser Gly Gly Gly Gly
                245                 250                 255

Ser Gly Gly Gly Gly Ser His Arg Arg Arg Lys Arg Ser Val Asp Glu
            260                 265                 270

Gln Val Gln Leu Gln Gln Ser Gly Pro Glu Leu Val Lys Pro Gly Ala
        275                 280                 285

Ser Val Lys Ile Ser Cys Lys Ala Ser Gly Tyr Ser Phe Thr Ser Tyr
    290                 295                 300

Trp Ile His Trp Ile Lys Gln Arg Pro Gly Gln Gly Leu Glu Trp Ile
305                 310                 315                 320

Gly Met Ile Asp Pro Ser Asp Gly Glu Thr Arg Leu Asn Gln Arg Phe
                325                 330                 335

Gln Gly Arg Ala Thr Leu Thr Val Asp Glu Ser Thr Ser Thr Ala Tyr
            340                 345                 350

Met Gln Leu Arg Ser Pro Thr Ser Glu Asp Ser Ala Val Tyr Tyr Cys
        355                 360                 365

Thr Arg Leu Lys Glu Tyr Gly Asn Tyr Asp Ser Phe Tyr Phe Asp Val
    370                 375                 380

Trp Gly Ala Gly Thr Leu Val Thr Val Ser Ser Ala Ser Thr Lys Gly
385                 390                 395                 400

Pro Ser Val Phe Pro Leu Ala Pro Ser Ser Lys Ser Thr Ser Gly Gly
                405                 410                 415

Thr Ala Ala Leu Gly Cys Leu Val Lys Asp Tyr Phe Pro Glu Pro Val
            420                 425                 430

Thr Val Ser Trp Asn Ser Gly Ala Leu Thr Ser Gly Val His Thr Phe
        435                 440                 445

Pro Ala Val Leu Gln Ser Ser Gly Leu Tyr Ser Leu Ser Ser Val Val
    450                 455                 460
```

```
Thr Val Pro Ser Ser Ser Leu Gly Thr Gln Thr Tyr Ile Cys Asn Val
465                 470                 475                 480

Asn His Lys Pro Ser Asn Thr Lys Val Asp Lys Lys Val Glu Pro Lys
                485                 490                 495

Ser Cys Asp Lys Thr His Thr Cys Pro Pro Cys Pro Ala Pro Glu Leu
            500                 505                 510

Leu Gly Gly Pro Ser Val Phe Leu Phe Pro Pro Lys Pro Lys Asp Thr
        515                 520                 525

Leu Met Ile Ser Arg Thr Pro Glu Val Thr Cys Val Val Val Asp Val
    530                 535                 540

Ser His Glu Asp Pro Glu Val Lys Phe Asn Trp Tyr Val Asp Gly Val
545                 550                 555                 560

Glu Val His Asn Ala Lys Thr Lys Pro Arg Glu Glu Gln Tyr Asn Ser
                565                 570                 575

Thr Tyr Arg Val Val Ser Val Leu Thr Val Leu His Gln Asp Trp Leu
            580                 585                 590

Asn Gly Lys Glu Tyr Lys Cys Lys Val Ser Asn Lys Ala Leu Pro Ala
        595                 600                 605

Pro Ile Glu Lys Thr Ile Ser Lys Ala Lys Gly Gln Pro Arg Glu Pro
    610                 615                 620

Gln Val Tyr Thr Leu Pro Pro Ser Arg Asp Glu Leu Thr Lys Asn Gln
625                 630                 635                 640

Val Ser Leu Thr Cys Leu Val Lys Gly Phe Tyr Pro Ser Asp Ile Ala
                645                 650                 655

Val Glu Trp Glu Ser Asn Gly Gln Pro Glu Asn Asn Tyr Lys Thr Thr
            660                 665                 670

Pro Pro Val Leu Asp Ser Asp Gly Ser Phe Phe Leu Tyr Ser Lys Leu
        675                 680                 685

Thr Val Asp Lys Ser Arg Trp Gln Gln Gly Asn Val Phe Ser Cys Ser
    690                 695                 700

Val Met His Glu Ala Leu His Asn His Tyr Thr Gln Lys Ser Leu Ser
705                 710                 715                 720

Leu Ser Pro Gly


<210> SEQ ID NO 10
<211> LENGTH: 724
<212> TYPE: PRT
<213> ORGANISM: Artificial Sequence
<220> FEATURE:
<223> OTHER INFORMATION: anti-IL4-VL-huIGKC-[PCS3]-<(G4S)4>-His(8)-
      <(G4S)4>-[PCS3]-anti-IL4-VH-huIGHG1

<400> SEQUENCE: 10

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95
```

```
Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Pro Met Lys Lys Arg Arg Ala Gly Val Pro
    210                 215                 220

Gly Gly Gly Gly Ser Gly Gly Gly Gly Ser Gly Gly Gly Gly Ser His
225                 230                 235                 240

His His His His His His His Gly Gly Gly Gly Ser Gly Gly Gly Gly
                245                 250                 255

Ser Gly Gly Gly Gly Ser Pro Met Lys Lys Arg Arg Ala Gly Val Pro
            260                 265                 270

Gln Val Gln Leu Gln Gln Ser Gly Pro Glu Leu Val Lys Pro Gly Ala
        275                 280                 285

Ser Val Lys Ile Ser Cys Lys Ala Ser Gly Tyr Ser Phe Thr Ser Tyr
    290                 295                 300

Trp Ile His Trp Ile Lys Gln Arg Pro Gly Gln Gly Leu Glu Trp Ile
305                 310                 315                 320

Gly Met Ile Asp Pro Ser Asp Gly Glu Thr Arg Leu Asn Gln Arg Phe
                325                 330                 335

Gln Gly Arg Ala Thr Leu Thr Val Asp Glu Ser Thr Ser Thr Ala Tyr
            340                 345                 350

Met Gln Leu Arg Ser Pro Thr Ser Glu Asp Ser Ala Val Tyr Tyr Cys
        355                 360                 365

Thr Arg Leu Lys Glu Tyr Gly Asn Tyr Asp Ser Phe Tyr Phe Asp Val
    370                 375                 380

Trp Gly Ala Gly Thr Leu Val Thr Val Ser Ser Ala Ser Thr Lys Gly
385                 390                 395                 400

Pro Ser Val Phe Pro Leu Ala Pro Ser Ser Lys Ser Thr Ser Gly Gly
                405                 410                 415

Thr Ala Ala Leu Gly Cys Leu Val Lys Asp Tyr Phe Pro Glu Pro Val
            420                 425                 430

Thr Val Ser Trp Asn Ser Gly Ala Leu Thr Ser Gly Val His Thr Phe
        435                 440                 445

Pro Ala Val Leu Gln Ser Ser Gly Leu Tyr Ser Leu Ser Ser Val Val
    450                 455                 460

Thr Val Pro Ser Ser Ser Leu Gly Thr Gln Thr Tyr Ile Cys Asn Val
465                 470                 475                 480

Asn His Lys Pro Ser Asn Thr Lys Val Asp Lys Lys Val Glu Pro Lys
                485                 490                 495

Ser Cys Asp Lys Thr His Thr Cys Pro Pro Cys Pro Ala Pro Glu Leu
            500                 505                 510

Leu Gly Gly Pro Ser Val Phe Leu Phe Pro Pro Lys Pro Lys Asp Thr
```

-continued 515 520 525

Leu Met Ile Ser Arg Thr Pro Glu Val Thr Cys Val Val Val Asp Val
530 535 540

Ser His Glu Asp Pro Glu Val Lys Phe Asn Trp Tyr Val Asp Gly Val
545 550 555 560

Glu Val His Asn Ala Lys Thr Lys Pro Arg Glu Glu Gln Tyr Asn Ser
565 570 575

Thr Tyr Arg Val Val Ser Val Leu Thr Val Leu His Gln Asp Trp Leu
580 585 590

Asn Gly Lys Glu Tyr Lys Cys Lys Val Ser Asn Lys Ala Leu Pro Ala
595 600 605

Pro Ile Glu Lys Thr Ile Ser Lys Ala Lys Gly Gln Pro Arg Glu Pro
610 615 620

Gln Val Tyr Thr Leu Pro Pro Ser Arg Asp Glu Leu Thr Lys Asn Gln
625 630 635 640

Val Ser Leu Thr Cys Leu Val Lys Gly Phe Tyr Pro Ser Asp Ile Ala
645 650 655

Val Glu Trp Glu Ser Asn Gly Gln Pro Glu Asn Asn Tyr Lys Thr Thr
660 665 670

Pro Pro Val Leu Asp Ser Asp Gly Ser Phe Phe Leu Tyr Ser Lys Leu
675 680 685

Thr Val Asp Lys Ser Arg Trp Gln Gln Gly Asn Val Phe Ser Cys Ser
690 695 700

Val Met His Glu Ala Leu His Asn His Tyr Thr Gln Lys Ser Leu Ser
705 710 715 720

Leu Ser Pro Gly

<210> SEQ ID NO 11
<211> LENGTH: 214
<212> TYPE: PRT
<213> ORGANISM: Artificial Sequence
<220> FEATURE:
<223> OTHER INFORMATION: anti-IL4-VL-huIGKC

<400> SEQUENCE: 11

Asp Ile Gln Met Thr Gln Ser Pro Ala Ser Leu Ser Val Ser Val Gly
1 5 10 15

Asp Thr Ile Thr Leu Thr Cys His Ala Ser Gln Asn Ile Asp Val Trp
20 25 30

Leu Ser Trp Phe Gln Gln Lys Pro Gly Asn Ile Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Gly Phe Thr Leu Thr Ile Ser Ser Leu Gln Pro
65 70 75 80

Glu Asp Ile Ala Thr Tyr Tyr Cys Gln Gln Ala His Ser Tyr Pro Phe
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 12
<211> LENGTH: 218
<212> TYPE: PRT
<213> ORGANISM: Artificial Sequence
<220> FEATURE:
<223> OTHER INFORMATION: anti-IL13-IGKC

<400> SEQUENCE: 12

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 13
<211> LENGTH: 693
<212> TYPE: PRT
<213> ORGANISM: Artificial Sequence
<220> FEATURE:
<223> OTHER INFORMATION: anti-IL4-VH-huIGH-G11-huIGH-H1-<(G4S)3>-anti-
      IL13-VH-huIGHG1

<400> SEQUENCE: 13

Gln Val Gln Leu Gln Gln Ser Gly Pro Glu Leu Val Lys Pro Gly Ala
1               5                   10                  15
```

-continued

```
Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Gly Gly Gly Gly Ser Gly Gly Gly Gly
225                 230                 235                 240

Ser Gly Gly Gly Gly Ser Glu Val Gln Leu Lys Glu Ser Gly Pro Gly
                245                 250                 255

Leu Val Ala Pro Gly Gly Ser Leu Ser Ile Thr Cys Thr Val Ser Gly
            260                 265                 270

Phe Ser Leu Thr Asp Ser Ser Ile Asn Trp Val Arg Gln Pro Pro Gly
        275                 280                 285

Lys Gly Leu Glu Trp Leu Gly Met Ile Trp Gly Asp Gly Arg Ile Asp
    290                 295                 300

Tyr Ala Asp Ala Leu Lys Ser Arg Leu Ser Ile Ser Lys Asp Ser Ser
305                 310                 315                 320

Lys Ser Gln Val Phe Leu Glu Met Thr Ser Leu Arg Thr Asp Asp Thr
                325                 330                 335

Ala Thr Tyr Tyr Cys Ala Arg Asp Gly Tyr Phe Pro Tyr Ala Met Asp
            340                 345                 350

Phe Trp Gly Gln Gly Thr Ser Val Thr Val Ser Ser Ala Ser Thr Lys
        355                 360                 365

Gly Pro Ser Val Phe Pro Leu Ala Pro Ser Ser Lys Ser Thr Ser Gly
    370                 375                 380

Gly Thr Ala Ala Leu Gly Cys Leu Val Lys Asp Tyr Phe Pro Glu Pro
385                 390                 395                 400

Val Thr Val Ser Trp Asn Ser Gly Ala Leu Thr Ser Gly Val His Thr
                405                 410                 415

Phe Pro Ala Val Leu Gln Ser Ser Gly Leu Tyr Ser Leu Ser Ser Val
            420                 425                 430

Val Thr Val Pro Ser Ser Ser Leu Gly Thr Gln Thr Tyr Ile Cys Asn
```

-continued

```
        435                 440                 445

Val Asn His Lys Pro Ser Asn Thr Lys Val Asp Lys Lys Val Glu Pro
    450                 455                 460

Lys Ser Cys Asp Lys Thr His Thr Cys Pro Pro Cys Pro Ala Pro Glu
465                 470                 475                 480

Leu Leu Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Pro
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Ser Arg Asp Glu Leu Thr Lys Asn
        595                 600                 605

Gln Val Ser Leu Thr Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly
    690


<210> SEQ ID NO 14
<211> LENGTH: 446
<212> TYPE: PRT
<213> ORGANISM: Artificial Sequence
<220> FEATURE:
<223> OTHER INFORMATION: anti-IL4-VL-huIGKC-<G4S>-[PCS1]-<G4S>-anti-
      IL13-VL-huIGKC

<400> SEQUENCE: 14

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95
```

-continued

```
Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Arg Arg Lys Arg Gly
    210                 215                 220

Gly Gly Gly Ser Asp Ile Val Leu Thr Gln Ser Pro Ala Ser Leu Ala
225                 230                 235                 240

Val Ser Leu Gly Gln Arg Ala Thr Ile Ser Cys Arg Ala Ser Glu Ser
                245                 250                 255

Val Asp Ser Tyr Gly Gln Ser Tyr Met His Trp Tyr Gln Gln Lys Ala
            260                 265                 270

Gly Gln Pro Pro Lys Leu Leu Ile Tyr Leu Ala Ser Asn Leu Glu Ser
        275                 280                 285

Gly Val Pro Ala Arg Phe Ser Gly Ser Gly Ser Arg Thr Asp Phe Thr
    290                 295                 300

Leu Thr Ile Asp Pro Val Gln Ala Glu Asp Ala Ala Thr Tyr Tyr Cys
305                 310                 315                 320

Gln Gln Asn Ala Glu Asp Ser Arg Thr Phe Gly Gly Gly Thr Lys Leu
                325                 330                 335

Glu Ile Lys Arg Thr Val Ala Ala Pro Ser Val Phe Ile Phe Pro Pro
            340                 345                 350

Ser Asp Glu Gln Leu Lys Ser Gly Thr Ala Ser Val Val Cys Leu Leu
        355                 360                 365

Asn Asn Phe Tyr Pro Arg Glu Ala Lys Val Gln Trp Lys Val Asp Asn
    370                 375                 380

Ala Leu Gln Ser Gly Asn Ser Gln Glu Ser Val Thr Glu Gln Asp Ser
385                 390                 395                 400

Lys Asp Ser Thr Tyr Ser Leu Ser Ser Thr Leu Thr Leu Ser Lys Ala
                405                 410                 415

Asp Tyr Glu Lys His Lys Val Tyr Ala Cys Glu Val Thr His Gln Gly
            420                 425                 430

Leu Ser Ser Pro Val Thr Lys Ser Phe Asn Arg Gly Glu Cys
        435                 440                 445


<210> SEQ ID NO 15
<211> LENGTH: 455
<212> TYPE: PRT
<213> ORGANISM: Artificial Sequence
<220> FEATURE:
<223> OTHER INFORMATION: anti-IL4-VL-huIGKC-[PCS1]-<(G4S)3>-[PCS1]-anti-
      IL13-VL-huIGKC

<400> SEQUENCE: 15

Asp Ile Gln Met Thr Gln Ser Pro Ala Ser Leu Ser Val Ser Val Gly
1               5                   10                  15
```

-continued

```
Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Gly Gly Gly Ser Gly
    210                 215                 220

Gly Gly Gly Ser Gly Gly Gly Gly Ser Arg Arg Lys Arg Asp Ile Val
225                 230                 235                 240

Leu Thr Gln Ser Pro Ala Ser Leu Ala Val Ser Leu Gly Gln Arg Ala
                245                 250                 255

Thr Ile Ser Cys Arg Ala Ser Glu Ser Val Asp Ser Tyr Gly Gln Ser
            260                 265                 270

Tyr Met His Trp Tyr Gln Gln Lys Ala Gly Gln Pro Pro Lys Leu Leu
        275                 280                 285

Ile Tyr Leu Ala Ser Asn Leu Glu Ser Gly Val Pro Ala Arg Phe Ser
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335

Arg Thr Phe Gly Gly Gly Thr Lys Leu Glu Ile Lys Arg Thr Val Ala
            340                 345                 350

Ala Pro Ser Val Phe Ile Phe Pro Pro Ser Asp Glu Gln Leu Lys Ser
        355                 360                 365

Gly Thr Ala Ser Val Val Cys Leu Leu Asn Asn Phe Tyr Pro Arg Glu
    370                 375                 380

Ala Lys Val Gln Trp Lys Val Asp Asn Ala Leu Gln Ser Gly Asn Ser
385                 390                 395                 400

Gln Glu Ser Val Thr Glu Gln Asp Ser Lys Asp Ser Thr Tyr Ser Leu
                405                 410                 415

Ser Ser Thr Leu Thr Leu Ser Lys Ala Asp Tyr Glu Lys His Lys Val
            420                 425                 430
```

```
Tyr Ala Cys Glu Val Thr His Gln Gly Leu Ser Ser Pro Val Thr Lys
        435                 440                 445

Ser Phe Asn Arg Gly Glu Cys
    450                 455


<210> SEQ ID NO 16
<211> LENGTH: 455
<212> TYPE: PRT
<213> ORGANISM: Artificial Sequence
<220> FEATURE:
<223> OTHER INFORMATION: anti-IL4-VL-huIGKC-[deltaPCS]-<(G4S)3>-
      [deltaPCS]-anti-IL13-VL-huIGKC

<400> SEQUENCE: 16

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Gln Gln Arg Gly Gly Gly Gly Ser Gly
    210                 215                 220

Gly Gly Gly Ser Gly Gly Gly Gly Ser Arg Gln Gln Arg Asp Ile Val
225                 230                 235                 240

Leu Thr Gln Ser Pro Ala Ser Leu Ala Val Ser Leu Gly Gln Arg Ala
                245                 250                 255

Thr Ile Ser Cys Arg Ala Ser Glu Ser Val Asp Ser Tyr Gly Gln Ser
            260                 265                 270

Tyr Met His Trp Tyr Gln Gln Lys Ala Gly Gln Pro Pro Lys Leu Leu
        275                 280                 285

Ile Tyr Leu Ala Ser Asn Leu Glu Ser Gly Val Pro Ala Arg Phe Ser
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335
```

Arg Thr Phe Gly Gly Gly Thr Lys Leu Glu Ile Lys Arg Thr Val Ala
340 345 350

Ala Pro Ser Val Phe Ile Phe Pro Pro Ser Asp Glu Gln Leu Lys Ser
355 360 365

Gly Thr Ala Ser Val Val Cys Leu Leu Asn Asn Phe Tyr Pro Arg Glu
370 375 380

Ala Lys Val Gln Trp Lys Val Asp Asn Ala Leu Gln Ser Gly Asn Ser
385 390 395 400

Gln Glu Ser Val Thr Glu Gln Asp Ser Lys Asp Ser Thr Tyr Ser Leu
405 410 415

Ser Ser Thr Leu Thr Leu Ser Lys Ala Asp Tyr Glu Lys His Lys Val
420 425 430

Tyr Ala Cys Glu Val Thr His Gln Gly Leu Ser Ser Pro Val Thr Lys
435 440 445

Ser Phe Asn Arg Gly Glu Cys
450 455

<210> SEQ ID NO 17
<211> LENGTH: 455
<212> TYPE: PRT
<213> ORGANISM: Artificial Sequence
<220> FEATURE:
<223> OTHER INFORMATION: anti-IL4-VL-huIGKC-[PCS1]-<GS>-His(8)-<G4S>-
[PCS1]-anti-IL13-VL-huIGKC

<400> SEQUENCE: 17

Asp Ile Gln Met Thr Gln Ser Pro Ala Ser Leu Ser Val Ser Val Gly
1 5 10 15

Asp Thr Ile Thr Leu Thr Cys His Ala Ser Gln Asn Ile Asp Val Trp
20 25 30

Leu Ser Trp Phe Gln Gln Lys Pro Gly Asn Ile Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Gly Phe Thr Leu Thr Ile Ser Ser Leu Gln Pro
65 70 75 80

Glu Asp Ile Ala Thr Tyr Tyr Cys Gln Gln Ala His Ser Tyr Pro Phe
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Arg Arg Lys Arg Gly Ser His His His His
210 215 220

His His His His Gly Gly Gly Gly Ser Arg Arg Lys Arg Asp Ile Val

-continued

```
225                 230                 235                 240

Leu Thr Gln Ser Pro Ala Ser Leu Ala Val Ser Leu Gly Gln Arg Ala
                245                 250                 255

Thr Ile Ser Cys Arg Ala Ser Glu Ser Val Asp Ser Tyr Gly Gln Ser
            260                 265                 270

Tyr Met His Trp Tyr Gln Gln Lys Ala Gly Gln Pro Pro Lys Leu Leu
        275                 280                 285

Ile Tyr Leu Ala Ser Asn Leu Glu Ser Gly Val Pro Ala Arg Phe Ser
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335

Arg Thr Phe Gly Gly Gly Thr Lys Leu Glu Ile Lys Arg Thr Val Ala
            340                 345                 350

Ala Pro Ser Val Phe Ile Phe Pro Pro Ser Asp Glu Gln Leu Lys Ser
        355                 360                 365

Gly Thr Ala Ser Val Val Cys Leu Leu Asn Asn Phe Tyr Pro Arg Glu
    370                 375                 380

Ala Lys Val Gln Trp Lys Val Asp Asn Ala Leu Gln Ser Gly Asn Ser
385                 390                 395                 400

Gln Glu Ser Val Thr Glu Gln Asp Ser Lys Asp Ser Thr Tyr Ser Leu
                405                 410                 415

Ser Ser Thr Leu Thr Leu Ser Lys Ala Asp Tyr Glu Lys His Lys Val
            420                 425                 430

Tyr Ala Cys Glu Val Thr His Gln Gly Leu Ser Ser Pro Val Thr Lys
        435                 440                 445

Ser Phe Asn Arg Gly Glu Cys
    450                 455


<210> SEQ ID NO 18
<211> LENGTH: 455
<212> TYPE: PRT
<213> ORGANISM: Artificial Sequence
<220> FEATURE:
<223> OTHER INFORMATION: anti-IL4-VL-huIGKC-[deltaPCS]-<GS>-His(8)-
      <G4S>-[deltaPCS]-anti-IL13-VL-huIGKC

<400> SEQUENCE: 18

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Gln Gln Arg Gly Ser His His His His
    210                 215                 220

His His His His Gly Gly Gly Gly Ser Arg Gln Gln Arg Asp Ile Val
225                 230                 235                 240

Leu Thr Gln Ser Pro Ala Ser Leu Ala Val Ser Leu Gly Gln Arg Ala
                245                 250                 255

Thr Ile Ser Cys Arg Ala Ser Glu Ser Val Asp Ser Tyr Gly Gln Ser
            260                 265                 270

Tyr Met His Trp Tyr Gln Gln Lys Ala Gly Gln Pro Pro Lys Leu Leu
        275                 280                 285

Ile Tyr Leu Ala Ser Asn Leu Glu Ser Gly Val Pro Ala Arg Phe Ser
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335

Arg Thr Phe Gly Gly Gly Thr Lys Leu Glu Ile Lys Arg Thr Val Ala
            340                 345                 350

Ala Pro Ser Val Phe Ile Phe Pro Pro Ser Asp Glu Gln Leu Lys Ser
        355                 360                 365

Gly Thr Ala Ser Val Val Cys Leu Leu Asn Asn Phe Tyr Pro Arg Glu
    370                 375                 380

Ala Lys Val Gln Trp Lys Val Asp Asn Ala Leu Gln Ser Gly Asn Ser
385                 390                 395                 400

Gln Glu Ser Val Thr Glu Gln Asp Ser Lys Asp Ser Thr Tyr Ser Leu
                405                 410                 415

Ser Ser Thr Leu Thr Leu Ser Lys Ala Asp Tyr Glu Lys His Lys Val
            420                 425                 430

Tyr Ala Cys Glu Val Thr His Gln Gly Leu Ser Ser Pro Val Thr Lys
        435                 440                 445

Ser Phe Asn Arg Gly Glu Cys
    450                 455


<210> SEQ ID NO 19
<211> LENGTH: 457
<212> TYPE: PRT
<213> ORGANISM: Artificial Sequence
<220> FEATURE:
<223> OTHER INFORMATION: anti-IL4-VL-huIGKC-[PCS2]-<(G4S)3>-[PCS2]-anti-
      IL13-VL-huIGKC

<400> SEQUENCE: 19

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30
```

-continued

```
Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Arg Lys Arg Ser Val Asp Glu
    210                 215                 220

Gly Gly Gly Gly Ser His Arg Arg Arg Lys Arg Ser Val Asp Glu Asp
225                 230                 235                 240

Ile Val Leu Thr Gln Ser Pro Ala Ser Leu Ala Val Ser Leu Gly Gln
                245                 250                 255

Arg Ala Thr Ile Ser Cys Arg Ala Ser Glu Ser Val Asp Ser Tyr Gly
            260                 265                 270

Gln Ser Tyr Met His Trp Tyr Gln Gln Lys Ala Gly Gln Pro Pro Lys
        275                 280                 285

Leu Leu Ile Tyr Leu Ala Ser Asn Leu Glu Ser Gly Val Pro Ala Arg
    290                 295                 300

Phe Ser Gly Ser Gly Ser Arg Thr Asp Phe Thr Leu Thr Ile Asp Pro
305                 310                 315                 320

Val Gln Ala Glu Asp Ala Ala Thr Tyr Tyr Cys Gln Gln Asn Ala Glu
                325                 330                 335

Asp Ser Arg Thr Phe Gly Gly Gly Thr Lys Leu Glu Ile Lys Arg Thr
            340                 345                 350

Val Ala Ala Pro Ser Val Phe Ile Phe Pro Pro Ser Asp Glu Gln Leu
        355                 360                 365

Lys Ser Gly Thr Ala Ser Val Val Cys Leu Leu Asn Asn Phe Tyr Pro
    370                 375                 380

Arg Glu Ala Lys Val Gln Trp Lys Val Asp Asn Ala Leu Gln Ser Gly
385                 390                 395                 400

Asn Ser Gln Glu Ser Val Thr Glu Gln Asp Ser Lys Asp Ser Thr Tyr
                405                 410                 415

Ser Leu Ser Ser Thr Leu Thr Leu Ser Lys Ala Asp Tyr Glu Lys His
            420                 425                 430

Lys Val Tyr Ala Cys Glu Val Thr His Gln Gly Leu Ser Ser Pro Val
        435                 440                 445
```

```
Thr Lys Ser Phe Asn Arg Gly Glu Cys
    450                 455


<210> SEQ ID NO 20
<211> LENGTH: 457
<212> TYPE: PRT
<213> ORGANISM: Artificial Sequence
<220> FEATURE:
<223> OTHER INFORMATION: anti-IL4-VL-huIGKC-[PCS3]-<(G4S)>-[PCS3]-anti-
      IL13-VL-huIGKC

<400> SEQUENCE: 20

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Pro Met Lys Lys Arg Arg Ala Gly Val Pro
    210                 215                 220

Gly Gly Gly Gly Ser Pro Met Lys Lys Arg Arg Ala Gly Val Pro Asp
225                 230                 235                 240

Ile Val Leu Thr Gln Ser Pro Ala Ser Leu Ala Val Ser Leu Gly Gln
                245                 250                 255

Arg Ala Thr Ile Ser Cys Arg Ala Ser Glu Ser Val Asp Ser Tyr Gly
            260                 265                 270

Gln Ser Tyr Met His Trp Tyr Gln Gln Lys Ala Gly Gln Pro Pro Lys
        275                 280                 285

Leu Leu Ile Tyr Leu Ala Ser Asn Leu Glu Ser Gly Val Pro Ala Arg
    290                 295                 300

Phe Ser Gly Ser Gly Ser Arg Thr Asp Phe Thr Leu Thr Ile Asp Pro
305                 310                 315                 320

Val Gln Ala Glu Asp Ala Ala Thr Tyr Tyr Cys Gln Gln Asn Ala Glu
                325                 330                 335

Asp Ser Arg Thr Phe Gly Gly Gly Thr Lys Leu Glu Ile Lys Arg Thr
            340                 345                 350
```

```
Val Ala Ala Pro Ser Val Phe Ile Phe Pro Pro Ser Asp Glu Gln Leu
        355                 360                 365

Lys Ser Gly Thr Ala Ser Val Val Cys Leu Leu Asn Asn Phe Tyr Pro
    370                 375                 380

Arg Glu Ala Lys Val Gln Trp Lys Val Asp Asn Ala Leu Gln Ser Gly
385                 390                 395                 400

Asn Ser Gln Glu Ser Val Thr Glu Gln Asp Ser Lys Asp Ser Thr Tyr
                405                 410                 415

Ser Leu Ser Ser Thr Leu Thr Leu Ser Lys Ala Asp Tyr Glu Lys His
            420                 425                 430

Lys Val Tyr Ala Cys Glu Val Thr His Gln Gly Leu Ser Ser Pro Val
        435                 440                 445

Thr Lys Ser Phe Asn Arg Gly Glu Cys
    450                 455


<210> SEQ ID NO 21
<211> LENGTH: 460
<212> TYPE: PRT
<213> ORGANISM: Artificial Sequence
<220> FEATURE:
<223> OTHER INFORMATION: anti-IL4-VL-huIGKC-[PCS1]-<G4S>-<(EAAAK)2>-
      <G4S>-[PCS1]-anti-IL13-VL-huIGKC

<400> SEQUENCE: 21

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Gly Gly Gly Ser Glu
    210                 215                 220

Ala Ala Ala Lys Glu Ala Ala Ala Lys Gly Gly Gly Gly Ser Arg Arg
225                 230                 235                 240

Lys Arg Asp Ile Val Leu Thr Gln Ser Pro Ala Ser Leu Ala Val Ser
```

```
                245                 250                 255

Leu Gly Gln Arg Ala Thr Ile Ser Cys Arg Ala Ser Glu Ser Val Asp
            260                 265                 270

Ser Tyr Gly Gln Ser Tyr Met His Trp Tyr Gln Gln Lys Ala Gly Gln
        275                 280                 285

Pro Pro Lys Leu Leu Ile Tyr Leu Ala Ser Asn Leu Glu Ser Gly Val
    290                 295                 300

Pro Ala Arg Phe Ser Gly Ser Gly Ser Arg Thr Asp Phe Thr Leu Thr
305                 310                 315                 320

Ile Asp Pro Val Gln Ala Glu Asp Ala Ala Thr Tyr Tyr Cys Gln Gln
                325                 330                 335

Asn Ala Glu Asp Ser Arg Thr Phe Gly Gly Gly Thr Lys Leu Glu Ile
            340                 345                 350

Lys Arg Thr Val Ala Ala Pro Ser Val Phe Ile Phe Pro Pro Ser Asp
        355                 360                 365

Glu Gln Leu Lys Ser Gly Thr Ala Ser Val Val Cys Leu Leu Asn Asn
    370                 375                 380

Phe Tyr Pro Arg Glu Ala Lys Val Gln Trp Lys Val Asp Asn Ala Leu
385                 390                 395                 400

Gln Ser Gly Asn Ser Gln Glu Ser Val Thr Glu Gln Asp Ser Lys Asp
                405                 410                 415

Ser Thr Tyr Ser Leu Ser Ser Thr Leu Thr Leu Ser Lys Ala Asp Tyr
            420                 425                 430

Glu Lys His Lys Val Tyr Ala Cys Glu Val Thr His Gln Gly Leu Ser
        435                 440                 445

Ser Pro Val Thr Lys Ser Phe Asn Arg Gly Glu Cys
    450                 455                 460


<210> SEQ ID NO 22
<211> LENGTH: 698
<212> TYPE: PRT
<213> ORGANISM: Artificial Sequence
<220> FEATURE:
<223> OTHER INFORMATION: anti-IL4-VH-huIGH-G11-huIGH-H1-<G4S>-
      <(EAAAK)2>-<G4S>-anti-IL13-VH-huIGHG1

<400> SEQUENCE: 22

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

-continued

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Gly Gly Gly Gly Ser Glu Ala Ala Ala
225                 230                 235                 240

Lys Glu Ala Ala Ala Lys Gly Gly Gly Gly Ser Glu Val Gln Leu Lys
                245                 250                 255

Glu Ser Gly Pro Gly Leu Val Ala Pro Gly Gly Ser Leu Ser Ile Thr
            260                 265                 270

Cys Thr Val Ser Gly Phe Ser Leu Thr Asp Ser Ser Ile Asn Trp Val
        275                 280                 285

Arg Gln Pro Pro Gly Lys Gly Leu Glu Trp Leu Gly Met Ile Trp Gly
    290                 295                 300

Asp Gly Arg Ile Asp Tyr Ala Asp Ala Leu Lys Ser Arg Leu Ser Ile
305                 310                 315                 320

Ser Lys Asp Ser Ser Lys Ser Gln Val Phe Leu Glu Met Thr Ser Leu
                325                 330                 335

Arg Thr Asp Asp Thr Ala Thr Tyr Tyr Cys Ala Arg Asp Gly Tyr Phe
            340                 345                 350

Pro Tyr Ala Met Asp Phe Trp Gly Gln Gly Thr Ser Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Lys Val Glu Pro Lys Ser Cys Asp Lys Thr His Thr Cys Pro Pro
465                 470                 475                 480

Cys Pro Ala Pro Glu Leu Leu Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
```

-continued

```
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Asp
        595                 600                 605

Glu Leu Thr Lys Asn Gln Val Ser Leu Thr Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695


<210> SEQ ID NO 23
<211> LENGTH: 455
<212> TYPE: PRT
<213> ORGANISM: Artificial Sequence
<220> FEATURE:
<223> OTHER INFORMATION: anti-IL4-VL-huIGKC-[PCS1]-<(AP)7A>-[PCS1]-anti-
      IL13-VL-huIGKC

<400> SEQUENCE: 23

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Ala Pro Ala Pro Ala Pro
    210                 215                 220
```

-continued

```
Ala Pro Ala Pro Ala Pro Ala Pro Ala Arg Arg Lys Arg Asp Ile Val
225                 230                 235                 240

Leu Thr Gln Ser Pro Ala Ser Leu Ala Val Ser Leu Gly Gln Arg Ala
                245                 250                 255

Thr Ile Ser Cys Arg Ala Ser Glu Ser Val Asp Ser Tyr Gly Gln Ser
            260                 265                 270

Tyr Met His Trp Tyr Gln Gln Lys Ala Gly Gln Pro Pro Lys Leu Leu
        275                 280                 285

Ile Tyr Leu Ala Ser Asn Leu Glu Ser Gly Val Pro Ala Arg Phe Ser
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335

Arg Thr Phe Gly Gly Gly Thr Lys Leu Glu Ile Lys Arg Thr Val Ala
            340                 345                 350

Ala Pro Ser Val Phe Ile Phe Pro Pro Ser Asp Glu Gln Leu Lys Ser
        355                 360                 365

Gly Thr Ala Ser Val Val Cys Leu Leu Asn Asn Phe Tyr Pro Arg Glu
    370                 375                 380

Ala Lys Val Gln Trp Lys Val Asp Asn Ala Leu Gln Ser Gly Asn Ser
385                 390                 395                 400

Gln Glu Ser Val Thr Glu Gln Asp Ser Lys Asp Ser Thr Tyr Ser Leu
                405                 410                 415

Ser Ser Thr Leu Thr Leu Ser Lys Ala Asp Tyr Glu Lys His Lys Val
            420                 425                 430

Tyr Ala Cys Glu Val Thr His Gln Gly Leu Ser Ser Pro Val Thr Lys
        435                 440                 445

Ser Phe Asn Arg Gly Glu Cys
    450                 455


<210> SEQ ID NO 24
<211> LENGTH: 454
<212> TYPE: PRT
<213> ORGANISM: Artificial Sequence
<220> FEATURE:
<223> OTHER INFORMATION: anti-IL4-VL-huIGKC-[PCS1]-<GS>-<(KQGKQ)2>-<GS>-
      [PCS1]-anti-IL13-VL-huIGKC

<400> SEQUENCE: 24

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Ser Lys Gln Gly Lys
    210                 215                 220

Gln Lys Gln Gly Lys Gln Gly Ser Arg Arg Lys Arg Asp Ile Val Leu
225                 230                 235                 240

Thr Gln Ser Pro Ala Ser Leu Ala Val Ser Leu Gly Gln Arg Ala Thr
                245                 250                 255

Ile Ser Cys Arg Ala Ser Glu Ser Val Asp Ser Tyr Gly Gln Ser Tyr
            260                 265                 270

Met His Trp Tyr Gln Gln Lys Ala Gly Gln Pro Pro Lys Leu Leu Ile
        275                 280                 285

Tyr Leu Ala Ser Asn Leu Glu Ser Gly Val Pro Ala Arg Phe Ser Gly
    290                 295                 300

Ser Gly Ser Arg Thr Asp Phe Thr Leu Thr Ile Asp Pro Val Gln Ala
305                 310                 315                 320

Glu Asp Ala Ala Thr Tyr Tyr Cys Gln Gln Asn Ala Glu Asp Ser Arg
                325                 330                 335

Thr Phe Gly Gly Gly Thr Lys Leu Glu Ile Lys Arg Thr Val Ala Ala
            340                 345                 350

Pro Ser Val Phe Ile Phe Pro Pro Ser Asp Glu Gln Leu Lys Ser Gly
        355                 360                 365

Thr Ala Ser Val Val Cys Leu Leu Asn Asn Phe Tyr Pro Arg Glu Ala
    370                 375                 380

Lys Val Gln Trp Lys Val Asp Asn Ala Leu Gln Ser Gly Asn Ser Gln
385                 390                 395                 400

Glu Ser Val Thr Glu Gln Asp Ser Lys Asp Ser Thr Tyr Ser Leu Ser
                405                 410                 415

Ser Thr Leu Thr Leu Ser Lys Ala Asp Tyr Glu Lys His Lys Val Tyr
            420                 425                 430

Ala Cys Glu Val Thr His Gln Gly Leu Ser Ser Pro Val Thr Lys Ser
        435                 440                 445

Phe Asn Arg Gly Glu Cys
    450
```

<210> SEQ ID NO 25
<211> LENGTH: 686
<212> TYPE: PRT
<213> ORGANISM: Artificial Sequence
<220> FEATURE:
<223> OTHER INFORMATION: anti-IL4-VL-huIGKC-[PCS1]-<(G4S)3>-[PCS1]-anti-IL13-VL-huIGKC-<G4S>-Fc-huIgG1(hole-RF)

<400> SEQUENCE: 25

```
Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
```

-continued

```
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Gly Gly Gly Ser Gly
    210                 215                 220

Gly Gly Gly Ser Gly Gly Gly Gly Ser Arg Arg Lys Arg Asp Ile Val
225                 230                 235                 240

Leu Thr Gln Ser Pro Ala Ser Leu Ala Val Ser Leu Gly Gln Arg Ala
                245                 250                 255

Thr Ile Ser Cys Arg Ala Ser Glu Ser Val Asp Ser Tyr Gly Gln Ser
            260                 265                 270

Tyr Met His Trp Tyr Gln Gln Lys Ala Gly Gln Pro Pro Lys Leu Leu
        275                 280                 285

Ile Tyr Leu Ala Ser Asn Leu Glu Ser Gly Val Pro Ala Arg Phe Ser
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335

Arg Thr Phe Gly Gly Gly Thr Lys Leu Glu Ile Lys Arg Thr Val Ala
            340                 345                 350

Ala Pro Ser Val Phe Ile Phe Pro Pro Ser Asp Glu Gln Leu Lys Ser
        355                 360                 365

Gly Thr Ala Ser Val Val Cys Leu Leu Asn Asn Phe Tyr Pro Arg Glu
    370                 375                 380

Ala Lys Val Gln Trp Lys Val Asp Asn Ala Leu Gln Ser Gly Asn Ser
385                 390                 395                 400

Gln Glu Ser Val Thr Glu Gln Asp Ser Lys Asp Ser Thr Tyr Ser Leu
                405                 410                 415

Ser Ser Thr Leu Thr Leu Ser Lys Ala Asp Tyr Glu Lys His Lys Val
            420                 425                 430

Tyr Ala Cys Glu Val Thr His Gln Gly Leu Ser Ser Pro Val Thr Lys
        435                 440                 445
```

```
Ser Phe Asn Arg Gly Glu Cys Gly Gly Gly Gly Ser Asp Lys Thr His
    450                 455                 460

Thr Cys Pro Pro Cys Pro Ala Pro Glu Leu Leu Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser His Glu Asp Pro Glu
            500                 505                 510

Val Lys Phe Asn Trp Tyr Val Asp Gly Val Glu Val His Asn Ala Lys
        515                 520                 525

Thr Lys Pro Arg Glu Glu Gln Tyr Asn Ser Thr Tyr Arg Val Val Ser
    530                 535                 540

Val Leu Thr Val Leu His Gln Asp Trp Leu Asn Gly Lys Glu Tyr Lys
545                 550                 555                 560

Cys Lys Val Ser Asn Lys Ala Leu Pro Ala Pro Ile Glu Lys Thr Ile
                565                 570                 575

Ser Lys Ala Lys Gly Gln Pro Arg Glu Pro Gln Val Cys Thr Leu Pro
            580                 585                 590

Pro Ser Arg Asp Glu Leu Thr Lys Asn Gln Val Ser Leu Ser Cys Ala
        595                 600                 605

Val Lys Gly Phe Tyr Pro Ser Asp Ile Ala Val Glu Trp Glu Ser Asn
    610                 615                 620

Gly Gln Pro Glu Asn Asn Tyr Lys Thr Thr Pro Pro Val Leu Asp Ser
625                 630                 635                 640

Asp Gly Ser Phe Phe Leu Val Ser Lys Leu Thr Val Asp Lys Ser Arg
                645                 650                 655

Trp Gln Gln Gly Asn Val Phe Ser Cys Ser Val Met His Glu Ala Leu
            660                 665                 670

His Asn Arg Phe Thr Gln Lys Ser Leu Ser Leu Ser Pro Gly
        675                 680                 685


<210> SEQ ID NO 26
<211> LENGTH: 693
<212> TYPE: PRT
<213> ORGANISM: Artificial Sequence
<220> FEATURE:
<223> OTHER INFORMATION: anti-IL4-VH-huIGH-G11-huIGH-H1-<(G4S)3>-anti-
      IL13-VH-huIGHG1(knob)

<400> SEQUENCE: 26

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala Ser Thr Lys Gly
```

-continued

```
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Gly Gly Gly Gly Ser Gly Gly Gly Gly
225                 230                 235                 240

Ser Gly Gly Gly Gly Ser Glu Val Gln Leu Lys Glu Ser Gly Pro Gly
                245                 250                 255

Leu Val Ala Pro Gly Gly Ser Leu Ser Ile Thr Cys Thr Val Ser Gly
            260                 265                 270

Phe Ser Leu Thr Asp Ser Ser Ile Asn Trp Val Arg Gln Pro Pro Gly
        275                 280                 285

Lys Gly Leu Glu Trp Leu Gly Met Ile Trp Gly Asp Gly Arg Ile Asp
    290                 295                 300

Tyr Ala Asp Ala Leu Lys Ser Arg Leu Ser Ile Ser Lys Asp Ser Ser
305                 310                 315                 320

Lys Ser Gln Val Phe Leu Glu Met Thr Ser Leu Arg Thr Asp Asp Thr
                325                 330                 335

Ala Thr Tyr Tyr Cys Ala Arg Asp Gly Tyr Phe Pro Tyr Ala Met Asp
            340                 345                 350

Phe Trp Gly Gln Gly Thr Ser Val Thr Val Ser Ser Ala Ser Thr Lys
        355                 360                 365

Gly Pro Ser Val Phe Pro Leu Ala Pro Ser Ser Lys Ser Thr Ser Gly
    370                 375                 380

Gly Thr Ala Ala Leu Gly Cys Leu Val Lys Asp Tyr Phe Pro Glu Pro
385                 390                 395                 400

Val Thr Val Ser Trp Asn Ser Gly Ala Leu Thr Ser Gly Val His Thr
                405                 410                 415

Phe Pro Ala Val Leu Gln Ser Ser Gly Leu Tyr Ser Leu Ser Ser Val
            420                 425                 430

Val Thr Val Pro Ser Ser Ser Leu Gly Thr Gln Thr Tyr Ile Cys Asn
        435                 440                 445

Val Asn His Lys Pro Ser Asn Thr Lys Val Asp Lys Lys Val Glu Pro
    450                 455                 460

Lys Ser Cys Asp Lys Thr His Thr Cys Pro Pro Cys Pro Ala Pro Glu
465                 470                 475                 480

Leu Leu Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540
```

```
Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Pro
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Cys Arg Asp Glu Leu Thr Lys Asn
        595                 600                 605

Gln Val Ser Leu Trp Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly
    690


<210> SEQ ID NO 27
<211> LENGTH: 677
<212> TYPE: PRT
<213> ORGANISM: Artificial Sequence
<220> FEATURE:
<223> OTHER INFORMATION: anti-IL4-VL-huIGKC-<G4S>-[PCS1]-<G4S>-anti-
      IL13-VL-huIGKC-<G4S>-Fc-huIgG1(hole-RF)

<400> SEQUENCE: 27

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

-continued

```
        195                 200                 205

Phe Asn Arg Gly Glu Cys Gly Gly Gly Gly Ser Arg Arg Lys Arg Gly
    210                 215                 220

Gly Gly Gly Ser Asp Ile Val Leu Thr Gln Ser Pro Ala Ser Leu Ala
225                 230                 235                 240

Val Ser Leu Gly Gln Arg Ala Thr Ile Ser Cys Arg Ala Ser Glu Ser
                245                 250                 255

Val Asp Ser Tyr Gly Gln Ser Tyr Met His Trp Tyr Gln Gln Lys Ala
            260                 265                 270

Gly Gln Pro Pro Lys Leu Leu Ile Tyr Leu Ala Ser Asn Leu Glu Ser
        275                 280                 285

Gly Val Pro Ala Arg Phe Ser Gly Ser Gly Ser Arg Thr Asp Phe Thr
    290                 295                 300

Leu Thr Ile Asp Pro Val Gln Ala Glu Asp Ala Ala Thr Tyr Tyr Cys
305                 310                 315                 320

Gln Gln Asn Ala Glu Asp Ser Arg Thr Phe Gly Gly Gly Thr Lys Leu
                325                 330                 335

Glu Ile Lys Arg Thr Val Ala Ala Pro Ser Val Phe Ile Phe Pro Pro
            340                 345                 350

Ser Asp Glu Gln Leu Lys Ser Gly Thr Ala Ser Val Val Cys Leu Leu
        355                 360                 365

Asn Asn Phe Tyr Pro Arg Glu Ala Lys Val Gln Trp Lys Val Asp Asn
    370                 375                 380

Ala Leu Gln Ser Gly Asn Ser Gln Glu Ser Val Thr Glu Gln Asp Ser
385                 390                 395                 400

Lys Asp Ser Thr Tyr Ser Leu Ser Ser Thr Leu Thr Leu Ser Lys Ala
                405                 410                 415

Asp Tyr Glu Lys His Lys Val Tyr Ala Cys Glu Val Thr His Gln Gly
            420                 425                 430

Leu Ser Ser Pro Val Thr Lys Ser Phe Asn Arg Gly Glu Cys Gly Gly
        435                 440                 445

Gly Gly Ser Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Asn
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Cys Thr Leu Pro Pro Ser Arg Asp Glu Leu Thr Lys Asn
            580                 585                 590

Gln Val Ser Leu Ser Cys Ala Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620
```

Thr Pro Pro Val Leu Asp Ser Asp Gly Ser Phe Phe Leu Val Ser Lys
625 630 635 640

Leu Thr Val Asp Lys Ser Arg Trp Gln Gln Gly Asn Val Phe Ser Cys
645 650 655

Ser Val Met His Glu Ala Leu His Asn Arg Phe Thr Gln Lys Ser Leu
660 665 670

Ser Leu Ser Pro Gly
675

<210> SEQ ID NO 28
<211> LENGTH: 686
<212> TYPE: PRT
<213> ORGANISM: Artificial Sequence
<220> FEATURE:
<223> OTHER INFORMATION: anti-IL4-VL-huIGKC-[deltaPCS]-<(G4S)3>-
[deltaPCS]-anti-IL13-VL-huIGKC-<G4S>-Fc-huIgG1(hole-RF)

<400> SEQUENCE: 28

Asp Ile Gln Met Thr Gln Ser Pro Ala Ser Leu Ser Val Ser Val Gly
1 5 10 15

Asp Thr Ile Thr Leu Thr Cys His Ala Ser Gln Asn Ile Asp Val Trp
20 25 30

Leu Ser Trp Phe Gln Gln Lys Pro Gly Asn Ile Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Gly Phe Thr Leu Thr Ile Ser Ser Leu Gln Pro
65 70 75 80

Glu Asp Ile Ala Thr Tyr Tyr Cys Gln Gln Ala His Ser Tyr Pro Phe
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Arg Gln Gln Arg Gly Gly Gly Gly Ser Gly
210 215 220

Gly Gly Gly Ser Gly Gly Gly Gly Ser Arg Gln Gln Arg Asp Ile Val
225 230 235 240

Leu Thr Gln Ser Pro Ala Ser Leu Ala Val Ser Leu Gly Gln Arg Ala
245 250 255

Thr Ile Ser Cys Arg Ala Ser Glu Ser Val Asp Ser Tyr Gly Gln Ser
260 265 270

Tyr Met His Trp Tyr Gln Gln Lys Ala Gly Gln Pro Pro Lys Leu Leu
275 280 285

Ile Tyr Leu Ala Ser Asn Leu Glu Ser Gly Val Pro Ala Arg Phe Ser

-continued

```
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335

Arg Thr Phe Gly Gly Gly Thr Lys Leu Glu Ile Lys Arg Thr Val Ala
            340                 345                 350

Ala Pro Ser Val Phe Ile Phe Pro Pro Ser Asp Glu Gln Leu Lys Ser
        355                 360                 365

Gly Thr Ala Ser Val Val Cys Leu Leu Asn Asn Phe Tyr Pro Arg Glu
    370                 375                 380

Ala Lys Val Gln Trp Lys Val Asp Asn Ala Leu Gln Ser Gly Asn Ser
385                 390                 395                 400

Gln Glu Ser Val Thr Glu Gln Asp Ser Lys Asp Ser Thr Tyr Ser Leu
                405                 410                 415

Ser Ser Thr Leu Thr Leu Ser Lys Ala Asp Tyr Glu Lys His Lys Val
            420                 425                 430

Tyr Ala Cys Glu Val Thr His Gln Gly Leu Ser Ser Pro Val Thr Lys
        435                 440                 445

Ser Phe Asn Arg Gly Glu Cys Gly Gly Gly Gly Ser Asp Lys Thr His
    450                 455                 460

Thr Cys Pro Pro Cys Pro Ala Pro Glu Leu Leu Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser His Glu Asp Pro Glu
            500                 505                 510

Val Lys Phe Asn Trp Tyr Val Asp Gly Val Glu Val His Asn Ala Lys
        515                 520                 525

Thr Lys Pro Arg Glu Glu Gln Tyr Asn Ser Thr Tyr Arg Val Val Ser
    530                 535                 540

Val Leu Thr Val Leu His Gln Asp Trp Leu Asn Gly Lys Glu Tyr Lys
545                 550                 555                 560

Cys Lys Val Ser Asn Lys Ala Leu Pro Ala Pro Ile Glu Lys Thr Ile
                565                 570                 575

Ser Lys Ala Lys Gly Gln Pro Arg Glu Pro Gln Val Cys Thr Leu Pro
            580                 585                 590

Pro Ser Arg Asp Glu Leu Thr Lys Asn Gln Val Ser Leu Ser Cys Ala
        595                 600                 605

Val Lys Gly Phe Tyr Pro Ser Asp Ile Ala Val Glu Trp Glu Ser Asn
    610                 615                 620

Gly Gln Pro Glu Asn Asn Tyr Lys Thr Thr Pro Pro Val Leu Asp Ser
625                 630                 635                 640

Asp Gly Ser Phe Phe Leu Val Ser Lys Leu Thr Val Asp Lys Ser Arg
                645                 650                 655

Trp Gln Gln Gly Asn Val Phe Ser Cys Ser Val Met His Glu Ala Leu
            660                 665                 670

His Asn Arg Phe Thr Gln Lys Ser Leu Ser Leu Ser Pro Gly
        675                 680                 685
```

<210> SEQ ID NO 29
<211> LENGTH: 686
<212> TYPE: PRT
<213> ORGANISM: Artificial Sequence
<220> FEATURE:
<223> OTHER INFORMATION: anti-IL4-VL-huIGKC-[PCS1]-<GS>-His(8)-<G4S>-
[PCS1]-anti-IL13-VL-huIGKC-<G4S>-Fc-huIgG1(hole-RF)

<400> SEQUENCE: 29

```
Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Ser His His His His
    210                 215                 220

His His His His Gly Gly Gly Gly Ser Arg Arg Lys Arg Asp Ile Val
225                 230                 235                 240

Leu Thr Gln Ser Pro Ala Ser Leu Ala Val Ser Leu Gly Gln Arg Ala
                245                 250                 255

Thr Ile Ser Cys Arg Ala Ser Glu Ser Val Asp Ser Tyr Gly Gln Ser
            260                 265                 270

Tyr Met His Trp Tyr Gln Gln Lys Ala Gly Gln Pro Pro Lys Leu Leu
        275                 280                 285

Ile Tyr Leu Ala Ser Asn Leu Glu Ser Gly Val Pro Ala Arg Phe Ser
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335

Arg Thr Phe Gly Gly Gly Thr Lys Leu Glu Ile Lys Arg Thr Val Ala
            340                 345                 350

Ala Pro Ser Val Phe Ile Phe Pro Pro Ser Asp Glu Gln Leu Lys Ser
        355                 360                 365

Gly Thr Ala Ser Val Val Cys Leu Leu Asn Asn Phe Tyr Pro Arg Glu
    370                 375                 380

Ala Lys Val Gln Trp Lys Val Asp Asn Ala Leu Gln Ser Gly Asn Ser
```

385 390 395 400

Gln Glu Ser Val Thr Glu Gln Asp Ser Lys Asp Ser Thr Tyr Ser Leu
405 410 415

Ser Ser Thr Leu Thr Leu Ser Lys Ala Asp Tyr Glu Lys His Lys Val
420 425 430

Tyr Ala Cys Glu Val Thr His Gln Gly Leu Ser Ser Pro Val Thr Lys
435 440 445

Ser Phe Asn Arg Gly Glu Cys Gly Gly Gly Gly Ser Asp Lys Thr His
450 455 460

Thr Cys Pro Pro Cys Pro Ala Pro Glu Leu Leu Gly Gly Pro Ser Val
465 470 475 480

Phe Leu Phe Pro Pro Lys Pro Lys Asp Thr Leu Met Ile Ser Arg Thr
485 490 495

Pro Glu Val Thr Cys Val Val Val Asp Val Ser His Glu Asp Pro Glu
500 505 510

Val Lys Phe Asn Trp Tyr Val Asp Gly Val Glu Val His Asn Ala Lys
515 520 525

Thr Lys Pro Arg Glu Glu Gln Tyr Asn Ser Thr Tyr Arg Val Val Ser
530 535 540

Val Leu Thr Val Leu His Gln Asp Trp Leu Asn Gly Lys Glu Tyr Lys
545 550 555 560

Cys Lys Val Ser Asn Lys Ala Leu Pro Ala Pro Ile Glu Lys Thr Ile
565 570 575

Ser Lys Ala Lys Gly Gln Pro Arg Glu Pro Gln Val Cys Thr Leu Pro
580 585 590

Pro Ser Arg Asp Glu Leu Thr Lys Asn Gln Val Ser Leu Ser Cys Ala
595 600 605

Val Lys Gly Phe Tyr Pro Ser Asp Ile Ala Val Glu Trp Glu Ser Asn
610 615 620

Gly Gln Pro Glu Asn Asn Tyr Lys Thr Thr Pro Pro Val Leu Asp Ser
625 630 635 640

Asp Gly Ser Phe Phe Leu Val Ser Lys Leu Thr Val Asp Lys Ser Arg
645 650 655

Trp Gln Gln Gly Asn Val Phe Ser Cys Ser Val Met His Glu Ala Leu
660 665 670

His Asn Arg Phe Thr Gln Lys Ser Leu Ser Leu Ser Pro Gly
675 680 685

<210> SEQ ID NO 30
<211> LENGTH: 686
<212> TYPE: PRT
<213> ORGANISM: Artificial Sequence
<220> FEATURE:
<223> OTHER INFORMATION: anti-IL4-VL-huIGKC-[deltaPCS]-<GS>-His(8)-
<G4S>-[deltaPCS]-anti-IL13-VL-huIGKC-<G4S>-Fc-huIgG1(hole-RF)

<400> SEQUENCE: 30

Asp Ile Gln Met Thr Gln Ser Pro Ala Ser Leu Ser Val Ser Val Gly
1 5 10 15

Asp Thr Ile Thr Leu Thr Cys His Ala Ser Gln Asn Ile Asp Val Trp
20 25 30

Leu Ser Trp Phe Gln Gln Lys Pro Gly Asn Ile Pro Lys Leu Leu Ile
35 40 45

Tyr Lys Ala Ser Asn Leu His Thr Gly Val Pro Ser Arg Phe Ser Gly
50 55 60

-continued

```
Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Gln Gln Arg Gly Ser His His His His
    210                 215                 220

His His His His Gly Gly Gly Gly Ser Arg Gln Gln Arg Asp Ile Val
225                 230                 235                 240

Leu Thr Gln Ser Pro Ala Ser Leu Ala Val Ser Leu Gly Gln Arg Ala
                245                 250                 255

Thr Ile Ser Cys Arg Ala Ser Glu Ser Val Asp Ser Tyr Gly Gln Ser
            260                 265                 270

Tyr Met His Trp Tyr Gln Gln Lys Ala Gly Gln Pro Pro Lys Leu Leu
        275                 280                 285

Ile Tyr Leu Ala Ser Asn Leu Glu Ser Gly Val Pro Ala Arg Phe Ser
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335

Arg Thr Phe Gly Gly Gly Thr Lys Leu Glu Ile Lys Arg Thr Val Ala
            340                 345                 350

Ala Pro Ser Val Phe Ile Phe Pro Pro Ser Asp Glu Gln Leu Lys Ser
        355                 360                 365

Gly Thr Ala Ser Val Val Cys Leu Leu Asn Asn Phe Tyr Pro Arg Glu
    370                 375                 380

Ala Lys Val Gln Trp Lys Val Asp Asn Ala Leu Gln Ser Gly Asn Ser
385                 390                 395                 400

Gln Glu Ser Val Thr Glu Gln Asp Ser Lys Asp Ser Thr Tyr Ser Leu
                405                 410                 415

Ser Ser Thr Leu Thr Leu Ser Lys Ala Asp Tyr Glu Lys His Lys Val
            420                 425                 430

Tyr Ala Cys Glu Val Thr His Gln Gly Leu Ser Ser Pro Val Thr Lys
        435                 440                 445

Ser Phe Asn Arg Gly Glu Cys Gly Gly Gly Gly Ser Asp Lys Thr His
    450                 455                 460

Thr Cys Pro Pro Cys Pro Ala Pro Glu Leu Leu Gly Gly Pro Ser Val
465                 470                 475                 480

Phe Leu Phe Pro Pro Lys Pro Lys Asp Thr Leu Met Ile Ser Arg Thr
```

```
                485                 490                 495

Pro Glu Val Thr Cys Val Val Val Asp Val Ser His Glu Asp Pro Glu
            500                 505                 510

Val Lys Phe Asn Trp Tyr Val Asp Gly Val Glu Val His Asn Ala Lys
        515                 520                 525

Thr Lys Pro Arg Glu Glu Gln Tyr Asn Ser Thr Tyr Arg Val Val Ser
    530                 535                 540

Val Leu Thr Val Leu His Gln Asp Trp Leu Asn Gly Lys Glu Tyr Lys
545                 550                 555                 560

Cys Lys Val Ser Asn Lys Ala Leu Pro Ala Pro Ile Glu Lys Thr Ile
                565                 570                 575

Ser Lys Ala Lys Gly Gln Pro Arg Glu Pro Gln Val Cys Thr Leu Pro
            580                 585                 590

Pro Ser Arg Asp Glu Leu Thr Lys Asn Gln Val Ser Leu Ser Cys Ala
        595                 600                 605

Val Lys Gly Phe Tyr Pro Ser Asp Ile Ala Val Glu Trp Glu Ser Asn
    610                 615                 620

Gly Gln Pro Glu Asn Asn Tyr Lys Thr Thr Pro Pro Val Leu Asp Ser
625                 630                 635                 640

Asp Gly Ser Phe Phe Leu Val Ser Lys Leu Thr Val Asp Lys Ser Arg
                645                 650                 655

Trp Gln Gln Gly Asn Val Phe Ser Cys Ser Val Met His Glu Ala Leu
            660                 665                 670

His Asn Arg Phe Thr Gln Lys Ser Leu Ser Leu Ser Pro Gly
        675                 680                 685


<210> SEQ ID NO 31
<211> LENGTH: 688
<212> TYPE: PRT
<213> ORGANISM: Artificial Sequence
<220> FEATURE:
<223> OTHER INFORMATION: anti-IL4-VL-huIGKC-[PCS2]-<(G4S)3>-[PCS2]-anti-
      IL13-VL-huIGKC-<G4S>-Fc-huIgG1(hole-RF)

<400> SEQUENCE: 31

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Arg Lys Arg Ser Val Asp Glu
    210                 215                 220

Gly Gly Gly Gly Ser His Arg Arg Arg Lys Arg Ser Val Asp Glu Asp
225                 230                 235                 240

Ile Val Leu Thr Gln Ser Pro Ala Ser Leu Ala Val Ser Leu Gly Gln
                245                 250                 255

Arg Ala Thr Ile Ser Cys Arg Ala Ser Glu Ser Val Asp Ser Tyr Gly
            260                 265                 270

Gln Ser Tyr Met His Trp Tyr Gln Gln Lys Ala Gly Gln Pro Pro Lys
        275                 280                 285

Leu Leu Ile Tyr Leu Ala Ser Asn Leu Glu Ser Gly Val Pro Ala Arg
    290                 295                 300

Phe Ser Gly Ser Gly Ser Arg Thr Asp Phe Thr Leu Thr Ile Asp Pro
305                 310                 315                 320

Val Gln Ala Glu Asp Ala Ala Thr Tyr Tyr Cys Gln Gln Asn Ala Glu
                325                 330                 335

Asp Ser Arg Thr Phe Gly Gly Gly Thr Lys Leu Glu Ile Lys Arg Thr
            340                 345                 350

Val Ala Ala Pro Ser Val Phe Ile Phe Pro Pro Ser Asp Glu Gln Leu
        355                 360                 365

Lys Ser Gly Thr Ala Ser Val Val Cys Leu Leu Asn Asn Phe Tyr Pro
    370                 375                 380

Arg Glu Ala Lys Val Gln Trp Lys Val Asp Asn Ala Leu Gln Ser Gly
385                 390                 395                 400

Asn Ser Gln Glu Ser Val Thr Glu Gln Asp Ser Lys Asp Ser Thr Tyr
                405                 410                 415

Ser Leu Ser Ser Thr Leu Thr Leu Ser Lys Ala Asp Tyr Glu Lys His
            420                 425                 430

Lys Val Tyr Ala Cys Glu Val Thr His Gln Gly Leu Ser Ser Pro Val
        435                 440                 445

Thr Lys Ser Phe Asn Arg Gly Glu Cys Gly Gly Gly Gly Ser Asp Lys
    450                 455                 460

Thr His Thr Cys Pro Pro Cys Pro Ala Pro Glu Leu Leu Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Pro Ala Pro Ile Glu Lys
                565                 570                 575

Thr Ile Ser Lys Ala Lys Gly Gln Pro Arg Glu Pro Gln Val Cys Thr
```

```
            580                 585                 590

Leu Pro Pro Ser Arg Asp Glu Leu Thr Lys Asn Gln Val Ser Leu Ser
        595                 600                 605

Cys Ala Val Lys Gly Phe Tyr Pro Ser Asp Ile Ala Val Glu Trp Glu
    610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Val Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn Arg Phe Thr Gln Lys Ser Leu Ser Leu Ser Pro Gly
        675                 680                 685


<210> SEQ ID NO 32
<211> LENGTH: 688
<212> TYPE: PRT
<213> ORGANISM: Artificial Sequence
<220> FEATURE:
<223> OTHER INFORMATION: anti-IL4-VL-huIGKC-[PCS3]-<(G4S)3>-[PCS3]-anti-
      IL13-VL-huIGKC-<G4S>-Fc-huIgG1(hole-RF)

<400> SEQUENCE: 32

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Pro Met Lys Lys Arg Arg Ala Gly Val Pro
    210                 215                 220

Gly Gly Gly Gly Ser Pro Met Lys Lys Arg Arg Ala Gly Val Pro Asp
225                 230                 235                 240

Ile Val Leu Thr Gln Ser Pro Ala Ser Leu Ala Val Ser Leu Gly Gln
                245                 250                 255
```

-continued

```
Arg Ala Thr Ile Ser Cys Arg Ala Ser Glu Ser Val Asp Ser Tyr Gly
            260                 265                 270

Gln Ser Tyr Met His Trp Tyr Gln Gln Lys Ala Gly Gln Pro Pro Lys
        275                 280                 285

Leu Leu Ile Tyr Leu Ala Ser Asn Leu Glu Ser Gly Val Pro Ala Arg
    290                 295                 300

Phe Ser Gly Ser Gly Ser Arg Thr Asp Phe Thr Leu Thr Ile Asp Pro
305                 310                 315                 320

Val Gln Ala Glu Asp Ala Ala Thr Tyr Tyr Cys Gln Gln Asn Ala Glu
                325                 330                 335

Asp Ser Arg Thr Phe Gly Gly Gly Thr Lys Leu Glu Ile Lys Arg Thr
            340                 345                 350

Val Ala Ala Pro Ser Val Phe Ile Phe Pro Pro Ser Asp Glu Gln Leu
        355                 360                 365

Lys Ser Gly Thr Ala Ser Val Val Cys Leu Leu Asn Asn Phe Tyr Pro
    370                 375                 380

Arg Glu Ala Lys Val Gln Trp Lys Val Asp Asn Ala Leu Gln Ser Gly
385                 390                 395                 400

Asn Ser Gln Glu Ser Val Thr Glu Gln Asp Ser Lys Asp Ser Thr Tyr
                405                 410                 415

Ser Leu Ser Ser Thr Leu Thr Leu Ser Lys Ala Asp Tyr Glu Lys His
            420                 425                 430

Lys Val Tyr Ala Cys Glu Val Thr His Gln Gly Leu Ser Ser Pro Val
        435                 440                 445

Thr Lys Ser Phe Asn Arg Gly Glu Cys Gly Gly Gly Gly Ser Asp Lys
    450                 455                 460

Thr His Thr Cys Pro Pro Cys Pro Ala Pro Glu Leu Leu Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Pro Ala Pro Ile Glu Lys
                565                 570                 575

Thr Ile Ser Lys Ala Lys Gly Gln Pro Arg Glu Pro Gln Val Cys Thr
            580                 585                 590

Leu Pro Pro Ser Arg Asp Glu Leu Thr Lys Asn Gln Val Ser Leu Ser
        595                 600                 605

Cys Ala Val Lys Gly Phe Tyr Pro Ser Asp Ile Ala Val Glu Trp Glu
    610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Val Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn Arg Phe Thr Gln Lys Ser Leu Ser Leu Ser Pro Gly
```

-continued

```
        675                 680                 685


<210> SEQ ID NO 33
<211> LENGTH: 691
<212> TYPE: PRT
<213> ORGANISM: Artificial Sequence
<220> FEATURE:
<223> OTHER INFORMATION: anti-IL4-VL-huIGKC-[PCS1]-<G4S>-<(EAAAK)2>-
      <G4S>-[PCS1]-anti-IL13-VL-huIGKC-<G4S>-Fc-huIgG1(hole-RF)

<400> SEQUENCE: 33

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Gly Gly Gly Gly Ser Glu
    210                 215                 220

Ala Ala Ala Lys Glu Ala Ala Ala Lys Gly Gly Gly Gly Ser Arg Arg
225                 230                 235                 240

Lys Arg Asp Ile Val Leu Thr Gln Ser Pro Ala Ser Leu Ala Val Ser
                245                 250                 255

Leu Gly Gln Arg Ala Thr Ile Ser Cys Arg Ala Ser Glu Ser Val Asp
            260                 265                 270

Ser Tyr Gly Gln Ser Tyr Met His Trp Tyr Gln Gln Lys Ala Gly Gln
        275                 280                 285

Pro Pro Lys Leu Leu Ile Tyr Leu Ala Ser Asn Leu Glu Ser Gly Val
    290                 295                 300

Pro Ala Arg Phe Ser Gly Ser Gly Ser Arg Thr Asp Phe Thr Leu Thr
305                 310                 315                 320

Ile Asp Pro Val Gln Ala Glu Asp Ala Ala Thr Tyr Tyr Cys Gln Gln
                325                 330                 335

Asn Ala Glu Asp Ser Arg Thr Phe Gly Gly Gly Thr Lys Leu Glu Ile
            340                 345                 350
```

-continued

```
Lys Arg Thr Val Ala Ala Pro Ser Val Phe Ile Phe Pro Pro Ser Asp
        355                 360                 365

Glu Gln Leu Lys Ser Gly Thr Ala Ser Val Val Cys Leu Leu Asn Asn
    370                 375                 380

Phe Tyr Pro Arg Glu Ala Lys Val Gln Trp Lys Val Asp Asn Ala Leu
385                 390                 395                 400

Gln Ser Gly Asn Ser Gln Glu Ser Val Thr Glu Gln Asp Ser Lys Asp
                405                 410                 415

Ser Thr Tyr Ser Leu Ser Ser Thr Leu Thr Leu Ser Lys Ala Asp Tyr
            420                 425                 430

Glu Lys His Lys Val Tyr Ala Cys Glu Val Thr His Gln Gly Leu Ser
        435                 440                 445

Ser Pro Val Thr Lys Ser Phe Asn Arg Gly Glu Cys Gly Gly Gly Gly
    450                 455                 460

Ser Asp Lys Thr His Thr Cys Pro Pro Cys Pro Ala Pro Glu Leu Leu
465                 470                 475                 480

Gly Gly Pro Ser Val Phe Leu Phe Pro Pro Lys Pro Lys Asp Thr Leu
                485                 490                 495

Met Ile Ser Arg Thr Pro Glu Val Thr Cys Val Val Val Asp Val Ser
            500                 505                 510

His Glu Asp Pro Glu Val Lys Phe Asn Trp Tyr Val Asp Gly Val Glu
        515                 520                 525

Val His Asn Ala Lys Thr Lys Pro Arg Glu Glu Gln Tyr Asn Ser Thr
    530                 535                 540

Tyr Arg Val Val Ser Val Leu Thr Val Leu His Gln Asp Trp Leu Asn
545                 550                 555                 560

Gly Lys Glu Tyr Lys Cys Lys Val Ser Asn Lys Ala Leu Pro Ala Pro
                565                 570                 575

Ile Glu Lys Thr Ile Ser Lys Ala Lys Gly Gln Pro Arg Glu Pro Gln
            580                 585                 590

Val Cys Thr Leu Pro Pro Ser Arg Asp Glu Leu Thr Lys Asn Gln Val
        595                 600                 605

Ser Leu Ser Cys Ala Val Lys Gly Phe Tyr Pro Ser Asp Ile Ala Val
    610                 615                 620

Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Val Ser Lys Leu Thr
                645                 650                 655

Val Asp Lys Ser Arg Trp Gln Gln Gly Asn Val Phe Ser Cys Ser Val
            660                 665                 670

Met His Glu Ala Leu His Asn Arg Phe Thr Gln Lys Ser Leu Ser Leu
        675                 680                 685

Ser Pro Gly
    690
```

<210> SEQ ID NO 34
<211> LENGTH: 698
<212> TYPE: PRT
<213> ORGANISM: Artificial Sequence
<220> FEATURE:
<223> OTHER INFORMATION: anti-IL4-VH-huIGH-G11-huIGH-H1-<G4S>-
<(EAAAK)2>-<G4S>-anti-IL13-VH-huIGHG1(knob)

<400> SEQUENCE: 34

```
Gln Val Gln Leu Gln Gln Ser Gly Pro Glu Leu Val Lys Pro Gly Ala
1               5                   10                  15
```

-continued

```
Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Gly Gly Gly Gly Ser Glu Ala Ala Ala
225                 230                 235                 240

Lys Glu Ala Ala Ala Lys Gly Gly Gly Gly Ser Glu Val Gln Leu Lys
                245                 250                 255

Glu Ser Gly Pro Gly Leu Val Ala Pro Gly Gly Ser Leu Ser Ile Thr
            260                 265                 270

Cys Thr Val Ser Gly Phe Ser Leu Thr Asp Ser Ser Ile Asn Trp Val
        275                 280                 285

Arg Gln Pro Pro Gly Lys Gly Leu Glu Trp Leu Gly Met Ile Trp Gly
    290                 295                 300

Asp Gly Arg Ile Asp Tyr Ala Asp Ala Leu Lys Ser Arg Leu Ser Ile
305                 310                 315                 320

Ser Lys Asp Ser Ser Lys Ser Gln Val Phe Leu Glu Met Thr Ser Leu
                325                 330                 335

Arg Thr Asp Asp Thr Ala Thr Tyr Tyr Cys Ala Arg Asp Gly Tyr Phe
            340                 345                 350

Pro Tyr Ala Met Asp Phe Trp Gly Gln Gly Thr Ser Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430
```

```
Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Lys Val Glu Pro Lys Ser Cys Asp Lys Thr His Thr Cys Pro Pro
465                 470                 475                 480

Cys Pro Ala Pro Glu Leu Leu Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Cys Arg Asp
        595                 600                 605

Glu Leu Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695


<210> SEQ ID NO 35
<211> LENGTH: 686
<212> TYPE: PRT
<213> ORGANISM: Artificial Sequence
<220> FEATURE:
<223> OTHER INFORMATION: anti-IL4-VL-huIGKC-[PCS1]-<(AP)7A>-[PCS1]-anti-
      IL13-VL-huIGKC-<G4S>-Fc-huIgG1(hole-RF)

<400> SEQUENCE: 35

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95
```

-continued

```
Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Arg Arg Lys Arg Ala Pro Ala Pro Ala Pro
    210                 215                 220

Ala Pro Ala Pro Ala Pro Ala Pro Ala Arg Arg Lys Arg Asp Ile Val
225                 230                 235                 240

Leu Thr Gln Ser Pro Ala Ser Leu Ala Val Ser Leu Gly Gln Arg Ala
                245                 250                 255

Thr Ile Ser Cys Arg Ala Ser Glu Ser Val Asp Ser Tyr Gly Gln Ser
            260                 265                 270

Tyr Met His Trp Tyr Gln Gln Lys Ala Gly Gln Pro Pro Lys Leu Leu
        275                 280                 285

Ile Tyr Leu Ala Ser Asn Leu Glu Ser Gly Val Pro Ala Arg Phe Ser
    290                 295                 300

Gly Ser Gly Ser Arg Thr Asp Phe Thr Leu Thr Ile Asp Pro Val Gln
305                 310                 315                 320

Ala Glu Asp Ala Ala Thr Tyr Tyr Cys Gln Gln Asn Ala Glu Asp Ser
                325                 330                 335

Arg Thr Phe Gly Gly Gly Thr Lys Leu Glu Ile Lys Arg Thr Val Ala
            340                 345                 350

Ala Pro Ser Val Phe Ile Phe Pro Pro Ser Asp Glu Gln Leu Lys Ser
        355                 360                 365

Gly Thr Ala Ser Val Val Cys Leu Leu Asn Asn Phe Tyr Pro Arg Glu
    370                 375                 380

Ala Lys Val Gln Trp Lys Val Asp Asn Ala Leu Gln Ser Gly Asn Ser
385                 390                 395                 400

Gln Glu Ser Val Thr Glu Gln Asp Ser Lys Asp Ser Thr Tyr Ser Leu
                405                 410                 415

Ser Ser Thr Leu Thr Leu Ser Lys Ala Asp Tyr Glu Lys His Lys Val
            420                 425                 430

Tyr Ala Cys Glu Val Thr His Gln Gly Leu Ser Ser Pro Val Thr Lys
        435                 440                 445

Ser Phe Asn Arg Gly Glu Cys Gly Gly Gly Gly Ser Asp Lys Thr His
    450                 455                 460

Thr Cys Pro Pro Cys Pro Ala Pro Glu Leu Leu Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser His Glu Asp Pro Glu
            500                 505                 510
```

Val Lys Phe Asn Trp Tyr Val Asp Gly Val Glu Val His Asn Ala Lys
515 520 525

Thr Lys Pro Arg Glu Glu Gln Tyr Asn Ser Thr Tyr Arg Val Val Ser
530 535 540

Val Leu Thr Val Leu His Gln Asp Trp Leu Asn Gly Lys Glu Tyr Lys
545 550 555 560

Cys Lys Val Ser Asn Lys Ala Leu Pro Ala Pro Ile Glu Lys Thr Ile
565 570 575

Ser Lys Ala Lys Gly Gln Pro Arg Glu Pro Gln Val Cys Thr Leu Pro
580 585 590

Pro Ser Arg Asp Glu Leu Thr Lys Asn Gln Val Ser Leu Ser Cys Ala
595 600 605

Val Lys Gly Phe Tyr Pro Ser Asp Ile Ala Val Glu Trp Glu Ser Asn
610 615 620

Gly Gln Pro Glu Asn Asn Tyr Lys Thr Thr Pro Pro Val Leu Asp Ser
625 630 635 640

Asp Gly Ser Phe Phe Leu Val Ser Lys Leu Thr Val Asp Lys Ser Arg
645 650 655

Trp Gln Gln Gly Asn Val Phe Ser Cys Ser Val Met His Glu Ala Leu
660 665 670

His Asn Arg Phe Thr Gln Lys Ser Leu Ser Leu Ser Pro Gly
675 680 685

<210> SEQ ID NO 36
<211> LENGTH: 685
<212> TYPE: PRT
<213> ORGANISM: Artificial Sequence
<220> FEATURE:
<223> OTHER INFORMATION: anti-IL4-VL-huIGKC-[PCS1]-<GS>-<(KQGKQ)2>-<GS>-[PCS1]-anti-IL13-VL-huIGKC-<G4S>-Fc-huIgG1(hole-RF)

<400> SEQUENCE: 36

Asp Ile Gln Met Thr Gln Ser Pro Ala Ser Leu Ser Val Ser Val Gly
1 5 10 15

Asp Thr Ile Thr Leu Thr Cys His Ala Ser Gln Asn Ile Asp Val Trp
20 25 30

Leu Ser Trp Phe Gln Gln Lys Pro Gly Asn Ile Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Gly Phe Thr Leu Thr Ile Ser Ser Leu Gln Pro
65 70 75 80

Glu Asp Ile Ala Thr Tyr Tyr Cys Gln Gln Ala His Ser Tyr Pro Phe
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

```
Ala Cys Glu Val Thr His Gln Gly Leu Ser Ser Pro Val Thr Lys Ser
        195                 200                 205

Phe Asn Arg Gly Glu Cys Arg Arg Lys Arg Gly Ser Lys Gln Gly Lys
    210                 215                 220

Gln Lys Gln Gly Lys Gln Gly Ser Arg Arg Lys Arg Asp Ile Val Leu
225                 230                 235                 240

Thr Gln Ser Pro Ala Ser Leu Ala Val Ser Leu Gly Gln Arg Ala Thr
                245                 250                 255

Ile Ser Cys Arg Ala Ser Glu Ser Val Asp Ser Tyr Gly Gln Ser Tyr
            260                 265                 270

Met His Trp Tyr Gln Gln Lys Ala Gly Gln Pro Pro Lys Leu Leu Ile
        275                 280                 285

Tyr Leu Ala Ser Asn Leu Glu Ser Gly Val Pro Ala Arg Phe Ser Gly
    290                 295                 300

Ser Gly Ser Arg Thr Asp Phe Thr Leu Thr Ile Asp Pro Val Gln Ala
305                 310                 315                 320

Glu Asp Ala Ala Thr Tyr Tyr Cys Gln Gln Asn Ala Glu Asp Ser Arg
                325                 330                 335

Thr Phe Gly Gly Gly Thr Lys Leu Glu Ile Lys Arg Thr Val Ala Ala
            340                 345                 350

Pro Ser Val Phe Ile Phe Pro Pro Ser Asp Glu Gln Leu Lys Ser Gly
        355                 360                 365

Thr Ala Ser Val Val Cys Leu Leu Asn Asn Phe Tyr Pro Arg Glu Ala
    370                 375                 380

Lys Val Gln Trp Lys Val Asp Asn Ala Leu Gln Ser Gly Asn Ser Gln
385                 390                 395                 400

Glu Ser Val Thr Glu Gln Asp Ser Lys Asp Ser Thr Tyr Ser Leu Ser
                405                 410                 415

Ser Thr Leu Thr Leu Ser Lys Ala Asp Tyr Glu Lys His Lys Val Tyr
            420                 425                 430

Ala Cys Glu Val Thr His Gln Gly Leu Ser Ser Pro Val Thr Lys Ser
        435                 440                 445

Phe Asn Arg Gly Glu Cys Gly Gly Gly Gly Ser Asp Lys Thr His Thr
    450                 455                 460

Cys Pro Pro Cys Pro Ala Pro Glu Leu Leu Gly Gly Pro Ser Val Phe
465                 470                 475                 480

Leu Phe Pro Pro Lys Pro Lys Asp Thr Leu Met Ile Ser Arg Thr Pro
                485                 490                 495

Glu Val Thr Cys Val Val Val Asp Val Ser His Glu Asp Pro Glu Val
            500                 505                 510

Lys Phe Asn Trp Tyr Val Asp Gly Val Glu Val His Asn Ala Lys Thr
        515                 520                 525

Lys Pro Arg Glu Glu Gln Tyr Asn Ser Thr Tyr Arg Val Val Ser Val
    530                 535                 540

Leu Thr Val Leu His Gln Asp Trp Leu Asn Gly Lys Glu Tyr Lys Cys
545                 550                 555                 560

Lys Val Ser Asn Lys Ala Leu Pro Ala Pro Ile Glu Lys Thr Ile Ser
                565                 570                 575

Lys Ala Lys Gly Gln Pro Arg Glu Pro Gln Val Cys Thr Leu Pro Pro
            580                 585                 590

Ser Arg Asp Glu Leu Thr Lys Asn Gln Val Ser Leu Ser Cys Ala Val
        595                 600                 605
```

-continued

```
Lys Gly Phe Tyr Pro Ser Asp Ile Ala Val Glu Trp Glu Ser Asn Gly
    610                 615                 620

Gln Pro Glu Asn Asn Tyr Lys Thr Thr Pro Pro Val Leu Asp Ser Asp
625                 630                 635                 640

Gly Ser Phe Phe Leu Val Ser Lys Leu Thr Val Asp Lys Ser Arg Trp
                645                 650                 655

Gln Gln Gly Asn Val Phe Ser Cys Ser Val Met His Glu Ala Leu His
            660                 665                 670

Asn Arg Phe Thr Gln Lys Ser Leu Ser Leu Ser Pro Gly
        675                 680                 685


<210> SEQ ID NO 37
<211> LENGTH: 768
<212> TYPE: PRT
<213> ORGANISM: Homo sapiens

<400> SEQUENCE: 37

Gln Lys Val Phe Thr Asn Thr Trp Ala Val Arg Ile Pro Gly Gly Pro
1               5                   10                  15

Ala Val Ala Asn Ser Val Ala Arg Lys His Gly Phe Leu Asn Leu Gly
            20                  25                  30

Gln Ile Phe Gly Asp Tyr Tyr His Phe Trp His Arg Gly Val Thr Lys
        35                  40                  45

Arg Ser Leu Ser Pro His Arg Pro Arg His Ser Arg Leu Gln Arg Glu
    50                  55                  60

Pro Gln Val Gln Trp Leu Glu Gln Gln Val Ala Lys Arg Arg Thr Lys
65                  70                  75                  80

Arg Asp Val Tyr Gln Glu Pro Thr Asp Pro Lys Phe Pro Gln Gln Trp
                85                  90                  95

Tyr Leu Ser Gly Val Thr Gln Arg Asp Leu Asn Val Lys Ala Ala Trp
            100                 105                 110

Ala Gln Gly Tyr Thr Gly His Gly Ile Val Val Ser Ile Leu Asp Asp
        115                 120                 125

Gly Ile Glu Lys Asn His Pro Asp Leu Ala Gly Asn Tyr Asp Pro Gly
    130                 135                 140

Ala Ser Phe Asp Val Asn Asp Gln Asp Pro Asp Pro Gln Pro Arg Tyr
145                 150                 155                 160

Thr Gln Met Asn Asp Asn Arg His Gly Thr Arg Cys Ala Gly Glu Val
                165                 170                 175

Ala Ala Val Ala Asn Asn Gly Val Cys Gly Val Gly Val Ala Tyr Asn
            180                 185                 190

Ala Arg Ile Gly Gly Val Arg Met Leu Asp Gly Glu Val Thr Asp Ala
        195                 200                 205

Val Glu Ala Arg Ser Leu Gly Leu Asn Pro Asn His Ile His Ile Tyr
    210                 215                 220

Ser Ala Ser Trp Gly Pro Glu Asp Asp Gly Lys Thr Val Asp Gly Pro
225                 230                 235                 240

Ala Arg Leu Ala Glu Glu Ala Phe Phe Arg Gly Val Ser Gln Gly Arg
                245                 250                 255

Gly Gly Leu Gly Ser Ile Phe Val Trp Ala Ser Gly Asn Gly Gly Arg
            260                 265                 270

Glu His Asp Ser Cys Asn Cys Asp Gly Tyr Thr Asn Ser Ile Tyr Thr
        275                 280                 285

Leu Ser Ile Ser Ser Ala Thr Gln Phe Gly Asn Val Pro Trp Tyr Ser
    290                 295                 300
```

```
Glu Ala Cys Ser Ser Thr Leu Ala Thr Thr Tyr Ser Ser Gly Asn Gln
305                 310                 315                 320

Asn Glu Lys Gln Ile Val Thr Thr Asp Leu Arg Gln Lys Cys Thr Glu
                325                 330                 335

Ser His Thr Gly Thr Ser Ala Ser Ala Pro Leu Ala Ala Gly Ile Ile
            340                 345                 350

Ala Leu Thr Leu Glu Ala Asn Lys Asn Leu Thr Trp Arg Asp Met Gln
        355                 360                 365

His Leu Val Val Gln Thr Ser Lys Pro Ala His Leu Asn Ala Asn Asp
    370                 375                 380

Trp Ala Thr Asn Gly Val Gly Arg Lys Val Ser His Ser Tyr Gly Tyr
385                 390                 395                 400

Gly Leu Leu Asp Ala Gly Ala Met Val Ala Leu Ala Gln Asn Trp Thr
                405                 410                 415

Thr Val Ala Pro Gln Arg Lys Cys Ile Ile Asp Ile Leu Thr Glu Pro
            420                 425                 430

Lys Asp Ile Gly Lys Arg Leu Glu Val Arg Lys Thr Val Thr Ala Cys
        435                 440                 445

Leu Gly Glu Pro Asn His Ile Thr Arg Leu Glu His Ala Gln Ala Arg
    450                 455                 460

Leu Thr Leu Ser Tyr Asn Arg Arg Gly Asp Leu Ala Ile His Leu Val
465                 470                 475                 480

Ser Pro Met Gly Thr Arg Ser Thr Leu Leu Ala Ala Arg Pro His Asp
                485                 490                 495

Tyr Ser Ala Asp Gly Phe Asn Asp Trp Ala Phe Met Thr Thr His Ser
            500                 505                 510

Trp Asp Glu Asp Pro Ser Gly Glu Trp Val Leu Glu Ile Glu Asn Thr
        515                 520                 525

Ser Glu Ala Asn Asn Tyr Gly Thr Leu Thr Lys Phe Thr Leu Val Leu
    530                 535                 540

Tyr Gly Thr Ala Pro Glu Gly Leu Pro Val Pro Pro Glu Ser Ser Gly
545                 550                 555                 560

Cys Lys Thr Leu Thr Ser Ser Gln Ala Cys Val Val Cys Glu Glu Gly
                565                 570                 575

Phe Ser Leu His Gln Lys Ser Cys Val Gln His Cys Pro Pro Gly Phe
            580                 585                 590

Ala Pro Gln Val Leu Asp Thr His Tyr Ser Thr Glu Asn Asp Val Glu
        595                 600                 605

Thr Ile Arg Ala Ser Val Cys Ala Pro Cys His Ala Ser Cys Ala Thr
    610                 615                 620

Cys Gln Gly Pro Ala Leu Thr Asp Cys Leu Ser Cys Pro Ser His Ala
625                 630                 635                 640

Ser Leu Asp Pro Val Glu Gln Thr Cys Ser Arg Gln Ser Gln Ser Ser
                645                 650                 655

Arg Glu Ser Pro Pro Gln Gln Gln Pro Pro Arg Leu Pro Pro Glu Val
            660                 665                 670

Glu Ala Gly Gln Arg Leu Arg Ala Gly Leu Leu Pro Ser His Leu Pro
        675                 680                 685

Glu Val Val Ala Gly Leu Ser Cys Ala Phe Ile Val Leu Val Phe Val
    690                 695                 700

Thr Val Phe Leu Val Leu Gln Leu Arg Ser Gly Phe Ser Phe Arg Gly
705                 710                 715                 720
```

```
Val Lys Val Tyr Thr Met Asp Arg Gly Leu Ile Ser Tyr Lys Gly Leu
            725                 730                 735

Pro Pro Glu Ala Trp Gln Glu Glu Cys Pro Ser Asp Ser Glu Glu Asp
        740                 745                 750

Glu Gly Arg Gly Glu Arg Thr Ala Phe Ile Lys Asp Gln Ser Ala Leu
    755                 760                 765


<210> SEQ ID NO 38
<211> LENGTH: 775
<212> TYPE: PRT
<213> ORGANISM: Artificial Sequence
<220> FEATURE:
<223> OTHER INFORMATION: Propeptide Furin-mature Furin-<GAA>-KDEL signal
      peptide

<400> SEQUENCE: 38

Gln Lys Val Phe Thr Asn Thr Trp Ala Val Arg Ile Pro Gly Gly Pro
1               5                   10                  15

Ala Val Ala Asn Ser Val Ala Arg Lys His Gly Phe Leu Asn Leu Gly
            20                  25                  30

Gln Ile Phe Gly Asp Tyr Tyr His Phe Trp His Arg Gly Val Thr Lys
        35                  40                  45

Arg Ser Leu Ser Pro His Arg Pro Arg His Ser Arg Leu Gln Arg Glu
    50                  55                  60

Pro Gln Val Gln Trp Leu Glu Gln Gln Val Ala Lys Arg Arg Thr Lys
65                  70                  75                  80

Arg Asp Val Tyr Gln Glu Pro Thr Asp Pro Lys Phe Pro Gln Gln Trp
                85                  90                  95

Tyr Leu Ser Gly Val Thr Gln Arg Asp Leu Asn Val Lys Ala Ala Trp
            100                 105                 110

Ala Gln Gly Tyr Thr Gly His Gly Ile Val Val Ser Ile Leu Asp Asp
        115                 120                 125

Gly Ile Glu Lys Asn His Pro Asp Leu Ala Gly Asn Tyr Asp Pro Gly
    130                 135                 140

Ala Ser Phe Asp Val Asn Asp Gln Asp Pro Asp Pro Gln Pro Arg Tyr
145                 150                 155                 160

Thr Gln Met Asn Asp Asn Arg His Gly Thr Arg Cys Ala Gly Glu Val
                165                 170                 175

Ala Ala Val Ala Asn Asn Gly Val Cys Gly Val Gly Val Ala Tyr Asn
            180                 185                 190

Ala Arg Ile Gly Gly Val Arg Met Leu Asp Gly Glu Val Thr Asp Ala
        195                 200                 205

Val Glu Ala Arg Ser Leu Gly Leu Asn Pro Asn His Ile His Ile Tyr
    210                 215                 220

Ser Ala Ser Trp Gly Pro Glu Asp Asp Gly Lys Thr Val Asp Gly Pro
225                 230                 235                 240

Ala Arg Leu Ala Glu Glu Ala Phe Phe Arg Gly Val Ser Gln Gly Arg
                245                 250                 255

Gly Gly Leu Gly Ser Ile Phe Val Trp Ala Ser Gly Asn Gly Gly Arg
            260                 265                 270

Glu His Asp Ser Cys Asn Cys Asp Gly Tyr Thr Asn Ser Ile Tyr Thr
        275                 280                 285

Leu Ser Ile Ser Ser Ala Thr Gln Phe Gly Asn Val Pro Trp Tyr Ser
    290                 295                 300

Glu Ala Cys Ser Ser Thr Leu Ala Thr Thr Tyr Ser Ser Gly Asn Gln
305                 310                 315                 320
```

-continued

```
Asn Glu Lys Gln Ile Val Thr Thr Asp Leu Arg Gln Lys Cys Thr Glu
                325                 330                 335

Ser His Thr Gly Thr Ser Ala Ser Ala Pro Leu Ala Ala Gly Ile Ile
            340                 345                 350

Ala Leu Thr Leu Glu Ala Asn Lys Asn Leu Thr Trp Arg Asp Met Gln
        355                 360                 365

His Leu Val Val Gln Thr Ser Lys Pro Ala His Leu Asn Ala Asn Asp
    370                 375                 380

Trp Ala Thr Asn Gly Val Gly Arg Lys Val Ser His Ser Tyr Gly Tyr
385                 390                 395                 400

Gly Leu Leu Asp Ala Gly Ala Met Val Ala Leu Ala Gln Asn Trp Thr
                405                 410                 415

Thr Val Ala Pro Gln Arg Lys Cys Ile Ile Asp Ile Leu Thr Glu Pro
            420                 425                 430

Lys Asp Ile Gly Lys Arg Leu Glu Val Arg Lys Thr Val Thr Ala Cys
        435                 440                 445

Leu Gly Glu Pro Asn His Ile Thr Arg Leu Glu His Ala Gln Ala Arg
    450                 455                 460

Leu Thr Leu Ser Tyr Asn Arg Arg Gly Asp Leu Ala Ile His Leu Val
465                 470                 475                 480

Ser Pro Met Gly Thr Arg Ser Thr Leu Leu Ala Ala Arg Pro His Asp
                485                 490                 495

Tyr Ser Ala Asp Gly Phe Asn Asp Trp Ala Phe Met Thr Thr His Ser
            500                 505                 510

Trp Asp Glu Asp Pro Ser Gly Glu Trp Val Leu Glu Ile Glu Asn Thr
        515                 520                 525

Ser Glu Ala Asn Asn Tyr Gly Thr Leu Thr Lys Phe Thr Leu Val Leu
    530                 535                 540

Tyr Gly Thr Ala Pro Glu Gly Leu Pro Val Pro Pro Glu Ser Ser Gly
545                 550                 555                 560

Cys Lys Thr Leu Thr Ser Ser Gln Ala Cys Val Val Cys Glu Glu Gly
                565                 570                 575

Phe Ser Leu His Gln Lys Ser Cys Val Gln His Cys Pro Pro Gly Phe
            580                 585                 590

Ala Pro Gln Val Leu Asp Thr His Tyr Ser Thr Glu Asn Asp Val Glu
        595                 600                 605

Thr Ile Arg Ala Ser Val Cys Ala Pro Cys His Ala Ser Cys Ala Thr
    610                 615                 620

Cys Gln Gly Pro Ala Leu Thr Asp Cys Leu Ser Cys Pro Ser His Ala
625                 630                 635                 640

Ser Leu Asp Pro Val Glu Gln Thr Cys Ser Arg Gln Ser Gln Ser Ser
                645                 650                 655

Arg Glu Ser Pro Pro Gln Gln Gln Pro Pro Arg Leu Pro Pro Glu Val
            660                 665                 670

Glu Ala Gly Gln Arg Leu Arg Ala Gly Leu Leu Pro Ser His Leu Pro
        675                 680                 685

Glu Val Val Ala Gly Leu Ser Cys Ala Phe Ile Val Leu Val Phe Val
    690                 695                 700

Thr Val Phe Leu Val Leu Gln Leu Arg Ser Gly Phe Ser Phe Arg Gly
705                 710                 715                 720

Val Lys Val Tyr Thr Met Asp Arg Gly Leu Ile Ser Tyr Lys Gly Leu
                725                 730                 735
```

-continued

```
Pro Pro Glu Ala Trp Gln Glu Glu Cys Pro Ser Asp Ser Glu Glu Asp
            740                 745                 750

Glu Gly Arg Gly Glu Arg Thr Ala Phe Ile Lys Asp Gln Ser Ala Leu
        755                 760                 765

Gly Ala Ala Lys Asp Glu Leu
    770                 775


<210> SEQ ID NO 39
<211> LENGTH: 1828
<212> TYPE: PRT
<213> ORGANISM: Homo sapiens

<400> SEQUENCE: 39

Arg Val Tyr Thr Asn His Trp Ala Val Lys Ile Ala Gly Gly Phe Pro
1               5                   10                  15

Glu Ala Asn Arg Ile Ala Ser Lys Tyr Gly Phe Ile Asn Ile Gly Gln
            20                  25                  30

Ile Gly Ala Leu Lys Asp Tyr Tyr His Phe Tyr His Ser Arg Thr Ile
        35                  40                  45

Lys Arg Ser Val Ile Ser Ser Arg Gly Thr His Ser Phe Ile Ser Met
    50                  55                  60

Glu Pro Lys Val Glu Trp Ile Gln Gln Gln Val Val Lys Lys Arg Thr
65                  70                  75                  80

Lys Arg Asp Tyr Asp Phe Ser Arg Ala Gln Ser Thr Tyr Phe Asn Asp
                85                  90                  95

Pro Lys Trp Pro Ser Met Trp Tyr Met His Cys Ser Asp Asn Thr His
            100                 105                 110

Pro Cys Gln Ser Asp Met Asn Ile Glu Gly Ala Trp Lys Arg Gly Tyr
        115                 120                 125

Thr Gly Lys Asn Ile Val Val Thr Ile Leu Asp Asp Gly Ile Glu Arg
    130                 135                 140

Thr His Pro Asp Leu Met Gln Asn Tyr Asp Ala Leu Ala Ser Cys Asp
145                 150                 155                 160

Val Asn Gly Asn Asp Leu Asp Pro Met Pro Arg Tyr Asp Ala Ser Asn
                165                 170                 175

Glu Asn Lys His Gly Thr Arg Cys Ala Gly Glu Val Ala Ala Ala Ala
            180                 185                 190

Asn Asn Ser His Cys Thr Val Gly Ile Ala Phe Asn Ala Lys Ile Gly
        195                 200                 205

Gly Val Arg Met Leu Asp Gly Asp Val Thr Asp Met Val Glu Ala Lys
    210                 215                 220

Ser Val Ser Phe Asn Pro Gln His Val His Ile Tyr Ser Ala Ser Trp
225                 230                 235                 240

Gly Pro Asp Asp Asp Gly Lys Thr Val Asp Gly Pro Ala Pro Leu Thr
                245                 250                 255

Arg Gln Ala Phe Glu Asn Gly Val Arg Met Gly Arg Arg Gly Leu Gly
            260                 265                 270

Ser Val Phe Val Trp Ala Ser Gly Asn Gly Gly Arg Ser Lys Asp His
        275                 280                 285

Cys Ser Cys Asp Gly Tyr Thr Asn Ser Ile Tyr Thr Ile Ser Ile Ser
    290                 295                 300

Ser Thr Ala Glu Ser Gly Lys Lys Pro Trp Tyr Leu Glu Glu Cys Ser
305                 310                 315                 320

Ser Thr Leu Ala Thr Thr Tyr Ser Ser Gly Glu Ser Tyr Asp Lys Lys
                325                 330                 335
```

-continued

```
Ile Ile Thr Thr Asp Leu Arg Gln Arg Cys Thr Asp Asn His Thr Gly
            340                 345                 350

Thr Ser Ala Ser Ala Pro Met Ala Ala Gly Ile Ile Ala Leu Ala Leu
        355                 360                 365

Glu Ala Asn Pro Phe Leu Thr Trp Arg Asp Val Gln His Val Ile Val
    370                 375                 380

Arg Thr Ser Arg Ala Gly His Leu Asn Ala Asn Asp Trp Lys Thr Asn
385                 390                 395                 400

Ala Ala Gly Phe Lys Val Ser His Leu Tyr Gly Phe Gly Leu Met Asp
                405                 410                 415

Ala Glu Ala Met Val Met Glu Ala Glu Lys Trp Thr Thr Val Pro Arg
            420                 425                 430

Gln His Val Cys Val Glu Ser Thr Asp Arg Gln Ile Lys Thr Ile Arg
        435                 440                 445

Pro Asn Ser Ala Val Arg Ser Ile Tyr Lys Ala Ser Gly Cys Ser Asp
    450                 455                 460

Asn Pro Asn Arg His Val Asn Tyr Leu Glu His Val Val Val Arg Ile
465                 470                 475                 480

Thr Ile Thr His Pro Arg Arg Gly Asp Leu Ala Ile Tyr Leu Thr Ser
                485                 490                 495

Pro Ser Gly Thr Arg Ser Gln Leu Leu Ala Asn Arg Leu Phe Asp His
            500                 505                 510

Ser Met Glu Gly Phe Lys Asn Trp Glu Phe Met Thr Ile His Cys Trp
        515                 520                 525

Gly Glu Arg Ala Ala Gly Asp Trp Val Leu Glu Val Tyr Asp Thr Pro
    530                 535                 540

Ser Gln Leu Arg Asn Phe Lys Thr Pro Gly Lys Leu Lys Glu Trp Ser
545                 550                 555                 560

Leu Val Leu Tyr Gly Thr Ser Val Gln Pro Tyr Ser Pro Thr Asn Glu
                565                 570                 575

Phe Pro Lys Val Glu Arg Phe Arg Tyr Ser Arg Val Glu Asp Pro Thr
            580                 585                 590

Asp Asp Tyr Gly Thr Glu Asp Tyr Ala Gly Pro Cys Asp Pro Glu Cys
        595                 600                 605

Ser Glu Val Gly Cys Asp Gly Pro Gly Pro Asp His Cys Asn Asp Cys
    610                 615                 620

Leu His Tyr Tyr Tyr Lys Leu Lys Asn Asn Thr Arg Ile Cys Val Ser
625                 630                 635                 640

Ser Cys Pro Pro Gly His Tyr His Ala Asp Lys Lys Arg Cys Arg Lys
                645                 650                 655

Cys Ala Pro Asn Cys Glu Ser Cys Phe Gly Ser His Gly Asp Gln Cys
            660                 665                 670

Met Ser Cys Lys Tyr Gly Tyr Phe Leu Asn Glu Glu Thr Asn Ser Cys
        675                 680                 685

Val Thr His Cys Pro Asp Gly Ser Tyr Gln Asp Thr Lys Lys Asn Leu
    690                 695                 700

Cys Arg Lys Cys Ser Glu Asn Cys Lys Thr Cys Thr Glu Phe His Asn
705                 710                 715                 720

Cys Thr Glu Cys Arg Asp Gly Leu Ser Leu Gln Gly Ser Arg Cys Ser
                725                 730                 735

Val Ser Cys Glu Asp Gly Arg Tyr Phe Asn Gly Gln Asp Cys Gln Pro
            740                 745                 750
```

```
Cys His Arg Phe Cys Ala Thr Cys Ala Gly Ala Gly Ala Asp Gly Cys
        755                 760                 765

Ile Asn Cys Thr Glu Gly Tyr Phe Met Glu Asp Gly Arg Cys Val Gln
    770                 775                 780

Ser Cys Ser Ile Ser Tyr Tyr Phe Asp His Ser Ser Glu Asn Gly Tyr
785                 790                 795                 800

Lys Ser Cys Lys Lys Cys Asp Ile Ser Cys Leu Thr Cys Asn Gly Pro
            805                 810                 815

Gly Phe Lys Asn Cys Thr Ser Cys Pro Ser Gly Tyr Leu Leu Asp Leu
            820                 825                 830

Gly Met Cys Gln Met Gly Ala Ile Cys Lys Asp Gly Glu Tyr Val Asp
        835                 840                 845

Glu His Gly His Cys Gln Thr Cys Glu Ala Ser Cys Ala Lys Cys Gln
    850                 855                 860

Gly Pro Thr Gln Glu Asp Cys Thr Thr Cys Pro Met Thr Arg Ile Phe
865                 870                 875                 880

Asp Asp Gly Arg Cys Val Ser Asn Cys Pro Ser Trp Lys Phe Glu Phe
            885                 890                 895

Glu Asn Gln Cys His Pro Cys His His Thr Cys Gln Arg Cys Gln Gly
            900                 905                 910

Ser Gly Pro Thr His Cys Thr Ser Cys Gly Ala Asp Asn Tyr Gly Arg
        915                 920                 925

Glu His Phe Leu Tyr Gln Gly Glu Cys Gly Asp Ser Cys Pro Glu Gly
    930                 935                 940

His Tyr Ala Thr Glu Gly Asn Thr Cys Leu Pro Cys Pro Asp Asn Cys
945                 950                 955                 960

Glu Leu Cys His Ser Val His Val Cys Thr Arg Cys Met Lys Gly Tyr
                965                 970                 975

Phe Ile Ala Pro Thr Asn His Thr Cys Gln Lys Leu Glu Cys Gly Gln
            980                 985                 990

Gly Glu Val Gln Asp Pro Asp Tyr  Glu Glu Cys Val Pro  Cys Glu Glu
        995                 1000                1005

Gly Cys  Leu Gly Cys Ser Leu  Asp Asp Pro Gly Thr  Cys Thr Ser
    1010                 1015                 1020

Cys Ala  Met Gly Tyr Tyr Arg  Phe Asp His His Cys  Tyr Lys Thr
    1025                 1030                 1035

Cys Pro  Glu Lys Thr Tyr Ser  Glu Glu Val Glu Cys  Lys Ala Cys
    1040                 1045                 1050

Asp Ser  Asn Cys Gly Ser Cys  Asp Gln Asn Gly Cys  Tyr Trp Cys
    1055                 1060                 1065

Glu Glu  Gly Phe Phe Leu Leu  Gly Gly Ser Cys Val  Arg Lys Cys
    1070                 1075                 1080

Gly Pro  Gly Phe Tyr Gly Asp  Gln Glu Met Gly Glu  Cys Glu Ser
    1085                 1090                 1095

Cys His  Arg Ala Cys Glu Thr  Cys Thr Gly Pro Gly  His Asp Glu
    1100                 1105                 1110

Cys Ser  Ser Cys Gln Glu Gly  Leu Gln Leu Leu Arg  Gly Met Cys
    1115                 1120                 1125

Val His  Ala Thr Lys Thr Gln  Glu Glu Gly Lys Phe  Trp Asn Asp
    1130                 1135                 1140

Ile Leu  Arg Lys Leu Gln Pro  Cys His Ser Ser Cys  Lys Thr Cys
    1145                 1150                 1155

Asn Gly  Ser Ala Thr Leu Cys  Thr Ser Cys Pro Lys  Gly Ala Tyr
```

-continued

```
    1160                1165                1170

Leu Leu  Ala Gln Ala Cys Val  Ser Ser Cys Pro Gln  Gly Thr Trp
    1175                1180                1185

Pro Ser  Val Arg Ser Gly Ser  Cys Glu Asn Cys Thr  Glu Ala Cys
    1190                1195                1200

Ala Ile  Cys Ser Gly Ala Asp  Leu Cys Lys Lys Cys  Gln Met Gln
    1205                1210                1215

Pro Gly  His Pro Leu Phe Leu  His Glu Gly Arg Cys  Tyr Ser Lys
    1220                1225                1230

Cys Pro  Glu Gly Ser Tyr Ala  Glu Asp Gly Ile Cys  Glu Arg Cys
    1235                1240                1245

Ser Ser  Pro Cys Arg Thr Cys  Glu Gly Asn Ala Thr  Asn Cys His
    1250                1255                1260

Ser Cys  Glu Gly Gly His Val  Leu His His Gly Val  Cys Gln Glu
    1265                1270                1275

Asn Cys  Pro Glu Arg His Val  Ala Val Lys Gly Val  Cys Lys His
    1280                1285                1290

Cys Pro  Glu Met Cys Gln Asp  Cys Ile His Glu Lys  Thr Cys Lys
    1295                1300                1305

Glu Cys  Thr Pro Glu Phe Phe  Leu His Asp Asp Met  Cys His Gln
    1310                1315                1320

Ser Cys  Pro Arg Gly Phe Tyr  Ala Asp Ser Arg His  Cys Val Pro
    1325                1330                1335

Cys His  Lys Asp Cys Leu Glu  Cys Ser Gly Pro Lys  Ala Asp Asp
    1340                1345                1350

Cys Glu  Leu Cys Leu Glu Ser  Ser Trp Val Leu Tyr  Asp Gly Leu
    1355                1360                1365

Cys Leu  Glu Glu Cys Pro Ala  Gly Thr Tyr Tyr Glu  Lys Glu Thr
    1370                1375                1380

Lys Glu  Cys Arg Asp Cys His  Lys Ser Cys Leu Thr  Cys Ser Ser
    1385                1390                1395

Ser Gly  Thr Cys Thr Thr Cys  Gln Lys Gly Leu Ile  Met Asn Pro
    1400                1405                1410

Arg Gly  Ser Cys Met Ala Asn  Glu Lys Cys Ser Pro  Ser Glu Tyr
    1415                1420                1425

Trp Asp  Glu Asp Ala Pro Gly  Cys Lys Pro Cys His  Val Lys Cys
    1430                1435                1440

Phe His  Cys Met Gly Pro Ala  Glu Asp Gln Cys Gln  Thr Cys Pro
    1445                1450                1455

Met Asn  Ser Leu Leu Leu Asn  Thr Thr Cys Val Lys  Asp Cys Pro
    1460                1465                1470

Glu Gly  Tyr Tyr Ala Asp Glu  Asp Ser Asn Arg Cys  Ala His Cys
    1475                1480                1485

His Ser  Ser Cys Arg Thr Cys  Glu Gly Arg His Ser  Arg Gln Cys
    1490                1495                1500

His Ser  Cys Arg Pro Gly Trp  Phe Gln Leu Gly Lys  Glu Cys Leu
    1505                1510                1515

Leu Gln  Cys Arg Glu Gly Tyr  Tyr Ala Asp Asn Ser  Thr Gly Arg
    1520                1525                1530

Cys Glu  Arg Cys Asn Arg Ser  Cys Lys Gly Cys Gln  Gly Pro Arg
    1535                1540                1545

Pro Thr  Asp Cys Leu Ser Cys  Asp Arg Phe Phe Phe  Leu Leu Arg
    1550                1555                1560
```

```
Ser Lys  Gly Glu Cys His Arg  Ser Cys Pro Asp His  Tyr Tyr Val
    1565                 1570                 1575

Glu Gln  Ser Thr Gln Thr Cys  Glu Arg Cys His Pro  Thr Cys Asp
    1580                 1585                 1590

Gln Cys  Lys Gly Lys Gly Ala  Leu Asn Cys Leu Ser  Cys Val Trp
    1595                 1600                 1605

Ser Tyr  His Leu Met Gly Gly  Ile Cys Thr Ser Asp  Cys Leu Val
    1610                 1615                 1620

Gly Glu  Tyr Arg Val Gly Glu  Gly Glu Lys Phe Asn  Cys Glu Lys
    1625                 1630                 1635

Cys His  Glu Ser Cys Met Glu  Cys Lys Gly Pro Gly  Ala Lys Asn
    1640                 1645                 1650

Cys Thr  Leu Cys Pro Ala Asn  Leu Val Leu His Met  Asp Asp Ser
    1655                 1660                 1665

His Cys  Leu His Cys Cys Asn  Thr Ser Asp Pro Pro  Ser Ala Gln
    1670                 1675                 1680

Glu Cys  Cys Asp Cys Gln Asp  Thr Thr Asp Glu Cys  Ile Leu Arg
    1685                 1690                 1695

Thr Ser  Lys Val Arg Pro Ala  Thr Glu His Phe Lys  Thr Ala Leu
    1700                 1705                 1710

Phe Ile  Thr Ser Ser Met Met  Leu Val Leu Leu Leu  Gly Ala Ala
    1715                 1720                 1725

Val Val  Val Trp Lys Lys Ser  Arg Gly Arg Val Gln  Pro Ala Ala
    1730                 1735                 1740

Lys Ala  Gly Tyr Glu Lys Leu  Ala Asp Pro Asn Lys  Ser Tyr Ser
    1745                 1750                 1755

Ser Tyr  Lys Ser Ser Tyr Arg  Glu Ser Thr Ser Phe  Glu Glu Asp
    1760                 1765                 1770

Gln Val  Ile Glu Tyr Arg Asp  Arg Asp Tyr Asp Glu  Asp Asp Asp
    1775                 1780                 1785

Asp Asp  Ile Val Tyr Met Gly  Gln Asp Gly Thr Val  Tyr Arg Lys
    1790                 1795                 1800

Phe Lys  Tyr Gly Leu Leu Asp  Asp Asp Asp Ile Asp  Glu Leu Glu
    1805                 1810                 1815

Tyr Asp  Asp Glu Ser Tyr Ser  Tyr Tyr Gln
    1820                 1825


<210> SEQ ID NO 40
<211> LENGTH: 748
<212> TYPE: PRT
<213> ORGANISM: Homo sapiens

<400> SEQUENCE: 40

Leu Ala Gly Thr Gly Gly Pro Asp Gly Gln Gly Thr Gly Gly Pro Ser
1               5                   10                  15

Trp Ala Val His Leu Glu Ser Leu Glu Gly Asp Gly Glu Glu Glu Thr
            20                  25                  30

Leu Glu Gln Gln Ala Asp Ala Leu Ala Gln Ala Ala Gly Leu Val Asn
        35                  40                  45

Ala Gly Arg Ile Gly Glu Leu Gln Gly His Tyr Leu Phe Val Gln Pro
    50                  55                  60

Ala Gly His Arg Pro Ala Leu Glu Val Glu Ala Ile Arg Gln Gln Val
65                  70                  75                  80

Glu Ala Val Leu Ala Gly His Glu Ala Val Arg Trp His Ser Glu Gln
```

```
                85                  90                  95

Arg Leu Leu Arg Arg Ala Lys Arg Ser Val His Phe Asn Asp Pro Lys
            100                 105                 110

Tyr Pro Gln Gln Trp His Leu Asn Asn Arg Arg Ser Pro Gly Arg Asp
        115                 120                 125

Ile Asn Val Thr Gly Val Trp Glu Arg Asn Val Thr Gly Arg Gly Val
    130                 135                 140

Thr Val Val Val Val Asp Asp Gly Val Glu His Thr Ile Gln Asp Ile
145                 150                 155                 160

Ala Pro Asn Tyr Ser Pro Glu Gly Ser Tyr Asp Leu Asn Ser Asn Asp
                165                 170                 175

Pro Asp Pro Met Pro His Pro Asp Val Glu Asn Gly Asn His His Gly
            180                 185                 190

Thr Arg Cys Ala Gly Glu Ile Ala Ala Val Pro Asn Asn Ser Phe Cys
        195                 200                 205

Ala Val Gly Val Ala Tyr Gly Ser Arg Ile Ala Gly Ile Arg Val Leu
    210                 215                 220

Asp Gly Pro Leu Thr Asp Ser Met Glu Ala Val Ala Phe Asn Lys His
225                 230                 235                 240

Tyr Gln Ile Asn Asp Ile Tyr Ser Cys Ser Trp Gly Pro Asp Asp Asp
                245                 250                 255

Gly Lys Thr Val Asp Gly Pro His Gln Leu Gly Lys Ala Ala Leu Gln
            260                 265                 270

His Gly Val Ile Ala Gly Arg Gln Gly Phe Gly Ser Ile Phe Val Val
        275                 280                 285

Ala Ser Gly Asn Gly Gly Gln His Asn Asp Asn Cys Asn Tyr Asp Gly
    290                 295                 300

Tyr Ala Asn Ser Ile Tyr Thr Val Thr Ile Gly Ala Val Asp Glu Glu
305                 310                 315                 320

Gly Arg Met Pro Phe Tyr Ala Glu Glu Cys Ala Ser Met Leu Ala Val
                325                 330                 335

Thr Phe Ser Gly Gly Asp Lys Met Leu Arg Ser Ile Val Thr Thr Asp
            340                 345                 350

Trp Asp Leu Gln Lys Gly Thr Gly Cys Thr Glu Gly His Thr Gly Thr
        355                 360                 365

Ser Ala Ala Ala Pro Leu Ala Ala Gly Met Ile Ala Leu Met Leu Gln
    370                 375                 380

Val Arg Pro Cys Leu Thr Trp Arg Asp Val Gln His Ile Ile Val Phe
385                 390                 395                 400

Thr Ala Thr Arg Tyr Glu Asp Arg Arg Ala Glu Trp Val Thr Asn Glu
                405                 410                 415

Ala Gly Phe Ser His Ser His Gln His Gly Phe Gly Leu Leu Asn Ala
            420                 425                 430

Trp Arg Leu Val Asn Ala Ala Lys Ile Trp Thr Ser Val Pro Tyr Leu
        435                 440                 445

Ala Ser Tyr Val Ser Pro Val Leu Lys Glu Asn Lys Ala Ile Pro Gln
    450                 455                 460

Ser Pro Arg Ser Leu Glu Val Leu Trp Asn Val Ser Arg Met Asp Leu
465                 470                 475                 480

Glu Met Ser Gly Leu Lys Thr Leu Glu His Val Ala Val Thr Val Ser
                485                 490                 495

Ile Thr His Pro Arg Arg Gly Ser Leu Glu Leu Lys Leu Phe Cys Pro
            500                 505                 510
```

```
Ser Gly Met Met Ser Leu Ile Gly Ala Pro Arg Ser Met Asp Ser Asp
        515                 520                 525

Pro Asn Gly Phe Asn Asp Trp Thr Phe Ser Thr Val Arg Cys Trp Gly
    530                 535                 540

Glu Arg Ala Arg Gly Thr Tyr Arg Leu Val Ile Arg Asp Val Gly Asp
545                 550                 555                 560

Glu Ser Phe Gln Val Gly Ile Leu Arg Gln Trp Gln Leu Thr Leu Tyr
                565                 570                 575

Gly Ser Val Trp Ser Ala Val Asp Ile Arg Asp Arg Gln Arg Leu Leu
            580                 585                 590

Glu Ser Ala Met Ser Gly Lys Tyr Leu His Asp Asp Phe Ala Leu Pro
        595                 600                 605

Cys Pro Pro Gly Leu Lys Ile Pro Glu Glu Asp Gly Tyr Thr Ile Thr
    610                 615                 620

Pro Asn Thr Leu Lys Thr Leu Val Leu Val Gly Cys Phe Thr Val Phe
625                 630                 635                 640

Trp Thr Val Tyr Tyr Met Leu Glu Val Tyr Leu Ser Gln Arg Asn Val
                645                 650                 655

Ala Ser Asn Gln Val Cys Arg Ser Gly Pro Cys His Trp Pro His Arg
            660                 665                 670

Ser Arg Lys Ala Lys Glu Glu Gly Thr Glu Leu Glu Ser Val Pro Leu
        675                 680                 685

Cys Ser Ser Lys Asp Pro Asp Glu Val Glu Thr Glu Ser Arg Gly Pro
    690                 695                 700

Pro Thr Thr Ser Asp Leu Leu Ala Pro Asp Leu Leu Glu Gln Gly Asp
705                 710                 715                 720

Trp Ser Leu Ser Gln Asn Lys Ser Ala Leu Asp Cys Pro His Gln His
                725                 730                 735

Leu Asp Val Pro His Gly Lys Glu Glu Gln Ile Cys
            740                 745
```

<210> SEQ ID NO 41
<211> LENGTH: 906
<212> TYPE: PRT
<213> ORGANISM: Homo sapiens

<400> SEQUENCE: 41

```
Pro Pro Pro Arg Pro Val Tyr Thr Asn His Trp Ala Val Gln Val Leu
1               5                   10                  15

Gly Gly Pro Ala Glu Ala Asp Arg Val Ala Ala Ala His Gly Tyr Leu
            20                  25                  30

Asn Leu Gly Gln Ile Gly Asn Leu Glu Asp Tyr Tyr His Phe Tyr His
        35                  40                  45

Ser Lys Thr Phe Lys Arg Ser Thr Leu Ser Ser Arg Gly Pro His Thr
    50                  55                  60

Phe Leu Arg Met Asp Pro Gln Val Lys Trp Leu Gln Gln Gln Glu Val
65                  70                  75                  80

Lys Arg Arg Val Lys Arg Gln Val Arg Ser Asp Pro Gln Ala Leu Tyr
                85                  90                  95

Phe Asn Asp Pro Ile Trp Ser Asn Met Trp Tyr Leu His Cys Gly Asp
            100                 105                 110

Lys Asn Ser Arg Cys Arg Ser Glu Met Asn Val Gln Ala Ala Trp Lys
        115                 120                 125

Arg Gly Tyr Thr Gly Lys Asn Val Val Val Thr Ile Leu Asp Asp Gly
```

-continued

```
    130                 135                 140

Ile Glu Arg Asn His Pro Asp Leu Ala Pro Asn Tyr Asp Ser Tyr Ala
145                 150                 155                 160

Ser Tyr Asp Val Asn Gly Asn Asp Tyr Asp Pro Ser Pro Arg Tyr Asp
                165                 170                 175

Ala Ser Asn Glu Asn Lys His Gly Thr Arg Cys Ala Gly Glu Val Ala
            180                 185                 190

Ala Ser Ala Asn Asn Ser Tyr Cys Ile Val Gly Ile Ala Tyr Asn Ala
        195                 200                 205

Lys Ile Gly Gly Ile Arg Met Leu Asp Gly Asp Val Thr Asp Val Val
    210                 215                 220

Glu Ala Lys Ser Leu Gly Ile Arg Pro Asn Tyr Ile Asp Ile Tyr Ser
225                 230                 235                 240

Ala Ser Trp Gly Pro Asp Asp Asp Gly Lys Thr Val Asp Gly Pro Gly
                245                 250                 255

Arg Leu Ala Lys Gln Ala Phe Glu Tyr Gly Ile Lys Lys Gly Arg Gln
            260                 265                 270

Gly Leu Gly Ser Ile Phe Val Trp Ala Ser Gly Asn Gly Gly Arg Glu
        275                 280                 285

Gly Asp Tyr Cys Ser Cys Asp Gly Tyr Thr Asn Ser Ile Tyr Thr Ile
    290                 295                 300

Ser Val Ser Ser Ala Thr Glu Asn Gly Tyr Lys Pro Trp Tyr Leu Glu
305                 310                 315                 320

Glu Cys Ala Ser Thr Leu Ala Thr Thr Tyr Ser Ser Gly Ala Phe Tyr
                325                 330                 335

Glu Arg Lys Ile Val Thr Thr Asp Leu Arg Gln Arg Cys Thr Asp Gly
            340                 345                 350

His Thr Gly Thr Ser Val Ser Ala Pro Met Val Ala Gly Ile Ile Ala
        355                 360                 365

Leu Ala Leu Glu Ala Asn Ser Gln Leu Thr Trp Arg Asp Val Gln His
    370                 375                 380

Leu Leu Val Lys Thr Ser Arg Pro Ala His Leu Lys Ala Ser Asp Trp
385                 390                 395                 400

Lys Val Asn Gly Ala Gly His Lys Val Ser His Phe Tyr Gly Phe Gly
                405                 410                 415

Leu Val Asp Ala Glu Ala Leu Val Val Glu Ala Lys Lys Trp Thr Ala
            420                 425                 430

Val Pro Ser Gln His Met Cys Val Ala Ala Ser Asp Lys Arg Pro Arg
        435                 440                 445

Ser Ile Pro Leu Val Gln Val Leu Arg Thr Thr Ala Leu Thr Ser Ala
    450                 455                 460

Cys Ala Glu His Ser Asp Gln Arg Val Val Tyr Leu Glu His Val Val
465                 470                 475                 480

Val Arg Thr Ser Ile Ser His Pro Arg Arg Gly Asp Leu Gln Ile Tyr
                485                 490                 495

Leu Val Ser Pro Ser Gly Thr Lys Ser Gln Leu Leu Ala Lys Arg Leu
            500                 505                 510

Leu Asp Leu Ser Asn Glu Gly Phe Thr Asn Trp Glu Phe Met Thr Val
        515                 520                 525

His Cys Trp Gly Glu Lys Ala Glu Gly Gln Trp Thr Leu Glu Ile Gln
    530                 535                 540

Asp Leu Pro Ser Gln Val Arg Asn Pro Glu Lys Gln Gly Lys Leu Lys
545                 550                 555                 560
```

```
Glu Trp Ser Leu Ile Leu Tyr Gly Thr Ala Glu His Pro Tyr His Thr
                565                 570                 575

Phe Ser Ala His Gln Ser Arg Ser Arg Met Leu Glu Leu Ser Ala Pro
            580                 585                 590

Glu Leu Glu Pro Pro Lys Ala Ala Leu Ser Pro Ser Gln Val Glu Val
        595                 600                 605

Pro Glu Asp Glu Glu Asp Tyr Thr Ala Gln Ser Thr Pro Gly Ser Ala
    610                 615                 620

Asn Ile Leu Gln Thr Ser Val Cys His Pro Glu Cys Gly Asp Lys Gly
625                 630                 635                 640

Cys Asp Gly Pro Asn Ala Asp Gln Cys Leu Asn Cys Val His Phe Ser
                645                 650                 655

Leu Gly Ser Val Lys Thr Ser Arg Lys Cys Val Ser Val Cys Pro Leu
            660                 665                 670

Gly Tyr Phe Gly Asp Thr Ala Ala Arg Arg Cys Arg Arg Cys His Lys
        675                 680                 685

Gly Cys Glu Thr Cys Ser Ser Arg Ala Ala Thr Gln Cys Leu Ser Cys
    690                 695                 700

Arg Arg Gly Phe Tyr His His Gln Glu Met Asn Thr Cys Val Thr Leu
705                 710                 715                 720

Cys Pro Ala Gly Phe Tyr Ala Asp Glu Ser Gln Lys Asn Cys Leu Lys
                725                 730                 735

Cys His Pro Ser Cys Lys Lys Cys Val Asp Glu Pro Glu Lys Cys Thr
            740                 745                 750

Val Cys Lys Glu Gly Phe Ser Leu Ala Arg Gly Ser Cys Ile Pro Asp
        755                 760                 765

Cys Glu Pro Gly Thr Tyr Phe Asp Ser Glu Leu Ile Arg Cys Gly Glu
    770                 775                 780

Cys His His Thr Cys Gly Thr Cys Val Gly Pro Gly Arg Glu Glu Cys
785                 790                 795                 800

Ile His Cys Ala Lys Asn Phe His Phe His Asp Trp Lys Cys Val Pro
                805                 810                 815

Ala Cys Gly Glu Gly Phe Tyr Pro Glu Glu Met Pro Gly Leu Pro His
            820                 825                 830

Lys Val Cys Arg Arg Cys Asp Glu Asn Cys Leu Ser Cys Ala Gly Ser
        835                 840                 845

Ser Arg Asn Cys Ser Arg Cys Lys Thr Gly Phe Thr Gln Leu Gly Thr
    850                 855                 860

Ser Cys Ile Thr Asn His Thr Cys Ser Asn Ala Asp Glu Thr Phe Cys
865                 870                 875                 880

Glu Met Val Lys Ser Asn Arg Leu Cys Glu Arg Lys Leu Phe Ile Gln
                885                 890                 895

Phe Cys Cys Arg Thr Cys Leu Leu Ala Gly
            900                 905
```

<210> SEQ ID NO 42
<211> LENGTH: 10
<212> TYPE: PRT
<213> ORGANISM: Artificial Sequence
<220> FEATURE:
<223> OTHER INFORMATION: PCS General Formula
<220> FEATURE:
<221> NAME/KEY: misc_feature
<222> LOCATION: (4)..(5)
<223> OTHER INFORMATION: Xaa can be any naturally occurring amino acid

<400> SEQUENCE: 42

His Arg Arg Xaa Xaa Arg Ser Val Asp Glu
1 5 10

<210> SEQ ID NO 43
<211> LENGTH: 10
<212> TYPE: PRT
<213> ORGANISM: Artificial Sequence
<220> FEATURE:
<223> OTHER INFORMATION: PCS2

<400> SEQUENCE: 43

His Arg Arg Arg Lys Arg Ser Val Asp Glu
1 5 10

<210> SEQ ID NO 44
<211> LENGTH: 10
<212> TYPE: PRT
<213> ORGANISM: Artificial Sequence
<220> FEATURE:
<223> OTHER INFORMATION: PCS2a

<400> SEQUENCE: 44

His Arg Arg Gln Gln Arg Ser Val Asp Glu
1 5 10

<210> SEQ ID NO 45
<211> LENGTH: 15
<212> TYPE: PRT
<213> ORGANISM: Artificial Sequence
<220> FEATURE:
<223> OTHER INFORMATION: Linker

<400> SEQUENCE: 45

Gly Ser His His His His His His His His Gly Gly Gly Gly Ser
1 5 10 15

<210> SEQ ID NO 46
<211> LENGTH: 20
<212> TYPE: PRT
<213> ORGANISM: Artificial Sequence
<220> FEATURE:
<223> OTHER INFORMATION: Linker

<400> SEQUENCE: 46

Gly Gly Gly Gly Ser Glu Ala Ala Ala Lys Glu Ala Ala Ala Lys Gly
1 5 10 15

Gly Gly Gly Ser
20

<210> SEQ ID NO 47
<211> LENGTH: 15
<212> TYPE: PRT
<213> ORGANISM: Artificial Sequence
<220> FEATURE:
<223> OTHER INFORMATION: Linker

<400> SEQUENCE: 47

Ala Pro Ala Pro Ala Pro Ala Pro Ala Pro Ala Pro Ala Pro Ala
1 5 10 15

<210> SEQ ID NO 48
<211> LENGTH: 14
<212> TYPE: PRT
<213> ORGANISM: Artificial Sequence
<220> FEATURE:

-continued

<223> OTHER INFORMATION: Linker

<400> SEQUENCE: 48

Gly Ser Lys Gln Gly Lys Gln Lys Gln Gly Lys Gln Gly Ser
1               5                   10

<210> SEQ ID NO 49
<211> LENGTH: 4
<212> TYPE: PRT
<213> ORGANISM: Artificial Sequence
<220> FEATURE:
<223> OTHER INFORMATION: PCS1

<400> SEQUENCE: 49

Arg Arg Lys Arg
1

<210> SEQ ID NO 50
<211> LENGTH: 10
<212> TYPE: PRT
<213> ORGANISM: Artificial Sequence
<220> FEATURE:
<223> OTHER INFORMATION: PCS3

<400> SEQUENCE: 50

Pro Met Lys Lys Arg Arg Ala Gly Val Pro
1               5                   10

<210> SEQ ID NO 51
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)

<400> SEQUENCE: 51

Gly Gly Gly Gly Ser
1               5

<210> SEQ ID NO 52
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)

<400> SEQUENCE: 52

Glu Ala Ala Ala Lys
1               5

<210> SEQ ID NO 53
<211> LENGTH: 3
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(2)

<400> SEQUENCE: 53

Ala Pro Ala

1

<210> SEQ ID NO 54
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)

<400> SEQUENCE: 54

```
Lys Gln Gly Lys Gln
1               5
```

<210> SEQ ID NO 55
<211> LENGTH: 15
<212> TYPE: PRT
<213> ORGANISM: Artificial Sequence
<220> FEATURE:
<223> OTHER INFORMATION: Linker

<400> SEQUENCE: 55

```
Gly Gly Gly Gly Ser Gly Gly Gly Gly Ser Gly Gly Gly Gly Ser
1               5                   10                  15
```

<210> SEQ ID NO 56
<211> LENGTH: 341
<212> TYPE: PRT
<213> ORGANISM: Artificial Sequence
<220> FEATURE:
<223> OTHER INFORMATION: anti-OX40-VL-<(G4S)2>-anti-PD1-VL-<(G4S)2>-
huIGKC

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Gly Gly Gly Gly Ser
            100                 105                 110

Gly Gly Gly Gly Ser Glu Ile Val Leu Thr Gln Ser Pro Ala Thr Leu
        115                 120                 125

Ser Leu Ser Pro Gly Glu Arg Ala Thr Leu Ser Cys Arg Ala Ser Gln
    130                 135                 140

Ser Val Ser Ser Tyr Leu Ala Trp Tyr Gln Gln Lys Pro Gly Gln Ala
145                 150                 155                 160

Pro Arg Leu Leu Ile Tyr Asp Ala Ser Asn Arg Ala Thr Gly Ile Pro
                165                 170                 175

Ala Arg Phe Ser Gly Ser Gly Ser Gly Thr Asp Phe Thr Leu Thr Ile
            180                 185                 190

Ser Ser Leu Glu Pro Glu Asp Phe Ala Val Tyr Tyr Cys Gln Gln Ser
```

```
        195                 200                 205

Ser Asn Trp Pro Arg Thr Phe Gly Gln Gly Thr Lys Val Glu Ile Lys
    210                 215                 220

Gly Gly Gly Gly Ser Gly Gly Gly Gly Ser Arg Thr Val Ala Ala Pro
225                 230                 235                 240

Ser Val Phe Ile Phe Pro Pro Ser Asp Glu Gln Leu Lys Ser Gly Thr
                245                 250                 255

Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
    290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys
            340


<210> SEQ ID NO 57
<211> LENGTH: 559
<212> TYPE: PRT
<213> ORGANISM: Artificial Sequence
<220> FEATURE:
<223> OTHER INFORMATION: anti-PD1-VH-anti-OX40-VH-huIGHG1(LALA-knob)

<400> SEQUENCE: 57

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Glu Val Gln Leu Val Gln Ser Gly Ala Glu Val Lys Lys Pro Gly
        115                 120                 125

Ala Ser Val Lys Val Ser Cys Lys Ala Ser Gly Tyr Thr Phe Thr Asp
    130                 135                 140

Ser Tyr Met Ser Trp Val Arg Gln Ala Pro Gly Gln Gly Leu Glu Trp
145                 150                 155                 160

Ile Gly Asp Met Tyr Pro Asp Asn Gly Asp Ser Ser Tyr Asn Gln Lys
                165                 170                 175

Phe Arg Glu Arg Val Thr Ile Thr Arg Asp Thr Ser Thr Ser Thr Ala
            180                 185                 190

Tyr Leu Glu Leu Ser Ser Leu Arg Ser Glu Asp Thr Ala Val Tyr Tyr
        195                 200                 205

Cys Val Leu Ala Pro Arg Trp Tyr Phe Ser Val Trp Gly Gln Gly Thr
```

-continued

```
    210                 215                 220

Leu Val Thr Val Ser Ser Ala Ser Thr Lys Gly Pro Ser Val Phe Pro
225                 230                 235                 240

Leu Ala Pro Ser Ser Lys Ser Thr Ser Gly Gly Thr Ala Ala Leu Gly
                245                 250                 255

Cys Leu Val Lys Asp Tyr Phe Pro Glu Pro Val Thr Val Ser Trp Asn
            260                 265                 270

Ser Gly Ala Leu Thr Ser Gly Val His Thr Phe Pro Ala Val Leu Gln
        275                 280                 285

Ser Ser Gly Leu Tyr Ser Leu Ser Ser Val Val Thr Val Pro Ser Ser
    290                 295                 300

Ser Leu Gly Thr Gln Thr Tyr Ile Cys Asn Val Asn His Lys Pro Ser
305                 310                 315                 320

Asn Thr Lys Val Asp Lys Lys Val Glu Pro Lys Ser Cys Asp Lys Thr
                325                 330                 335

His Thr Cys Pro Pro Cys Pro Ala Pro Glu Ala Ala Gly Gly Pro Ser
            340                 345                 350

Val Phe Leu Phe Pro Pro Lys Pro Lys Asp Thr Leu Met Ile Ser Arg
        355                 360                 365

Thr Pro Glu Val Thr Cys Val Val Val Asp Val Ser His Glu Asp Pro
    370                 375                 380

Glu Val Lys Phe Asn Trp Tyr Val Asp Gly Val Glu Val His Asn Ala
385                 390                 395                 400

Lys Thr Lys Pro Arg Glu Glu Gln Tyr Asn Ser Thr Tyr Arg Val Val
                405                 410                 415

Ser Val Leu Thr Val Leu His Gln Asp Trp Leu Asn Gly Lys Glu Tyr
            420                 425                 430

Lys Cys Lys Val Ser Asn Lys Ala Leu Pro Ala Pro Ile Glu Lys Thr
        435                 440                 445

Ile Ser Lys Ala Lys Gly Gln Pro Arg Glu Pro Gln Val Tyr Thr Leu
    450                 455                 460

Pro Pro Cys Arg Asp Glu Leu Thr Lys Asn Gln Val Ser Leu Trp Cys
465                 470                 475                 480

Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
        515                 520                 525

Arg Trp Gln Gln Gly Asn Val Phe Ser Cys Ser Val Met His Glu Ala
    530                 535                 540

Leu His Asn His Tyr Thr Gln Lys Ser Leu Ser Leu Ser Pro Gly
545                 550                 555


<210> SEQ ID NO 58
<211> LENGTH: 214
<212> TYPE: PRT
<213> ORGANISM: Artificial Sequence
<220> FEATURE:
<223> OTHER INFORMATION: anti-GITR-VL-huIGKC

<400> SEQUENCE: 58

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
```

-continued

```
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 59
<211> LENGTH: 453
<212> TYPE: PRT
<213> ORGANISM: Artificial Sequence
<220> FEATURE:
<223> OTHER INFORMATION: anti-GITR-VH-huIGHG1(LALA-hole-RF)

<400> SEQUENCE: 59

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
```

-continued

```
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Asp Glu Leu Thr Lys Asn
        355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn Arg Phe Thr Gln Lys Ser Leu
        435                 440                 445

Ser Leu Ser Pro Gly
    450


<210> SEQ ID NO 60
<211> LENGTH: 717
<212> TYPE: PRT
<213> ORGANISM: Artificial Sequence
<220> FEATURE:
<223> OTHER INFORMATION: anti-GITR-VL-huIGKC-[PCS2]-<(G4S)6>-[PCS2]-
      anti-GITR-VH-huIGHG1(LALA-hole-RF)

<400> SEQUENCE: 60

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60
```

-continued

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Arg Lys Arg Ser Val Asp Glu
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gly Gly Ser Gly Gly Gly Gly Ser His Arg
                245                 250                 255

Arg Arg Lys Arg Ser Val Asp Glu Gln Val Gln Leu Val Glu Ser Gly
            260                 265                 270

Gly Gly Val Val Gln Pro Gly Arg Ser Leu Arg Leu Ser Cys Ala Ala
        275                 280                 285

Ser Gly Phe Thr Phe Ser Ser Tyr Gly Met His Trp Val Arg Gln Ala
    290                 295                 300

Pro Gly Lys Gly Leu Glu Trp Val Ala Val Ile Trp Tyr Glu Gly Ser
305                 310                 315                 320

Asn Lys Tyr Tyr Ala Asp Ser Val Lys Gly Arg Phe Thr Ile Ser Arg
                325                 330                 335

Asp Asn Ser Lys Asn Thr Leu Tyr Leu Gln Met Asn Ser Leu Arg Ala
            340                 345                 350

Glu Asp Thr Ala Val Tyr Tyr Cys Ala Arg Gly Gly Ser Met Val Arg
        355                 360                 365

Gly Asp Tyr Tyr Tyr Gly Met Asp Val Trp Gly Gln Gly Thr Thr Val
    370                 375                 380

Thr Val Ser Ser Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
            420                 425                 430

Ala Leu Thr Ser Gly Val His Thr Phe Pro Ala Val Leu Gln Ser Ser
        435                 440                 445

Gly Leu Tyr Ser Leu Ser Ser Val Val Thr Val Pro Ser Ser Ser Leu
    450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys Asp Lys Thr His Thr
```

```
                485                 490                 495

Cys Pro Pro Cys Pro Ala Pro Glu Ala Ala Gly Gly Pro Ser Val Phe
            500                 505                 510

Leu Phe Pro Pro Lys Pro Lys Asp Thr Leu Met Ile Ser Arg Thr Pro
        515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
        595                 600                 605

Lys Ala Lys Gly Gln Pro Arg Glu Pro Gln Val Cys Thr Leu Pro Pro
    610                 615                 620

Ser Arg Asp Glu Leu Thr Lys Asn Gln Val Ser Leu Ser Cys Ala Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Val Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn Arg Phe Thr Gln Lys Ser Leu Ser Leu Ser Pro Gly
705                 710                 715


<210> SEQ ID NO 61
<211> LENGTH: 717
<212> TYPE: PRT
<213> ORGANISM: Artificial Sequence
<220> FEATURE:
<223> OTHER INFORMATION: anti-GITR-VL-huIGKC-[PCS2a]-<(G4S)6>-[PCS2a]-
      anti-GITR-VH-huIGHG1(LALA-hole-RF)

<400> SEQUENCE: 61

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Gln Gln Arg Ser Val Asp Glu
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gly Gly Ser Gly Gly Gly Gly Ser His Arg
                245                 250                 255

Arg Gln Gln Arg Ser Val Asp Glu Gln Val Gln Leu Val Glu Ser Gly
            260                 265                 270

Gly Gly Val Val Gln Pro Gly Arg Ser Leu Arg Leu Ser Cys Ala Ala
        275                 280                 285

Ser Gly Phe Thr Phe Ser Ser Tyr Gly Met His Trp Val Arg Gln Ala
    290                 295                 300

Pro Gly Lys Gly Leu Glu Trp Val Ala Val Ile Trp Tyr Glu Gly Ser
305                 310                 315                 320

Asn Lys Tyr Tyr Ala Asp Ser Val Lys Gly Arg Phe Thr Ile Ser Arg
                325                 330                 335

Asp Asn Ser Lys Asn Thr Leu Tyr Leu Gln Met Asn Ser Leu Arg Ala
            340                 345                 350

Glu Asp Thr Ala Val Tyr Tyr Cys Ala Arg Gly Gly Ser Met Val Arg
        355                 360                 365

Gly Asp Tyr Tyr Tyr Gly Met Asp Val Trp Gly Gln Gly Thr Thr Val
    370                 375                 380

Thr Val Ser Ser Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
            420                 425                 430

Ala Leu Thr Ser Gly Val His Thr Phe Pro Ala Val Leu Gln Ser Ser
        435                 440                 445

Gly Leu Tyr Ser Leu Ser Ser Val Val Thr Val Pro Ser Ser Ser Leu
    450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys Asp Lys Thr His Thr
                485                 490                 495

Cys Pro Pro Cys Pro Ala Pro Glu Ala Ala Gly Gly Pro Ser Val Phe
            500                 505                 510

Leu Phe Pro Pro Lys Pro Lys Asp Thr Leu Met Ile Ser Arg Thr Pro
        515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
```

-continued

```
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
        595                 600                 605

Lys Ala Lys Gly Gln Pro Arg Glu Pro Gln Val Cys Thr Leu Pro Pro
    610                 615                 620

Ser Arg Asp Glu Leu Thr Lys Asn Gln Val Ser Leu Ser Cys Ala Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Val Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn Arg Phe Thr Gln Lys Ser Leu Ser Leu Ser Pro Gly
705                 710                 715


<210> SEQ ID NO 62
<211> LENGTH: 341
<212> TYPE: PRT
<213> ORGANISM: Artificial Sequence
<220> FEATURE:
<223> OTHER INFORMATION: anti-PD1-VL-<(G4S)2>-anti-GITR-VL-<(G4S)2>-
      huIGKC

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Gly Gly Gly Gly Ser
            100                 105                 110

Gly Gly Gly Gly Ser Ala Ile Gln Leu Thr Gln Ser Pro Ser Ser Leu
        115                 120                 125

Ser Ala Ser Val Gly Asp Arg Val Thr Ile Thr Cys Arg Ala Ser Gln
    130                 135                 140

Gly Ile Ser Ser Ala Leu Ala Trp Tyr Gln Gln Lys Pro Gly Lys Ala
145                 150                 155                 160

Pro Lys Leu Leu Ile Tyr Asp Ala Ser Ser Leu Glu Ser Gly Val Pro
                165                 170                 175

Ser Arg Phe Ser Gly Ser Gly Ser Gly Thr Asp Phe Thr Leu Thr Ile
            180                 185                 190
```

```
Ser Ser Leu Gln Pro Glu Asp Phe Ala Thr Tyr Tyr Cys Gln Gln Phe
        195                 200                 205

Asn Ser Tyr Pro Tyr Thr Phe Gly Gln Gly Thr Lys Leu Glu Ile Lys
    210                 215                 220

Gly Gly Gly Gly Ser Gly Gly Gly Gly Ser Arg Thr Val Ala Ala Pro
225                 230                 235                 240

Ser Val Phe Ile Phe Pro Pro Ser Asp Glu Gln Leu Lys Ser Gly Thr
                245                 250                 255

Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
    290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys
            340


<210> SEQ ID NO 63
<211> LENGTH: 566
<212> TYPE: PRT
<213> ORGANISM: Artificial Sequence
<220> FEATURE:
<223> OTHER INFORMATION: anti-GITR-VH-anti-PD1-VH-huIGHG1(LALA-knob)

<400> SEQUENCE: 63

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser Gln Val Gln Leu
        115                 120                 125

Val Glu Ser Gly Gly Gly Val Val Gln Pro Gly Arg Ser Leu Arg Leu
    130                 135                 140

Asp Cys Lys Ala Ser Gly Ile Thr Phe Ser Asn Ser Gly Met His Trp
145                 150                 155                 160

Val Arg Gln Ala Pro Gly Lys Gly Leu Glu Trp Val Ala Val Ile Trp
                165                 170                 175

Tyr Asp Gly Ser Lys Arg Tyr Tyr Ala Asp Ser Val Lys Gly Arg Phe
            180                 185                 190

Thr Ile Ser Arg Asp Asn Ser Lys Asn Thr Leu Phe Leu Gln Met Asn
        195                 200                 205
```

-continued

```
Ser Leu Arg Ala Glu Asp Thr Ala Val Tyr Tyr Cys Ala Thr Asn Asp
    210                 215                 220

Asp Tyr Trp Gly Gln Gly Thr Leu Val Thr Val Ser Ser Ala Ser Thr
225                 230                 235                 240

Lys Gly Pro Ser Val Phe Pro Leu Ala Pro Ser Ser Lys Ser Thr Ser
                245                 250                 255

Gly Gly Thr Ala Ala Leu Gly Cys Leu Val Lys Asp Tyr Phe Pro Glu
            260                 265                 270

Pro Val Thr Val Ser Trp Asn Ser Gly Ala Leu Thr Ser Gly Val His
        275                 280                 285

Thr Phe Pro Ala Val Leu Gln Ser Ser Gly Leu Tyr Ser Leu Ser Ser
    290                 295                 300

Val Val Thr Val Pro Ser Ser Ser Leu Gly Thr Gln Thr Tyr Ile Cys
305                 310                 315                 320

Asn Val Asn His Lys Pro Ser Asn Thr Lys Val Asp Lys Lys Val Glu
                325                 330                 335

Pro Lys Ser Cys Asp Lys Thr His Thr Cys Pro Pro Cys Pro Ala Pro
            340                 345                 350

Glu Ala Ala Gly Gly Pro Ser Val Phe Leu Phe Pro Pro Lys Pro Lys
        355                 360                 365

Asp Thr Leu Met Ile Ser Arg Thr Pro Glu Val Thr Cys Val Val Val
    370                 375                 380

Asp Val Ser His Glu Asp Pro Glu Val Lys Phe Asn Trp Tyr Val Asp
385                 390                 395                 400

Gly Val Glu Val His Asn Ala Lys Thr Lys Pro Arg Glu Glu Gln Tyr
                405                 410                 415

Asn Ser Thr Tyr Arg Val Val Ser Val Leu Thr Val Leu His Gln Asp
            420                 425                 430

Trp Leu Asn Gly Lys Glu Tyr Lys Cys Lys Val Ser Asn Lys Ala Leu
        435                 440                 445

Pro Ala Pro Ile Glu Lys Thr Ile Ser Lys Ala Lys Gly Gln Pro Arg
    450                 455                 460

Glu Pro Gln Val Tyr Thr Leu Pro Pro Cys Arg Asp Glu Leu Thr Lys
465                 470                 475                 480

Asn Gln Val Ser Leu Trp Cys Leu Val Lys Gly Phe Tyr Pro Ser Asp
                485                 490                 495

Ile Ala Val Glu Trp Glu Ser Asn Gly Gln Pro Glu Asn Asn Tyr Lys
            500                 505                 510

Thr Thr Pro Pro Val Leu Asp Ser Asp Gly Ser Phe Phe Leu Tyr Ser
        515                 520                 525

Lys Leu Thr Val Asp Lys Ser Arg Trp Gln Gln Gly Asn Val Phe Ser
    530                 535                 540

Cys Ser Val Met His Glu Ala Leu His Asn His Tyr Thr Gln Lys Ser
545                 550                 555                 560

Leu Ser Leu Ser Pro Gly
                565
```

<210> SEQ ID NO 64
<211> LENGTH: 710
<212> TYPE: PRT
<213> ORGANISM: Artificial Sequence
<220> FEATURE:
<223> OTHER INFORMATION: anti-OX40-VL-huIGKC-[PCS2]-<(G4S)6>-[PCS2]-
anti-OX40-VH-huIGHG1(LALA-hole-RF)

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Arg Lys Arg Ser Val Asp Glu
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gly Gly Ser Gly Gly Gly Gly Ser His Arg
                245                 250                 255

Arg Arg Lys Arg Ser Val Asp Glu Glu Val Gln Leu Val Gln Ser Gly
            260                 265                 270

Ala Glu Val Lys Lys Pro Gly Ala Ser Val Lys Val Ser Cys Lys Ala
        275                 280                 285

Ser Gly Tyr Thr Phe Thr Asp Ser Tyr Met Ser Trp Val Arg Gln Ala
    290                 295                 300

Pro Gly Gln Gly Leu Glu Trp Ile Gly Asp Met Tyr Pro Asp Asn Gly
305                 310                 315                 320

Asp Ser Ser Tyr Asn Gln Lys Phe Arg Glu Arg Val Thr Ile Thr Arg
                325                 330                 335

Asp Thr Ser Thr Ser Thr Ala Tyr Leu Glu Leu Ser Ser Leu Arg Ser
            340                 345                 350

Glu Asp Thr Ala Val Tyr Tyr Cys Val Leu Ala Pro Arg Trp Tyr Phe
        355                 360                 365

Ser Val Trp Gly Gln Gly Thr Leu Val Thr Val Ser Ser Ala Ser Thr
    370                 375                 380

Lys Gly Pro Ser Val Phe Pro Leu Ala Pro Ser Ser Lys Ser Thr Ser
385                 390                 395                 400

Gly Gly Thr Ala Ala Leu Gly Cys Leu Val Lys Asp Tyr Phe Pro Glu
                405                 410                 415
```

```
Pro Val Thr Val Ser Trp Asn Ser Gly Ala Leu Thr Ser Gly Val His
            420                 425                 430

Thr Phe Pro Ala Val Leu Gln Ser Ser Gly Leu Tyr Ser Leu Ser Ser
        435                 440                 445

Val Val Thr Val Pro Ser Ser Ser Leu Gly Thr Gln Thr Tyr Ile Cys
    450                 455                 460

Asn Val Asn His Lys Pro Ser Asn Thr Lys Val Asp Lys Lys Val Glu
465                 470                 475                 480

Pro Lys Ser Cys Asp Lys Thr His Thr Cys Pro Pro Cys Pro Ala Pro
                485                 490                 495

Glu Ala Ala Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser His Glu Asp Pro Glu Val Lys Phe Asn Trp Tyr Val Asp
    530                 535                 540

Gly Val Glu Val His Asn Ala Lys Thr Lys Pro Arg Glu Glu Gln Tyr
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
            580                 585                 590

Pro Ala Pro Ile Glu Lys Thr Ile Ser Lys Ala Lys Gly Gln Pro Arg
        595                 600                 605

Glu Pro Gln Val Cys Thr Leu Pro Pro Ser Arg Asp Glu Leu Thr Lys
    610                 615                 620

Asn Gln Val Ser Leu Ser Cys Ala Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Val Ser
            660                 665                 670

Lys Leu Thr Val Asp Lys Ser Arg Trp Gln Gln Gly Asn Val Phe Ser
        675                 680                 685

Cys Ser Val Met His Glu Ala Leu His Asn Arg Phe Thr Gln Lys Ser
    690                 695                 700

Leu Ser Leu Ser Pro Gly
705                 710


<210> SEQ ID NO 65
<211> LENGTH: 710
<212> TYPE: PRT
<213> ORGANISM: Artificial Sequence
<220> FEATURE:
<223> OTHER INFORMATION: anti-OX40-VL-huIGKC-[PCS2a]-<(G4S)6>-[PCS2a]-
      anti-OX40-VH-huIGHG1(LALA-hole-RF)

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Gln Gln Arg Ser Val Asp Glu
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gly Gly Ser Gly Gly Gly Gly Ser His Arg
                245                 250                 255

Arg Gln Gln Arg Ser Val Asp Glu Glu Val Gln Leu Val Gln Ser Gly
            260                 265                 270

Ala Glu Val Lys Lys Pro Gly Ala Ser Val Lys Val Ser Cys Lys Ala
        275                 280                 285

Ser Gly Tyr Thr Phe Thr Asp Ser Tyr Met Ser Trp Val Arg Gln Ala
    290                 295                 300

Pro Gly Gln Gly Leu Glu Trp Ile Gly Asp Met Tyr Pro Asp Asn Gly
305                 310                 315                 320

Asp Ser Ser Tyr Asn Gln Lys Phe Arg Glu Arg Val Thr Ile Thr Arg
                325                 330                 335

Asp Thr Ser Thr Ser Thr Ala Tyr Leu Glu Leu Ser Ser Leu Arg Ser
            340                 345                 350

Glu Asp Thr Ala Val Tyr Tyr Cys Val Leu Ala Pro Arg Trp Tyr Phe
        355                 360                 365

Ser Val Trp Gly Gln Gly Thr Leu Val Thr Val Ser Ser Ala Ser Thr
    370                 375                 380

Lys Gly Pro Ser Val Phe Pro Leu Ala Pro Ser Ser Lys Ser Thr Ser
385                 390                 395                 400

Gly Gly Thr Ala Ala Leu Gly Cys Leu Val Lys Asp Tyr Phe Pro Glu
                405                 410                 415

Pro Val Thr Val Ser Trp Asn Ser Gly Ala Leu Thr Ser Gly Val His
            420                 425                 430

Thr Phe Pro Ala Val Leu Gln Ser Ser Gly Leu Tyr Ser Leu Ser Ser
        435                 440                 445

Val Val Thr Val Pro Ser Ser Ser Leu Gly Thr Gln Thr Tyr Ile Cys
    450                 455                 460

Asn Val Asn His Lys Pro Ser Asn Thr Lys Val Asp Lys Lys Val Glu
465                 470                 475                 480
```

```
Pro Lys Ser Cys Asp Lys Thr His Thr Cys Pro Pro Cys Pro Ala Pro
                485                 490                 495

Glu Ala Ala Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser His Glu Asp Pro Glu Val Lys Phe Asn Trp Tyr Val Asp
    530                 535                 540

Gly Val Glu Val His Asn Ala Lys Thr Lys Pro Arg Glu Glu Gln Tyr
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
            580                 585                 590

Pro Ala Pro Ile Glu Lys Thr Ile Ser Lys Ala Lys Gly Gln Pro Arg
        595                 600                 605

Glu Pro Gln Val Cys Thr Leu Pro Pro Ser Arg Asp Glu Leu Thr Lys
    610                 615                 620

Asn Gln Val Ser Leu Ser Cys Ala Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Val Ser
            660                 665                 670

Lys Leu Thr Val Asp Lys Ser Arg Trp Gln Gln Gly Asn Val Phe Ser
        675                 680                 685

Cys Ser Val Met His Glu Ala Leu His Asn Arg Phe Thr Gln Lys Ser
    690                 695                 700

Leu Ser Leu Ser Pro Gly
705                 710


<210> SEQ ID NO 66
<211> LENGTH: 341
<212> TYPE: PRT
<213> ORGANISM: Artificial Sequence
<220> FEATURE:
<223> OTHER INFORMATION: anti-GITR-VL-<(G4S)2>-anti-PD1-VL-<(G4S)2>-
      huIGKC

<400> SEQUENCE: 66

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Glu Ile Val Leu Thr Gln Ser Pro Ala Thr Leu
        115                 120                 125
```

Ser Leu Ser Pro Gly Glu Arg Ala Thr Leu Ser Cys Arg Ala Ser Gln
    130                 135                 140

Ser Val Ser Ser Tyr Leu Ala Trp Tyr Gln Gln Lys Pro Gly Gln Ala
145                 150                 155                 160

Pro Arg Leu Leu Ile Tyr Asp Ala Ser Asn Arg Ala Thr Gly Ile Pro
                165                 170                 175

Ala Arg Phe Ser Gly Ser Gly Ser Gly Thr Asp Phe Thr Leu Thr Ile
            180                 185                 190

Ser Ser Leu Glu Pro Glu Asp Phe Ala Val Tyr Tyr Cys Gln Gln Ser
        195                 200                 205

Ser Asn Trp Pro Arg Thr Phe Gly Gln Gly Thr Lys Val Glu Ile Lys
    210                 215                 220

Gly Gly Gly Gly Ser Gly Gly Gly Gly Ser Arg Thr Val Ala Ala Pro
225                 230                 235                 240

Ser Val Phe Ile Phe Pro Pro Ser Asp Glu Gln Leu Lys Ser Gly Thr
                245                 250                 255

Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
    290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys
            340

<210> SEQ ID NO 67
<211> LENGTH: 566
<212> TYPE: PRT
<213> ORGANISM: Artificial Sequence
<220> FEATURE:
<223> OTHER INFORMATION: anti-PD1-VH-anti-GITR-VH-huIGHG1(LALA-knob)

<400> SEQUENCE: 67

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Gln Val Gln Leu Val Glu Ser Gly Gly Gly Val Val Gln Pro Gly
        115                 120                 125

Arg Ser Leu Arg Leu Ser Cys Ala Ala Ser Gly Phe Thr Phe Ser Ser
    130                 135                 140

```
Tyr Gly Met His Trp Val Arg Gln Ala Pro Gly Lys Gly Leu Glu Trp
145                 150                 155                 160

Val Ala Val Ile Trp Tyr Glu Gly Ser Asn Lys Tyr Tyr Ala Asp Ser
                165                 170                 175

Val Lys Gly Arg Phe Thr Ile Ser Arg Asp Asn Ser Lys Asn Thr Leu
            180                 185                 190

Tyr Leu Gln Met Asn Ser Leu Arg Ala Glu Asp Thr Ala Val Tyr Tyr
        195                 200                 205

Cys Ala Arg Gly Gly Ser Met Val Arg Gly Asp Tyr Tyr Tyr Gly Met
    210                 215                 220

Asp Val Trp Gly Gln Gly Thr Thr Val Thr Val Ser Ser Ala Ser Thr
225                 230                 235                 240

Lys Gly Pro Ser Val Phe Pro Leu Ala Pro Ser Ser Lys Ser Thr Ser
                245                 250                 255

Gly Gly Thr Ala Ala Leu Gly Cys Leu Val Lys Asp Tyr Phe Pro Glu
            260                 265                 270

Pro Val Thr Val Ser Trp Asn Ser Gly Ala Leu Thr Ser Gly Val His
        275                 280                 285

Thr Phe Pro Ala Val Leu Gln Ser Ser Gly Leu Tyr Ser Leu Ser Ser
    290                 295                 300

Val Val Thr Val Pro Ser Ser Ser Leu Gly Thr Gln Thr Tyr Ile Cys
305                 310                 315                 320

Asn Val Asn His Lys Pro Ser Asn Thr Lys Val Asp Lys Lys Val Glu
                325                 330                 335

Pro Lys Ser Cys Asp Lys Thr His Thr Cys Pro Pro Cys Pro Ala Pro
            340                 345                 350

Glu Ala Ala Gly Gly Pro Ser Val Phe Leu Phe Pro Pro Lys Pro Lys
        355                 360                 365

Asp Thr Leu Met Ile Ser Arg Thr Pro Glu Val Thr Cys Val Val Val
    370                 375                 380

Asp Val Ser His Glu Asp Pro Glu Val Lys Phe Asn Trp Tyr Val Asp
385                 390                 395                 400

Gly Val Glu Val His Asn Ala Lys Thr Lys Pro Arg Glu Glu Gln Tyr
                405                 410                 415

Asn Ser Thr Tyr Arg Val Val Ser Val Leu Thr Val Leu His Gln Asp
            420                 425                 430

Trp Leu Asn Gly Lys Glu Tyr Lys Cys Lys Val Ser Asn Lys Ala Leu
        435                 440                 445

Pro Ala Pro Ile Glu Lys Thr Ile Ser Lys Ala Lys Gly Gln Pro Arg
    450                 455                 460

Glu Pro Gln Val Tyr Thr Leu Pro Pro Cys Arg Asp Glu Leu Thr Lys
465                 470                 475                 480

Asn Gln Val Ser Leu Trp Cys Leu Val Lys Gly Phe Tyr Pro Ser Asp
                485                 490                 495

Ile Ala Val Glu Trp Glu Ser Asn Gly Gln Pro Glu Asn Asn Tyr Lys
            500                 505                 510

Thr Thr Pro Pro Val Leu Asp Ser Asp Gly Ser Phe Phe Leu Tyr Ser
        515                 520                 525

Lys Leu Thr Val Asp Lys Ser Arg Trp Gln Gln Gly Asn Val Phe Ser
    530                 535                 540

Cys Ser Val Met His Glu Ala Leu His Asn His Tyr Thr Gln Lys Ser
545                 550                 555                 560
```

```
Leu Ser Leu Ser Pro Gly
                565


<210> SEQ ID NO 68
<211> LENGTH: 710
<212> TYPE: PRT
<213> ORGANISM: Artificial Sequence
<220> FEATURE:
<223> OTHER INFORMATION: anti-OX40-VL-huIGKC-[PCS2]-<(G4S)6>-[PCS2]-
      anti-OX40-VH-huIGHG1(LALA-hole-RF)

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Arg Lys Arg Ser Val Asp Glu
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gly Gly Ser Gly Gly Gly Gly Ser His Arg
                245                 250                 255

Arg Arg Lys Arg Ser Val Asp Glu Glu Val Gln Leu Val Gln Ser Gly
            260                 265                 270

Ala Glu Val Lys Lys Pro Gly Ala Ser Val Lys Val Ser Cys Lys Ala
        275                 280                 285

Ser Gly Tyr Thr Phe Thr Asp Ser Tyr Met Ser Trp Val Arg Gln Ala
    290                 295                 300

Pro Gly Gln Gly Leu Glu Trp Ile Gly Asp Met Tyr Pro Asp Asn Gly
305                 310                 315                 320

Asp Ser Ser Tyr Asn Gln Lys Phe Arg Glu Arg Val Thr Ile Thr Arg
                325                 330                 335

Asp Thr Ser Thr Ser Thr Ala Tyr Leu Glu Leu Ser Ser Leu Arg Ser
            340                 345                 350
```

-continued

```
Glu Asp Thr Ala Val Tyr Tyr Cys Val Leu Ala Pro Arg Trp Tyr Phe
        355                 360                 365

Ser Val Trp Gly Gln Gly Thr Leu Val Thr Val Ser Ser Ala Ser Thr
    370                 375                 380

Lys Gly Pro Ser Val Phe Pro Leu Ala Pro Ser Ser Lys Ser Thr Ser
385                 390                 395                 400

Gly Gly Thr Ala Ala Leu Gly Cys Leu Val Lys Asp Tyr Phe Pro Glu
                405                 410                 415

Pro Val Thr Val Ser Trp Asn Ser Gly Ala Leu Thr Ser Gly Val His
            420                 425                 430

Thr Phe Pro Ala Val Leu Gln Ser Ser Gly Leu Tyr Ser Leu Ser Ser
        435                 440                 445

Val Val Thr Val Pro Ser Ser Ser Leu Gly Thr Gln Thr Tyr Ile Cys
    450                 455                 460

Asn Val Asn His Lys Pro Ser Asn Thr Lys Val Asp Lys Lys Val Glu
465                 470                 475                 480

Pro Lys Ser Cys Asp Lys Thr His Thr Cys Pro Pro Cys Pro Ala Pro
                485                 490                 495

Glu Ala Ala Gly Gly Pro Ser Val Phe Leu Phe Pro Pro Lys Pro Lys
            500                 505                 510

Asp Thr Leu Met Ile Ser Arg Thr Pro Glu Val Thr Cys Val Val Val
        515                 520                 525

Asp Val Ser His Glu Asp Pro Glu Val Lys Phe Asn Trp Tyr Val Asp
    530                 535                 540

Gly Val Glu Val His Asn Ala Lys Thr Lys Pro Arg Glu Glu Gln Tyr
545                 550                 555                 560

Asn Ser Thr Tyr Arg Val Val Ser Val Leu Thr Val Leu His Gln Asp
                565                 570                 575

Trp Leu Asn Gly Lys Glu Tyr Lys Cys Lys Val Ser Asn Lys Ala Leu
            580                 585                 590

Pro Ala Pro Ile Glu Lys Thr Ile Ser Lys Ala Lys Gly Gln Pro Arg
        595                 600                 605

Glu Pro Gln Val Cys Thr Leu Pro Pro Ser Arg Asp Glu Leu Thr Lys
    610                 615                 620

Asn Gln Val Ser Leu Ser Cys Ala Val Lys Gly Phe Tyr Pro Ser Asp
625                 630                 635                 640

Ile Ala Val Glu Trp Glu Ser Asn Gly Gln Pro Glu Asn Asn Tyr Lys
                645                 650                 655

Thr Thr Pro Pro Val Leu Asp Ser Asp Gly Ser Phe Phe Leu Val Ser
            660                 665                 670

Lys Leu Thr Val Asp Lys Ser Arg Trp Gln Gln Gly Asn Val Phe Ser
        675                 680                 685

Cys Ser Val Met His Glu Ala Leu His Asn Arg Phe Thr Gln Lys Ser
    690                 695                 700

Leu Ser Leu Ser Pro Gly
705                 710
```

<210> SEQ ID NO 69
<211> LENGTH: 710
<212> TYPE: PRT
<213> ORGANISM: Artificial Sequence
<220> FEATURE:
<223> OTHER INFORMATION: anti-OX40-VL-huIGKC-[PCS2a]-<(G4S)6>-[PCS2a]-
anti-OX40-VH-huIGHG1(LALA-hole-RF)

-continued

<400> SEQUENCE: 69

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Gln Gln Arg Ser Val Asp Glu
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gly Gly Ser Gly Gly Gly Gly Ser His Arg
                245                 250                 255

Arg Gln Gln Arg Ser Val Asp Glu Glu Val Gln Leu Val Gln Ser Gly
            260                 265                 270

Ala Glu Val Lys Lys Pro Gly Ala Ser Val Lys Val Ser Cys Lys Ala
        275                 280                 285

Ser Gly Tyr Thr Phe Thr Asp Ser Tyr Met Ser Trp Val Arg Gln Ala
    290                 295                 300

Pro Gly Gln Gly Leu Glu Trp Ile Gly Asp Met Tyr Pro Asp Asn Gly
305                 310                 315                 320

Asp Ser Ser Tyr Asn Gln Lys Phe Arg Glu Arg Val Thr Ile Thr Arg
                325                 330                 335

Asp Thr Ser Thr Ser Thr Ala Tyr Leu Glu Leu Ser Ser Leu Arg Ser
            340                 345                 350

Glu Asp Thr Ala Val Tyr Tyr Cys Val Leu Ala Pro Arg Trp Tyr Phe
        355                 360                 365

Ser Val Trp Gly Gln Gly Thr Leu Val Thr Val Ser Ser Ala Ser Thr
    370                 375                 380

Lys Gly Pro Ser Val Phe Pro Leu Ala Pro Ser Ser Lys Ser Thr Ser
385                 390                 395                 400

Gly Gly Thr Ala Ala Leu Gly Cys Leu Val Lys Asp Tyr Phe Pro Glu
                405                 410                 415
```

Pro Val Thr Val Ser Trp Asn Ser Gly Ala Leu Thr Ser Gly Val His
420 425 430

Thr Phe Pro Ala Val Leu Gln Ser Ser Gly Leu Tyr Ser Leu Ser Ser
435 440 445

Val Val Thr Val Pro Ser Ser Ser Leu Gly Thr Gln Thr Tyr Ile Cys
450 455 460

Asn Val Asn His Lys Pro Ser Asn Thr Lys Val Asp Lys Lys Val Glu
465 470 475 480

Pro Lys Ser Cys Asp Lys Thr His Thr Cys Pro Pro Cys Pro Ala Pro
485 490 495

Glu Ala Ala Gly Gly Pro Ser Val Phe Leu Phe Pro Pro Lys Pro Lys
500 505 510

Asp Thr Leu Met Ile Ser Arg Thr Pro Glu Val Thr Cys Val Val Val
515 520 525

Asp Val Ser His Glu Asp Pro Glu Val Lys Phe Asn Trp Tyr Val Asp
530 535 540

Gly Val Glu Val His Asn Ala Lys Thr Lys Pro Arg Glu Glu Gln Tyr
545 550 555 560

Asn Ser Thr Tyr Arg Val Val Ser Val Leu Thr Val Leu His Gln Asp
565 570 575

Trp Leu Asn Gly Lys Glu Tyr Lys Cys Lys Val Ser Asn Lys Ala Leu
580 585 590

Pro Ala Pro Ile Glu Lys Thr Ile Ser Lys Ala Lys Gly Gln Pro Arg
595 600 605

Glu Pro Gln Val Cys Thr Leu Pro Pro Ser Arg Asp Glu Leu Thr Lys
610 615 620

Asn Gln Val Ser Leu Ser Cys Ala Val Lys Gly Phe Tyr Pro Ser Asp
625 630 635 640

Ile Ala Val Glu Trp Glu Ser Asn Gly Gln Pro Glu Asn Asn Tyr Lys
645 650 655

Thr Thr Pro Pro Val Leu Asp Ser Asp Gly Ser Phe Phe Leu Val Ser
660 665 670

Lys Leu Thr Val Asp Lys Ser Arg Trp Gln Gln Gly Asn Val Phe Ser
675 680 685

Cys Ser Val Met His Glu Ala Leu His Asn Arg Phe Thr Gln Lys Ser
690 695 700

Leu Ser Leu Ser Pro Gly
705 710

<210> SEQ ID NO 70
<211> LENGTH: 465
<212> TYPE: PRT
<213> ORGANISM: Artificial Sequence
<220> FEATURE:
<223> OTHER INFORMATION: anti-PD1-VL-huIGKC-[PCS2]-<(G4S)3>-[PCS2]-anti-4.1BB-VL-huIGKC

<400> SEQUENCE: 70

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly

-continued

```
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Arg Lys Arg Ser Val Asp Glu
    210                 215                 220

Gly Gly Gly Gly Ser Gly Gly Gly Gly Ser Gly Gly Gly Gly Ser His
225                 230                 235                 240

Arg Arg Arg Lys Arg Ser Val Asp Glu Glu Ile Val Leu Thr Gln Ser
                245                 250                 255

Pro Ala Thr Leu Ser Leu Ser Pro Gly Glu Arg Ala Thr Leu Ser Cys
            260                 265                 270

Arg Ala Ser Gln Ser Val Ser Ser Tyr Leu Ala Trp Tyr Gln Gln Lys
        275                 280                 285

Pro Gly Gln Ala Pro Arg Leu Leu Ile Tyr Asp Ala Ser Asn Arg Ala
    290                 295                 300

Thr Gly Ile Pro Ala Arg Phe Ser Gly Ser Gly Ser Gly Thr Asp Phe
305                 310                 315                 320

Thr Leu Thr Ile Ser Ser Leu Glu Pro Glu Asp Phe Ala Val Tyr Tyr
                325                 330                 335

Cys Gln Gln Arg Ser Asn Trp Pro Pro Ala Leu Thr Phe Gly Gly Gly
            340                 345                 350

Thr Lys Val Glu Ile Lys Arg Thr Val Ala Ala Pro Ser Val Phe Ile
        355                 360                 365

Phe Pro Pro Ser Asp Glu Gln Leu Lys Ser Gly Thr Ala Ser Val Val
    370                 375                 380

Cys Leu Leu Asn Asn Phe Tyr Pro Arg Glu Ala Lys Val Gln Trp Lys
385                 390                 395                 400

Val Asp Asn Ala Leu Gln Ser Gly Asn Ser Gln Glu Ser Val Thr Glu
                405                 410                 415

Gln Asp Ser Lys Asp Ser Thr Tyr Ser Leu Ser Ser Thr Leu Thr Leu
            420                 425                 430

Ser Lys Ala Asp Tyr Glu Lys His Lys Val Tyr Ala Cys Glu Val Thr
        435                 440                 445

His Gln Gly Leu Ser Ser Pro Val Thr Lys Ser Phe Asn Arg Gly Glu
    450                 455                 460

Cys
465
```

<210> SEQ ID NO 71
<211> LENGTH: 686
<212> TYPE: PRT
<213> ORGANISM: Artificial Sequence
<220> FEATURE:
<223> OTHER INFORMATION: anti-PD1-VH-huIGH-G11-huIGH-H1-<(G4S)3>-anti-4.1BB-VH-huIGHG1-(LALA)

<400> SEQUENCE: 71

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Gly Gly Gly
    210                 215                 220

Gly Ser Gly Gly Gly Gly Ser Gly Gly Gly Gly Ser Gln Val Gln Leu
225                 230                 235                 240

Gln Gln Trp Gly Ala Gly Leu Leu Lys Pro Ser Glu Thr Leu Ser Leu
                245                 250                 255

Thr Cys Ala Val Tyr Gly Gly Ser Phe Ser Gly Tyr Tyr Trp Ser Trp
            260                 265                 270

Ile Arg Gln Ser Pro Glu Lys Gly Leu Glu Trp Ile Gly Glu Ile Asn
        275                 280                 285

His Gly Gly Tyr Val Thr Tyr Asn Pro Ser Leu Glu Ser Arg Val Thr
    290                 295                 300

Ile Ser Val Asp Thr Ser Lys Asn Gln Phe Ser Leu Lys Leu Ser Ser
305                 310                 315                 320

Val Thr Ala Ala Asp Thr Ala Val Tyr Tyr Cys Ala Arg Asp Tyr Gly
                325                 330                 335

Pro Gly Asn Tyr Asp Trp Tyr Phe Asp Leu Trp Gly Arg Gly Thr Leu
            340                 345                 350

Val Thr Val Ser Ser Ala Ser Thr Lys Gly Pro Ser Val Phe Pro Leu
```

```
        355                 360                 365

Ala Pro Ser Ser Lys Ser Thr Ser Gly Gly Thr Ala Ala Leu Gly Cys
    370                 375                 380

Leu Val Lys Asp Tyr Phe Pro Glu Pro Val Thr Val Ser Trp Asn Ser
385                 390                 395                 400

Gly Ala Leu Thr Ser Gly Val His Thr Phe Pro Ala Val Leu Gln Ser
                405                 410                 415

Ser Gly Leu Tyr Ser Leu Ser Ser Val Val Thr Val Pro Ser Ser Ser
            420                 425                 430

Leu Gly Thr Gln Thr Tyr Ile Cys Asn Val Asn His Lys Pro Ser Asn
        435                 440                 445

Thr Lys Val Asp Lys Lys Val Glu Pro Lys Ser Cys Asp Lys Thr His
    450                 455                 460

Thr Cys Pro Pro Cys Pro Ala Pro Glu Ala Ala Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser His Glu Asp Pro Glu
            500                 505                 510

Val Lys Phe Asn Trp Tyr Val Asp Gly Val Glu Val His Asn Ala Lys
        515                 520                 525

Thr Lys Pro Arg Glu Glu Gln Tyr Asn Ser Thr Tyr Arg Val Val Ser
    530                 535                 540

Val Leu Thr Val Leu His Gln Asp Trp Leu Asn Gly Lys Glu Tyr Lys
545                 550                 555                 560

Cys Lys Val Ser Asn Lys Ala Leu Pro Ala Pro Ile Glu Lys Thr Ile
                565                 570                 575

Ser Lys Ala Lys Gly Gln Pro Arg Glu Pro Gln Val Tyr Thr Leu Pro
            580                 585                 590

Pro Ser Arg Asp Glu Leu Thr Lys Asn Gln Val Ser Leu Thr Cys Leu
        595                 600                 605

Val Lys Gly Phe Tyr Pro Ser Asp Ile Ala Val Glu Trp Glu Ser Asn
    610                 615                 620

Gly Gln Pro Glu Asn Asn Tyr Lys Thr Thr Pro Pro Val Leu Asp Ser
625                 630                 635                 640

Asp Gly Ser Phe Phe Leu Tyr Ser Lys Leu Thr Val Asp Lys Ser Arg
                645                 650                 655

Trp Gln Gln Gly Asn Val Phe Ser Cys Ser Val Met His Glu Ala Leu
            660                 665                 670

His Asn His Tyr Thr Gln Lys Ser Leu Ser Leu Ser Pro Gly
        675                 680                 685


<210> SEQ ID NO 72
<211> LENGTH: 465
<212> TYPE: PRT
<213> ORGANISM: Artificial Sequence
<220> FEATURE:
<223> OTHER INFORMATION: anti-PD1-VL-huIGKC-[PCS2a]-<(G4S)3>-[PCS2a]-
      anti-4.1BB-VL-huIGKC

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

-continued

```
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Gln Gln Arg Ser Val Asp Glu
    210                 215                 220

Gly Gly Gly Gly Ser Gly Gly Gly Gly Ser Gly Gly Gly Gly Ser His
225                 230                 235                 240

Arg Arg Gln Gln Arg Ser Val Asp Glu Glu Ile Val Leu Thr Gln Ser
                245                 250                 255

Pro Ala Thr Leu Ser Leu Ser Pro Gly Glu Arg Ala Thr Leu Ser Cys
            260                 265                 270

Arg Ala Ser Gln Ser Val Ser Ser Tyr Leu Ala Trp Tyr Gln Gln Lys
        275                 280                 285

Pro Gly Gln Ala Pro Arg Leu Leu Ile Tyr Asp Ala Ser Asn Arg Ala
    290                 295                 300

Thr Gly Ile Pro Ala Arg Phe Ser Gly Ser Gly Ser Gly Thr Asp Phe
305                 310                 315                 320

Thr Leu Thr Ile Ser Ser Leu Glu Pro Glu Asp Phe Ala Val Tyr Tyr
                325                 330                 335

Cys Gln Gln Arg Ser Asn Trp Pro Pro Ala Leu Thr Phe Gly Gly Gly
            340                 345                 350

Thr Lys Val Glu Ile Lys Arg Thr Val Ala Ala Pro Ser Val Phe Ile
        355                 360                 365

Phe Pro Pro Ser Asp Glu Gln Leu Lys Ser Gly Thr Ala Ser Val Val
    370                 375                 380

Cys Leu Leu Asn Asn Phe Tyr Pro Arg Glu Ala Lys Val Gln Trp Lys
385                 390                 395                 400

Val Asp Asn Ala Leu Gln Ser Gly Asn Ser Gln Glu Ser Val Thr Glu
                405                 410                 415

Gln Asp Ser Lys Asp Ser Thr Tyr Ser Leu Ser Ser Thr Leu Thr Leu
            420                 425                 430

Ser Lys Ala Asp Tyr Glu Lys His Lys Val Tyr Ala Cys Glu Val Thr
        435                 440                 445

His Gln Gly Leu Ser Ser Pro Val Thr Lys Ser Phe Asn Arg Gly Glu
```

```
    450                 455                 460

Cys
465


<210> SEQ ID NO 73
<211> LENGTH: 463
<212> TYPE: PRT
<213> ORGANISM: Artificial Sequence
<220> FEATURE:
<223> OTHER INFORMATION: anti-PD1-VL-huIGKC-[PCS2]-<(G4S)3>-[PCS2]-anti-
      OX40-VL-huIGKC

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys His Arg Arg Arg Lys Arg Ser Val Asp Glu
    210                 215                 220

Gly Gly Gly Gly Ser Gly Gly Gly Gly Ser Gly Gly Gly Gly Ser His
225                 230                 235                 240

Arg Arg Arg Lys Arg Ser Val Asp Glu Asp Ile Gln Met Thr Gln Ser
                245                 250                 255

Pro Ser Ser Leu Ser Ala Ser Val Gly Asp Arg Val Thr Ile Thr Cys
            260                 265                 270

Arg Ala Ser Gln Asp Ile Ser Asn Tyr Leu Asn Trp Tyr Gln Gln Lys
        275                 280                 285

Pro Gly Lys Ala Pro Lys Leu Leu Ile Tyr Tyr Thr Ser Arg Leu Arg
    290                 295                 300

Ser Gly Val Pro Ser Arg Phe Ser Gly Ser Gly Ser Gly Thr Asp Phe
305                 310                 315                 320

Thr Leu Thr Ile Ser Ser Leu Gln Pro Glu Asp Phe Ala Thr Tyr Tyr
                325                 330                 335
```

Cys Gln Gln Gly His Thr Leu Pro Pro Thr Phe Gly Gln Gly Thr Lys
340 345 350

Val Glu Ile Lys Arg Thr Val Ala Ala Pro Ser Val Phe Ile Phe Pro
355 360 365

Pro Ser Asp Glu Gln Leu Lys Ser Gly Thr Ala Ser Val Val Cys Leu
370 375 380

Leu Asn Asn Phe Tyr Pro Arg Glu Ala Lys Val Gln Trp Lys Val Asp
385 390 395 400

Asn Ala Leu Gln Ser Gly Asn Ser Gln Glu Ser Val Thr Glu Gln Asp
405 410 415

Ser Lys Asp Ser Thr Tyr Ser Leu Ser Ser Thr Leu Thr Leu Ser Lys
420 425 430

Ala Asp Tyr Glu Lys His Lys Val Tyr Ala Cys Glu Val Thr His Gln
435 440 445

Gly Leu Ser Ser Pro Val Thr Lys Ser Phe Asn Arg Gly Glu Cys
450 455 460

<210> SEQ ID NO 74
<211> LENGTH: 682
<212> TYPE: PRT
<213> ORGANISM: Artificial Sequence
<220> FEATURE:
<223> OTHER INFORMATION: anti-PD1-VH-huIGH-G11-huIGH-H1-<(G4S)3>-anti-OX40-VH-huIGHG1-(LALA)

<400> SEQUENCE: 74

Gln Val Gln Leu Val Glu Ser Gly Gly Gly Val Val Gln Pro Gly Arg
1 5 10 15

Ser Leu Arg Leu Asp Cys Lys Ala Ser Gly Ile Thr Phe Ser Asn Ser
20 25 30

Gly Met His Trp Val Arg Gln Ala Pro Gly Lys Gly Leu Glu Trp Val
35 40 45

Ala Val Ile Trp Tyr Asp Gly Ser Lys Arg Tyr Tyr Ala Asp Ser Val
50 55 60

Lys Gly Arg Phe Thr Ile Ser Arg Asp Asn Ser Lys Asn Thr Leu Phe
65 70 75 80

Leu Gln Met Asn Ser Leu Arg Ala Glu Asp Thr Ala Val Tyr Tyr Cys
85 90 95

Ala Thr Asn Asp Asp Tyr Trp Gly Gln Gly Thr Leu Val Thr Val Ser
100 105 110

Ser Ala Ser Thr Lys Gly Pro Ser Val Phe Pro Leu Ala Pro Ser Ser
115 120 125

Lys Ser Thr Ser Gly Gly Thr Ala Ala Leu Gly Cys Leu Val Lys Asp
130 135 140

Tyr Phe Pro Glu Pro Val Thr Val Ser Trp Asn Ser Gly Ala Leu Thr
145 150 155 160

Ser Gly Val His Thr Phe Pro Ala Val Leu Gln Ser Ser Gly Leu Tyr
165 170 175

Ser Leu Ser Ser Val Val Thr Val Pro Ser Ser Ser Leu Gly Thr Gln
180 185 190

Thr Tyr Ile Cys Asn Val Asn His Lys Pro Ser Asn Thr Lys Val Asp
195 200 205

Lys Lys Val Glu Pro Lys Ser Cys Asp Lys Thr His Thr Gly Gly Gly
210 215 220

Gly Ser Gly Gly Gly Gly Ser Gly Gly Gly Gly Ser Glu Val Gln Leu
225 230 235 240

-continued

```
Val Gln Ser Gly Ala Glu Val Lys Lys Pro Gly Ala Ser Val Lys Val
                245                 250                 255

Ser Cys Lys Ala Ser Gly Tyr Thr Phe Thr Asp Ser Tyr Met Ser Trp
            260                 265                 270

Val Arg Gln Ala Pro Gly Gln Gly Leu Glu Trp Ile Gly Asp Met Tyr
        275                 280                 285

Pro Asp Asn Gly Asp Ser Ser Tyr Asn Gln Lys Phe Arg Glu Arg Val
    290                 295                 300

Thr Ile Thr Arg Asp Thr Ser Thr Ser Thr Ala Tyr Leu Glu Leu Ser
305                 310                 315                 320

Ser Leu Arg Ser Glu Asp Thr Ala Val Tyr Tyr Cys Val Leu Ala Pro
                325                 330                 335

Arg Trp Tyr Phe Ser Val Trp Gly Gln Gly Thr Leu Val Thr Val Ser
            340                 345                 350

Ser Ala Ser Thr Lys Gly Pro Ser Val Phe Pro Leu Ala Pro Ser Ser
        355                 360                 365

Lys Ser Thr Ser Gly Gly Thr Ala Ala Leu Gly Cys Leu Val Lys Asp
    370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Ser Ser Leu Gly Thr Gln
            420                 425                 430

Thr Tyr Ile Cys Asn Val Asn His Lys Pro Ser Asn Thr Lys Val Asp
        435                 440                 445

Lys Lys Val Glu Pro Lys Ser Cys Asp Lys Thr His Thr Cys Pro Pro
    450                 455                 460

Cys Pro Ala Pro Glu Ala Ala Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Asn Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Ser Arg Asp
            580                 585                 590

Glu Leu Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655
```

Asn Val Phe Ser Cys Ser Val Met His Glu Ala Leu His Asn His Tyr
660 665 670

Thr Gln Lys Ser Leu Ser Leu Ser Pro Gly
675 680

<210> SEQ ID NO 75
<211> LENGTH: 463
<212> TYPE: PRT
<213> ORGANISM: Artificial Sequence
<220> FEATURE:
<223> OTHER INFORMATION: anti-PD1-VL-huIGKC-[PCS2a]-<(G4S)3>-[PCS2a]-
anti-OX40-VL-huIGKC

<400> SEQUENCE: 75

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser Ser Asn Trp Pro Arg
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys His Arg Arg Gln Gln Arg Ser Val Asp Glu
210 215 220

Gly Gly Gly Gly Ser Gly Gly Gly Gly Ser Gly Gly Gly Gly Ser His
225 230 235 240

Arg Arg Gln Gln Arg Ser Val Asp Glu Asp Ile Gln Met Thr Gln Ser
245 250 255

Pro Ser Ser Leu Ser Ala Ser Val Gly Asp Arg Val Thr Ile Thr Cys
260 265 270

Arg Ala Ser Gln Asp Ile Ser Asn Tyr Leu Asn Trp Tyr Gln Gln Lys
275 280 285

Pro Gly Lys Ala Pro Lys Leu Leu Ile Tyr Tyr Thr Ser Arg Leu Arg
290 295 300

Ser Gly Val Pro Ser Arg Phe Ser Gly Ser Gly Ser Gly Thr Asp Phe
305 310 315 320

Thr Leu Thr Ile Ser Ser Leu Gln Pro Glu Asp Phe Ala Thr Tyr Tyr
325 330 335

-continued

```
Cys Gln Gln Gly His Thr Leu Pro Pro Thr Phe Gly Gln Gly Thr Lys
            340                 345                 350

Val Glu Ile Lys Arg Thr Val Ala Ala Pro Ser Val Phe Ile Phe Pro
        355                 360                 365

Pro Ser Asp Glu Gln Leu Lys Ser Gly Thr Ala Ser Val Val Cys Leu
    370                 375                 380

Leu Asn Asn Phe Tyr Pro Arg Glu Ala Lys Val Gln Trp Lys Val Asp
385                 390                 395                 400

Asn Ala Leu Gln Ser Gly Asn Ser Gln Glu Ser Val Thr Glu Gln Asp
                405                 410                 415

Ser Lys Asp Ser Thr Tyr Ser Leu Ser Ser Thr Leu Thr Leu Ser Lys
            420                 425                 430

Ala Asp Tyr Glu Lys His Lys Val Tyr Ala Cys Glu Val Thr His Gln
        435                 440                 445

Gly Leu Ser Ser Pro Val Thr Lys Ser Phe Asn Arg Gly Glu Cys
    450                 455                 460
```